US012780875B2

(12) United States Patent
Alvarez

(10) Patent No.: US 12,780,875 B2
(45) Date of Patent: Nov. 3, 2026

(54) POLYPEPTIDES INCLUDING A BETA-TRICALCIUM PHOSPHATE-BINDING SEQUENCE AND USES THEREOF

(71) Applicant: THERADAPTIVE, INC., Frederick, MD (US)

(72) Inventor: Luis Alvarez, Lexington, MA (US)

(73) Assignee: THERADAPTIVE, INC., Frederick, MD (US)

( * ) Notice: Subject to any disclaimer, the term of this patent is extended or adjusted under 35 U.S.C. 154(b) by 547 days.

(21) Appl. No.: 18/451,003

(22) Filed: Aug. 16, 2023

(65) Prior Publication Data

US 2024/0018187 A1 Jan. 18, 2024

Related U.S. Application Data

(63) Continuation of application No. 17/506,523, filed on Oct. 20, 2021, now Pat. No. 11,773,138, which is a continuation of application No. 16/892,141, filed on Jun. 3, 2020, now Pat. No. 11,192,923, which is a continuation of application No. PCT/US2019/055939, filed on Oct. 11, 2019.

(60) Provisional application No. 62/744,941, filed on Oct. 12, 2018.

(51) Int. Cl.

| | |
|---|---|
| ***A61K 38/04*** | (2006.01) |
| ***A61K 38/16*** | (2006.01) |
| ***A61K 38/18*** | (2006.01) |
| ***A61P 19/00*** | (2006.01) |
| ***C07K 7/08*** | (2006.01) |
| ***C07K 14/00*** | (2006.01) |
| ***C07K 14/475*** | (2006.01) |
| ***C07K 14/51*** | (2006.01) |

(52) U.S. Cl.

CPC ................ *C07K 7/08* (2013.01); *A61K 38/04* (2013.01); *A61K 38/16* (2013.01); *A61K 38/1875* (2013.01); *A61P 19/00* (2018.01); *C07K 14/001* (2013.01); *C07K 14/475* (2013.01); *C07K 14/51* (2013.01)

(58) Field of Classification Search

CPC ...... C07K 7/08; C07K 14/001; C07K 14/475; C07K 14/51; C07K 2319/20; C07K 7/06; C07K 2319/00; A61K 38/04; A61K 38/16; A61K 38/1875; A61K 38/00; A61K 47/64; A61K 47/642; A61P 19/00; A61P 19/02; A61P 19/08

See application file for complete search history.

(56) References Cited

U.S. PATENT DOCUMENTS

| | | | | |
|---|---|---|---|---|
| 5,122,458 | A | 6/1992 | Post et al. | |
| 5,152,791 | A | 10/1992 | Hakamatsuka et al. | |
| 5,219,740 | A | 6/1993 | Miller et al. | |
| 5,491,082 | A | 2/1996 | Suzuki et al. | |
| 5,820,632 | A | 10/1998 | Constantz et al. | |
| 5,906,828 | A | 5/1999 | Cima et al. | |
| 6,207,453 | B1 | 3/2001 | Maass et al. | |
| 6,455,495 | B1 | 9/2002 | Orgel et al. | |
| 6,949,251 | B2 | 9/2005 | Dalal et al. | |
| 7,172,629 | B2 | 2/2007 | Mckay | |
| 7,323,542 | B2 | 1/2008 | Balian | |
| 7,572,766 | B2 | 8/2009 | Beyer, Jr. et al. | |
| 7,871,978 | B2 | 1/2011 | Balian | |
| 7,977,313 | B2 | 7/2011 | Gron et al. | |
| 8,022,040 | B2 | 9/2011 | Bertozzi et al. | |
| 8,075,562 | B2 | 12/2011 | Murphy et al. | |
| 8,137,664 | B2 | 3/2012 | Nycz et al. | |
| 8,383,769 | B2 | 2/2013 | Peled et al. | |
| 8,420,774 | B2 | 4/2013 | Murphy et al. | |
| 8,778,869 | B2 | 7/2014 | Murphy et al. | |
| 8,846,860 | B2 | 9/2014 | Murphy et al. | |
| 9,295,755 | B2 | 3/2016 | Murphy | |
| 9,809,635 | B2 | 11/2017 | Qin et al. | |
| 10,329,327 | B2 | 6/2019 | Alvarez et al. | |
| 10,675,330 | B2 | 6/2020 | Li | |
| 11,066,444 | B2 | 7/2021 | Stupp et al. | |
| 11,192,923 | B2 * | 12/2021 | Alvarez | C07K 14/001 |
| 11,773,138 | B2 * | 10/2023 | Alvarez | C07K 14/51 530/200 |
| 12,264,187 | B2 | 4/2025 | Alvarez et al. | |
| 2004/0171552 | A1 | 9/2004 | Peled et al. | |
| 2004/0197892 | A1 | 10/2004 | Moore et al. | |
| 2005/0084962 | A1 | 4/2005 | Simon | |
| 2005/0085623 | A1 | 4/2005 | Balian | |
| 2006/0040354 | A1 | 2/2006 | O'Keefe | |
| 2006/0193916 | A1 | 8/2006 | Lazarova et al. | |
| 2006/0292198 | A1 | 12/2006 | Dalal et al. | |
| 2008/0095817 | A1 | 4/2008 | Murphy | |
| 2008/0214468 | A1 | 9/2008 | Balian | |

(Continued)

FOREIGN PATENT DOCUMENTS

| | | | |
|---|---|---|---|
| CN | 102532272 | A | 7/2012 |
| CN | 104193803 | A | 12/2014 |

(Continued)

OTHER PUBLICATIONS

Bowie et al (Science, 1990, 247: 1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Alonso-Camino et al.: CARbodies: Human Antibodies Against Cell Surface Tumor Antigens Selected From Repertoires Displayed on T Cell Chimeric Antigen Receptors. Mol. Ther. Nucleic Acids. 2(5):e93 (2013).
Alvarez et al.: Tethering of epidermal growth factor (EGF) to beta tricalcium phosphate (βTCP) via fusion to a high affinity, multimeric BTCP-binding peptide: effects on human multipotent stromal cells/connective tissue progenitors. PLoS One. 10(6):e0129600:1-21 (2015).

(Continued)

*Primary Examiner* — Sudhakar Katakam
(74) *Attorney, Agent, or Firm* — Wilson Sonsini Goodrich & Rosati

(57) ABSTRACT

Provided herein are polypeptides that include one or more β-tricalcium phosphate (βTCP)-binding sequence(s) and uses thereof.

11 Claims, 12 Drawing Sheets

Specification includes a Sequence Listing.

(56) References Cited

U.S. PATENT DOCUMENTS

| | | | | |
|---|---|---|---|---|
| 2008/0279908 | A1 | 11/2008 | Bertozzi et al. | |
| 2009/0087472 | A1 | 4/2009 | Murphy et al. | |
| 2009/0305352 | A1 | 12/2009 | Dai et al. | |
| 2010/0049322 | A1 | 2/2010 | Mckay | |
| 2010/0080850 | A1 | 4/2010 | Hubbell et al. | |
| 2010/0092955 | A1 | 4/2010 | Harriman | |
| 2010/0260673 | A1 | 10/2010 | Cao et al. | |
| 2011/0129611 | A1 | 6/2011 | Murphy et al. | |
| 2011/0165132 | A1 | 7/2011 | Cool et al. | |
| 2011/0305760 | A1 | 12/2011 | Murphy et al. | |
| 2012/0028913 | A1 | 2/2012 | Peled et al. | |
| 2013/0149457 | A1 | 6/2013 | Murphy et al. | |
| 2014/0037593 | A1* | 2/2014 | Alvarez | A61P 19/00 435/6.12 |
| 2019/0322702 | A1 | 10/2019 | Alvarez et al. | |
| 2020/0031896 | A1 | 1/2020 | Cao | |
| 2020/0102458 | A1 | 4/2020 | Alemseghed et al. | |
| 2020/0182872 | A1 | 6/2020 | Reinke et al. | |
| 2020/0254061 | A1 | 8/2020 | Li | |
| 2021/0023269 | A1 | 1/2021 | Taira et al. | |
| 2021/0214408 | A1 | 7/2021 | Low et al. | |
| 2022/0220154 | A1 | 7/2022 | Alvarez | |
| 2022/0323641 | A1 | 10/2022 | Alvarez et al. | |
| 2022/0395610 | A1 | 12/2022 | Taira et al. | |
| 2023/0203115 | A1 | 6/2023 | Alvarez et al. | |
| 2023/0233740 | A1 | 7/2023 | Alvarez et al. | |
| 2023/0235002 | A1 | 7/2023 | Alvarez et al. | |
| 2024/0226383 | A9 | 7/2024 | Alvarez et al. | |
| 2025/0179136 | A1 | 6/2025 | Alvarez et al. | |

FOREIGN PATENT DOCUMENTS

| | | | |
|---|---|---|---|
| JP | 2014508555 | A | 4/2014 |
| WO | WO-0202593 | A2 | 1/2002 |
| WO | WO-03026590 | A2 | 4/2003 |
| WO | WO-2005039616 | A1 | 5/2005 |
| WO | WO-2006012414 | A2 | 2/2006 |
| WO | WO-2006078464 | A2 | 7/2006 |
| WO | WO-2007038683 | A2 | 4/2007 |
| WO | WO-2009020550 | A2 | 2/2009 |
| WO | WO-2009108934 | A2 | 9/2009 |
| WO | WO-2009126648 | A1 | 10/2009 |
| WO | WO-2010051032 | A1 | 5/2010 |
| WO | WO-2010052715 | A2 | 5/2010 |
| WO | WO-2012078671 | A2 | 6/2012 |
| WO | WO-2017096328 | A1 | 6/2017 |
| WO | WO-2020077265 | A1 | 4/2020 |
| WO | WO-2020139901 | A1 | 7/2020 |
| WO | WO-2020163766 | A1 | 8/2020 |
| WO | WO-2021194604 | A2 | 9/2021 |
| WO | WO-2021211683 | A2 | 10/2021 |
| WO | WO-2021211683 | A3 | 10/2021 |

OTHER PUBLICATIONS

Bateman et al.: Platelet-derived growth factor enhancement of two alloplastic bone matrices. J. Periodontology 76(11):1833-1841 (2005).

Batt et al.: Characterization of the Polyomavirus Late Polyadenylation Signal. Mol. Cell Biol. 15(9):4783-4790 (1995).

Boris-Lawrie et al.: Recent advances in retrovirus vector technology. Cur. Opin. Genet. Development. 3:102-109 (1993).

Bradshaw et al.: SPaRC-null mice exhibit increased adiposity without significant differences in overall body weight. PNaS 100(10):6045-6050 (2003).

Bublil et al.: The EGF receptor family: spearheading a merger of signaling and therapeutics. Current Opinion in Cell Biology 19:124-134 (2007).

Burns et al.: Vesicular Stomatitis Virus G Glycoprotein Pseudotyped Retroviral Vectors: Concentration to Very High Titer and Efficient Gene Transfer into Mammalian and Nonmammalian Cells. Proc. Natl. Acad. Sci. USA 90(17):8033-8037 (1993).

Cao et al.: Phage display peptide probes for imaging early response to bevacizumab treatment. Amino Acids. 41(5):1103-1112 (2011).

Carlens et al.: Ex vivo T lymphoccyte expansion for retroviral transduction: Influence of serum-free media on variations in cell expansion rates and lymphocyte subset distribution. Exp. Hematol. 28(10):1137-1146 (2000).

Carrodeguas et al.: Alpha-tricalcium phosphate: synthesis, properties and biomedical applications. Acta Biomaterialia 7:3536-3546 (2011).

Cavalieri, et al.: Human T lymphocytes transduced by lentiviral vectors in the absence of TCR activation maintain an intact immune competence. Blood 102(2):497-505 (2003).

Chan et al.: Expression of epidermal growth factor in transgenic mice causes growth retardation. Journal of Biological Chemistry 275(49):38693-38698 (2000).

Cheng et al.: A new protocol for high-yield purification of recombinant human CXCL8(3-72)K11R/G31P expressed in *Escherichia coli*. Protein Expression and Purification 61:65-72 (2008).

Chhabra et al.: BMP-14 Deficiency Inhibits Long Bone Fracture Healing. A Biochemical, Histologic, and Radiographic Assessment. J Orthop Trauma 19(9):629-634 (2005).

Cho et al.: The effects of synthetic peptide derived from hBMP-2 on bone formation in rabbit calvarial defect. Tissue Engineering and Regenerative Medicine 5(3):488-497 (2008).

Citri et al.: EGF-ERBB signalling: towards the systems level. Molecular Cell Biology 7:505-516 (2006).

Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.

Dickens et al.: Crystallographic studies of the role of Mg as a stabilizing impurity in beta-Ca3(PO4)2. I. The crystal structure of pure beta-Ca3(PO4)2. Journal of Solid State Chemistry 10(3):232-248 (1974).

Dickerson et al.: Identification and design of peptides for the rapid, high-yield formation of nanoparticulate TiO2 from aqueous solutions at room temperature. Chemistry of Materials 20(4):1578-1584 (2008).

Drosse et al.: Tissue Engineering Part C 14(1):79-88 (2008).

Dudak et al.: Enhancing the affinity of SEB-binding peptides by repeating their sequence. Biopolymers 98(2):145-154 (2011).

Erbe et al.: Potential of an ultraporous beta-tricalcium phosphate synthetic cancellous bone void filler and bone marrow aspirate composite graft. Eur. Spine J. 10:S141-S146 (2001).

Fan et al.: Tethered epidermal growth factor provides a survival advantage to mesenchymal stem cells. Stem Cells 25:1241-1251 (2007).

Fleming Jr. et al.: Intraoperative harvest and concentration of human bone marrow osteoprogenitors for enhancement of spinal fusion. In Orthopedic Tissue Engineering Basic Science and Practice, V.M. Goldberg and A.I. Caplan eds. (NY: Marcel Dekker, Inc.). pp. 51-65 (2004).

Freeman M., Reiterative use of the EGF receptor triggers differentiation of all cell types in the drosophila eye. Cell 87:651-660 (1996).

Friedlaender et al.: Osteogenic protein-1 (bone morphogenctic protein-7) in the treatment of tibial nonunions. J. Bone Joint Surg. Am., 83(A Suppl 1, Pt 2):S151-S158 (2001).

Gao et al.: Molecular cloning, structure, expression, and chomosomal localization of the human osterix (SP7) gene. Gene 2341:101-110 (2004).

Gibbs et al.: Epidermal growth factor and keratinocyte growth factor differentially regulate epidermal migration, growth, and differentiation. Wound Repair and Regeneration 8(3):192-203 (2000).

Glick et al.: Ligand recognition by influenza virus. The Journal of Biological Chemistry 266(35):23660-23669 (1991).

Griffith L.G., Emerging design principles in biomaterials and scaffolds for tissue engineering. Ann. N.Y. Acad. Sci. 961:83-95 (2002).

Gronthos et al.: The growth factor requirements of STRO-1-positive human bone marrow stromal precursosrs under serum-deprived conditions in vitro. Blood 85(4):929-940 (1995).

Gungormus et al.: Regulation of in vitro calcium phosphate mineralization by combinatorially selected hydroxyapatite-binding peptides. Biomacromolecules 9(3):966-973 (2008).

(56) References Cited

OTHER PUBLICATIONS

Hamilton et al.: Improved bone morphogenetic protein-2 retention in an injectable collagen matrix Using Bifunctional Peptides. PLoS One 8(8):e70715 [1-10] (2013).
Handl et al.: Hitting multiple targets with multimeric ligands. Expert Opin. 8(6):565-586 (2004).
Histing et al.: Small animal bone healing models: standards, tips, and pitfalls results of a consensus meeting. Bone. 49:591-599 (2011).
Hoang et al.: Bone recognition mechanism of porcine osteocalcin from crystal structure. Nature 425:977-980 (2003).
Huang et al.: MimoDB 2.0: a mimotope database and beyond. Nucleic Acids Research 40(Database issue):D271-D277 (2012).
Jay et al.: Engineered bivalent ligands to bias ErbB receptor-mediated signaling and phenotypes. J. Biol. Chem. 286:27729-27740 (2011).
Kenan et al.: Peptide-PEG amphiphiles as brief communication cytophobic coatings for mammalian and bacterial cells. Chemistry & Biology 13:695-700 (2006).
Kim et al.: Extracellular calcium-binding peptide-modified ceramics stimulate regeneration of calvarial bone defects. Tissue Engineering and Regenerative Medicine 13:57-65 (2016).
Kim et al.: In vitro and in vivo osteogenic activity of licochalcone A. Amino Acids. 42:1455-1465 (2012).
Kimura et al.: Effects of platelet derived growth factor, epidermal growth factor and transforming growth factor-beta on the growth of human marrow fibroblasts. British Journal of Haematology 69(1):9-12 (1988).
Kitov et al.: Optimization of tether length in nonglycosidically linked bivalent ligands that target sites 2 and 1 of a shiga-like toxin. J. Am. Chem. Soc. 125:3284-3294 (2003).
Kratchmarova et al.: Mechanism of divergent growth factor effects in mesenchymal stem cell differentiation. Science 308:1472-1477 (2005).
Krueger et al.: Tailoring chimeric ligands for studying and biasing ErbB receptor family interactions. Angew. Chem. Int. Ed. 53:2662-2666 (2014).
Kuhl et al.: Tethered epidermal growth factor as a paradigm for growth factor-induced stimulation from the solid phase. Nature Medicine 2(9):1022-1027 (1996).
Kuznetsov et al.: Factors required for bone marrow stromal fibroblast colony formation in vitro. British Journal of Haematology 97:561-570 (1997).
Lee et al.: In Vitro and In Vivo Osteogenic Activity of Largazole. ACS Med. Chem. Lett. 2(3):248-251 (2011).
Levitt et al.: Definition of an efficient synthetic poly(A) site. Genes Dev. 3(7):1019-1025 (1989).
Maheshwari et al.: Biophysical integration of effects of epidermal growth factor and fibronectin on fibroblast migration. Biophysical Journal 76:2814-2823 (1999).
Makley et al.: The Effect of Reduced Barometric Pressure on Fracture Healing in Rats. J Bone Joint Surg Am 49(5):903-914 (1967).
Marcantonio et al.: The influence of tethered epidermal growth factor on connective tissue progenitor colony formation. Biomaterials 30(27):4629-4638 (2009).
Marino et al.: Fracture Healing in Rats Exposed to Extremely Low-Frequency Electric Fields. Clin Orthop Relat Res. (145):239-244 (1979).
Martino et al.: Extracellular matrix-inspired growth factor delivery systems for bone regeneration. Advanced Drug Delivery Reviews 94:41-52 (2015).
Martino et al.: Growth factors engineered for super-affinity to the extracellular matrix enhance tissue healing. Science 343(6173):885-888 (2014).
Martyre et al.: Increased intraplatelet levels of platelet-derived growth factor and transforming growth factor-β in patients with myelofibrosis with myeloid metaplasia. British Journal of Haematology. 77:80-86 (1991).
Matsubara et al.: BMP2 regulates osterix through Msx2 and Runx2 during osteoblast differentiation. Journal of Biological Chemistry 283:29119-29125 (2008).
Mehta et al.: Synergistic effects of tethered growth factors and adhesion ligands on DNA synthesis and function of primary hepatocytes cultured on soft synthetic hydrogels. Biomaterials 31(17):4657-4671 (2010).
Miettinen et al.: Epidermal growth factor receptor function is necessary for normal craniofacial development and palate closure. Nature Genetics 22:69-73 (1999).
Mikami et al.: Inductive effects of dexamethasone on the mineralization and the osteoblastic gene expressions in mature osteoblast-like ROS17/2.8 cells. Biochem Biophys Res Comm 362(2):368-372 (2007).
Miller, A.D. Retrovirus packaging cells. Human Gene Therapy 1990; 1(1): 5-14.
Miller et al.: Improved retroviral vectors for gene transfer and expression. Biotechniques Oct. 1989; 7(9):980-982; 984-986; 989-990.
Moll et al.: Designed heterodimerizing leucine zippers with a range of pls and stabilities up to 10exp(-15) M. Protein Science 10:649-655 (2001).
Muschler et al.: Engineering principles of clinical cell-based tissue engineering. J Bone Joint Surg Am 86-A:1541-1558 (2004).
Muschler et al.: Engineering principles of clinical cell-based tissue engineering. Journal of Bone Joint Surg. 86-A(7):1541-1558 (2004).
NCBI. GenBank Accession No. NP_001191.1: Bone morphogentic protein 2 preproprotein [*Homo sapiens*]. entire document (2018).
Nuschke et al.: Epidermal growth factor tethered to beta-tricalcium phosphate bone scaffolds via a high-affinity binding peptide enhances survival of human mesenchymal stem cells/multipotent stromal cells in an immune-competent parafascial implantation assay in mice. Stem Cells Translation Medicine 5:1580-1586 (2016).
Ogose et al.: Comparison of hydroxyapatite and beta tricalcium phosphate as bone substitutes after exclusion of bone tumors. Biomedical Materials Research Part B: Applied Biomaterials 72B:94-101 (2005).
Orii et al.: Beta-tricalcium phosphate (beta-TCP) graft combined with bone marrow stromal cells (MSCs) for posterolateral spine fusion. J Med Dent Sci 52:51-57 (2005).
Orkin et al.: Thalassemia due to a mutation in the cleavage-polyadenylation signal of the human beta-globin gene. EMBO J. 4(2):453-456 (1985).
Owen et al.: Clonal analysis in vitro of osteogenic differentiation of marrow DFU-F. J Cell Science 87:731-738 (1987).
Park et al.: Treating cancer with genetically engineered T cells. Trends Biotechnol., 29(11):550-557 (2011).
PCT/US2011/063592 international Preliminary Report on Patentability dated Jun. 20, 2013.
PCT/US2011/063592 international Search Report and Written Opinion dated Feb. 14, 2013.
PCT/US2019/055939 International Preliminary Report on Patentability dated Apr. 22, 2021.
PCT/US2019/055939 International Search Report and Written Opinion dated Feb. 5, 2020.
PCT/US2021/012219 International Invitation to Pay Additional Fees dated Aug. 27, 2021.
PCT/US2021/012219 International Preliminary Report on Patentability dated Sep. 15, 2022.
PCT/US2021/012219 International Search Report and Written Opinion dated Nov. 23, 2021.
PCT/US2021/027230 International Invitation to Pay Additional Fees dated Jul. 20, 2021.
PCT/US2021/027230 International Preliminary Report on Patentability dated Oct. 26, 2022.
PCT/US2021/027230 International Search Report and Written Opinion dated Oct. 4, 2021.
Pickens et al.: Nonspanning bivalent ligands as improved surface receptor binding inhibitors of the cholera toxin B pentamer. Chemistry & Biology 11:1205-1215 (2004).
Pinkas-Kramarski et al.: Diversification of neu differentiation factor and epidermal growth factor signaling by combinatorial receptor interactions. The EMBO Journal 15(10):2452-2467 (1996).

(56) References Cited

OTHER PUBLICATIONS

Platt et al.: Sustained epidermal growth factor receptor levels and activation by tethered ligand binding enhances osteogenic differentiation of multi-potent marrow stromal cells. J. Cell Physiol. 221(2):306-317 (2009).
Poser et al.: A Standardized Critical Size Defect Model in Normal and Osteoporotic Rats to Evaluate Bone Tissue Engineered Constructs. Hindawi Publishing Corporation. BioMed Research International; Article ID 348635 (2014).
Qin et al.: Amphiregulin is a novel growth factor involved in normal bone development and in the cellular response to parathyroid hormone stimulation. Journal of Biological Chemistry 280:3974-3981 (2005).
Rieker et al.: Molecular applications of fusions to leucine zippers. Methods in Enzymology 328:282-296 (2000).
Roy et al.: Identification of a Highly Specific Hydroxyapatite-binding Peptide using Phage Display. Advanced Materials. VCH Publishers. 20(10):1830-1836 (2008).
Sanghvi et al.: Biomaterials functionalization using a novel peptide that selectively binds to a conducting polymer. Nature Materials 4:496-502 (2005).
Satomura et al.: Receptor tyrosine kinase expression in human bone marrow stromal cells. Journal of Cellular Physiology 177(3):426-438 (1998).
Scarpa et al.: Characterization of recombinant helper retroviruses from moloney-based vectors in ecotropic and amphotropic packaging cell lines. Virology. 180(2):849-852 (1991).
Schek et al.: Definition of the Upstream Efficiency Element of the Simian virus 40 Late Polyadenylation Signal by Using In Vitro Analyses. Mol. Cell Biol. 12(12):5386-5393 (1992).
Segvich, S.J. Design of peptides with targeted apatite and human bone marrow stromal cell adhesion for bone tissue engineering. (Doctoral Dissertation), Proquest UMI Publication No. 3343205 (2009).
Seker et al.: Quantitative affinity of genetically engineered repeating polypeptides to inorganic surfaces. Biomacromolecules 10:250-257 (2009).
Shen et al.: Tuning the erosion rate of artificial protein hydrogels through control of network topology. Nature Materials 5:153-158 (2006).
Sibilia et al.: Mice humanized for the EGF receptor display hypomorphic phenotypes in skin, bone and heart. Development 130(19):4515-4525 (2003).
Stemcell Technologies product description for human bone marrow stromal cells, frozen, Cat No. 70022 (2014; made of record).
Su et al.: Conformational Selectivity of Peptides for Single-Walled Carbon Nanotubes. J. Phys. Chem. B 110(47):23623-23627 (2006).
Szymanski et al.: Development and Validation of a Robust and Versatile One-plasmid Regulated Gene Expression System. Mol. Therapy. 15(7):1340-1347 (2007).
Tamama et al.: Epidermal growth factor as a candidate for ex vivo expansion of bone marrow-derived mesenchymal stem cells. Stem Cells 24:686-695 (2006).
Termine et al.: Osteonetin, a bone-specific protein linking mineral to collagen. Cell 26:99-105 (1981).
Tokumaru et al.: Ectodomain shedding of epidermal growth factor receptor ligands is required for keratinocyte migration in cutaneous wound healing. Journal of Cell Biology 151(2):209-219 (2000).
Traverse et al.: EGF triggers neuronal differentiation of PC12 cells that overexpress the EGF receptor. Curr Biol., 4(8):694-701 (1994).
Tzahar et al.: A hierarchical network of interreceptor interactions determines signal transduction by neu differentiation factor/ neuregulin and epidermal growth factor. Molecular and Cellular Biology 16(10):5276-5287 (1996).
U.S. Appl. No. 13/991,842 Office Action dated Jul. 1, 2015.
U.S. Appl. No. 13/991,842 Office Action dated Jul. 13, 2017.
U.S. Appl. No. 13/991,842 Office Action dated Nov. 18, 2016.
U.S. Appl. No. 13/991,842 Office Action dated Nov. 21, 2014.
U.S. Appl. No. 16/892,141 Office Action dated Feb. 5, 2021.
U.S. Appl. No. 16/892,141 Office Action dated Oct. 26, 2020.
U.S. Appl. No. 16/892,141 Restriction Requirement dated Jul. 10, 2020.
Verhoeyen et al.: Lentiviral Vector Gene Transfer into Human T Cells, Methods in Molecular Biology, Methods and Protocols 506:97-114, 2009.
Wang et al.: Epidermal growth factor receptor-deficient mice have delayed primary encochondral ossification because of defective ostcoclast recruitment. Journal of Biological Chemistry 279(51):53848-53856 (2004).
Wang et al.: In vivo osteogenic activity of bone marrow stromal stem cells transfected with Ad-GFP-hBMP-2. Genetics Mol. Res. 13(2):4456-4465 (2014).
Wang et al.: Phenotypic and Functional Attributes of Lentivirus-modified CD19-specific Human CD8+ Central Memory T Cells Manufactured at Clinical Scale. J. Immunother. 35(9):689-701 (2012).
Whaley et al.: Selection of peptides with semiconductor binding specificity for directed nanocrystal assembly. Nature 405:665-668 (2000).
Woychik et al.: Requirement for the 3' flanking region of the bovine growth hormone gene for accurate polyadenylylation. Proc. Natl. Acad. Sci. U.S.A. 81(13):3944-3948 (1984).
Yashima et al.: Crystal structure analysis of beta-tricalcium phosphate Ca3(PO4)2 by neutron powder diffraction. Journal of Solid State Chemistry 175(2):272-277 (2003).
Yazici et al.: Bi-functional chimeric peptide coatings for improved osteointegration of titanium implants. Minerals, Metals and Materials Society / AIME 2011 Meeting (2011).
Yuca et al.: In vitro labeling of hydroxyapatite minerals by an engineered protein. Biotechnology and Bioengineering 108:1021-1030 (2011).
Zeltinger et al.: Effect of pore size and void fraction on cellular adhesion, proliferation, and matrix deposition. Tissue Engineering 7(5):557-572 (2001).
Zhang et al.: Artificial polypeptide scaffold for protein immobilization. J Am Chem Soc. 127:10136-10137 (2005).
Ziros et al.: The bone-specific transcriptional regulator Cbfal is a target of mechanical signals in osteoblastic cells, Journal of Biological Chemistry 277(26):23934-23941 (2002).
Bang, et al. Selection and Identification of a Novel Bone-targeting Peptide for Biomedical Imaging of Bone. Scientific Reports 10(1):10576, 1-10 (2020).
Christou, Chris. et al. In vivo Assessment of AMP2, a Novel Ceramic-Binding BMP-2, in Ovine Lumbar Interbody Fusion. Spine 49(19):1381-1390 (2024).
Hoff, Samuel E. et al. Binding mechanism and binding free energy of amino acids and citrate to hydroxyapatite surfaces as a function of crystallographic facet, pH, and electrolytes. Journal of colloid and interface science 605:685-700 (2022).
Karoulias, et al. Specific Amino Acids From the Broad C-terminal Region of BMP-2 Are Crucial for Osteogenesis. Bone Reports 14:101092, 1-9 (2021).
Osta, Bilal. et al. Classical and paradoxical effects of TNF-α on bone homeostasis. Frontiers in immunology 5:48, 1-9 (2014).
Peng, Chun. et al. Potential role of bone morphogenetic protein-15 in zebrafish follicle development and oocyte maturation. Comparative Biochemistry and Physiology Part A: Molecular & Integrative Physiology 153(1):83-87 (2009).
Qu, Xiuxia. et al. BMP10 preserves cardiac function through its dual activation of SMAD-mediated and STAT3-mediated pathways. Journal of Biological Chemistry 294(52):19877-19888 (2019).
Starr, Tyler N, and Joseph W Thornton. Epistasis in protein evolution. Protein science 25(7):1204-1218 (2016).
U.S. Appl. No. 17/636,527, filed Feb. 18, 2022, entitled Materials for Delivery of Tetherable Proteins in Bone Implants, inventors Luis Alvarez et al.
U.S. Appl. No. 17/871,734, filed Jul. 22, 2022, entitled Bone Regeneration Material Having a Cotton-Wool Like Structure Formed of a Plurality of Electrospun Fibers, inventors Hiroyuki Taira et al.
U.S. Appl. No. 17/908,835, filed Sep. 1, 2022, entitled Therapeutic Compositions Comprising Graft Materials and Beta-TCP Binding Peptides and Uses Thereof, inventors Luis Alvarez et al.

(56) References Cited

OTHER PUBLICATIONS

U.S. Appl. No. 18/002,608, filed Dec. 20, 2022, entitled Osteoinductive Bone Regeneration Material and Production Method of the Same, inventors Luis Alvarez et al.
U.S. Appl. No. 18/451,003, filed Aug. 16, 2023, entitled Polypeptides Including a Beta-Tricalcium Phosphate-Binding Sequence and Uses Thereof, inventor Luis Alvarez.
U.S. Appl. No. 18/547,668, filed Aug. 23, 2023, entitled Ceramic Compositions and Methods of Use, inventors Luis Alvarez et al.
U.S. Appl. No. 19/105,766, filed Feb. 21, 2025, entitled 3D Printed Ceramic Compositions and Methods of Use, inventors Luis Alvarez et al.
U.S. Appl. No. 18/046,810 Office Action dated Jun. 12, 2024.
U.S. Appl. No. 18/046,810 Office Action dated Sep. 11, 2024.
Zhao, Weilong. et al. Predicting the Structure-Activity Relationship of Hydroxyapatite-Binding Peptides by Enhanced-Sampling Molecular Simulation. Langmuir : the ACS journal of surfaces and colloids 32(27):7009-7022 (2016).
Bae et al.: Transient Local Bone Remodeling Effects of rhBMP-2 in an Ovine Interbody Spine Fusion Model. J Bone Joint Surg Am. 98(24):2061-2070 (2016).
Chen et al.: Mechanisms of quenching of Alexa fluorophores by natural amino acids. J Am Chem So. 132(21):7244-7245 (2010).
Chloros et al.: Induced membrane technique for acute bone loss and nonunion management of the tibia. OTA International. 5(2S):e170 (2022).
Fredericks et al.: In Vivo Assessment of AMP2, a Novel Ceramic-Binding BMP-2 in two Spinal Fusion Models, in ORS 2023 Annual Meeting. (2023).
Fredericks et al.: In Vivo Assessment of AMP2, a Novel Ceramic-Binding BMP-2 in two Spinal Fusion Models, in ORS 2023 Annual Meeting. (2023) Final.
Glaeser et al.: Electrospun, synthetic bone void filler promotes human MSC function and BMP-2 mediated spinal fusion. J Biomater Appl. 35(4-5):532-543 (2020).
Kirley et al.: Characterization and optimization of fluorescein isothiocyanate labeling of humanized h2E2 anti-cocaine mAb. Biochem Biophys Rep. 35:101520 (2023).
Kretschy et al.: Sequence-Dependent Fluorescence of Cy3- and Cy5- Labeled Double-Stranded DNA. Bioconjug Chem. 27(3):840-848 (2016).
Lee et al.: Bone regeneration with low dose BMP-2 amplified by biomimetic supramolecular nanofibers within collagen scaffolds. Biomaterials. 34(2):452-459 (2013).
Lietard et al.: Sequence-dependent quenching of fluorescein fluorescence on single-stranded and double-stranded DNA. RSC Adv. 12(9):5629-5637 (2022).
Luppen et al.: Recombinant human bone morphogenetic protein-2 enhances osteotomy healing in glucocorticoid-treated rabbits. J Bone Miner Res. 17(2):301-310 (2002).
Medtronic Sofamor Danek, Inc. USA: Summary of Safety and Effectiveness Data. Food and Drug Administration. FDA PMA Database. 1-40 (2002).
Parker et al.: Comparison of a calcium phosphate bone substitute with recombinant human bone morphogenetic protein-2: a prospective study of fusion rates, clinical outcomes and complications with 24-month follow-up. Eur Spine J. 26(3):754-763 (2017).
Sandhu et al.: Histologic evaluation of the efficacy of rhBMP-2 compared with autograft bone in sheep spinal anterior interbody fusion. Spine (Phila Pa 1976). 27(2):567-575 (2002).
Shakesheff et al.: Interbody fusion using a new controlled release BMP-2 matrix. The Spine Journal. 23(9, Supplement): S46 (2023).
Slavin et al.: An evaluation of novel AMP2-coated electrospun composite scaffolds for intraoral bone regeneration: a proof-of-concept in vivo study. Front Bioeng Biotechnol. 13:1443280 (2025).
Walsh et al.: Does implantation site influence bone ingrowth into 3D-printed porous implants? The spine journal: official journal of the North American Spine Society. 19(11):1885-1898 (2019).
Welch et al.: Effect of Recombinant Human Bone Morphogenetic Protein-2 on Fracture Healing in a Goat Tibial Fracture Model. Journal of Bone and Mineral Research. 13(9):1483-1490 (1998).
Yang et al.: Comparison between heparin-conjugated fibrin and collagen sponge as bone morphogenetic protein-2 carriers for bone regeneration. Experimental & Molecular Medicine. 44(5):350-355 (2012).
Baldwin, Paul. et al. Autograft, Allograft, and Bone Graft Substitutes: Clinical Evidence and Indications for Use in the Setting of Orthopaedic Trauma Surgery. Journal of Orthopaedic Trauma 33(4):203-213 (2019).
U.S. Appl. No. 16/892,141 Application filed Jun. 3, 2020.
U.S. Appl. No. 17/506,523 Application filed Oct. 20, 2021.
U.S. Appl. No. 18/046,810 Application filed Oct. 14, 2022.
U.S. Appl. No. 19/059,012 Application filed Feb. 20, 2025.
U.S. Appl. No. 17/908,835 Office Action dated Aug. 19, 2025.
Zhang et al.: New Ouabain-Conjugated Peptide Found From Phage Displayed Peptide Library. American Journal of Hypertension, Ltd. 17:619-623 (2004).

* cited by examiner

Group A tBMP+bTCP Putty

Rat # 31 BL Wk2 Wk4 Wk8

Group C β-TCP Putty

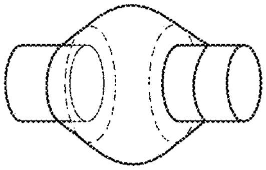
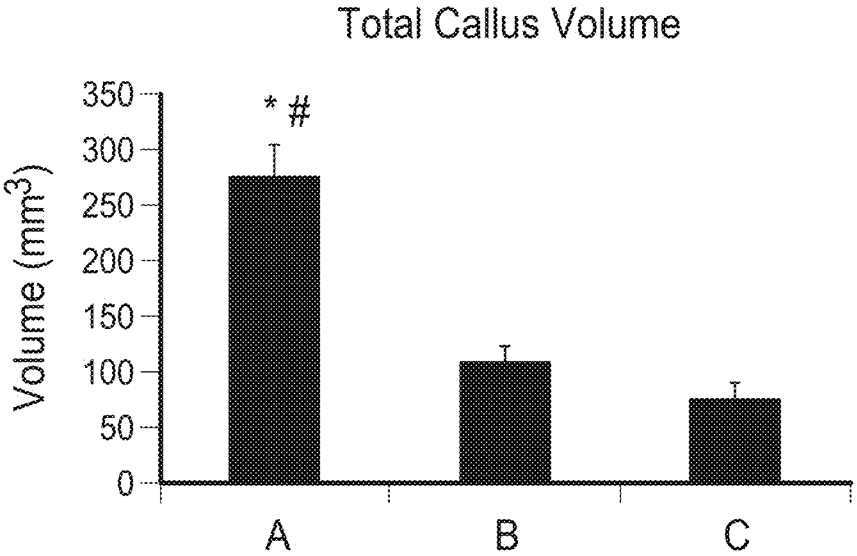
FIG. 7A
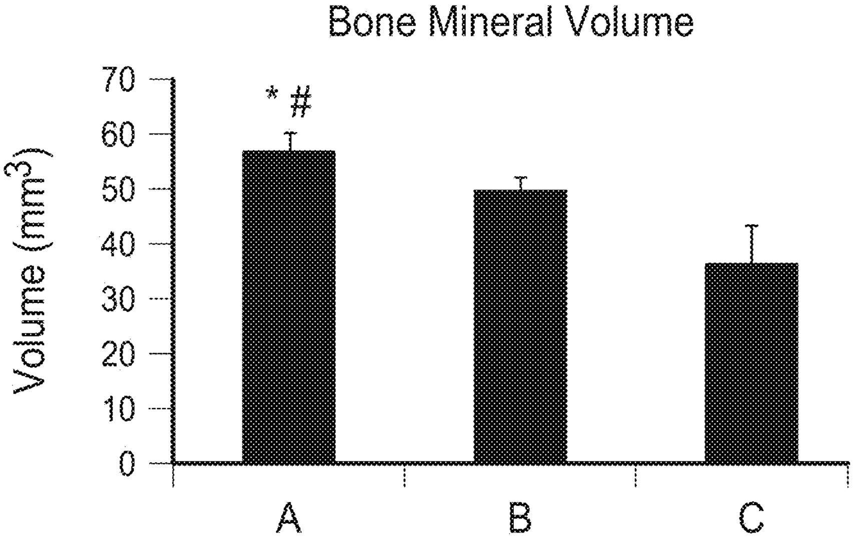
FIG. 7B

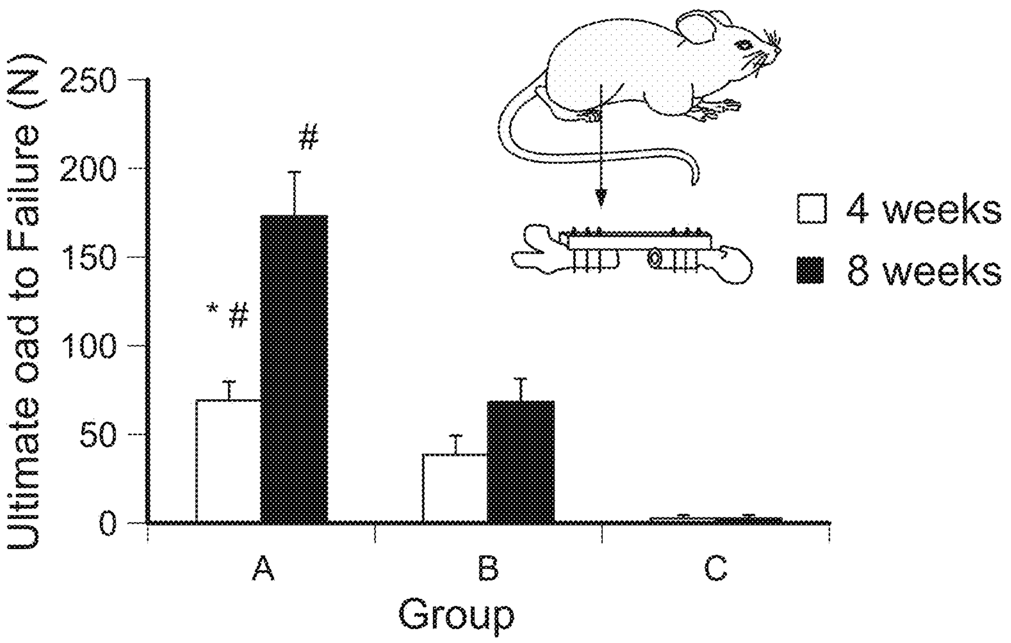
FIG. 8
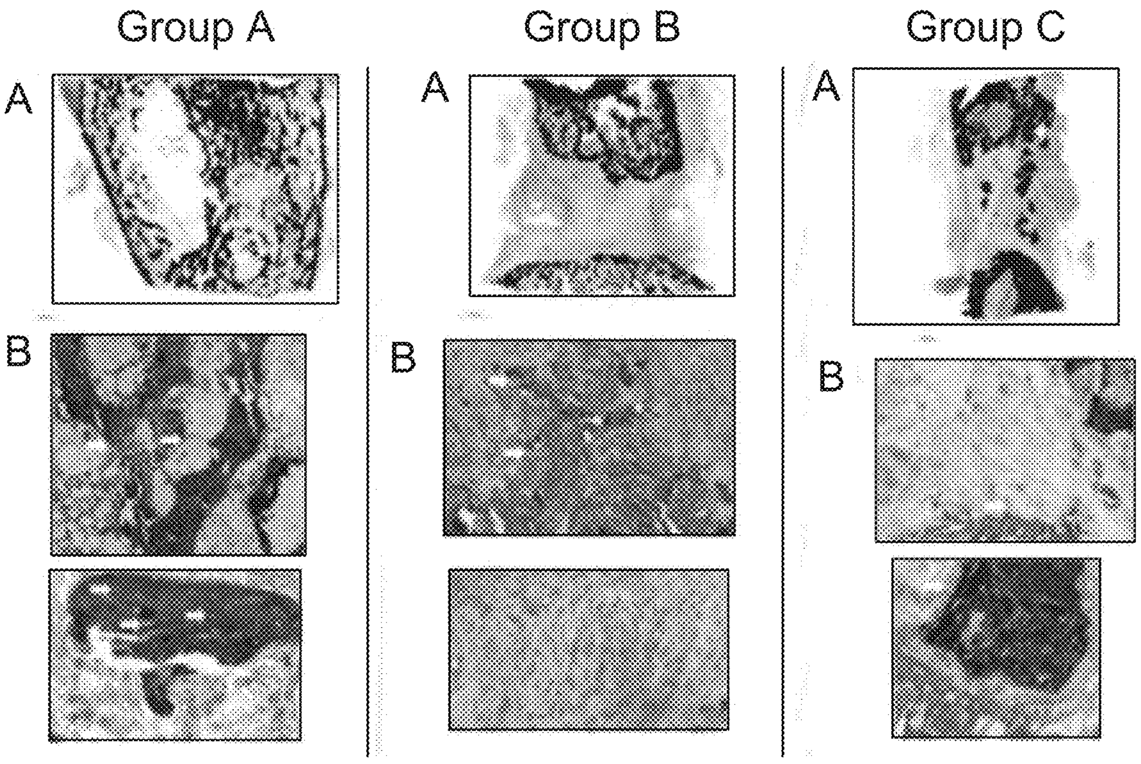
FIG. 9A-B

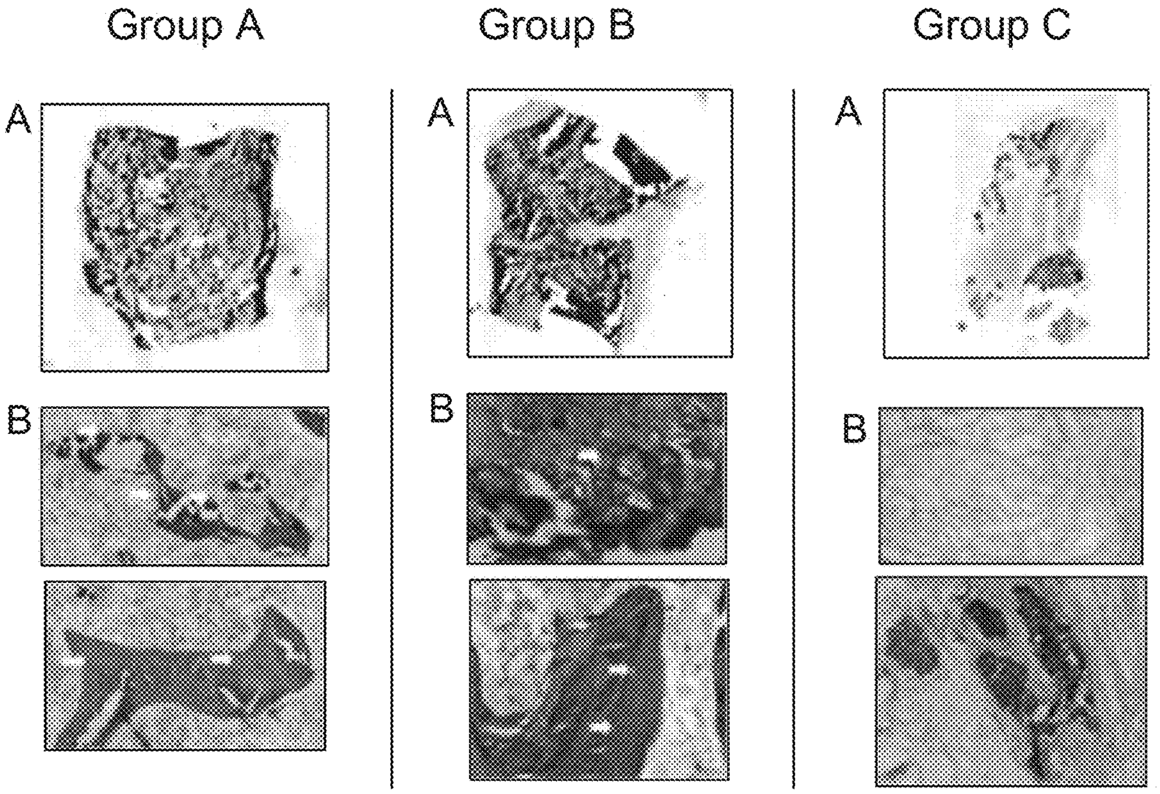
FIG. 10A-B
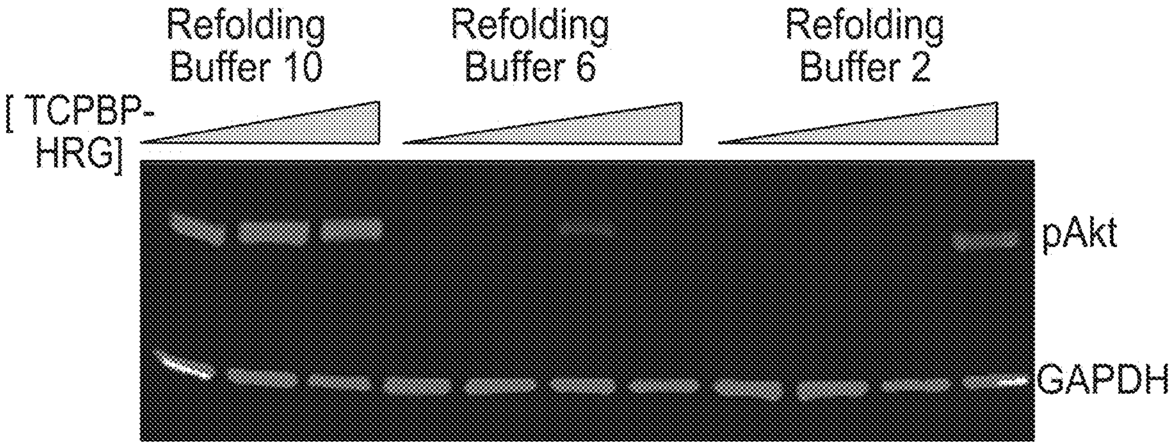
FIG. 11

POLYPEPTIDES INCLUDING A BETA-TRICALCIUM PHOSPHATE-BINDING SEQUENCE AND USES THEREOF

CROSS-REFERENCE TO RELATED APPLICATIONS

This application is a Continuation Application of U.S. patent application Ser. No. 17/506,523, filed Oct. 20, 2021, which is a Continuation of U.S. patent application Ser. No. 16/892,141, filed Jun. 3, 2020, now U.S. Pat. No. 11,192, 923, issued Dec. 7, 2021, which is a Continuation of PCT International Application No. PCT/US2019/055939, filed Oct. 11, 2019, which claims the benefit of U.S. Provisional Patent Application Ser. No. 62/744,941, filed Oct. 12, 2018; all of which are incorporated herein by reference in their entirety.

STATEMENT AS TO FEDERALLY SPONSORED RESEARCH

This invention was made with government support under grant numbers W81XWH-18-C-0182 and W81XWH-18-C-0325 awarded by the United States Army Medical Research and Materiel Command. The government has certain rights in the invention.

SEQUENCE LISTING

The instant application contains a Sequence Listing which has been submitted electronically in XML format and is hereby incorporated by reference in its entirety. Said XML copy, created on Aug. 16, 2023 is named 50222-702_303_SL.xml and is 141,746 bytes in size.

TECHNICAL FIELD

The present disclosure relates generally to the field of molecular biology, and more specifically, to methods of treating bone and cartilage loss of defects in a mammal.

BACKGROUND

In the U.S., an average of six million people break a bone annually. Of these bone defects, the majority heal without problems. However, 5-10% will heal poorly or not at all (American Academy of Orthopaedic Surgeons). Large defects, also known as critical-sized bone defects, may not heal spontaneously and can lead to non-unions. A non-union occurs when there is no indication of healing for at least three months and no expectation of further healing (American Academy of Orthopaedic Surgeons). Currently, bone grafting is regarded as the "gold standard" for treating large or segmental bone defects. However, there are limitations with this treatment such as donor site pain, risk of rejection, limited donor supply and risk of transmission of infectious disease.

The repair of critical and complex bone and cartilage defects is also limited by poor tissue regrowth on implanted orthopedic substrates. Reasons for poor tissue regrowth include the loss of implanted progenitor cells within 48 hours post-implantation and the scarcity of progenitor cells. Another contributing factor is that current orthopedic substrates fail to facilitate sufficient tissue regeneration.

SUMMARY

The present invention is based on the discovery that the use of composition including β-tricalcium phosphate (β-TCP) and a chimeric polypeptide including at least one β-TCP binding sequence and a mammalian growth factor (e.g., bone morphogenetic protein 2 (BMP-2) can vastly improve bone healing and accelerate tissue regrowth. Thus, provided herein are chimeric polypeptides that include one or more β-TCP binding sequences, and a mammalian growth factor, compositions comprising any of these chimeric polypeptides (and optionally, β-TCP), and methods of promoting bone or cartilage formulation, methods of replacing and/or repairing bone or cartilage, and methods of treating a bone fraction or bone loss that include administration of any of these compositions. The compositions and methods provided herein can increase and sustain the number of progenitor cells at sites of bone and/or cartilage injury through stem cell capture. The compositions and methods provided herein can also be applied to soft tissue repair or localized delivery of a therapeutic.

Provided herein are chimeric polypeptides that include: (i) one or more β-tricalcium phosphate (βTCP)-binding sequence(s), wherein at least one of the one or more β-TCP-binding sequence(s) is selected from the group consisting of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19); and (ii) a mammalian growth factor.

In some embodiments, the chimeric polypeptide includes two or more β-TCP-binding sequences.

In some embodiments, each neighboring pair of the two or more β-TCP binding sequences directly abut each other.

In some embodiments, each neighboring pair of the two or more β-TCP binding sequences are separated by a linker sequence.

In some embodiments, the chimeric polypeptide includes at least two different β-TCP-binding sequences.

In some embodiments, the chimeric polypeptide includes two or more copies of the same β-TCP-binding sequence.

In some embodiments, at least one of the two or more β-TCP-binding sequences is

```
                                  (SEQ ID NO: 1)
LLADTTHHRPWT
or
                                 (SEQ ID NO: 103)
GQVLPTTTPSSP.
```

In some embodiments, the at least two different β-TCP-binding sequences include

```
                                  (SEQ ID NO: 1)
LLADTTHHRPWT
and
                                  (SEQ ID NO: 2)
VIGESTHHRPWS.
```

In some embodiments, the chimeric polypeptide includes the sequence of (SEQ ID NO: 20)
LLADTTHHRPWTVIGESTHHRPWS.

In some embodiments, the at least two different β-TCP-binding sequences include (SEQ ID NO: 1)
LLADTTHHRPWT, (SEQ ID NO: 2)
VIGESTHHRPWS,
and (SEQ ID NO: 6)
IIGESSHHKPFT.

In some embodiments, the chimeric polypeptide includes the sequence of (SEQ ID NO: 21)
LLADTTHHRPWTVIGESTHHRPWSIIGESSHHKPFT.

In some embodiments, the at least two different β-TCP-binding sequences include (SEQ ID NO: 1)
LLADTTHHRPWT, (SEQ ID NO: 2)
VIGESTHHRPWS, (SEQ ID NO: 6)
IIGESSHHKPFT, (SEQ ID NO: 7)
GLGDTTHHRPWG,
and (SEQ ID NO: 4)
ILAESTHHKPWT.

In some embodiments, the chimeric polypeptide includes the sequence of (SEQ ID NO: 22)
LLADTTHHRPWTVIGESTHHRPWSIIGESSHHKPFTGLGDTTHEIRPWGI

LAESTHHKPWT.

In some embodiments, the at least two β-TCP-binding sequences include (SEQ ID NO: 1)
LLADTTHHRPWT
and (SEQ ID NO: 4)
ILAESTHHKPWT.

In some embodiments, the chimeric polypeptide includes at least one copy of the sequence LLADTTTHHRPWTI-LAESTHHKPWT (SEQ ID NO: 23).

In some embodiments, the chimeric polypeptide includes the sequence of (SEQ ID NO: 24)
LLADTTHHRPWTILAESTHHKPWTLLADTTHHRPWTILAESTHHKPWTL

LADTTHHRPWT.

In some embodiments, the at least two β-TCP-binding sequences include (SEQ ID NO: 1)
LLADTTHHRPWT
and (SEQ ID NO: 7)
GLGDTTHHRPWG.

In some embodiments, the chimeric polypeptide includes at least one copy of the sequence of LLADTTHHRPWTGLGDTTTHHRPWG (SEQ ID NO: 25).

In some embodiments, the chimeric polypeptide includes the sequence of (SEQ ID NO: 26)
LLADTTHHRPWTGLGDTTHHRPWGLLADTTHHRPWT.

In some embodiments, the chimeric polypeptide includes the sequence of (SEQ ID NO: 27)
LLADTTHHRPWTGLGDTTHHRPWGLLADTTHHRPWTGLGDTTHHRPWG

LLADTTHHRPWT.

In some embodiments, the chimeric polypeptide includes the sequence of (SEQ ID NO: 28)
LLADTTHHRPWTGLGDTTHHRPWGLLADTTHHRPWTGLGDTTHHRPWGLL

ADTTHHRPWTGLGDTTHERPWGLLADTTHHRPWT.

In some embodiments, the at least two β-TCP-binding sequences include (SEQ ID NO: 10)
STADTSHHRPS, (SEQ ID NO: 11)
TSGGESTHHRPS, (SEQ ID NO: 12)
TSGGESSHHKPS, (SEQ ID NO: 13)
TGSGDSSHHRPS,
and (SEQ ID NO: 14)
GSSGESTHHKPST.

In some embodiments, the chimeric polypeptide includes the sequence of (SEQ ID NO: 29)
STADTSHHRPSTSGGESTHHRPSTSGGESSHHKPSTGSGDSSHHRPSGSS

GESTHHKPST.

In some embodiments, the at least two β-TCP-binding sequences include (SEQ ID NO: 15)
VGADSTHHRPVT,

SEQ ID NO: 16)
GAADTTHHRPVT, (SEQ ID NO: 17)
AGADTTHHRPVT, (SEQ ID NO: 18)
GGADTTHHRPAT
and (SEQ ID NO: 19)
GGADTTHHRPGT.

In some embodiments, the chimeric polypeptide includes the sequence of (SEQ ID NO: 30)
VGADSTHHRPVTGAADTTHHRPVTAGADTTHHRPVTGGADTTHHRPATG

GADTTHHRPGT.

In some embodiments, the at least two different β-TCP-binding sequences include (SEQ ID NO: 10)
STADTSHHRPS, (SEQ ID NO: 1)
LLADTTHHRPWT, (SEQ ID NO: 11)
TSGGESTHHRPS, (SEQ ID NO: 15)
VGADSTHHRPVT, (SEQ ID NO: 12)
TSGGESSHHKPS, (SEQ ID NO: 16)
GAADTTHHRPVT, (SEQ ID NO: 13)
TGSGDSSHHRPS, (SEQ ID NO: 101)
GSSGESTHHKPS,
and (SEQ ID NO: 102)
TGGADTTHHRPAT.

In some embodiments, the chimeric polypeptide includes the sequence of (SEQ ID NO: 31)
STADTSHHRPSLLADTTHHRPWTTSGGESTHHRPSVGADSTHHRPVTTSG

GESSHHKPSGAADTTHHRPVTTGSGDSSHHRPSGSSGESTHHKPSTGGAD

TTHHRPAT.

In some embodiments of any the chimeric polypeptides described herein, the mammalian growth factor is selected from the group consisting of: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12) bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF11), growth differentiation factor 15 (GDF15), vascular endothelial growth factor (VEGF), hyaluronic acid binding protein (HABP), collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT9B), wnt family member 10A (WNT10A), wnt family member 10B (WNT10B), wnt family member 11 (WNT11), and wnt family member 16 (WNT16).

In some embodiments, the mammalian growth factor is BMP-2.

In some embodiments, the BMP-2 includes an amino acid sequence of (SEQ ID NO: 32)
MVAGTRCLLALLLPQVLLGGAAGLVPELGRRKFAAASSGRPSSQPSDEVL

SEFELRLLSMFGLKQRPTPSRDAVVPPYMLDLYRRHSGQPGSPAPDHRLE

RAASRANTVRSFHHEESLEELPETSGKTTRRFFFNLSSIPTEEFITSAEL

QVFREQMQDALGNNSSFHHRINIYEIIKPATANSKFPVTRLLDTRLVNQN

-continued

ASRWESFDVTPAVMRWTAQGHANHGFVVEVAHLEEKQGVSKRHVRISRSL

HQDEHSWSQIRPLLVTFGHDGKGHPLHKREKRQAKHKQRKRLKSSCKRHP

LYVDFSDVGWNDWIVAPPGYHAFYCHGECPFPLADHLNSTNHAIVQTLVN

SVNSKIPKACCVPTELSAISMLYLDENEKVVLKNYQDMVVEGCGCR.

In some embodiments, the BMP-2 consists of the amino acid of SEQ ID NO: 32.

In some embodiments of any of the chimeric polypeptides described herein, the chimeric polypeptide further comprises a linker sequence between a neighboring pair of a β-TCP-binding sequence and the growth factor.

In some embodiments, the linker sequence includes (SEQ ID NO: 33)
TGGSGEGGTGASTGGSAGTGGSGGTTSGEAGGSSGAG.

In some embodiments, the linker sequence consists of SEQ ID NO: 33.

In some embodiments, the linker sequence includes GAGTG (SEQ ID NO: 104).

In some embodiments, the linker sequence consists of SEQ ID NO: 34.

In some embodiments of any of the chimeric polypeptides described herein, chimeric polypeptide binds to β-TCP with a $K_D$ of about 1 picomolar to about 100 micromolar.

Also provided herein are compositions includes any of one of the chimeric polypeptides described herein.

In some embodiments, the composition further includes β-TCP. In some embodiments, the β-TCP is formulated as a powder, a putty, or a paste. In some embodiments, the β-TCP is disposed on or in a scaffold, a mesh, or a sponge.

In some embodiments of any of the compositions described herein, the composition is a pharmaceutical composition.

Also provided herein are kits that include any of the compositions described herein.

Provided herein are chimeric polypeptides that include: (i) one or more β-TCP-binding sequence(s) comprising an amino acid sequence of Formula I: $A_0B_0C_0D_0E_0F_0G_0H_0I_0J_0K_0L_0$ (Formula I) (SEQ ID NO: 35), wherein: $A_0$ is V, L, I, G, S, T or A; $B_0$ is I, L, V, Q, T, S, G or A; $C_0$ is G, A, V or S; Do is E, D, L or G; $E_0$ is S, T, P T, E or D; $F_0$ is T or S; $G_0$ is H, T or S; $H_0$ is H or T; $I_0$ is R, S, K, P or H; $J_0$ is P, S, R or K; $K_0$ is W, F, S, P, V, A or G; and $L_0$ is absent or is S, T G, (or A); and (ii) a mammalian growth factor, wherein Formula I does not include (SEQ ID NO: 1)
LLADTTHHRPWT.

In some embodiments, the chimeric polypeptide includes two or more β-TCP-binding sequences of Formula I.

In some embodiments, each neighboring pair of the two or more β-TCP binding sequences of Formula I directly abut each other.

In some embodiments, each neighboring pair of the two or more β-TCP binding sequences of Formula I are separated by a linker sequence.

In some embodiments, the chimeric polypeptide includes at least two different β-TCP-binding sequences of Formula I.

In some embodiments, the chimeric polypeptide includes two or more copies of the same β-TCP-binding sequence of Formula I.

In some embodiments, the chimeric polypeptide further includes a β-TCP-binding sequence that does not includes a sequence of Formula I.

In some embodiments of any of the chimeric polypeptides described herein, the mammalian growth factor is selected from the group consisting of: EGF, PDGF, IGF-1, FGF, FGF2, FGF18, TGF-α, TGF-β, TGF-β1, TGF-β3, OP-1, OP-2, OP-3, BMP-2, BMP-3, BMP-4, BMP-5, BMP-6, BMP-7, BMP-9, BMP-10, BMP-12, BMP-11, BMP-13, BMP-15, DPP, Vgr, GDF-1, GDF-3, GDF-5, GDF-6, GDF-7, GDF8, GDF11, GDF15, VEGF, HABP, CBP, FGF-18, KGF, TNFα, TRAIL, WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the mammalian growth factor is BMP-2. In some embodiments, the BMP-2 includes an amino acid sequence of (SEQ ID NO: 32)
MVAGTRCLLALLLPQVLLGGAAGLVPELGRRKFAAASSGRPSSQPSDEVL

SEFELRLLSMFGLKQRPTPSRDAVVPPYMLDLYRRHSGQPGSPAPDHRLE

RAASRANTVRSFHHEESLEELPETSGKTTRRFFFNLSSIPTEEFITSAEL

QVFREQMQDALGNNSSFHHRINIYEIIKPATANSKFPVTRLLDTRLVNQN

ASRWESFDVTPAVMRWTAQGHANHGFVVEVAHLEEKQGVSKRHVRISRSL

HQDEHSWSQIRPLLVTFGHDGKGHPLHKREKRQAKHKQRKRLKSSCKRHP

LYVDFSDVGWNDWIVAPPGYHAFYCHGECPFPLADHLNSTNHAIVQTLVN

SVNSKIPKACCVPTELSAISMLYLDENEKVVLKNYQDMVVEGCGCR.

In some embodiments, the BMP-2 consists of the amino acid of SEQ ID NO: 32.

In some embodiments of any of the chimeric polypetides described herein, the chimeric polypeptide further includes a linker sequence between a neighboring pair of a β-TCP-binding sequence and the growth factor.

In some embodiments, the linker sequence includes (SEQ ID NO: 33)
TGGSGEGGTGASTGGSAGTGGSGGTTSGEAGGSSGAG.

In some embodiments, the linker sequence consists of SEQ ID NO: 33.

In some embodiments, the linker sequence includes GSGATG (SEQ ID NO: 34).

In some embodiments, the linker sequence consists of SEQ ID NO: 34.

In some embodiments of any of the chimeric polypetides described herein, the chimeric polypeptide binds to β-TCP with a $K_D$ of about 1 picomolar to about 100 micromolar.

Also provided herein are compositions including any of one of the chimeric polypeptides described herein.

In some embodiments, the composition further includes β-TCP. In some embodiments, the β-TCP is formulated as a powder, a putty, or a paste. In some embodiments, the β-TCP is disposed on or in a scaffold, a mesh, or a sponge.

In some embodiments of any of the compostions described herein, the composition is a pharmaceutical composition.

Also provided herein are kits includes any of the compositions described herein.

Provided herein are methods of promoting bone or cartilage formation in a subject in need thereof that include: administering to the subject a therapeutically effective amount of any of the compositions described herein.

Also provided herein are methods of replacing and/or repairing bone or cartilage in a subject in need thereof that include: administering to the subject a therapeutically effective amount of any of the compositions described herein.

Also provided herein are methods of treating a bone fracture or bone loss in a subject in need thereof, that include: administering to the subject a therapeutically effective amount of any of the compositions described herein.

In some embodiments of any of the methods described herein, the subject has a bone fracture. In some embodiments of any of the methods described herein, the subject has a bone defect. In some embodiments of any of the methods described herein, the subject has a cartilage tear or cartilage defect. In some embodiments of any of the methods described herein, the subject has cartilage loss.

Also provided herein are β-tricalcium phosphate-binding polypeptides including at least one sequence selected from the group consisting of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19).

Also provided herein are β-tricalcium phosphate-binding polypeptides including an amino acid sequence of Formula I: $A_0B_0C_0D_0E_0F_0G_0H_0I_0J_0K_0L_0$ (Formula I) (SEQ ID NO: 35), wherein: $A_0$ is V, L, I, G, S, T or A; $B_0$ is I, L, V, Q, T, S, G or A; $C_0$ is G, A, V or S; Do is E, D, L or G; $E_0$ is S, T, P T, E or D; $F_0$ is T or S; $G_0$ is H, T or S; $H_0$ is H or T; $I_0$ is R, S, K, P or H; $J_0$ is P, S, R or K; $K_0$ is W, F, S, P, V, A or G; and $L_0$ is absent or is S, T G, (or A); wherein Formula I does not include LLADTTHHRPWT (SEQ ID NO: 1).

The term "subject" as used herein refers to any mammal. A subject therefore refers to, for example, mice, rats, dogs, cats, horses, cows, pigs, guinea pigs, rats, humans, monkeys, and the like. When the subject is a human, the subject may be referred to herein as a patient. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon), a human, or a rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine, or primate animals) may be employed.

The term "bone defect" refers to the absence or loss (e.g., partial loss) of bone at an anatomical location in a subject where it would otherwise be present in a control healthy subject. A bone defect may be the result of, e.g., an infection (e.g., osteomyelitis), a tumor, a trauma, or an adverse event of a treatment. A bone defect may also affect the muscles, soft tissue, tendons, or joints surrounding the bone defect and cause injury. In some embodiments, a bone defect includes damage to a soft tissue.

The term "cartilage defect" refers to the absence or loss (e.g., partial loss) of cartilage at an anatomical location in a subject where it would otherwise be present in a control healthy subject. A cartilage defect may be the result of, e.g., disease, osteochondritis, osteonecrosis, or trauma. For example, a cartilage defect may affect the knee joint.

"Affinity" refers to the strength of the sum total of non-covalent interactions between a β-TCP binding sequence (or a chimeric polypeptide or polypeptide comprising a β-TCP binding sequence) and its binding partner (e.g., 3-TCP). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining affinity are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 7A is a representative graph of micro-CT analyses of total callus volume in bone specimens obtained 8 weeks post-surgery from animals in Group A (n=9), B (n=7), or C (n=8). The data are represented as Mean±SEM; * P<0.01 vs B, #P<0.0.1 vs C.

FIG. 7B is a representative graph of micro-CT analyses of bone mineral volume in bone specimens obtained 8 weeks post-surgery from animals in Group A (n=9), B (n=7), or C (n=8). The data are represented as Mean±SEM; * P<0.01 vs B, #P<0.0.1 vs C.

FIG. 8 is a representative graph of ultimate load to failure (ULF) at 4- and 8-weeks post-surgery for animals in Group A, B, or C. Data are represented as the mean+/−S.E.M. *P<0.05 vs 4-week groups; #P<0.01 vs 8-week groups.

FIG. 9A are representative histological images of Von Kossa- and H&E-stained bone specimens obtained at 4 weeks post-surgery from animals in Group A, B, or C.

FIG. 9B are representative histological images of TRAP+ osteoclast-stained bone specimens obtained at 4 weeks post-surgery from animals in Groups A, B, or C. White arrows indicate osteoclasts, and yellow arrows indicate osteocytes.

FIG. 10A are representative Von Kossa- and H&E-stained histological images of bone specimens obtained at 8 weeks post-surgery from animals in Group A, B, or C.

FIG. 10B are representative TRAP+ osteoclast-stained histological images of bone specimens obtained at 8 weeks post-surgery from animals in Group A, B, or C. White arrows indicate osteoclasts, and yellow arrows indicate osteocytes.

FIG. 11 is a representative immunoblot of MCF-7 cell lysate probed with an anti-P-Akt antibody, wherein the MCF-7 cells were incubated with β-TCBP-HRG.

DETAILED DESCRIPTION

Figure 1A:
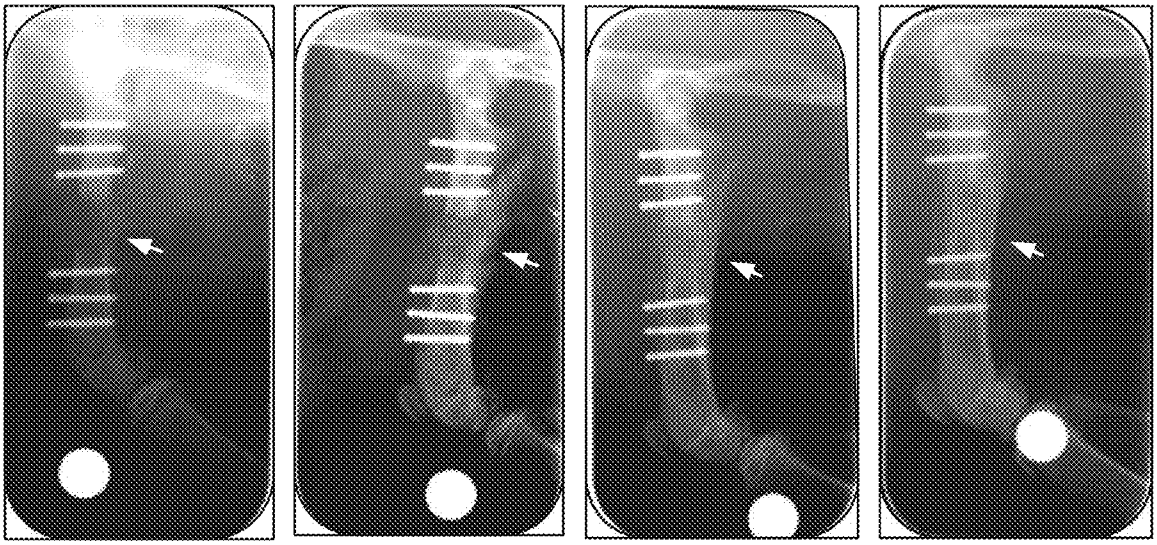
FIG. 1A are representative in vivo radiographs (lateromedial orientation) of animals from experimental Group A.

Provided herein are chimeric polypeptides that include: (i) one or more (e.g., two, three, four, five, six, seven, eight, nine, or ten) β-tricalcium phosphate (βTCP)-binding sequence(s), where at least one of the one or more β-TCP-binding sequence(s) is selected from the group of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19); and (ii) a mammalian growth factor (e.g., any of the exemplary mammalian growth factors described herein or known in the art).

Also provided herein are chimeric polypeptides that include (i) one or more β-TCP-binding sequence(s) including an amino acid sequence of Formula I:

$A_0B_0C_0D_0E_0F_0G_0H_0I_0J_0K_0L_0$ (Formula I) (SEQ ID NO: 35), where:

$A_0$ is V, L, I, G, S, T or A;

$B_0$ is I, L, V, Q, T, S, G or A;

$C_0$ is G, A, V or S;

$D_0$ is E, D, L or G;

$E_0$ is S, T, P T, E or D;

$F_0$ is T or S;

$G_0$ is H, T or S;

$H_0$ is H or T;

$I_0$ is R, S, K, P or H;

$J_0$ is P, S, R or K;

$K_0$ is W, F, S, P, V, A or G; and $L_0$ is absent or is S, T G, (or A); and (ii) a mammalian growth factor (e.g., any of the exemplary mammalian growth factors described herein or known in the art), where Formula I does not include LLADTTHHRPWT (SEQ ID NO: 1).

Also provided herein are β-tricalcium phosphate-binding polypeptides that include at least one (e.g., two, three, four, five, six, seven, eight, nine, or ten) sequence selected from the group of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTTHHRPGT (SEQ ID NO: 19). Some embodiments of these polypeptides can further include a mammalian growth factor (e.g., any of the exemplary mammalian growth factors described herein or known in the art).

Also provided herein are β-tricalcium phosphate-binding polypeptides that include an amino acid sequence of Formula I:

$A_0B_0C_0D_0E_0F_0G_0H_0I_0J_0K_0L_0$ (Formula I) (SEQ ID NO: 35), where:

$A_0$ is V, L, I, G, S, T or A;

$B_0$ is I, L, V, Q, T, S, G or A;

$C_0$ is G, A, V or S;

$D_0$ is E, D, L or G;

$E_0$ is S, T, P T, E or D;

$F_0$ is T or S;

$G_0$ is H, T or S;

$H_0$ is H or T;

$I_0$ is R, S, K, P or H;

$J_0$ is P, S, R or K;

$K_0$ is W, F, S, P, V, A or G; and $L_0$ is absent or is S, T G, (or A);

where Formula I does not include LLADTTHHRPWT (SEQ ID NO: 1). Some embodiments of these polypeptides can further include a mammalian growth factor (e.g., any of the exemplary mammalian growth factors described herein or known in the art). In some embodiments, any of the chimeric polypeptides described herein can bind to one or more substrates comprising ϑTCP (e.g., a Mastergraft strip, Vitoss Foam Pack, chronOS Strip, Vitoss Micromorsels, LifeInk500, Hyperelastic Bone, bioactive glass, ϑTCP powder, ϑTCP spray dried powder, hydroxyapaptite powder, hydroxyapatite-coated bone screw, ϑTCP granules, hydroxyapatite granules, and ReBOSSIS). In some embodiments, any of the chimeric polypeptides described herein can bind to silicon nitride or a substrante comprising silicon nitride.

Also provided herein are compositions that include any of the chimeric polypeptides or β-tricalcium phosphate-binding polypeptides described herein. In some embodiments, the compositions can further include a substrate including ϑTCP (e.g., (e.g., a Mastergraft strip, Vitoss Foam Pack, chronOS Strip, Vitoss Micromorsels, LifeInk500, Hyperelastic Bone, bioactive glass, ϑTCP powder, ϑTCP spray dried powder, hydroxyapaptite powder, hydroxyapatite-coated bone screw, ϑTCP granules, hydroxyapatite granules, and ReBOSSIS). In some embodiments, the compositions can further include a substrante comprising silicon nitride.

Also provided herein are kits that include any of these compositions. Also provided are methods of promoting bone or cartilage formation in a subject in need thereof, methods of replacing and/or repairing bone or cartilage in a subject in need thereof, and methods of treating a bone fraction or bone loss in a subject in need thereof that include administering to the subject any of the compositions described herein.

Non-limiting aspects of these polypeptides, compositions, kits, and methods are described below, and can be used in any combination without limitation. Additional aspects of these polypeptides, compositions, kits, and methods are known in the art.

Chimeric Polypeptides

The chimeric polypeptides described herein include a β-TCP binding sequence and can bind β-TCP (e.g., any of the exemplary types of β-TCP described herein or known in the art). In some examples, the chimeric polypeptides can include: (i) one or more (e.g., two, three, four, five, six, seven, eight, nine, or ten) β-tricalcium phosphate (βTCP)-binding sequence(s), where at least one of the one or more β-TCP-binding sequence(s) is selected from the group of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), and GGADTTHHRPGT (SEQ ID NO: 19); and (ii) a mammalian growth factor (e.g., any of the exemplary mammalian growth factors described herein or known in the art).

In some examples, the chimeric polypeptides can include: (i) one or more β-TCP-binding sequence(s) including an amino acid sequence of Formula I: $A_0B_0C_0D_0E_0F_0G_0H_0I_0J_0K_0L_0$ (Formula I) (SEQ ID NO: 35), wherein:

$A_0$ is V, L, I, G, S, T, or A;
$B_0$ is I, L, V, Q, T, S, G, or A;
$C_0$ is G, A, V, or S;
$D_0$ is E, D, L, or G;
$E_0$ is S, T, P T, E, or D;
$F_0$ is T or S;
$G_0$ is H, T, or S;
$H_0$ is H or T;
$I_0$ is R, S, K, P, or H;
$J_0$ is P, S, R, or K;
$K_0$ is W, F, S, P, V, A, or G; and
$L_0$ is absent or is S, T, G, or A; and (ii) a mammalian growth factor (e.g., any of the exemplary mammalian growth factors described herein or known in the art), where Formula I does not include LLADTTHHIRPWT (SEQ TD NO: 1).

Non-limiting examples of β-TCP binding sequences that may be present in any of the chimeric polypeptides described herein are listed in Table A below.

TABLE A

Exemplary β-TCP binding sequences

| β-TCP binding sequence | SEQ ID NO: |
|---|---|
| LLADTTHHRPWT | 1 |
| VIGESTHHRPWS | 2 |
| LIADSTHESPWT | 3 |
| ILAESTHHKPWT | 4 |
| ILAETTHHRPWS | 5 |
| IIGESSHHKPFT | 6 |
| GLGDTTHHRPWG | 7 |
| VLGDTTHHKPWT | 8 |
| IVADSTHHRPWT | 9 |
| STADTSHHRPS | 10 |
| TSGGESTHHRPS | 11 |
| TSGGESSHHKPS | 12 |
| TGSGDSSHHRPS | 13 |
| GSSGESTHHKPST | 14 |
| VGADSTHHRPVT | 15 |
| GAADTTHHRPVT | 16 |
| AGADTTHHRPVT | 17 |
| GGADTTHHRPAT | 18 |
| GGADTTHHRPGT | 19 |
| LLADTTHHRPWTVIGESTHHRPWS | 20 |
| LLADTTHHRPWTVIGESTHHRPWSIIGESSHHKPFT | 21 |
| LLADTTHHRPWTVIGESTHHRPWSIIGESSHHKPFTGLGDTTHHRPWGILAESTHHKPWT | 22 |
| LLADTTHHRPWTILAESTHHKPWT | 23 |

TABLE A-continued

| Exemplary β-TCP binding sequences | |
|---|---|
| β-TCP binding sequence | SEQ ID NO: |
| LLADTTHHRPWTILAESTHHKPWTLLADTTHHRPWTILAESTHHKPWTLLADTTHHRPWT | 24 |
| LLADTTHHRPWTGLGDTTHHRPWG | 25 |
| LLADTTHHRPWTGLGDTTHHRPWGLLADTTHHRPWT | 26 |
| LLADTTHHRPWTGLGDTTHHRPWGLLADTTHHRPWTGLGDTTHHRPWGLLADTTHHRPWT | 27 |
| LLADTTHHRPWTGLGDTTHHRPWGLLADTTHHRPWTGLGDTTHHRPWGLLADTTHHRPWTGLGDTTHEIRPWGLLADTTHHRPWT | 28 |
| STADTSHEIRPSTSGGESTHHRPSTSGGESSHHKPSTGSGDSSHHRPSGSSGESTHHKPST | 29 |
| VGADSTHEIRPVTGAADTTHHRPVTAGADTTHHRPVTGGADTTHHRPATGGADTTHHRPGT | 30 |
| STADTSHEIRPSLLADTTHHRPWTTSGGESTHHRPSVGADSTHHRPVTTSGGESSHHKPSGAADTTHHRPVTTGSGDSSHHRPSGSSGESTHHKPSTGGADTTHHRPAT | 31 |
| AAADTTHHRPWT | 36 |
| AAADTTHHRPWTAAADTTHHRPWTAAADTTHHRPWTAAADTTHHRPWTAAADTTHHRPWT | 37 |
| LLADAAHHRPWTLLADAAHHRPWTLLADAAHHRPWTLLADAAHHRPWTLLADAAHHRPWT | 38 |
| LLADTTAARPWTLLADTTAARPWTLLADTTAARPWTLLADTTAARPWTLLADTTAARPWT | 39 |
| LLADTTHHRPWTLLADTTHHRPWT | 40 |
| LLADTTHHRPWTLLADTTHHRPWTLLADTTHHRPWT | 41 |
| LLADTTHHRPWTLLADTTHHRPWTLLADTTHHRPWTLLADTTHHRPWTLLADTTHHRPWT | 42 |
| STSGSTVIGESTHHRPWSLIADSTHHSPWTILAESTHHKPWTILAETTHHRPWSIIGESSHHKPFTGLGDTTHHRPWGVLGDTTHHKPWTIVADSTHHRPWTGQVLPTTTPSSPSTTSGS | 43 |

In some embodiments, any of the chimeric polypeptides described herein can includes two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, 20, 21, or 22) 0-TCP-binding sequences (e.g., any of the exemplary β-TCP-binding sequences described herein).

In some embodiments, each neighboring pair of the two or more β-TCP binding sequences directly abut each other. In some embodiments, each neighboring pair of the two or more 3-TCP binding sequences (e.g., any of the exemplary β-TCP-binding sequences described herein) are separated by a linker sequence.

In some embodiments, the chimeric polypeptides can include at least two (e.g., at least three, at least four, at least five, at least six, at least seven, at least eight, at least nine, or at least ten; or 2, 3, 4, 5, 6, 7, 8, 9, or 10) different β-TCP-binding sequences (e.g., any of the exemplary β-TCP-binding sequences described herein).

In some embodiments, at least one of the two or more different β-TCP-binding sequences is LLADTTHHRPWT (SEQ ID NO: 1) or GQVLPTTTPSSP (SEQ ID NO: 103). In some embodiments, the at least two different β-TCP-binding sequences include LLADTTHHRPWT (SEQ ID NO: 1) and VIGESTHHRPWS (SEQ ID NO: 2). In some embodiments, the chimeric polypeptide includes the sequence of LLADTTHHRPWTVIGESTHHRPWS (SEQ ID NO: 20).

In some embodiments, the at least two different β-TCP-binding sequences include LLADTTHHRPWT (SEQ ID NO: 1), VIGESTHHRPWS (SEQ ID NO: 2), and IIGESSHHKPFT (SEQ ID NO: 6). In some embodiments, the chimeric polypeptide includes the sequence of LLADTTHHRPWTVIGESTHHRPWSIIGESSHHKPFT (SEQ ID NO: 21).

In some embodiments, the at least two different β-TCP-binding sequences include LLADTTHHRPWT (SEQ ID NO: 1), VIGESTHHRPWS (SEQ ID NO: 2), IIGESSHHKPFT (SEQ ID NO: 6), GLGDTTHHRPWG (SEQ ID NO: 7), and ILAESTHHKPWT (SEQ ID NO: 4). In some embodiments, the chimeric polypeptide includes the sequence of:

(SEQ ID NO: 22)
LLADTTHHRPWTVIGESTHHRPWSIIGESSHHKPFTGLGDTTHEIRPWGI

LAESTHHKPWT.

In some embodiments, the at least two β-TCP-binding sequences include LLADTTHHRPWT (SEQ ID NO: 1) and ILAESTHHKPWT (SEQ ID NO: 4). In some embodiments, the chimeric polypeptide includes at least one copy of the sequence LLADTTHHRPWTILAESTHHKPWT (SEQ ID NO: 23). In some embodiments, the chimeric polypeptide includes the sequence of (SEQ ID NO: 24)
LLADTTHEIRPWTILAESTHHKPWTLLADTTHHRPWTILAESTHHKPWTL

LADTTHHRPWT.

In some embodiments, the at least two β-TCP-binding sequences include LLADTTHHRPWT (SEQ ID NO: 1) and GLGDTTHHRPWG (SEQ ID NO: 7). In some embodiments, the chimeric polypeptide includes at least one copy of the sequence of LLADTTHHRPWTGLGDTTHHRPWG (SEQ ID NO: 25). In some embodiments, the chimeric polypeptide includes the sequence of LLADTTHHRPWTGLGDTTHHRPWGL-LADTTHHRPWT (SEQ ID NO: 26). In some embodiments, the chimeric polypeptide includes the sequence of LLADTTHHRPWTGLGDTTHHRPWGL-LADTTHHRPWTGLGDTTHHRPWGLLADTTHHR PWT (SEQ ID NO: 27). In some embodiments, the chimeric polypeptide includes the sequence of (SEQ ID NO: 28)
LLADTTHERPWTGLGDTTHHRPWGLLADTTHHRPWTGLGDTTHHRPWGLL

ADTTHHRPWTGLGDTTHERPWGLLADTTHHRPWT.

In some embodiments, the at least two different β-TCP-binding sequences include STADTSHHRPS (SEQ ID NO: 10), TSGGESTHHRPS (SEQ ID NO: 11), TSG-GESSHHKPS (SEQ ID NO: 12), TGSGDSSHHRPS (SEQ ID NO: 13), and GSSGESTHHKPST (SEQ ID NO: 14). In some embodiments, the chimeric polypeptide includes the sequence of

```
                                      (SEQ ID NO: 29)
STADTSHHRPSTSGGESTHHRPSTSGGESSHHKPSTGSGDSSHHRPSGSS

GESTHHKPST.
```

In some embodiments, the at least two different β-TCP-binding sequences include VGADSTHHRPVT (SEQ ID NO: 15), GAADTTHHRPVT SEQ ID NO: 16), AGADTTHHRPVT (SEQ ID NO: 17), GGADTTHHRPAT (SEQ ID NO: 18) and GGADTTHHRPGT (SEQ ID NO: 19). In some embodiments, the chimeric polypeptide includes the sequence of

```
                                      (SEQ ID NO: 30)
VGADSTHHRPVTGAADTTHHRPVTAGADTTHHRPVTGGADTTHHRPATGG

ADTTHHRPGT.
```

In some embodiments, the at least two different β-TCP-binding sequences include STADTSHHRPS (SEQ ID NO: 10), LLADTTHHRPWT (SEQ ID NO: 1), TSGGESTHHRPS (SEQ ID NO: 11), VGADSTHHRPVT (SEQ ID NO: 15), TSGGESSHHKPS (SEQ ID NO: 12), GAADTTHHRPVT (SEQ ID NO: 16), TGSGDSSHHRPS (SEQ ID NO: 13), GSSGESTHHKPS (SEQ ID NO: 101), and TGGADTTHHRPAT (SEQ ID NO: 102). In some embodiments, the chimeric polypeptide includes the sequence of:

```
                                      (SEQ ID NO: 31)
STADTSHHRPSLLADTTHHRPWTTSGGESTHHRPSVGADSTHHRPVTTSG

GESSHHKPSGAADTTHHRPVTTGSGDSSHHRPSGSSGESTHHKPSTGGAD

TTHHRPAT.
```

In some embodiments, the chimeric polypeptides can include two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, or 20) copies of the same β-TCP-binding sequence (e.g., any of the exemplary β-TCP-binding sequences described herein).

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 1.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 2.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 3.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 4.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 5.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 6.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 7.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 8.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 9.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 10.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 11.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 12.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 13.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 14.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 15.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 16.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 17.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 18.

In some embodiments, the chimeric polypeptides can include a β-TCP-binding sequence that has or includes an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 19.

In some embodiments, the chimeric polypeptide further comprises a linker sequence (e.g., any of the exemplary linker sequences described herein or known in the art) between a neighboring pair of a β-TCP-binding sequence (e.g., any of the exemplary β-TCP binding sequences described herein) and the mammalian growth factor (e.g., any of the exemplary mammalian growth factor described herein). In some embodiments, the linker sequence can include the sequence of TGGSGEGGT-GASTGGSAGTGGSGGTTSGEAGGSSGAG (SEQ ID NO: 33). In some embodiments, the linker sequence consists of TGGSGEGGT-GASTGGSAGTGGSGGTTSGEAGGSSGAG (SEQ ID NO: 33). In some embodiments, the linker sequence includes the sequence of GSGATG (SEQ ID NO: 34). In some embodiments, the linker sequence consists of GSGATG (SEQ ID NO: 34).

In some embodiments, where the chimeric polypeptide comprises two or more β-TCP-binding sequences, a linker sequence (e.g., any of the exemplary linker sequences described herein or known in the art) can be between any of the pairs (e.g., all of the pairs) of neighboring β-TCP-binding sequences.

In some embodiments, the chimeric polypeptide can include a signal sequence at its N-terminus. In some embodiments, the chimeric polypeptide can further include a tag sequence (e.g., a poly-His tag, chitin-binding protein (CBP), maltose-binding protein (MBP), strep-tag, glutathione-S-transferase (GST), thioredoxin, or Fc region). Additional examples of tags are known in the art.

The chimeric polypeptide described herein can bind to β-TCP (e.g., any of the types of β-TCP described herein) with a dissociation equilibrium constant ($K_d$) of about 1 pM to about 100 μM (e.g., about 1 pM to about 95 μM, about 1 pM to about 90 μM, about 1 pM to about 85 μM, about 1 pM to about 80 pM, about 1 pM to about 75 μM, about 1 pM to about 70 μM, about 1 pM to about 65 pM, about 1 pM to about 60 pM, about 1 pM to about 55 μM, about 1 pM to about 50 μM, about 1 pM to about 45 μM, about 1 pM to about 40 μM, about 1 pM to about 45 M, about 1 pM to about 40 μM, about 1 pM to about 35 pM, about 1 pM to about 30 μM, about 1 pM to about 25 μM, about 1 pM to about 20 μM, about 1 pM to about 15 pM, about 1 pM to about 10 μM, about 1 pM to about 5 μM, about 1 pM to about 2 μM, about 1 pM to about 1 μM, about 1 pM to about 950 nM, about 1 pM to about 900 nM, about 1 pM to about 850 nM, about 1 pM to about 800 nM, about 1 pM to about 750 nM, about 1 pM to about 700 nM, about 1 pM to about 650 nM, about 1 pM to about 600 nM, about 1 pM to about 550 nM, about 1 pM to about 500 nM, about 1 pM to about 450 nM, about 1 pM to about 400 nM, about 1 pM to about 350 nM, about 1 pM to about 300 nM, about 1 pM to about 250 nM, about 1 pM to about 200 nM, about 1 pM to about 150 nM, about 1 pM to about 100 nM, about 1 pM to about 95 nM, about 1 pM to about 90 nM, about 1 pM to about 85 nM, about 1 pM to about 80 nM, about 1 pM to about 75 nM, about 1 pM to about 70 nM, about 1 pM to about 75 nM, about 1 pM to about 70 nM, about 1 pM to about 65 nM, about 1 pM to about 60 nM, about 1 pM to about 55 nM, about 1 pM to about 50 nM, about 1 pM to about 45 nM, about 1 pM to about 40 nM, about 1 pM to about 35 nM, about 1 pM to about 30 nM, about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 95 pM, about 1 pM to about 90 pM, about 1 pM to about 85 pM, about 1 pM to about 80 pM, about 1 pM to about 75 pM, about 1 pM to about 70 pM, about 1 pM to about 75 pM, about 1 pM to about 70 pM, about 1 pM to about 65 pM, about 1 pM to about 60 pM, about 1 pM to about 55 pM, about 1 pM to about 50 pM, about 1 pM to about 45 pM, about 1 pM to about 40 pM, about 1 pM to about 35 pM, about 1 pM to about 30 pM, about 1 pM to about 25 pM, about 1 pM to about 20 pM, about 1 pM to about 15 pM, about 1 pM to about 10 pM, about 1 pM to about 5 pM, about 1 pM to about 2 pM, about 2 pM to about 100 M, about 2 pM to about 95 μM, about 2 pM to about 90 pM, about 2 pM to about 85 μM, about 2 pM to about 80 μM, about 2 pM to about 75 μM, about 2 pM to about 70 PM, about 2 pM to about 65 μM, about 2 pM to about 60 μM, about 2 pM to about 55 μM, about 2 pM to about 50 M, about 2 pM to about 45 μM, about 2 pM to about 40 pM, about 2 pM to about 45 μM, about 2 pM to about 40 μM, about 2 pM to about 35 μM, about 2 pM to about 30 pM, about 2 pM to about 25 μM, about 2 pM to about 20 μM, about 2 pM to about 15 μM, about 2 pM to about 10 M, about 2 pM to about 5 μM, about 2 pM to about 2 pM, about 2 pM to about 1 PM, about 2 pM to about 950 nM, about 2 pM to about 900 nM, about 2 pM to about 850 nM, about 2 pM to about 800 nM, about 2 pM to about 750 nM, about 2 pM to about 700 nM, about 2 pM to about 650 nM, about 2 pM to about 600 nM, about 2 pM to about 550 nM, about 2 pM to about 500 nM, about 2 pM to about 450 nM, about 2 pM to about 400 nM, about 2 pM to about 350 nM, about 2 pM to about 300 nM, about 2 pM to about 250 nM, about 2 pM to about 200 nM, about 2 pM to about 150 nM, about 2 pM to about 100 nM, about 2 pM to about 95 nM, about 2 pM to about 90 nM, about 2 pM to about 85 nM, about 2 pM to about 80 nM, about 2 pM to about 75 nM, about 2 pM to about 70 nM, about 2 pM to about 75 nM, about 2 pM to about 70 nM, about 2 pM to about 65 nM, about 2 pM to about 60 nM, about 2 pM to about 55 nM, about 2 pM to about 50 nM, about 2 pM to about 45 nM, about 2 pM to about 40 nM, about 2 pM to about 35 nM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 95 pM, about 2 pM to about 90 pM, about 2 pM to about 85 pM, about 2 pM to about 80 pM, about 2 pM to about 75 pM, about 2 pM to about 70 pM, about 2 pM to about 75 pM, about 2 pM to about 70 pM, about 2 pM to about 65 pM, about 2 pM to about 60 pM, about 2 pM to about 55 pM, about 2 pM to about 50 pM, about 2 pM to about 45 pM, about 2 pM to about 40 pM, about 2 pM to about 35 pM, about 2 pM to about 30 pM, about 2 pM to about 25 pM, about 2 pM to about 20 pM, about 2 pM to about 15 pM, about 2 pM to about 10 pM, about 2 pM to about 5 pM, about 5 pM to about 100 μM, about 5 pM to about 95 μM, about 5 pM to about 90 μM, about 5 pM to about 85 μM, about 5 pM to about 80 PM, about 5 pM to about 75 μM, about 5 pM to about 70 μM, about 5 pM to about 65 μM, about 5 pM to about 60 M, about 5 pM to about 55 μM, about 5 pM to about 50 pM, about 5 pM to about 45 μM, about 5 pM to about 40 μM, about 5 pM to about 45 μM, about 5 pM to about 40 pM, about 5 pM to about 35 μM, about 5 pM to about 30 μM, about 5 pM to about 25 μM, about 5 pM to about 20 M, about 5 pM to about 15 μM, about 5 pM to about 10 pM, about 5 pM to about 5 μM, about 5 pM to about 2 μM, about 5 pM to about 1 μM, about 5 pM to about 950 nM, about 5 pM to about 900 nM, about 5 pM to about 850 nM, about 5 pM to about 800 nM, about 5 pM to about 750 nM, about 5 pM to about 700 nM, about 5 pM to about 650 nM, about 5 pM to about 600 nM, about 5 pM to about 550 nM, about 5 pM to about 500 nM, about 5 pM to about 450 nM, about 5 pM to about 400 nM, about 5 pM to about 350 nM, about 5 pM to about 300 nM, about 5 pM to about 250 nM, about 5 pM to about 200 nM, about 5 pM to about 150 nM, about 5 pM to about 100 nM, about 5 pM to about 95 nM, about 5 pM to about 90 nM, about 5 pM to about 85 nM, about 5 pM to about 80 nM, about 5 pM to about 75 nM, about 5 pM to about 70 nM, about 5 pM to about 75 nM, about 5 pM to about 70 nM, about 5 pM to about 65 nM, about 5 pM to about 60 nM, about 5 pM to about 55 nM, about 5 pM to about 50 nM, about 5 pM to about 45 nM, about 5 pM to about 40 nM, about 5 pM to about 35 nM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 95 pM, about 5 pM to about 90 pM, about 5 pM to about 85 pM, about 5 pM to about 80 pM, about 5 pM to about 75 pM, about 5 pM to about 70 pM, about 5 pM to about 75 pM, about 5 pM to about 70 pM, about 5 pM to about 65 pM, about 5 pM to about 60 pM, about 5 pM to about 55 pM, about 5 pM to about 50 pM, about 5 pM to about 45 pM, about 5 pM to about 40 pM, about 5 pM to about 35 pM, about 5 pM to about 30 pM, about 5 pM to about 25 pM, about 5 pM to about 20 pM, about 5 pM to about 15 pM, about 5 pM to about 10 pM, about 10 pM to about 100 μM, about 10 pM to about 95 pM, about 10 pM to about 90 μM, about 10 pM to about 85 μM, about 10 pM to about 80 μM, about 10 pM to about 75 μM, about 10 pM to about 70 PM, about 10 pM to about 65 pM, about 10 pM to about 60 μM, about 10 pM to about 55 μM, about 10 pM to about 50 μM, about 10 pM to about 45 μM, about 10 pM to about 40 μM, about 10 pM to about 45 pM, about 10 pM to about 40 pM, about 10 pM to about 35 μM, about 10 pM to about 30 M, about 10 pM to about 25 μM, about 10 pM to about 20 μM, about 10 pM to about 15 μM, about 10 pM to about 10 pM, about 10 pM to about 5 μM, about 10 pM to about 2 μM, about 10 pM to about 1 pM, about 10 pM to about 950 nM, about 10 pM to about 900 nM, about 10 pM to about 850 nM, about 10 pM to about 800 nM, about 10 pM to about 750 nM, about 10 pM to about 700 nM, about 10 pM to about 650 nM, about 10 pM to about 600 nM, about 10 pM to about 550 nM, about 10 pM to about 500 nM, about 10 pM to about 450 nM, about 10 pM to about 400 nM, about 10 pM to about 350 nM, about 10 pM to about 300 nM, about 10 pM to about 250 nM, about 10 pM to about 200 nM, about 10 pM to about 150 nM, about 10 pM to about 100 nM, about 10 pM to about 95 nM, about 10 pM to about 90 nM, about 10 pM to about 85 nM, about 10 pM to about 80 nM, about 10 pM to about 75 nM, about 10 pM to about 70 nM, about 10 pM to about 75 nM, about 10 pM to about 70 nM, about 10 pM to about 65 nM, about 10 pM to about 60 nM, about 10 pM to about 55 nM, about 10 pM to about 50 nM, about 10 pM to about 45 nM, about 10 pM to about 40 nM, about 10 pM to about 35 nM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 95 pM, about 10 pM to about 90 pM, about 10 pM to about 85 pM, about 10 pM to about 80 pM, about 10 pM to about 75 pM, about 10 pM to about 70 pM, about 10 pM to about 75 pM, about 10 pM to about 70 pM, about 10 pM to about 65 pM, about 10 pM to about 60 pM, about 10 pM to about 55 pM, about 10 pM to about 50 pM, about 10 pM to about 45 pM, about 10 pM to about 40 pM, about 10 pM to about 35 pM, about 10 pM to about 30 pM, about 10 pM to about 25 pM, about 10 pM to about 20 pM, about 10 pM to about 15 pM, about 20 pM to about 100 μM, about 20 pM to about 95 pM, about 20 pM to about 90 M, about 20 pM to about 85 μM, about 20 pM to about 80 μM, about 20 pM to about 75 μM, about 20 pM to about 70 pM, about 20 pM to about 65 μM, about 20 pM to about 60 μM, about 20 pM to about 55 μM, about 20 pM to about 50 μM, about 20 pM to about 45 PM, about 20 pM to about 40 pM, about 20 pM to about 45 μM, about 20 pM to about 40 μM, about 20 pM to about 35 μM, about 20 pM to about 30 μM, about 20 pM to about 25 μM, about 20 pM to about 20 pM, about 20 pM to about 15 pM, about 20 pM to about 10 μM, about 20 pM to about 5 μM, about 20 pM to about 2 pM, about 20 pM to about 1 μM, about 20 pM to about 950 nM, about 20 pM to about 900 nM, about 20 pM to about 850 nM, about 20 pM to about 800 nM, about 20 pM to about 750 nM, about 20 pM to about 700 nM, about 20 pM to about 650 nM, about 20 pM to about 600 nM, about 20 pM to about 550 nM, about 20 pM to about 500 nM, about 20 pM to about 450 nM, about 20 pM to about 400 nM, about 20 pM to about 350 nM, about 20 pM to about 300 nM, about 20 pM to about 250 nM, about 20 pM to about 200 nM, about 20 pM to about 150 nM, about 20 pM to about 100 nM, about 20 pM to about 95 nM, about 20 pM to about 90 nM, about 20 pM to about 85 nM, about 20 pM to about 80 nM, about 20 pM to about 75 nM, about 20 pM to about 70 nM, about 20 pM to about 75 nM, about 20 pM to about 70 nM, about 20 pM to about 65 nM, about 20 pM to about 60 nM, about 20 pM to about 55 nM, about 20 pM to about 50 nM, about 20 pM to about 45 nM, about 20 pM to about 40 nM, about 20 pM to about 35 nM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 200 pM, about 20 pM to about 150 pM, about 20 pM to about 100 pM, about 20 pM to about 95 pM, about 20 pM to about 90 pM, about 20 pM to about 85 pM, about 20 pM to about 80 pM, about 20 pM to about 75 pM, about 20 pM to about 70 pM, about 20 pM to about 75 pM, about 20 pM to about 70 pM, about 20 pM to about 65 pM, about 20 pM to about 60 pM, about 20 pM to about 55 pM, about 20 pM to about 50 pM, about 20 pM to about 45 pM, about 20 pM to about 40 pM, about 20 pM to about 35 pM, about 20 pM to about 30 pM, about 20 pM to about 25 pM, about 50 pM to about 100 pM, about 50 pM to about 95 μM, about 50 pM to about 90 μM, about 50 pM to about 85 μM, about 50 pM to about 80 μM, about 50 pM to about 75 pM, about 50 pM to about 70 pM, about 50 pM to about 65 μM, about 50 pM to about 60 μM, about 50 pM to about 55 μM, about 50 pM to about 50 μM, about 50 pM to about 45 μM, about 50 pM to about 40 pM, about 50 pM to about 45 pM, about 50 pM to about 40 μM, about 50 pM to about 35 M, about 50 pM to about 30 μM, about 50 pM to about 25 μM, about 50 pM to about 20 μM, about 50 pM to about 15 pM, about 50 pM to about 10 μM, about 50 pM to about 5 μM, about 50 pM to about 2 μM, about 50 pM to about 1 pM, about 50 pM to about 950 nM, about 50 pM to about 900 nM, about 50 pM to about 850 nM, about 50 pM to about 800 nM, about 50 pM to about 750 nM, about 50 pM to about 700 nM, about 50 pM to about 650 nM, about 50 pM to about 600 nM, about 50 pM to about 550 nM, about 50 pM to about 500 nM, about 50 pM to about 450 nM, about 50 pM to about 400 nM, about 50 pM to about 350 nM, about 50 pM to about 300 nM, about 50 pM to about 250 nM, about 50 pM to about 200 nM, about 50 pM to about 150 nM, about 50 pM to about 100 nM, about 50 pM to about 95 nM, about 50 pM to about 90 nM, about 50 pM to about 85 nM, about 50 pM to about 80 nM, about 50 pM to about 75 nM, about 50 pM to about 70 nM, about 50 pM to about 75 nM, about 50 pM to about 70 nM, about 50 pM to about 65 nM, about 50 pM to about 60 nM, about 50 pM to about 55 nM, about 50 pM to about 50 nM, about 50 pM to about 45 nM, about 50 pM to about 40 nM, about 50 pM to about 35 nM, about 50 pM to about 30 nM, about 50 pM to about 25 nM, about 50 pM to about 20 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 95 pM, about 50 pM to about 90 pM, about 50 pM to about 85 pM, about 50 pM to about 80 pM, about 50 pM to about 75 pM, about 50 pM to about 70 pM, about 50 pM to about 75 pM, about 50 pM to about 70 pM, about 50 pM to about 65 pM, about 50 pM to about 60 pM, about 50 pM to about 55 pM, about 100 pM to about 100 μM, about 100 pM to about 95 μM, about 100 pM to about 90 μM, about 100 pM to about 85 μM, about 100 pM to about 80 μM, about 100 pM to about 75 μM, about 100 pM to about 70 μM, about 100 pM to about 65 μM, about 100 pM to about 60 μM, about 100 pM to about 55 μM, about 100 pM to about 50 μM, about 100 pM to about 45 μM, about 100 pM to about 40 μM, about 100 pM to about 45 μM, about 100 pM to about 40 μM, about 100 pM to about 35 μM, about 100 pM to about 30 μM, about 100 pM to about 25 μM, about 100 pM to about 20 μM, about 100 pM to about 15 μM, about 100 pM to about 10 μM, about 100 pM to about 5 μM, about 100 pM to about 2 PM, about 100 pM to about 1 pM, about 100 pM to about 950 nM, about 100 pM to about 900 nM, about 100 pM to about 850 nM, about 100 pM to about 800 nM, about 100 pM to about 750 nM, about 100 pM to about 700 nM, about 100 pM to about 650 nM, about 100 pM to about 600 nM, about 100 pM to about 550 nM, about 100 pM to about 500 nM, about 100 pM to about 450 nM, about 100 pM to about 400 nM, about 100 pM to about 350 nM, about 100 pM to about 300 nM, about 100 pM to about 250 nM, about 100 pM to about 200 nM, about 100 pM to about 150 nM, about 100 pM to about 100 nM, about 100 pM to about 95 nM, about 100 pM to about 90 nM, about 100 pM to about 85 nM, about 100 pM to about 80 nM, about 100 pM to about 75 nM, about 100 pM to about 70 nM, about 100 pM to about 75 nM, about 100 pM to about 70 nM, about 100 pM to about 65 nM, about 100 pM to about 60 nM, about 100 pM to about 55 nM, about 100 pM to about 50 nM, about 100 pM to about 45 nM, about 100 pM to about 40 nM, about 100 pM to about 35 nM, about 100 pM to about 30 nM, about 100 pM to about 25 nM, about 100 pM to about 20 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 200 pM to about 100 pM, about 200 pM to about 95 μM, about 200 pM to about 90 pM, about 200 pM to about 85 pM, about 200 pM to about 80 μM, about 200 pM to about 75 pM, about 200 pM to about 70 pM, about 200 pM to about 65 μM, about 200 pM to about 60 pM, about 200 pM to about 55 pM, about 200 pM to about 50 μM, about 200 pM to about 45 pM, about 200 pM to about 40 pM, about 200 pM to about 45 μM, about 200 pM to about 40 pM, about 200 pM to about 35 pM, about 200 pM to about 30 μM, about 200 pM to about 25 pM, about 200 pM to about 20 pM, about 200 pM to about 15 μM, about 200 pM to about 10 pM, about 200 pM to about 5 pM, about 200 pM to about 2 μM, about 200 pM to about 1 μM, about 200 pM to about 950 nM, about 200 pM to about 900 nM, about 200 pM to about 850 nM, about 200 pM to about 800 nM, about 200 pM to about 750 nM, about 200 pM to about 700 nM, about 200 pM to about 650 nM, about 200 pM to about 600 nM, about 200 pM to about 550 nM, about 200 pM to about 500 nM, about 200 pM to about 450 nM, about 200 pM to about 400 nM, about 200 pM to about 350 nM, about 200 pM to about 300 nM, about 200 pM to about 250 nM, about 200 pM to about 200 nM, about 200 pM to about 150 nM, about 200 pM to about 100 nM, about 200 pM to about 95 nM, about 200 pM to about 90 nM, about 200 pM to about 85 nM, about 200 pM to about 80 nM, about 200 pM to about 75 nM, about 200 pM to about 70 nM, about 200 pM to about 75 nM, about 200 pM to about 70 nM, about 200 pM to about 65 nM, about 200 pM to about 60 nM, about 200 pM to about 55 nM, about 200 pM to about 50 nM, about 200 pM to about 45 nM, about 200 pM to about 40 nM, about 200 pM to about 35 nM, about 200 pM to about 30 nM, about 200 pM to about 25 nM, about 200 pM to about 20 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 100 pM, about 300 pM to about 95 μM, about 300 pM to about 90 μM, about 300 pM to about 85 pM, about 300 pM to about 80 pM, about 300 pM to about 75 μM, about 300 pM to about 70 M, about 300 pM to about 65 μM, about 300 pM to about 60 PM, about 300 pM to about 55 M, about 300 pM to about 50 μM, about 300 pM to about 45 pM, about 300 pM to about 40 M, about 300 pM to about 45 μM, about 300 pM to about 40 PM, about 300 pM to about 35 M, about 300 pM to about 30 μM, about 300 pM to about 25 pM, about 300 pM to about 20 M, about 300 pM to about 15 μM, about 300 pM to about 10 pM, about 300 pM to about 5 μM, about 300 pM to about 2 pM, about 300 pM to about 1 μM, about 300 pM to about 950 nM, about 300 pM to about 900 nM, about 300 pM to about 850 nM, about 300 pM to about 800 nM, about 300 pM to about 750 nM, about 300 pM to about 700 nM, about 300 pM to about 650 nM, about 300 pM to about 600 nM, about 300 pM to about 550 nM, about 300 pM to about 500 nM, about 300 pM to about 450 nM, about 300 pM to about 400 nM, about 300 pM to about 350 nM, about 300 pM to about 300 nM, about 300 pM to about 250 nM, about 300 pM to about 200 nM, about 300 pM to about 150 nM, about 300 pM to about 100 nM, about 300 pM to about 95 nM, about 300 pM to about 90 nM, about 300 pM to about 85 nM, about 300 pM to about 80 nM, about 300 pM to about 75 nM, about 300 pM to about 70 nM, about 300 pM to about 75 nM, about 300 pM to about 70 nM, about 300 pM to about 65 nM, about 300 pM to about 60 nM, about 300 pM to about 55 nM, about 300 pM to about 50 nM, about 300 pM to about 45 nM, about 300 pM to about 40 nM, about 300 pM to about 35 nM, about 300 pM to about 30 nM, about 300 pM to about 25 nM, about 300 pM to about 20 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 100 μM, about 400 pM to about 95 μM, about 400 pM to about 90 μM, about 400 pM to about 85 μM, about 400 pM to about 80 μM, about 400 pM to about 75 μM, about 400 pM to about 70 μM, about 400 pM to about 65 μM, about 400 pM to about 60 μM, about 400 pM to about 55 μM, about 400 pM to about 50 μM, about 400 pM to about 45 μM, about 400 pM to about 40 μM, about 400 pM to about 45 μM, about 400 pM to about 40 μM, about 400 pM to about 35 μM, about 400 pM to about 30 μM, about 400 pM to about 25 μM, about 400 pM to about 20 μM, about 400 pM to about 15 μM, about 400 pM to about 10 μM, about 400 pM to about 5 μM, about 400 pM to about 2 pM, about 400 pM to about 1 pM, about 400 pM to about 950 nM, about 400 pM to about 900 nM, about 400 pM to about 850 nM, about 400 pM to about 800 nM, about 400 pM to about 750 nM, about 400 pM to about 700 nM, about 400 pM to about 650 nM, about 400 pM to about 600 nM, about 400 pM to about 550 nM, about 400 pM to about 500 nM, about 400 pM to about 450 nM, about 400 pM to about 400 nM, about 400 pM to about 350 nM, about 400 pM to about 300 nM, about 400 pM to about 250 nM, about 400 pM to about 200 nM, about 400 pM to about 150 nM, about 400 pM to about 100 nM, about 400 pM to about 95 nM, about 400 pM to about 90 nM, about 400 pM to about 85 nM, about 400 pM to about 80 nM, about 400 pM to about 75 nM, about 400 pM to about 70 nM, about 400 pM to about 75 nM, about 400 pM to about 70 nM, about 400 pM to about 65 nM, about 400 pM to about 60 nM, about 400 pM to about 55 nM, about 400 pM to about 50 nM, about 400 pM to about 45 nM, about 400 pM to about 40 nM, about 400 pM to about 35 nM, about 400 pM to about 30 nM, about 400 pM to about 25 nM, about 400 pM to about 20 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 400 pM to about 450 pM, about 500 pM to about 100 pM, about 500 pM to about 95 μM, about 500 pM to about 90 μM, about 500 pM to about 85 pM, about 500 pM to about 80 pM, about 500 pM to about 75 μM, about 500 pM to about 70 M, about 500 pM to about 65 μM, about 500 pM to about 60 PM, about 500 pM to about 55 M, about 500 pM to about 50 μM, about 500 pM to about 45 pM, about 500 pM to about 40 M, about 500 pM to about 45 μM, about 500 pM to about 40 PM, about 500 pM to about 35 M, about 500 pM to about 30 μM, about 500 pM to about 25 pM, about 500 pM to about 20 M, about 500 pM to about 15 μM, about 500 pM to about 10 pM, about 500 pM to about 5 μM, about 500 pM to about 2 pM, about 500 pM to about 1 μM, about 500 pM to about 950 nM, about 500 pM to about 900 nM, about 500 pM to about 850 nM, about 500 pM to about 800 nM, about 500 pM to about 750 nM, about 500 pM to about 700 nM, about 500 pM to about 650 nM, about 500 pM to about 600 nM, about 500 pM to about 550 nM, about 500 pM to about 500 nM, about 500 pM to about 450 nM, about 500 pM to about 400 nM, about 500 pM to about 350 nM, about 500 pM to about 300 nM, about 500 pM to about 250 nM, about 500 pM to about 200 nM, about 500 pM to about 150 nM, about 500 pM to about 100 nM, about 500 pM to about 95 nM, about 500 pM to about 90 nM, about 500 pM to about 85 nM, about 500 pM to about 80 nM, about 500 pM to about 75 nM, about 500 pM to about 70 nM, about 500 pM to about 75 nM, about 500 pM to about 70 nM, about 500 pM to about 65 nM, about 500 pM to about 60 nM, about 500 pM to about 55 nM, about 500 pM to about 50 nM, about 500 pM to about 45 nM, about 500 pM to about 40 nM, about 500 pM to about 35 nM, about 500 pM to about 30 nM, about 500 pM to about 25 nM, about 500 pM to about 20 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 100 μM, about 600 pM to about 95 μM, about 600 pM to about 90 μM, about 600 pM to about 85 μM, about 600 pM to about 80 μM, about 600 pM to about 75 μM, about 600 pM to about 70 μM, about 600 pM to about 65 μM, about 600 pM to about 60 μM, about 600 pM to about 55 μM, about 600 pM to about 50 μM, about 600 pM to about 45 μM, about 600 pM to about 40 μM, about 600 pM to about 45 μM, about 600 pM to about 40 μM, about 600 pM to about 35 μM, about 600 pM to about 30 μM, about 600 pM to about 25 μM, about 600 pM to about 20 μM, about 600 pM to about 15 μM, about 600 pM to about 10 μM, about 600 pM to about 5 μM, about 600 pM to about 2 PM, about 600 pM to about 1 pM, about 600 pM to about 950 nM, about 600 pM to about 900 nM, about 600 pM to about 850 nM, about 600 pM to about 800 nM, about 600 pM to about 750 nM, about 600 pM to about 700 nM, about 600 pM to about 650 nM, about 600 pM to about 600 nM, about 600 pM to about 550 nM, about 600 pM to about 500 nM, about 600 pM to about 450 nM, about 600 pM to about 400 nM, about 600 pM to about 350 nM, about 600 pM to about 300 nM, about 600 pM to about 250 nM, about 600 pM to about 200 nM, about 600 pM to about 150 nM, about 600 pM to about 100 nM, about 600 pM to about 95 nM, about 600 pM to about 90 nM, about 600 pM to about 85 nM, about 600 pM to about 80 nM, about 600 pM to about 75 nM, about 600 pM to about 70 nM, about 600 pM to about 75 nM, about 600 pM to about 70 nM, about 600 pM to about 65 nM, about 600 pM to about 60 nM, about 600 pM to about 55 nM, about 600 pM to about 50 nM, about 600 pM to about 45 nM, about 600 pM to about 40 nM, about 600 pM to about 35 nM, about 600 pM to about 30 nM, about 600 pM to about 25 nM, about 600 pM to about 20 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 100 pM, about 700 pM to about 95 μM, about 700 pM to about 90 pM, about 700 pM to about 85 pM, about 700 pM to about 80 μM, about 700 pM to about 75 M, about 700 pM to about 70 μM, about 700 pM to about 65 pM, about 700 pM to about 60 M, about 700 pM to about 55 μM, about 700 pM to about 50 PM, about 700 pM to about 45 M, about 700 pM to about 40 μM, about 700 pM to about 45 pM, about 700 pM to about 40 M, about 700 pM to about 35 μM, about 700 pM to about 30 PM, about 700 pM to about 25 M, about 700 pM to about 20 μM, about 700 pM to about 15 pM, about 700 pM to about 10 M, about 700 pM to about 5 μM, about 700 pM to about 2 pM, about 700 pM to about 1 μM, about 700 pM to about 950 nM, about 700 pM to about 900 nM, about 700 pM to about 850 nM, about 700 pM to about 800 nM, about 700 pM to about 750 nM, about 700 pM to about 700 nM, about 700 pM to about 650 nM, about 700 pM to about 600 nM, about 700 pM to about 550 nM, about 700 pM to about 500 nM, about 700 pM to about 450 nM, about 700 pM to about 400 nM, about 700 pM to about 350 nM, about 700 pM to about 300 nM, about 700 pM to about 250 nM, about 700 pM to about 200 nM, about 700 pM to about 150 nM, about 700 pM to about 100 nM, about 700 pM to about 95 nM, about 700 pM to about 90 nM, about 700 pM to about 85 nM, about 700 pM to about 80 nM, about 700 pM to about 75 nM, about 700 pM to about 70 nM, about 700 pM to about 75 nM, about 700 pM to about 70 nM, about 700 pM to about 65 nM, about 700 pM to about 60 nM, about 700 pM to about 55 nM, about 700 pM to about 50 nM, about 700 pM to about 45 nM, about 700 pM to about 40 nM, about 700 pM to about 35 nM, about 700 pM to about 30 nM, about 700 pM to about 25 nM, about 700 pM to about 20 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 100 pM, about 800 pM to about 95 μM, about 800 pM to about 90 pM, about 800 pM to about 85 pM, about 800 pM to about 80 μM, about 800 pM to about 75 pM, about 800 pM to about 70 pM, about 800 pM to about 65 μM, about 800 pM to about 60 pM, about 800 pM to about 55 pM, about 800 pM to about 50 μM, about 800 pM to about 45 pM, about 800 pM to about 40 pM, about 800 pM to about 45 μM, about 800 pM to about 40 pM, about 800 pM to about 35 pM, about 800 pM to about 30 μM, about 800 pM to about 25 pM, about 800 pM to about 20 pM, about 800 pM to about 15 μM, about 800 pM to about 10 pM, about 800 pM to about 5 pM, about 800 pM to about 2 μM, about 800 pM to about 1 μM, about 800 pM to about 950 nM, about 800 pM to about 900 nM, about 800 pM to about 850 nM, about 800 pM to about 800 nM, about 800 pM to about 750 nM, about 800 pM to about 700 nM, about 800 pM to about 650 nM, about 800 pM to about 600 nM, about 800 pM to about 550 nM, about 800 pM to about 500 nM, about 800 pM to about 450 nM, about 800 pM to about 400 nM, about 800 pM to about 350 nM, about 800 pM to about 300 nM, about 800 pM to about 250 nM, about 800 pM to about 200 nM, about 800 pM to about 150 nM, about 800 pM to about 100 nM, about 800 pM to about 95 nM, about 800 pM to about 90 nM, about 800 pM to about 85 nM, about 800 pM to about 80 nM, about 800 pM to about 75 nM, about 800 pM to about 70 nM, about 800 pM to about 75 nM, about 800 pM to about 70 nM, about 800 pM to about 65 nM, about 800 pM to about 60 nM, about 800 pM to about 55 nM, about 800 pM to about 50 nM, about 800 pM to about 45 nM, about 800 pM to about 40 nM, about 800 pM to about 35 nM, about 800 pM to about 30 nM, about 800 pM to about 25 nM, about 800 pM to about 20 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 100 pM, about 900 pM to about 95 μM, about 900 pM to about 90 μM, about 900 pM to about 85 pM, about 900 pM to about 80 pM, about 900 pM to about 75 μM, about 900 pM to about 70 M, about 900 pM to about 65 μM, about 900 pM to about 60 PM, about 900 pM to about 55 M, about 900 pM to about 50 μM, about 900 pM to about 45 pM, about 900 pM to about 40 M, about 900 pM to about 45 μM, about 900 pM to about 40 PM, about 900 pM to about 35 M, about 900 pM to about 30 μM, about 900 pM to about 25 pM, about 900 pM to about 20 M, about 900 pM to about 15 μM, about 900 pM to about 10 pM, about 900 pM to about 5 μM, about 900 pM to about 2 pM, about 900 pM to about 1 μM, about 900 pM to about 950 nM, about 900 pM to about 900 nM, about 900 pM to about 850 nM, about 900 pM to about 800 nM, about 900 pM to about 750 nM, about 900 pM to about 700 nM, about 900 pM to about 650 nM, about 900 pM to about 600 nM, about 900 pM to about 550 nM, about 900 pM to about 500 nM, about 900 pM to about 450 nM, about 900 pM to about 400 nM, about 900 pM to about 350 nM, about 900 pM to about 300 nM, about 900 pM to about 250 nM, about 900 pM to about 200 nM, about 900 pM to about 150 nM, about 900 pM to about 100 nM, about 900 pM to about 95 nM, about 900 pM to about 90 nM, about 900 pM to about 85 nM, about 900 pM to about 80 nM, about 900 pM to about 75 nM, about 900 pM to about 70 nM, about 900 pM to about 75 nM, about 900 pM to about 70 nM, about 900 pM to about 65 nM, about 900 pM to about 60 nM, about 900 pM to about 55 nM, about 900 pM to about 50 nM, about 900 pM to about 45 nM, about 900 pM to about 40 nM, about 900 pM to about 35 nM, about 900 pM to about 30 nM, about 900 pM to about 25 nM, about 900 pM to about 20 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 100 μM, about 1 nM to about 95 pM, about 1 nM to about 90 pM, about 1 nM to about 85 μM, about 1 nM to about 80 μM, about 1 nM to about 75 μM, about 1 nM to about 70 μM, about 1 nM to about 65 M, about 1 nM to about 60 μM, about 1 nM to about 55 pM, about 1 nM to about 50 μM, about 1 nM to about 45 μM, about 1 nM to about 40 μM, about 1 nM to about 45 pM, about 1 nM to about 40 μM, about 1 nM to about 35 μM, about 1 nM to about 30 μM, about 1 nM to about 25 M, about 1 nM to about 20 μM, about 1 nM to about 15 pM, about 1 nM to about 10 μM, about 1 nM to about 5 μM, about 1 nM to about 2 μM, about 1 nM to about 1 pM, about 1 nM to about 950 nM, about 1 nM to about 900 nM, about 1 nM to about 850 nM, about 1 nM to about 800 nM, about 1 nM to about 750 nM, about 1 nM to about 700 nM, about 1 nM to about 650 nM, about 1 nM to about 600 nM, about 1 nM to about 550 nM, about 1 nM to about 500 nM, about 1 nM to about 450 nM, about 1 nM to about 400 nM, about 1 nM to about 350 nM, about 1 nM to about 300 nM, about 1 nM to about 250 nM, about 1 nM to about 200 nM, about 1 nM to about 150 nM, about 1 nM to about 100 nM, about 1 nM to about 95 nM, about 1 nM to about 90 nM, about 1 nM to about 85 nM, about 1 nM to about 80 nM, about 1 nM to about 75 nM, about 1 nM to about 70 nM, about 1 nM to about 75 nM, about 1 nM to about 70 nM, about 1 nM to about 65 nM, about 1 nM to about 60 nM, about 1 nM to about 55 nM, about 1 nM to about 50 nM, about 1 nM to about 45 nM, about 1 nM to about 40 nM, about 1 nM to about 35 nM, about 1 nM to about 30 nM, about 1 nM to about 25 nM, about 1 nM to about 20 nM, about 1 nM to about 15 nM, about 1 nM to about 10 nM, about 1 nM to about 5 nM, about 1 nM to about 2 nM, about 2 nM to about 100 pM, about 2 nM to about 95 μM, about 2 nM to about 90 μM, about 2 nM to about 85 pM, about 2 nM to about 80 pM, about 2 nM to about 75 μM, about 2 nM to about 70 μM, about 2 nM to about 65 μM, about 2 nM to about 60 μM, about 2 nM to about 55 M, about 2 nM to about 50 μM, about 2 nM to about 45 pM, about 2 nM to about 40 μM, about 2 nM to about 45 μM, about 2 nM to about 40 μM, about 2 nM to about 35 pM, about 2 nM to about 30 μM, about 2 nM to about 25 μM, about 2 nM to about 20 μM, about 2 nM to about 15 M, about 2 nM to about 10 μM, about 2 nM to about 5 pM, about 2 nM to about 2 μM, about 2 nM to about 1 pM, about 2 nM to about 950 nM, about 2 nM to about 900 nM, about 2 nM to about 850 nM, about 2 nM to about 800 nM, about 2 nM to about 750 nM, about 2 nM to about 700 nM, about 2 nM to about 650 nM, about 2 nM to about 600 nM, about 2 nM to about 550 nM, about 2 nM to about 500 nM, about 2 nM to about 450 nM, about 2 nM to about 400 nM, about 2 nM to about 350 nM, about 2 nM to about 300 nM, about 2 nM to about 250 nM, about 2 nM to about 200 nM, about 2 nM to about 150 nM, about 2 nM to about 100 nM, about 2 nM to about 95 nM, about 2 nM to about 90 nM, about 2 nM to about 85 nM, about 2 nM to about 80 nM, about 2 nM to about 75 nM, about 2 nM to about 70 nM, about 2 nM to about 75 nM, about 2 nM to about 70 nM, about 2 nM to about 65 nM, about 2 nM to about 60 nM, about 2 nM to about 55 nM, about 2 nM to about 50 nM, about 2 nM to about 45 nM, about 2 nM to about 40 nM, about 2 nM to about 35 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 5 nM to about 100 μM, about 5 nM to about 95 μM, about 5 nM to about 90 M, about 5 nM to about 85 μM, about 5 nM to about 80 μM, about 5 nM to about 75 μM, about 5 nM to about 70 μM, about 5 nM to about 65 μM, about 5 nM to about 60 PM, about 5 nM to about 55 μM, about 5 nM to about 50 μM, about 5 nM to about 45 μM, about 5 nM to about 40 M, about 5 nM to about 45 μM, about 5 nM to about 40 μM, about 5 nM to about 35 μM, about 5 nM to about 30 μM, about 5 nM to about 25 μM, about 5 nM to about 20 PM, about 5 nM to about 15 μM, about 5 nM to about 10 μM, about 5 nM to about 5 μM, about 5 nM to about 2 M, about 5 nM to about 1 μM, about 5 nM to about 950 nM, about 5 nM to about 900 nM, about 5 nM to about 850 nM, about 5 nM to about 800 nM, about 5 nM to about 750 nM, about 5 nM to about 700 nM, about 5 nM to about 650 nM, about 5 nM to about 600 nM, about 5 nM to about 550 nM, about 5 nM to about 500 nM, about 5 nM to about 450 nM, about 5 nM to about 400 nM, about 5 nM to about 350 nM, about 5 nM to about 300 nM, about 5 nM to about 250 nM, about 5 nM to about 200 nM, about 5 nM to about 150 nM, about 5 nM to about 100 nM, about 5 nM to about 95 nM, about 5 nM to about 90 nM, about 5 nM to about 85 nM, about 5 nM to about 80 nM, about 5 nM to about 75 nM, about 5 nM to about 70 nM, about 5 nM to about 75 nM, about 5 nM to about 70 nM, about 5 nM to about 65 nM, about 5 nM to about 60 nM, about 5 nM to about 55 nM, about 5 nM to about 50 nM, about 5 nM to about 45 nM, about 5 nM to about 40 nM, about 5 nM to about 35 nM, about 5 nM to about 30 nM, about 5 nM to about 25 nM, about 5 nM to about 20 nM, about 5 nM to about 15 nM, about 5 nM to about 10 nM, about 10 nM to about 100 μM, about 10 nM to about 95 μM, about 10 nM to about 90 PM, about 10 nM to about 85 μM, about 10 nM to about 80 μM, about 10 nM to about 75 μM, about 10 nM to about 70 μM, about 10 nM to about 65 μM, about 10 nM to about 60 PM, about 10 nM to about 55 μM, about 10 nM to about 50 μM, about 10 nM to about 45 μM, about 10 nM to about 40 μM, about 10 nM to about 45 μM, about 10 nM to about 40 μM, about 10 nM to about 35 μM, about 10 nM to about 30 μM, about 10 nM to about 25 μM, about 10 nM to about 20 M, about 10 nM to about 15 μM, about 10 nM to about 10 μM, about 10 nM to about 5 μM, about 10 nM to about 2 μM, about 10 nM to about 1 μM, about 10 nM to about 950 nM, about 10 nM to about 900 nM, about 10 nM to about 850 nM, about 10 nM to about 800 nM, about 10 nM to about 750 nM, about 10 nM to about 700 nM, about 10 nM to about 650 nM, about 10 nM to about 600 nM, about 10 nM to about 550 nM, about 10 nM to about 500 nM, about 10 nM to about 450 nM, about 10 nM to about 400 nM, about 10 nM to about 350 nM, about 10 nM to about 300 nM, about 10 nM to about 250 nM, about 10 nM to about 200 nM, about 10 nM to about 150 nM, about 10 nM to about 100 nM, about 10 nM to about 95 nM, about 10 nM to about 90 nM, about 10 nM to about 85 nM, about 10 nM to about 80 nM, about 10 nM to about 75 nM, about 10 nM to about 70 nM, about 10 nM to about 75 nM, about 10 nM to about 70 nM, about 10 nM to about 65 nM, about 10 nM to about 60 nM, about 10 nM to about 55 nM, about 10 nM to about 50 nM, about 10 nM to about 45 nM, about 10 nM to about 40 nM, about 10 nM to about 35 nM, about 10 nM to about 30 nM, about 10 nM to about 25 nM, about 10 nM to about 20 nM, about 10 nM to about 15 nM, about 20 nM to about 100 μM, about 20 nM to about 95 μM, about 20 nM to about 90 μM, about 20 nM to about 85 μM, about 20 nM to about 80 M, about 20 nM to about 75 μM, about 20 nM to about 70 μM, about 20 nM to about 65 μM, about 20 nM to about 60 μM, about 20 nM to about 55 μM, about 20 nM to about 50 μM, about 20 nM to about 45 μM, about 20 nM to about 40 μM, about 20 nM to about 45 μM, about 20 nM to about 40 μM, about 20 nM to about 35 μM, about 20 nM to about 30 μM, about 20 nM to about 25 μM, about 20 nM to about 20 μM, about 20 nM to about 15 μM, about 20 nM to about 10 μM, about 20 nM to about 5 μM, about 20 nM to about 2 μM, about 20 nM to about 1 μM, about 20 nM to about 950 nM, about 20 nM to about 900 nM, about 20 nM to about 850 nM, about 20 nM to about 800 nM, about 20 nM to about 750 nM, about 20 nM to about 700 nM, about 20 nM to about 650 nM, about 20 nM to about 600 nM, about 20 nM to about 550 nM, about 20 nM to about 500 nM, about 20 nM to about 450 nM, about 20 nM to about 400 nM, about 20 nM to about 350 nM, about 20 nM to about 300 nM, about 20 nM to about 250 nM, about 20 nM to about 200 nM, about 20 nM to about 150 nM, about 20 nM to about 100 nM, about 20 nM to about 95 nM, about 20 nM to about 90 nM, about 20 nM to about 85 nM, about 20 nM to about 80 nM, about 20 nM to about 75 nM, about 20 nM to about 70 nM, about 20 nM to about 75 nM, about 20 nM to about 70 nM, about 20 nM to about 65 nM, about 20 nM to about 60 nM, about 20 nM to about 55 nM, about 20 nM to about 50 nM, about 20 nM to about 45 nM, about 20 nM to about 40 nM, about 20 nM to about 35 nM, about 20 nM to about 30 nM, about 20 nM to about 25 nM, about 50 nM to about 100 μM, about 50 nM to about 95 μM, about 50 nM to about 90 μM, about 50 nM to about 85 μM, about 50 nM to about 80 PM, about 50 nM to about 75 μM, about 50 nM to about 70 μM, about 50 nM to about 65 μM, about 50 nM to about 60 μM, about 50 nM to about 55 μM, about 50 nM to about 50 μM, about 50 nM to about 45 μM, about 50 nM to about 40 μM, about 50 nM to about 45 μM, about 50 nM to about 40 M, about 50 nM to about 35 μM, about 50 nM to about 30 μM, about 50 nM to about 25 μM, about 50 nM to about 20 μM, about 50 nM to about 15 μM, about 50 nM to about 10 μM, about 50 nM to about 5 μM, about 50 nM to about 2 μM, about 50 nM to about 1 μM, about 50 nM to about 950 nM, about 50 nM to about 900 nM, about 50 nM to about 850 nM, about 50 nM to about 800 nM, about 50 nM to about 750 nM, about 50 nM to about 700 nM, about 50 nM to about 650 nM, about 50 nM to about 600 nM, about 50 nM to about 550 nM, about 50 nM to about 500 nM, about 50 nM to about 450 nM, about 50 nM to about 400 nM, about 50 nM to about 350 nM, about 50 nM to about 300 nM, about 50 nM to about 250 nM, about 50 nM to about 200 nM, about 50 nM to about 150 nM, about 50 nM to about 100 nM, about 50 nM to about 95 nM, about 50 nM to about 90 nM, about 50 nM to about 85 nM, about 50 nM to about 80 nM, about 50 nM to about 75 nM, about 50 nM to about 70 nM, about 50 nM to about 75 nM, about 50 nM to about 70 nM, about 50 nM to about 65 nM, about 50 nM to about 60 nM, about 50 nM to about 55 nM, about 100 nM to about 100 μM, about 100 nM to about 95 μM, about 100 nM to about 90 μM, about 100 nM to about 85 μM, about 100 nM to about 80 μM, about 100 nM to about 75 μM, about 100 nM to about 70 μM, about 100 nM to about 65 μM, about 100 nM to about 60 μM, about 100 nM to about 55 μM, about 100 nM to about 50 μM, about 100 nM to about 45 μM, about 100 nM to about 40 μM, about 100 nM to about 45 μM, about 100 nM to about 40 μM, about 100 nM to about 35 μM, about 100 nM to about 30 μM, about 100 nM to about 25 μM, about 100 nM to about 20 μM, about 100 nM to about 15 μM, about 100 nM to about 10 μM, about 100 nM to about 5 μM, about 100 nM to about 2 PM, about 100 nM to about 1 μM, about 100 nM to about 950 nM, about 100 nM to about 900 nM, about 100 nM to about 850 nM, about 100 nM to about 800 nM, about 100 nM to about 750 nM, about 100 nM to about 700 nM, about 100 nM to about 650 nM, about 100 nM to about 600 nM, about 100 nM to about 550 nM, about 100 nM to about 500 nM, about 100 nM to about 450 nM, about 100 nM to about 400 nM, about 100 nM to about 350 nM, about 100 nM to about 300 nM, about 100 nM to about 250 nM, about 100 nM to about 200 nM, about 100 nM to about 150 nM, about 200 nM to about 100 μM, about 200 nM to about 95 μM, about 200 nM to about 90 μM, about 200 nM to about 85 μM, about 200 nM to about 80 μM, about 200 nM to about 75 μM, about 200 nM to about 70 μM, about 200 nM to about 65 μM, about 200 nM to about 60 μM, about 200 nM to about 55 μM, about 200 nM to about 50 μM, about 200 nM to about 45 μM, about 200 nM to about 40 μM, about 200 nM to about 45 μM, about 200 nM to about 40 μM, about 200 nM to about 35 μM, about 200 nM to about 30 μM, about 200 nM to about 25 μM, about 200 nM to about 20 μM, about 200 nM to about 15 μM, about 200 nM to about 10 μM, about 200 nM to about 5 μM, about 200 nM to about 2 μM, about 200 nM to about 1 μM, about 200 nM to about 950 nM, about 200 nM to about 900 nM, about 200 nM to about 850 nM, about 200 nM to about 800 nM, about 200 nM to about 750 nM, about 200 nM to about 700 nM, about 200 nM to about 650 nM, about 200 nM to about 600 nM, about 200 nM to about 550 nM, about 200 nM to about 500 nM, about 200 nM to about 450 nM, about 200 nM to about 400 nM, about 200 nM to about 350 nM, about 200 nM to about 300 nM, about 200 nM to about 250 nM, about 300 nM to about 100 μM, about 300 nM to about 95 μM, about 300 nM to about 90 μM, about 300 nM to about 85 μM, about 300 nM to about 80 μM, about 300 nM to about 75 μM, about 300 nM to about 70 M, about 300 nM to about 65 μM, about 300 nM to about 60 PM, about 300 nM to about 55 M, about 300 nM to about 50 μM, about 300 nM to about 45 μM, about 300 nM to about 40 M, about 300 nM to about 45 μM, about 300 nM to about 40 PM, about 300 nM to about 35 M, about 300 nM to about 30 μM, about 300 nM to about 25 μM, about 300 nM to about 20 M, about 300 nM to about 15 μM, about 300 nM to about 10 μM, about 300 nM to about 5 M, about 300 nM to about 2 μM, about 300 nM to about 1 μM, about 300 nM to about 950 nM, about 300 nM to about 900 nM, about 300 nM to about 850 nM, about 300 nM to about 800 nM, about 300 nM to about 750 nM, about 300 nM to about 700 nM, about 300 nM to about 650 nM, about 300 nM to about 600 nM, about 300 nM to about 550 nM, about 300 nM to about 500 nM, about 300 nM to about 450 nM, about 300 nM to about 400 nM, about 300 nM to about 350 nM, about 400 nM to about 100 μM, about 400 nM to about 95 μM, about 400 nM to about 90 μM, about 400 nM to about 85 μM, about 400 nM to about 80 μM, about 400 nM to about 75 μM, about 400 nM to about 70 μM, about 400 nM to about 65 μM, about 400 nM to about 60 μM, about 400 nM to about 55 μM, about 400 nM to about 50 μM, about 400 nM to about 45 μM, about 400 nM to about 40 μM, about 400 nM to about 45 μM, about 400 nM to about 40 μM, about 400 nM to about 35 μM, about 400 nM to about 30 μM, about 400 nM to about 25 μM, about 400 nM to about 20 μM, about 400 nM to about 15 μM, about 400 nM to about 10 μM, about 400 nM to about 5 μM, about 400 nM to about 2 μM, about 400 nM to about 1 μM, about 400 nM to about 950 nM, about 400 nM to about 900 nM, about 400 nM to about 850 nM, about 400 nM to about 800 nM, about 400 nM to about 750 nM, about 400 nM to about 700 nM, about 400 nM to about 650 nM, about 400 nM to about 600 nM, about 400 nM to about 550 nM, about 400 nM to about 500 nM, about 400 nM to about 450 nM, about 500 nM to about 100 μM, about 500 nM to about 95 μM, about 500 nM to about 90 μM, about 500 nM to about 85 μM, about 500 nM to about 80 μM, about 500 nM to about 75 μM, about 500 nM to about 70 μM, about 500 nM to about 65 μM, about 500 nM to about 60 μM, about 500 nM to about 55 μM, about 500 nM to about 50 μM, about 500 nM to about 45 μM, about 500 nM to about 40 μM, about 500 nM to about 45 μM, about 500 nM to about 40 μM, about 500 nM to about 35 μM, about 500 nM to about 30 μM, about 500 nM to about 25 μM, about 500 nM to about 20 μM, about 500 nM to about 15 μM, about 500 nM to about 10 μM, about 500 nM to about 5 μM, about 500 nM to about 2 μM, about 500 nM to about 1 μM, about 500 nM to about 950 nM, about 500 nM to about 900 nM, about 500 nM to about 850 nM, about 500 nM to about 800 nM, about 500 nM to about 750 nM, about 500 nM to about 700 nM, about 500 nM to about 650 nM, about 500 nM to about 600 nM, about 500 nM to about 550 nM, about 600 nM to about 100 M, about 600 nM to about 95 μM, about 600 nM to about 90 μM, about 600 nM to about 85 μM, about 600 nM to about 80 μM, about 600 nM to about 75 μM, about 600 nM to about 70 μM, about 600 nM to about 65 μM, about 600 nM to about 60 μM, about 600 nM to about 55 μM, about 600 nM to about 50 μM, about 600 nM to about 45 μM, about 600 nM to about 40 μM, about 600 nM to about 45 μM, about 600 nM to about 40 μM, about 600 nM to about 35 μM, about 600 nM to about 30 μM, about 600 nM to about 25 μM, about 600 nM to about 20 μM, about 600 nM to about 15 μM, about 600 nM to about 10 μM, about 600 nM to about 5 μM, about 600 nM to about 2 μM, about 600 nM to about 1 μM, about 600 nM to about 950 nM, about 600 nM to about 900 nM, about 600 nM to about 850 nM, about 600 nM to about 800 nM, about 600 nM to about 750 nM, about 600 nM to about 700 nM, about 600 nM to about 650 nM, about 700 nM to about 100 μM, about 700 nM to about 95 μM, about 700 nM to about 90 μM, about 700 nM to about 85 μM, about 700 nM to about 80 μM, about 700 nM to about 75 μM, about 700 nM to about 70 μM, about 700 nM to about 65 μM, about 700 nM to about 60 μM, about 700 nM to about 55 μM, about 700 nM to about 50 μM, about 700 nM to about 45 μM, about 700 nM to about 40 μM, about 700 nM to about 45 μM, about 700 nM to about 40 μM, about 700 nM to about 35 μM, about 700 nM to about 30 μM, about 700 nM to about 25 μM, about 700 nM to about 20 μM, about 700 nM to about 15 μM, about 700 nM to about 10 μM, about 700 nM to about 5 μM, about 700 nM to about 2 μM, about 700 nM to about 1 μM, about 700 nM to about 950 nM, about 700 nM to about 900 nM, about 700 nM to about 850 nM, about 700 nM to about 800 nM, about 700 nM to about 750 nM, about 800 nM to about 100 μM, about 800 nM to about 95 μM, about 800 nM to about 90 μM, about 800 nM to about 85 μM, about 800 nM to about 80 μM, about 800 nM to about 75 μM, about 800 nM to about 70 μM, about 800 nM to about 65 μM, about 800 nM to about 60 μM, about 800 nM to about 55 μM, about 800 nM to about 50 μM, about 800 nM to about 45 μM, about 800 nM to about 40 μM, about 800 nM to about 45 μM, about 800 nM to about 40 μM, about 800 nM to about 35 μM, about 800 nM to about 30 μM, about 800 nM to about 25 μM, about 800 nM to about 20 μM, about 800 nM to about 15 μM, about 800 nM to about 10 μM, about 800 nM to about 5 μM, about 800 nM to about 2 μM, about 800 nM to about 1 μM, about 800 nM to about 950 nM, about 800 nM to about 900 nM, about 800 nM to about 850 nM, about 900 nM to about 100 μM, about 900 nM to about 95 μM, about 900 nM to about 90 μM, about 900 nM to about 85 μM, about 900 nM to about 80 μM, about 900 nM to about 75 μM, about 900 nM to about 70 μM, about 900 nM to about 65 μM, about 900 nM to about 60 μM, about 900 nM to about 55 μM, about 900 nM to about 50 μM, about 900 nM to about 45 μM, about 900 nM to about 40 μM, about 900 nM to about 45 μM, about 900 nM to about 40 μM, about 900 nM to about 35 μM, about 900 nM to about 30 μM, about 900 nM to about 25 μM, about 900 nM to about 20 μM, about 900 nM to about 15 μM, about 900 nM to about 10 μM, about 900 nM to about 5 μM, about 900 nM to about 2 μM, about 900 nM to about 1 μM, about 900 nM to about 950 nM, about 1 μM to about 100 μM, about 1 μM to about 95 μM, about 1 μM to about 90 μM, about 1 μM to about 85 M, about 1 μM to about 80 μM, about 1 μM to about 75 μM, about 1 μM to about 70 μM, about 1 M to about 65 μM, about 1 μM to about 60 μM, about 1 μM to about 55 μM, about 1 μM to about 50 μM, about 1 μM to about 45 μM, about 1 μM to about 40 μM, about 1 μM to about 45 M, about 1 μM to about 40 μM, about 1 μM to about 35 μM, about 1 μM to about 30 μM, about 1 μM to about 25 μM, about 1 μM to about 20 μM, about 1 μM to about 15 μM, about 1 μM to about 10 μM, about 1 μM to about 5 μM, about 1 μM to about 2 μM, about 2 M to about 100 M, about 2 M to about 95 μM, about 2 M to about 90 μM, about 2 M to about 85 μM, about 2 M to about 80 μM, about 2 M to about 75 μM, about 2 M to about 70 μM, about 2 M to about 65 μM, about 2 M to about 60 μM, about 2 M to about 55 μM, about 2 μM to about 50 M, about 2 M to about 45 μM, about 2 M to about 40 μM, about 2 M to about 45 μM, about 2 M to about 40 μM, about 2 M to about 35 μM, about 2 M to about 30 μM, about 2 M to about 25 μM, about 2 M to about 20 μM, about 2 M to about 15 μM, about 2 μM to about 10 M, about 2 M to about 5 μM, about 5 μM to about 100 μM, about 5 μM to about 95 μM, about 5 μM to about 90 μM, about 5 μM to about 85 μM, about 5 μM to about 80 μM, about 5 μM to about 75 μM, about 5 μM to about 70 μM, about 5 μM to about 65 μM, about 5 μM to about 60 M, about 5 μM to about 55 μM, about 5 μM to about 50 μM, about 5 μM to about 45 μM, about 5 μM to about 40 μM, about 5 μM to about 45 μM, about 5 μM to about 40 μM, about 5 M to about 35 μM, about 5 μM to about 30 μM, about 5 μM to about 25 μM, about 5 μM to about 20 μM, about 5 μM to about 15 μM, about 5 μM to about 10 μM, about 10 μM to about 100 μM, about 10 μM to about 95 μM, about 10 μM to about 90 μM, about 10 μM to about 85 M, about 10 μM to about 80 μM, about 10 μM to about 75 μM, about 10 μM to about 70 M, about 10 μM to about 65 μM, about 10 μM to about 60 μM, about 10 μM to about 55 μM, about M to about 50 μM, about 10 μM to about 45 μM, about 10 μM to about 40 μM, about 10 μM to about 45 μM, about 10 μM to about 40 μM, about 10 μM to about 35 PM, about 10 μM to about 30 μM, about 10 μM to about 25 μM, about 10 μM to about 20 μM, about 10 μM to about 15 μM, about 20 μM to about 100 μM, about 20 μM to about 95 μM, about 20 μM to about 90 M, about 20 μM to about 85 μM, about 20 μM to about 80 μM, about 20 μM to about 75 M, about 20 μM to about 70 μM, about 20 μM to about 65 μM, about 20 μM to about 60 μM, about 20 μM to about 55 μM, about 20 μM to about 50 μM, about 20 μM to about 45 μM, about 20 μM to about 40 μM, about 20 μM to about 45 μM, about 20 μM to about 40 μM, about 20 μM to about 35 μM, about 20 μM to about 30 μM, about 20 μM to about 25 μM, about 30 μM to about 100 μM, about 30 μM to about 95 μM, about 30 μM to about 90 μM, about 30 μM to about 85 M, about 30 μM to about 80 μM, about 30 μM to about 75 μM, about 30 μM to about 70 μM, about 30 μM to about 65 μM, about 30 μM to about 60 μM, about 30 μM to about 55 μM, about 30 μM to about 50 μM, about 30 μM to about 45 μM, about 30 μM to about 40 μM, about 30 μM to about 45 pM, about 30 μM to about 40 μM, about 30 μM to about 35 PM, about 40 μM to about 100 μM, about 40 pM to about 95 μM, about 40 μM to about 90 pM, about 40 μM to about 85 pM, about 40 μM to about 80 μM, about 40 pM to about 75 μM, about 40 μM to about 70 M, about 40 μM to about 65 pM, about 40 μM to about 60 μM, about 40 μM to about 55 PM, about 40 μM to about 50 pM, about 40 μM to about 45 μM, about 50 pM to about 100 μM, about 50 pM to about 95 μM, about 50 μM to about 90 pM, about 50 μM to about 85 μM, about 50 μM to about 80 pM, about 50 μM to about 75 μM, about 50 μM to about 70 pM, about 50 μM to about 65 μM, about 50 pM to about 60 μM, about 50 μM to about 55 PM, about 60 μM to about 100 pM, about 60 μM to about 95 μM, about 60 pM to about 90 μM, about 60 μM to about 85 M, about 60 μM to about 80 pM, about 60 μM to about 75 μM, about 60 μM to about 70 M, about 60 μM to about 65 pM, about 70 μM to about 100 μM, about 70 pM to about 95 μM, about 70 pM to about 90 μM, about 70 μM to about 85 pM, about 70 μM to about 80 μM, about 70 pM to about 75 pM, about 80 μM to about 100 μM, about 80 pM to about 95 μM, about 80 μM to about 90 μM, about 80 pM to about 85 μM, about 90 μM to about 100 pM, or about 90 μM to about 95 μM) (e.g., as measured using SPR in phosphate buffered saline).

In some embodiments, the chimeric polypeptides described herein can have a total length of about 20 amino acids to about 1400 amino acids, about 20 amino acids to about 1350 amino acids, about 20 amino acids to about 1300 amino acids, about 20 amino acids to about 1250 amino acids, about 20 amino acids to about 1200 amino acids, about 20 amino acids to about 1150 amino acids, about 20 amino acids to about 1100 amino acids, about 20 amino acid to about 1050 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 250 amino acids, about 20 amino acids to about 200 amino acids, about 20 amino acids to about 150 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1400 amino acids, about 25 amino acids to about 1350 amino acids, about 25 amino acids to about 1300 amino acids, about 25 amino acids to about 1250 amino acids, about 25 amino acids to about 1200 amino acids, about 25 amino acids to about 1150 amino acids, about 25 amino acids to about 1100 amino acids, about 25 amino acid to about 1050 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 250 amino acids, about 25 amino acids to about 200 amino acids, about 25 amino acids to about 150 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1400 amino acids, about 30 amino acids to about 1350 amino acids, about 30 amino acids to about 1300 amino acids, about 30 amino acids to about 1250 amino acids, about 30 amino acids to about 1200 amino acids, about 30 amino acids to about 1150 amino acids, about 30 amino acids to about 1100 amino acids, about 30 amino acid to about 1050 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 250 amino acids, about 30 amino acids to about 200 amino acids, about 30 amino acids to about 150 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1400 amino acids, about 35 amino acids to about 1350 amino acids, about 35 amino acids to about 1300 amino acids, about 35 amino acids to about 1250 amino acids, about 35 amino acids to about 1200 amino acids, about 35 amino acids to about 1150 amino acids, about 35 amino acids to about 1100 amino acids, about 35 amino acid to about 1050 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 250 amino acids, about 35 amino acids to about 200 amino acids, about 35 amino acids to about 150 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 1400 amino acids, about 40 amino acids to about 1350 amino acids, about 40 amino acids to about 1300 amino acids, about 40 amino acids to about 1250 amino acids, about 40 amino acids to about 1200 amino acids, about 40 amino acids to about 1150 amino acids, about 40 amino acids to about 1100 amino acids, about 40 amino acid to about 1050 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 250 amino acids, about 40 amino acids to about 200 amino acids, about 40 amino acids to about 150 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 1400 amino acids, about 45 amino acids to about 1350 amino acids, about 45 amino acids to about 1300 amino acids, about 45 amino acids to about 1250 amino acids, about 45 amino acids to about 1200 amino acids, about 45 amino acids to about 1150 amino acids, about 45 amino acids to about 1100 amino acids, about 45 amino acid to about 1050 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 250 amino acids, about 45 amino acids to about 200 amino acids, about 45 amino acids to about 150 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 1400 amino acids, about 50 amino acids to about 1350 amino acids, about 50 amino acids to about 1300 amino acids, about 50 amino acids to about 1250 amino acids, about 50 amino acids to about 1200 amino acids, about 50 amino acids to about 1150 amino acids, about 50 amino acids to about 1100 amino acids, about 50 amino acid to about 1050 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 1400 amino acids, about 60 amino acids to about 1350 amino acids, about 60 amino acids to about 1300 amino acids, about 60 amino acids to about 1250 amino acids, about 60 amino acids to about 1200 amino acids, about 60 amino acids to about 1150 amino acids, about 60 amino acids to about 1100 amino acids, about 60 amino acid to about 1050 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 250 amino acids, about 60 amino acids to about 200 amino acids, about 60 amino acids to about 150 amino acids, about 60 amino acids to about 100 amino acids, about 60 amino acids to about 90 amino acids, about 60 amino acids to about 80 amino acids, about 60 amino acids to about 70 amino acids, about 70 amino acids to about 1400 amino acids, about 70 amino acids to about 1350 amino acids, about 70 amino acids to about 1300 amino acids, about 70 amino acids to about 1250 amino acids, about 70 amino acids to about 1200 amino acids, about 70 amino acids to about 1150 amino acids, about 70 amino acids to about 1100 amino acids, about 70 amino acid to about 1050 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 250 amino acids, about 70 amino acids to about 200 amino acids, about 70 amino acids to about 150 amino acids, about 70 amino acids to about 100 amino acids, about 70 amino acids to about 90 amino acids, about 70 amino acids to about 80 amino acids, about 80 amino acids to about 1400 amino acids, about 80 amino acids to about 1350 amino acids, about 80 amino acids to about 1300 amino acids, about 80 amino acids to about 1250 amino acids, about 80 amino acids to about 1200 amino acids, about 80 amino acids to about 1150 amino acids, about 80 amino acids to about 1100 amino acids, about 80 amino acid to about 1050 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 250 amino acids, about 80 amino acids to about 200 amino acids, about 80 amino acids to about 150 amino acids, about 80 amino acids to about 100 amino acids, about 80 amino acids to about 90 amino acids, about 90 amino acids to about 1400 amino acids, about 90 amino acids to about 1350 amino acids, about 90 amino acids to about 1300 amino acids, about 90 amino acids to about 1250 amino acids, about 90 amino acids to about 1200 amino acids, about 90 amino acids to about 1150 amino acids, about 90 amino acids to about 1100 amino acids, about 90 amino acid to about 1050 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 250 amino acids, about 90 amino acids to about 200 amino acids, about 90 amino acids to about 150 amino acids, about 90 amino acids to about 100 amino acids, about 100 amino acids to about 1400 amino acids, about 100 amino acids to about 1350 amino acids, about 100 amino acids to about 1300 amino acids, about 100 amino acids to about 1250 amino acids, about 100 amino acids to about 1200 amino acids, about 100 amino acids to about 1150 amino acids, about 100 amino acids to about 1100 amino acids, about 100 amino acid to about 1050 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 1400 amino acids, about 150 amino acids to about 1350 amino acids, about 150 amino acids to about 1300 amino acids, about 150 amino acids to about 1250 amino acids, about 150 amino acids to about 1200 amino acids, about 150 amino acids to about 1150 amino acids, about 150 amino acids to about 1100 amino acids, about 150 amino acid to about 1050 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 1400 amino acids, about 200 amino acids to about 1350 amino acids, about 200 amino acids to about 1300 amino acids, about 200 amino acids to about 1250 amino acids, about 200 amino acids to about 1200 amino acids, about 200 amino acids to about 1150 amino acids, about 200 amino acids to about 1100 amino acids, about 200 amino acid to about 1050 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 1400 amino acids, about 250 amino acids to about 1350 amino acids, about 250 amino acids to about 1300 amino acids, about 250 amino acids to about 1250 amino acids, about 250 amino acids to about 1200 amino acids, about 250 amino acids to about 1150 amino acids, about 250 amino acids to about 1100 amino acids, about 250 amino acid to about 1050 amino acids, about 250 amino acids to about 1000 amino acids, about 250 amino acids to about 950 amino acids, about 250 amino acids to about 900 amino acids, about 250 amino acids to about 850 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 1400 amino acids, about 300 amino acids to about 1350 amino acids, about 300 amino acids to about 1300 amino acids, about 300 amino acids to about 1250 amino acids, about 300 amino acids to about 1200 amino acids, about 300 amino acids to about 1150 amino acids, about 300 amino acids to about 1100 amino acids, about 300 amino acid to about 1050 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1400 amino acids, about 350 amino acids to about 1350 amino acids, about 350 amino acids to about 1300 amino acids, about 350 amino acids to about 1250 amino acids, about 350 amino acids to about 1200 amino acids, about 350 amino acids to about 1150 amino acids, about 350 amino acids to about 1100 amino acids, about 350 amino acid to about 1050 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1400 amino acids, about 400 amino acids to about 1350 amino acids, about 400 amino acids to about 1300 amino acids, about 400 amino acids to about 1250 amino acids, about 400 amino acids to about 1200 amino acids, about 400 amino acids to about 1150 amino acids, about 400 amino acids to about 1100 amino acids, about 400 amino acid to about 1050 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1400 amino acids, about 450 amino acids to about 1350 amino acids, about 450 amino acids to about 1300 amino acids, about 450 amino acids to about 1250 amino acids, about 450 amino acids to about 1200 amino acids, about 450 amino acids to about 1150 amino acids, about 450 amino acids to about 1100 amino acids, about 450 amino acid to about 1050 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1400 amino acids, about 500 amino acids to about 1350 amino acids, about 500 amino acids to about 1300 amino acids, about 500 amino acids to about 1250 amino acids, about 500 amino acids to about 1200 amino acids, about 500 amino acids to about 1150 amino acids, about 500 amino acids to about 1100 amino acids, about 500 amino acid to about 1050 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1400 amino acids, about 550 amino acids to about 1350 amino acids, about 550 amino acids to about 1300 amino acids, about 550 amino acids to about 1250 amino acids, about 550 amino acids to about 1200 amino acids, about 550 amino acids to about 1150 amino acids, about 550 amino acids to about 1100 amino acids, about 550 amino acid to about 1050 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1400 amino acids, about 600 amino acids to about 1350 amino acids, about 600 amino acids to about 1300 amino acids, about 600 amino acids to about 1250 amino acids, about 600 amino acids to about 1200 amino acids, about 600 amino acids to about 1150 amino acids, about 600 amino acids to about 1100 amino acids, about 600 amino acid to about 1050 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1400 amino acids, about 650 amino acids to about 1350 amino acids, about 650 amino acids to about 1300 amino acids, about 650 amino acids to about 1250 amino acids, about 650 amino acids to about 1200 amino acids, about 650 amino acids to about 1150 amino acids, about 650 amino acids to about 1100 amino acids, about 650 amino acid to about 1050 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1400 amino acids, about 700 amino acids to about 1350 amino acids, about 700 amino acids to about 1300 amino acids, about 700 amino acids to about 1250 amino acids, about 700 amino acids to about 1200 amino acids, about 700 amino acids to about 1150 amino acids, about 700 amino acids to about 1100 amino acids, about 700 amino acid to about 1050 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1400 amino acids, about 750 amino acids to about 1350 amino acids, about 750 amino acids to about 1300 amino acids, about 750 amino acids to about 1250 amino acids, about 750 amino acids to about 1200 amino acids, about 750 amino acids to about 1150 amino acids, about 750 amino acids to about 1100 amino acids, about 750 amino acid to about 1050 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1400 amino acids, about 800 amino acids to about 1350 amino acids, about 800 amino acids to about 1300 amino acids, about 800 amino acids to about 1250 amino acids, about 800 amino acids to about 1200 amino acids, about 800 amino acids to about 1150 amino acids, about 800 amino acids to about 1100 amino acids, about 800 amino acid to about 1050 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1400 amino acids, about 850 amino acids to about 1350 amino acids, about 850 amino acids to about 1300 amino acids, about 850 amino acids to about 1250 amino acids, about 850 amino acids to about 1200 amino acids, about 850 amino acids to about 1150 amino acids, about 850 amino acids to about 1100 amino acids, about 850 amino acid to about 1050 amino acids, about 850 amino acids to about 1000 amino acids, about 850 amino acids to about 950 amino acids, about 850 amino acids to about 900 amino acids, about 900 amino acids to about 1400 amino acids, about 900 amino acids to about 1350 amino acids, about 900 amino acids to about 1300 amino acids, about 900 amino acids to about 1250 amino acids, about 900 amino acids to about 1200 amino acids, about 900 amino acids to about 1150 amino acids, about 900 amino acids to about 1100 amino acids, about 900 amino acid to about 1050 amino acids, about 900 amino acids to about 1000 amino acids, about 900 amino acids to about 950 amino acids, about 950 amino acids to about 1400 amino acids, about 950 amino acids to about 1350 amino acids, about 950 amino acids to about 1300 amino acids, about 950 amino acids to about 1250 amino acids, about 950 amino acids to about 1200 amino acids, about 950 amino acids to about 1150 amino acids, about 950 amino acids to about 1100 amino acids, about 950 amino acid to about 1050 amino acids, about 950 amino acids to about 1000 amino acids, about 1000 amino acids to about 1400 amino acids, about 1000 amino acids to about 1350 amino acids, about 1000 amino acids to about 1300 amino acids, about 1000 amino acids to about 1250 amino acids, about 1000 amino acids to about 1200 amino acids, about 1000 amino acids to about 1150 amino acids, about 1000 amino acids to about 1100 amino acids, about 1000 amino acid to about 1050 amino acids, about 1050 amino acids to about 1400 amino acids, about 1050 amino acids to about 1350 amino acids, about 1050 amino acids to about 1300 amino acids, about 1050 amino acids to about 1250 amino acids, about 1050 amino acids to about 1200 amino acids, about 1050 amino acids to about 1150 amino acids, about 1050 amino acids to about 1100 amino acids, about 1100 amino acids to about 1400 amino acids, about 1100 amino acids to about 1350 amino acids, about 1100 amino acids to about 1300 amino acids, about 1100 amino acids to about 1250 amino acids, about 1100 amino acids to about 1200 amino acids, about 1100 amino acids to about 1150 amino acids, about 1150 amino acids to about 1400 amino acids, about 1150 amino acids to about 1350 amino acids, about 1150 amino acids to about 1300 amino acids, about 1150 amino acids to about 1250 amino acids, about 1150 amino acids to about 1200 amino acids, about 1200 amino acids to about 1400 amino acids, about 1200 amino acids to about 1350 amino acids, about 1200 amino acids to about 1300 amino acids, about 1200 amino acids to about 1250 amino acids, about 1250 amino acids to about 1400 amino acids, about 1250 amino acids to about 1350 amino acids, about 1250 amino acids to about 1300 amino acids, about 1300 amino acids to about 1400 amino acids, about 1300 amino acids to about 1350 amino acids, or about 1350 amino acids to about 1400 amino acids.

For example, the chimeric polypeptide may include: LLADTTHHRPWTVIGESTHHRPWSII-GESSHHKPFTGLGDTTHHRPWGILAESTHHKPWT A TGGSGEGGT-GASTGGSAGTGGSGGTTSGEAGGSSGAG (SEQ ID NO: 44). In some instances the chimeric polypeptide includes a β-TCP binding sequence and a linker that has an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 44.

For example, the chimeric polypeptide may include: LLADTTHHRPWTGLGDTTHHRPWGL-LADTTHHRPWTGLGDTTHHRPWGLLADTTTHHR PWT TGGSGEGGT-GASTGGSAGTGGSGGTTSGEAGGSSGAG (SEQ ID NO: 45. In some instances the chimeric polypeptide includes a β-TCP binding sequence and a linker that has an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 45.

A variety of different methods known in the art can be used to determine the $K_D$ values of any of the chimeric polypeptides described herein for binding to β-TCP (e.g., any of the types of β-TCP described herein) (e.g., an electrophoretic mobility shift assay, a filter binding assay, surface plasmon resonance, and a biomolecular binding kinetics assay, etc.) The chimeric polypeptides provided herein are useful orthopedic materials, and can be used as bone void fillers and for bone reconstructions. The chimeric polypeptides described herein are osteo-conductive and easily resorbed.

Linkers

In some instances, a neighboring pair (or each neighboring pair) of two β-TCP binding sequences directly abut each other. In other instances, a neighboring pair (or each neighboring pair) of two β-TCP binding sequences are separated by a linker sequence. For example, a linker sequence can be 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 95 amino acids, about 2 amino acids to about 90 amino acids, about 2 amino acids to about 85 amino acids, about 2 amino acids to about 80 amino acids, about 2 amino acids to about 75 amino acids, about 2 amino acids to about 70 amino acids, about 2 amino acids to about 65 amino acids, about 2 amino acids to about 60 amino acids, about 2 amino acids to about 55 amino acids, about 2 amino acids to about 50 amino acids, about 2 amino acids to about 45 amino acids, about 2 amino acids to about 40 amino acids, about 2 amino acids to about 38 amino acids, about 2 amino acids to about 36 amino acids, about 2 amino acids to about 34 amino acids, about 2 amino acids to about 32 amino acids, about 2 amino acids to about 30 amino acids, about 2 amino acids to about 28 amino acids, about 2 amino acids to about 26 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 95 amino acids, about 4 amino acids to about 90 amino acids, about 4 amino acids to about 85 amino acids, about 4 amino acids to about 80 amino acids, about 4 amino acids to about 75 amino acids, about 4 amino acids to about 70 amino acids, about 4 amino acids to about 65 amino acids, about 4 amino acids to about 60 amino acids, about 4 amino acids to about 55 amino acids, about 4 amino acids to about 50 amino acids, about 4 amino acids to about 45 amino acids, about 4 amino acids to about 40 amino acids, about 4 amino acids to about 38 amino acids, about 4 amino acids to about 36 amino acids, about 4 amino acids to about 34 amino acids, about 4 amino acids to about 32 amino acids, about 4 amino acids to about 30 amino acids, about 4 amino acids to about 28 amino acids, about 4 amino acids to about 26 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 95 amino acids, about 6 amino acids to about 90 amino acids, about 6 amino acids to about 85 amino acids, about 6 amino acids to about 80 amino acids, about 6 amino acids to about 75 amino acids, about 6 amino acids to about 70 amino acids, about 6 amino acids to about 65 amino acids, about 6 amino acids to about 60 amino acids, about 6 amino acids to about 55 amino acids, about 6 amino acids to about 50 amino acids, about 6 amino acids to about 45 amino acids, about 6 amino acids to about 40 amino acids, about 6 amino acids to about 38 amino acids, about 6 amino acids to about 36 amino acids, about 6 amino acids to about 34 amino acids, about 6 amino acids to about 32 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 95 amino acids, about 8 amino acids to about 90 amino acids, about 8 amino acids to about 85 amino acids, about 8 amino acids to about 80 amino acids, about 8 amino acids to about 75 amino acids, about 8 amino acids to about 70 amino acids, about 8 amino acids to about 65 amino acids, about 8 amino acids to about 60 amino acids, about 8 amino acids to about 55 amino acids, about 8 amino acids to about 50 amino acids, about 8 amino acids to about 45 amino acids, about 8 amino acids to about 40 amino acids, about 8 amino acids to about 38 amino acids, about 8 amino acids to about 36 amino acids, about 8 amino acids to about 34 amino acids, about 8 amino acids to about 32 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 38 amino acids, about 10 amino acids to about 36 amino acids, about 10 amino acids to about 34 amino acids, about 10 amino acids to about 32 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 95 amino acids, about 12 amino acids to about 90 amino acids, about 12 amino acids to about 85 amino acids, about 12 amino acids to about 80 amino acids, about 12 amino acids to about 75 amino acids, about 12 amino acids to about 70 amino acids, about 12 amino acids to about 65 amino acids, about 12 amino acids to about 60 amino acids, about 12 amino acids to about 55 amino acids, about 12 amino acids to about 50 amino acids, about 12 amino acids to about 45 amino acids, about 12 amino acids to about 40 amino acids, about 12 amino acids to about 38 amino acids, about 12 amino acids to about 36 amino acids, about 12 amino acids to about 34 amino acids, about 12 amino acids to about 32 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 95 amino acids, about 14 amino acids to about 90 amino acids, about 14 amino acids to about 85 amino acids, about 14 amino acids to about 80 amino acids, about 14 amino acids to about 75 amino acids, about 14 amino acids to about 70 amino acids, about 14 amino acids to about 65 amino acids, about 14 amino acids to about 60 amino acids, about 14 amino acids to about 55 amino acids, about 14 amino acids to about 50 amino acids, about 14 amino acids to about 45 amino acids, about 14 amino acids to about 40 amino acids, about 14 amino acids to about 38 amino acids, about 14 amino acids to about 36 amino acids, about 14 amino acids to about 34 amino acids, about 14 amino acids to about 32 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 95 amino acids, about 16 amino acids to about 90 amino acids, about 16 amino acids to about 85 amino acids, about 16 amino acids to about 80 amino acids, about 16 amino acids to about 75 amino acids, about 16 amino acids to about 70 amino acids, about 16 amino acids to about 65 amino acids, about 16 amino acids to about 60 amino acids, about 16 amino acids to about 55 amino acids, about 16 amino acids to about 50 amino acids, about 16 amino acids to about 45 amino acids, about 16 amino acids to about 40 amino acids, about 16 amino acids to about 38 amino acids, about 16 amino acids to about 36 amino acids, about 16 amino acids to about 34 amino acids, about 16 amino acids to about 32 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 95 amino acids, about 18 amino acids to about 90 amino acids, about 18 amino acids to about 85 amino acids, about 18 amino acids to about 80 amino acids, about 18 amino acids to about 75 amino acids, about 18 amino acids to about 70 amino acids, about 18 amino acids to about 65 amino acids, about 18 amino acids to about 60 amino acids, about 18 amino acids to about 55 amino acids, about 18 amino acids to about 50 amino acids, about 18 amino acids to about 45 amino acids, about 18 amino acids to about 40 amino acids, about 18 amino acids to about 38 amino acids, about 18 amino acids to about 36 amino acids, about 18 amino acids to about 34 amino acids, about 18 amino acids to about 32 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 38 amino acids, about 20 amino acids to about 36 amino acids, about 20 amino acids to about 34 amino acids, about 20 amino acids to about 32 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 100 amino acids, about 22 amino acids to about 95 amino acids, about 22 amino acids to about 90 amino acids, about 22 amino acids to about 85 amino acids, about 22 amino acids to about 80 amino acids, about 22 amino acids to about 75 amino acids, about 22 amino acids to about 70 amino acids, about 22 amino acids to about 65 amino acids, about 22 amino acids to about 60 amino acids, about 22 amino acids to about 55 amino acids, about 22 amino acids to about 50 amino acids, about 22 amino acids to about 45 amino acids, about 22 amino acids to about 40 amino acids, about 22 amino acids to about 38 amino acids, about 22 amino acids to about 36 amino acids, about 22 amino acids to about 34 amino acids, about 22 amino acids to about 32 amino acids, about 22 amino acids to about 30 amino acids, about 22 amino acids to about 28 amino acids, about 22 amino acids to about 26 amino acids, about 22 amino acids to about 24 amino acids, about 24 amino acids to about 100 amino acids, about 24 amino acids to about 95 amino acids, about 24 amino acids to about 90 amino acids, about 24 amino acids to about 85 amino acids, about 24 amino acids to about 80 amino acids, about 24 amino acids to about 75 amino acids, about 24 amino acids to about 70 amino acids, about 24 amino acids to about 65 amino acids, about 24 amino acids to about 60 amino acids, about 24 amino acids to about 55 amino acids, about 24 amino acids to about 50 amino acids, about 24 amino acids to about 45 amino acids, about 24 amino acids to about 40 amino acids, about 24 amino acids to about 38 amino acids, about 24 amino acids to about 36 amino acids, about 24 amino acids to about 34 amino acids, about 24 amino acids to about 32 amino acids, about 24 amino acids to about 30 amino acids, about 24 amino acids to about 28 amino acids, about 24 amino acids to about 26 amino acids, about 26 amino acids to about 100 amino acids, about 26 amino acids to about 95 amino acids, about 26 amino acids to about 90 amino acids, about 26 amino acids to about 85 amino acids, about 26 amino acids to about 80 amino acids, about 26 amino acids to about 75 amino acids, about 26 amino acids to about 70 amino acids, about 26 amino acids to about 65 amino acids, about 26 amino acids to about 60 amino acids, about 26 amino acids to about 55 amino acids, about 26 amino acids to about 50 amino acids, about 26 amino acids to about 45 amino acids, about 26 amino acids to about 40 amino acids, about 26 amino acids to about 38 amino acids, about 26 amino acids to about 36 amino acids, about 26 amino acids to about 34 amino acids, about 26 amino acids to about 32 amino acids, about 26 amino acids to about 30 amino acids, about 26 amino acids to about 28 amino acids, about 28 amino acids to about 100 amino acids, about 28 amino acids to about 95 amino acids, about 28 amino acids to about 90 amino acids, about 28 amino acids to about 85 amino acids, about 28 amino acids to about 80 amino acids, about 28 amino acids to about 75 amino acids, about 28 amino acids to about 70 amino acids, about 28 amino acids to about 65 amino acids, about 28 amino acids to about 60 amino acids, about 28 amino acids to about 55 amino acids, about 28 amino acids to about 50 amino acids, about 28 amino acids to about 45 amino acids, about 28 amino acids to about 40 amino acids, about 28 amino acids to about 38 amino acids, about 28 amino acids to about 36 amino acids, about 28 amino acids to about 34 amino acids, about 28 amino acids to about 32 amino acids, about 28 amino acids to about 30 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 38 amino acids, about 30 amino acids to about 36 amino acids, about 30 amino acids to about 34 amino acids, about 30 amino acids to about 32 amino acids, about 32 amino acids to about 100 amino acids, about 32 amino acids to about 95 amino acids, about 32 amino acids to about 90 amino acids, about 32 amino acids to about 85 amino acids, about 32 amino acids to about 80 amino acids, about 32 amino acids to about 75 amino acids, about 32 amino acids to about 70 amino acids, about 32 amino acids to about 65 amino acids, about 32 amino acids to about 60 amino acids, about 32 amino acids to about 55 amino acids, about 32 amino acids to about 50 amino acids, about 32 amino acids to about 45 amino acids, about 32 amino acids to about 40 amino acids, about 32 amino acids to about 38 amino acids, about 32 amino acids to about 36 amino acids, about 32 amino acids to about 34 amino acids, about 34 amino acids to about 100 amino acids, about 34 amino acids to about 95 amino acids, about 34 amino acids to about 90 amino acids, about 34 amino acids to about 85 amino acids, about 34 amino acids to about 80 amino acids, about 34 amino acids to about 75 amino acids, about 34 amino acids to about 70 amino acids, about 34 amino acids to about 65 amino acids, about 34 amino acids to about 60 amino acids, about 34 amino acids to about 55 amino acids, about 34 amino acids to about 50 amino acids, about 34 amino acids to about 45 amino acids, about 34 amino acids to about 40 amino acids, about 34 amino acids to about 38 amino acids, about 34 amino acids to about 36 amino acids, about 36 amino acids to about 100 amino acids, about 36 amino acids to about 95 amino acids, about 36 amino acids to about 90 amino acids, about 36 amino acids to about 85 amino acids, about 36 amino acids to about 80 amino acids, about 36 amino acids to about 75 amino acids, about 36 amino acids to about 70 amino acids, about 36 amino acids to about 65 amino acids, about 36 amino acids to about 60 amino acids, about 36 amino acids to about 55 amino acids, about 36 amino acids to about 50 amino acids, about 36 amino acids to about 45 amino acids, about 36 amino acids to about 40 amino acids, about 36 amino acids to about 38 amino acids, about 38 amino acids to about 100 amino acids, about 38 amino acids to about 95 amino acids, about 38 amino acids to about 90 amino acids, about 38 amino acids to about 85 amino acids, about 38 amino acids to about 80 amino acids, about 38 amino acids to about 75 amino acids, about 38 amino acids to about 70 amino acids, about 38 amino acids to about 65 amino acids, about 38 amino acids to about 60 amino acids, about 38 amino acids to about 55 amino acids, about 38 amino acids to about 50 amino acids, about 38 amino acids to about 45 amino acids, about 38 amino acids to about 40 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 100 amino acids, about 80 amino acids to about 95 amino acids, about 80 amino acids to about 90 amino acids, about 80 amino acids to about 85 amino acids, about 85 amino acids to about 100 amino acids, about 85 amino acids to about 95 amino acids, about 85 amino acids to about 90 amino acids, about 90 amino acids to about 100 amino acids, about 90 amino acids to about 95 amino acids, or about 95 amino acids to about 100 amino acids.

For example, a linker sequence can comprise or consist of TGGSGEGGT-GASTGGSAGTGGSGGTTSGEAGGSSGAG (SEQ ID NO: 33) or GSGATG (SEQ ID NO: 34). In some instances the chimeric polypeptide includes a linker that has an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 33. For example, a linker sequence can comprise or consist of the sequences of (SEQ ID NO: 105)
GSGS, (SEQ ID NO: 106)
GSGSGS, (SEQ ID NO: 107)
SGSG, (SEQ ID NO: 108)
SGSGSG, (SEQ ID NO: 109)
GSSG, (SEQ ID NO: 112)
SS,
or (SEQ ID NO: 110)
GGGGS.

Growth Factors

A β-TCP-binding sequence as described herein can be tethered to a mammalian growth factor. In some instances, a linker sequence (e.g., any of the linker sequences described herein or known in the art) is disposed between the β-TCP-binding sequence and the mammalian growth factor.

Mammalian growth factors can be osteoinductive molecules that are capable of initiating and enhancing the bone repair process. Bone morphogenetic proteins (BMP) represent a distinct subset of the transforming growth factor-β family. A number of these BMP (BMP-2, BMP-7, and BMP-14) enhance the speed of bone healing in defects and non-unions.

Non-limiting examples of mammalian growth factors are described herein. In some instances, the mammalian growth factor is selected from the group of: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12), bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF 11), growth differentiation factor 15 (GDF15), vascular endothelial growth factor (VEGF), hyaluronic acid binding protein (HABP), and collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT91B), wnt family member 10A (WNT10A), wnt family member 10B (WNT101B), wnt family member 11 (WNT11), and wnt family member 16 (WNT16).

For example, the mammalian growth factor can be a human growth factor. Non-limiting examples of human growth factors are provided in Table B.

TABLE B

Exemplary human growth factors

| Name | Exemplary Human Protein Sequence | SEQ ID NO: |
|---|---|---|
| EGF | MLLTLIILLPVVSKFSFVSLSAPQHWSCPEGTLAGNGNSTCVG<br>PAPFLIFSHGNSIFRIDTEGTNYEQLVVDAGVSVIMDFHYNEK<br>RIYWVDLERQLLQRVFLNGSRQERVCNIEKNVSGMAINWIN<br>EEVIWSNQQEGIITVTDMKGNNSHILLSALKYPANVAVDPVE<br>RFIFWSSEVAGSLYRADLDGVGVKALLETSEKITAVSLDVLD<br>KRLFWIQYNREGSNSLICSCDYDGGSVHISKHPTQHNLFAMS<br>LFGDRIFYSTWKMKTIWIANKHTGKDMVRINLHSSFVPLGEL<br>KVVHPLAQPKAEDDTWEPEQKLCKLRKGNCSSTVCGQDLQ | 46 |

TABLE B-continued

Exemplary human growth factors

| Name | Exemplary Human Protein Sequence | SEQ ID NO: |
|---|---|---|
| | SHLCMCAEGYALSRDRKYCEDVNECAFWNHGCTLGCKNTP GSYYCTCPVGFVLLPDGKRCHQLVSCPRNVSECSHDCVLTSE GPLCFCPEGSVLERDGKTCSGCSSPDNGGCSQLCVPLSPVSW ECDCFPGYDLQLDEKSCAASGPQPFLLFANSQDIRHMHFDGT DYGTLLSQQMGMVYALDHDPVENKIYFAHTALKWIERANM DGSQRERLIEEGVDVPEGLAVDWIGRRFYWTDRGKSLIGRSD LNGKRSKIITKENISQPRGIAVHPMAKRLFWTDTGINPRIESSS LQGLGRLVIASSDLIWPSGITIDFLTDKLYWCDAKQSVIEMA NLDGSKRRRLTQNDVGHPFAVAVFEDYVWFSDWAMPSVM RVNKRTGKDRVRLQGSMLKPSSLVVVHPLAKPGADPCLYQ NGGCEHICKKRLGTAWCSCREGFMKASDGKTCLALDGHQL LAGGEVDLKNQVTPLDILSKTRVSEDNITESQHMLVAEIMVS DQDDCAPVGCSMYARCISEGEDATCQCLKGFAGDGKLCSDI DECEMGVPVCPPASSKCINTEGGYVCRCSEGYQGDGIHCLDI DECQLGEHSCGENASCTNTEGGYTCMCAGRLSEPGLICPDST PPPHLREDDHHYSVRNSDSECPLSHDGYCLHDGVCMYIEAL DKYACNCVVGYIGERCQYRDLKWWELRHAGHGQQQKVIV VAVCVVVLVMLLLLSLWGAHYYRTQKLLSKNPKNPYEESS RDVRSRRPADTEDGMSSCPQPWFVVIKEHQDLKNGGQPVAG EDGQAADGSMQPTSWRQEPQLCGMGTEQGCWIPVSSDKGS CPQVMERSFHMPSYGTQTLEGGVEKPHSLLSANPLWQQRAL DPPHQMELTQ | |
| PDGF | MRTLACLLLLGCGYLAHVLAEEAEIPREVIERLARSQIHSIRD LQRLLEIDSVGSEDSLDTSLRAHGVHATKHVPEKRPLPIRRKR SIEEAVPAVCKTRTVIYEIPRSQVDPTSANFLIWPPCVEVKRC TGCCNTSSVKCQPSRVHHRSVKVAKVEYVRKKPKLKEVQV RLEEHLECACATTSLNPDYREEDTGRPRESGKKRKRKRLKPT | 47 |
| IGF-1 | MGKISSLPTQLFKCCFCDFLKVKMHTMSSSHLFYLALCLLTF TSSATAGPETLCGAELVDALQFVCGDRGFYFNKPTGYGSSSR RAPQTGIVDECCFRSCDLRRLEMYCAPLKPAKSARSVRAQR HTDMPKTQKYQPPSTNKNTKSQRRKGSTFEERK | 48 |
| FGF | MAEGEITTFTALTEKFNLPPGNYKKPKLLYCSNGGHFLRILPD GTVDGTRDRSDQHIQLQLSAESVGEVYIKSTETGQYLAMDT DGLLYGSQTPNEECLFLERLEENHYNTYISKKHAEKNWFVG LKKNGSCKRGPRTHYGQKAILFLPLPVSSD | 49 |
| FGF2 | MVGVGGGDVEDVTPRPGGCQISGRGARGCNGIPGAAAWEA ALPRRRPRRHPSVNPRSRAAGSPRTRGRRTEERPSGSRLGDR GRGRALPGGRLGGRGRGRAPERVGGRGRGRGTAAPRAAPA ARGSRPGPAGTMAAGSITTLPALPEDGGSGAFPPGHFKDPKR LYCKNGGFFLRIHPDGRVDGVREKSDPHIKLQLQAEERGVVS IKGVCANRYLAMKEDGRLLASKCVTDECFFFERLESNNYNT YRSRKYTSWYVALKRTGQYKLGSKTGPGQKAILFLPMSAKS | 50 |
| FGF18 | MYSAPSACTCLCLHFLLLCFQVQVLVAEENVDFRIHVENQTR ARDDVSRKQLRLYQLYSRTSGKHIQVLGRRISARGEDGDKY AQLLVETDTFGSQVRIKGKETEFYLCMNRKGKLVGKPDGTS KECVFIEKVLENNYTALMSAKYSGWYVGFTKKGRPRKGPKT RENQQDVHFMKRYPKGQPELQKPFKYTTVTKRSRRIRPTHP A | 51 |
| TGF-α | MVPSAGQLALFALGIVLAACQALENSTSPLSADPPVAAAVVS HFNDCPDSHTQFCFHGTCRFLVQEDKPACVCHSGYVGARCE HADLLAVVAASQKKQAITALVVVSIVALAVLIITCVLIHCCQ VRKHCEWCRALICRHEKPSALLKGRTACCHSETVV | 52 |
| TGF-β1 | MPPSGLRLLPLLLPLLWLLVLTPGRPAAGLSTCKTIDMELVK RKRIEAIRGQILSKLRLASPPSQGEVPPGPLPEAVLALYNSTRD RVAGESAEPEPEPEADYYAKEVTRVLMVETHNEIYDKFKQS THSIYMFFNTSELREAVPEPVLLSRAELRLLRLKLKVEQHVEL YQKYSNNSWRYLSNRLLAPSDSPEWLSFDVTGVVRQWLSR GGEIEGFRLSAHCSCDSRDNTLQVDINGFTTGRRGDLATIHG MNRPFLLLMATPLERAQHLQSSRHRRALDTNYCFSSTEKNC CVRQLYIDFRKDLGWKWIHEPKGYHANFCLGPCPYIWSLDT QYSKVLALYNQHNPGASAAPCCVPQALEPLPIVYYVGRKPK VEQLSNMIVRSCKCS | 53 |
| TGF-β3 | MKMHLQRALVVLALLNFATVSLSLSTCTTLDFGHIKKKRVE AIRGQILSKLRLTSPPEPTVMTHVPYQVLALYNSTRELLEEM HGEREEGCTQENTESEYYAKEIHKFDMIQGLAEHNELAVCP KGITSKVFRFNVSSVEKNRTNLFRAEFRVLRVPNPSSKRNEQ RIELFQILRPDEHIAKQRYIGGKNLPTRGTAEWLSFDVTDTVR | 54 |

TABLE B-continued

Exemplary human growth factors

| Name | Exemplary Human Protein Sequence | SEQ ID NO: |
|---|---|---|
| | EWLLRRESNLGLEISIHCPCHTFQPNGDILENIHEVMEIKFKG VDNEDDHGRGDLGRLKKQKDHHNPHLILMMIPPHRLDNPG QGGQRKKRALDTNYCFRNLEENCCVRPLYIDFRQDLGWKW VHEPKGYYANFCSGPCPYLRSADTTHSTVLGLYNTLNPEASA SPCCVPQDLEPLTILYYVGRTPKVEQLSNMVVKSCKCS | |
| OP-2 (BMP-8) | MTALPGPLWLLGLALCALGGGGPGLRPPPGCPQRRLGARER RDVQREILAVLGLPGRPRPRAPPAASRLPASAPLFMLDLYHA MAGDDDEDGAPAERRLGRADLVMSFVNMVERDRALGHQE PHWKEFRFDLTQIPAGEAVTAAEFRIYKVPSIHLLNRTLHVS MFQVVQEQSNRESDLEFLDLQTLRAGDEGWLVLDVTAASD CWLLKRHKDLGLRLYVETEDGHSVDPGLAGLLGQRAPRSQ QPFVVTFFRASPSPIRTPRAVRPLRRRQPKKSNELPQANRLPGI FDDVHGSHGRQVCRRHELYVSFQDLGWLDWVIAPQGYSAY YCEGECSFPLDSCMNATNHAILQSLVHLMMPDAVPKACCAP TKLSATSVLYYDSSNNVILRKHRNMVVKACGCH | 55 |
| OP-3 | MAARPGLLWLLGLALCVLGGGHLSHPPHVFPQRRLGVREPR DMQREIREVLGLPGRPRSRAPVGAAQQPASAPLFMLDLYRA MTDDSGGGTPQPHLDRADLIMSFVNIVERDRTLGYQEPHWK EFHFDLTQIPAGEAVTAAEFRIYKEPSTHPLNTTLHISMFEVV QEHSNRESDLEFLDLQTLRSGDEGWLVLDITAASDRWLLNH HKDLGLRLYVETEDGHSIDPGLAGLLGRQAPRSRQPFMVGFF RANQSPVRAPRTARPLKKKQLNQINQLPHSNKHLGILDDGH GSHGREVCRRHELYVSFRDLGWLDSVIAPQGYSAYYCAGEC IYPLNSCMNSTNHATMQALVHLMKPDIIPKVCCVPTELSAISL LYYDRNNNVILRRERNMVVQACGCH | 56 |
| BMP-2 | MVAGTRCLLALLLPQVLLGGAAGLVPELGRRKFAAASSGRP SSQPSDEVLSEFELRLLSMEGLKQRPTPSRDAVVPPYMLDLY RRHSGQPGSPAPDHRLERAASRANTVRSFHHEESLEELPETS GKTTRRFFFNLSSIPTEEFITSAELQVFREQMQDALGNNSSFH HRINIYEIIKPATANSKFPVTRLLDTRLVNQNASRWESEDVTP AVMRWTAQGHANHGFVVEVAHLEEKQGVSKRHVRISRSLH QDEHSWSQIRPLLVTFGHDGKGHPLHKREKRQAKHKQRKRL KSSCKRHPLYVDFSDVGWNDWIVAPPGYHAFYCHGECPFPL ADHLNSTNHAIVQTLVNSVNSKIPKACCVPTELSAISMLYLD ENEKVVLKNYQDMVVEGCGCR | 32 |
| BMP-3 | MAGASRLLFLWLGCFCVSLAQGERPKPPFPELRKAVPGDRT AGGGPDSELQPQDKVSEHMLRLYDRYSTVQAARTPGSLEGG SQPWRPRLLREGNTVRSFRAAAAETLERKGLYIFNLTSLTKS ENILSATLYFCIGELGNISLSCPVSGGCSHHAQRKHIQIDLSA WTLKFSRNQSQLLGHLSVDMAKSHRDIMSWLSKDITQFLRK AKENEEFLIGFNITSKGRQLPKRRLPFPEPYILVYANDAAISEP ESVVSSLQGHRNFPTGTVPKWDSHIRAALSIERRKKRSTGVL LPLQNNELPGAEYQYKKDEVWEERKPYKTLQAQAPEKSKN KKKQRKGPHRKSQTLQFDEQTLKKARRKQWIEPRNCARRYL KVDFADIGWSEWIISPKSFDAYYCSGACQFPMPKSLKPSNHA TIQSIVRAVGVVPGIPEPCCVPEKMSSLSILFFDENKNVVLKV YPNMTVESCACR | 57 |
| BMP-4 | MIPGNRMLMVVLLCQVLLGGASHASLIPETGKKKVAEIQGH AGGRRSGQSHELLRDFEATLLQMFGLRRRPQPSKSAVIPDYM RDLYRLQSGEEEEEQIHSTGLEYPERPASRANTVRSFHHEEHL ENIPGTSENSAFRFLFNLSSIPENEVISSAELRLFREQVDQGPD WERGEHRINIYEVMKPPAEVVPGHLITRLLDTRLVHENVTR WETFDVSPAVLRWTREKQPNYGLAIEVTHLHQTRTHQGQH VRISRSLPQGSGNWAQLRPLLVTFGHDGRGHALTRRRRAKR SPKHEISQRARKKNKNCRRHSLYVDFSDVGWNDWIVAPPGY QAFYCHGDCPFPLADHLNSTNHAIVQTLVNSVNSSIPKACCV PTELSAISMLYLDEYDKVVLKNYQEMVVEGCGCR | 58 |
| BMP-5 | MHLTVFLLKGIVGFLWSCWVLVGYAKGGLGDNHVHSSFIYR RLRNHERREIQREILSILGLPHRPRPFSPGKQASSAPLFMLDLY NAMTNEENPEESEYSVRASLAEETRGARKGYPASPNGYPRRI QLSRTTPLTTQSPPLASLHDTNFLNDADMVMSFVNLVERDK DFSHQRRHYKEFRFDLTQIPHGEAVTAAEFRIYKDRSNNRFE NETIKISIYQIIKEYTNRDADLELLDTRKAQALDVGWLVEDIT VTSNHWVINPQNNLGLQLCAETGDGRSINVKSAGLVGRQGP QSKQPFMVAFFKASEVLLRSVRAANKRKNQNRNKSSSHQDS SRMSSVGDYNTSEQKQACKKHELYVSFRDLGWQDWIIAPEG YAAFYCDGECSFPLNAHMNATNHAIVQTLVHLMFPDHVPKP CCAPTKLNAISVLYFDDSSNVILKKYRNMVVRSCGCH | 59 |

TABLE B-continued

| Name | Exemplary Human Protein Sequence | SEQ ID NO: |
|---|---|---|
| | Exemplary human growth factors | |
| BMP-6/VGR | MPGLGRRAQWLCWWWGLLCSCCGPPPLRPPLPAAAAAAAG GQLLGDGGSPGRTEQPPPSPQSSSGFLYRRLKTQEKREMQKE ILSVLGLPHRPRPLHGLQQPQPPALRQQEEQQQQQLPRGEP PPGRLKSAPLFMLDLYNALSADNDEDGASEGERQQSWPHEA ASSSQRRQPPPGAAHPLNRKSLLAPGSGSGGASPLTSAQDSA FLNDADMVMSFVNLVEYDKEFSPRQRHHKEFKFNLSQIPEG EVVTAAEFRIYKDCVMGSFKNQTFLISIYQVLQEHQHRDSDL FLLDTRVVWASEEGWLEFDITATSNLWVVTPQHNMGLQLSV VTRDGVHVHPRAAGLVGRDGPYDKQPFMVAFFKVSEVHVR TTRSASSRRRQQSRNRSTQSQDVARVSSASDYNSSELKTACR KHELYVSFQDLGWQDWIIAPKGYAANYCDGECSFPLNAHM NATNHAIVQTLVHLMNPEYVPKPCCAPTKLNAISVLYFDDNS NVILKKYRNMVVRACGCH | 60 |
| BMP-7/OP-1 | MHVRSLRAAAPHSFVALWAPLFLLRSALADFSLDNEVHSSFI HRRLRSQERREMQREILSILGLPHRPRPHLQGKHNSAPMFML DLYNAMAVEEGGGPGGQGFSYPYKAVFSTQGPPLASLQDSH FLTDADMVMSFVNLVEHDKEFFHPRYHHREFRFDLSKIPEGE AVTAAEFRIYKDYIRERFDNETFRISVYQVLQEHLGRESDLFL LDSRTLWASEEGWLVFDITATSNHWVVNPRHNLGLQLSVET LDGQSINPKLAGLIGRHGPQNKQPFMVAFFKATEVHFRSIRST GSKQRSQNRSKTPKNQEALRMANVAENSSSDQRQACKKHE LYVSFRDLGWQDWIIAPEGYAAYYCEGECAFPLNSYMNATN HAIVQTLVHFINPETVPKPCCAPTQLNAISVLYFDDSSNVILK KYRNMVVRACGCH | 61 |
| BMP-9 | MCPGALWVALPLLSLLAGSLQGKPLQSWGRGSAGGNAHSP LGVPGGGLPEHTFNLKMFLENVKVDFLRSLNLSGVPSQDKT RVEPPQYMIDLYNRYTSDKSTTPASNIVRSFSMEDAISITATE DFPFQKHILLFNISIPRHEQITRAELRLYVSCQNHVDPSHDLK GSVVIYDVLDGTDAWDSATETKTFLVSQDIQDEGWETLEVS SAVKRWVRSDSTKSKNKLEVTVESHRKGCDTLDISVPPGSR NLPFFVVFSNDHSSGTKETRLELREMISHEQESVLKKLSKDGS TEAGESSHEEDTDGHVAAGSTLARRKRSAGAGSHCQKTSLR VNFEDIGWDSWIIAPKEYEAYECKGGCFFPLADDVTPTKHAI VQTLVHLKFPTKVGKACCVPTKLSPISVLYKDDMGVPTLKY HYEGMSVAECGCR | 62 |
| BMP-10 | MGSLVLTLCALFCLAAYLVSGSPIMNLEQSPLEEDMSLFGDV FSEQDGVDFNTLLQSMKDEFLKTLNLSDIPTQDSAKVDPPEY MLELYNKFATDRTSNIPSANIIRSEKNEDLFSQPVSFNGLRKYP LLFNVSIPHHEEVIMAELRLYTLVQRDRMIYDGVDRKITIFEV LESKGDNEGERNMLVLVSGEIYGTNSEWETFDVTDAIRRWQ KSGSSTHQLEVHIESKHDEAEDASSGRLEIDTSAQNKHNPLLI VFSDDQSSDKERKEELNEMISHEQLPELDNLGLDSFSSGPGEE ALLQMRSNIIYDSTARIRRNAKGNYCKRTPLYIDFKEIGWDS WIIAPPGYEAYECRGVCNYPLAEHLTPTKHAIIQALVHLKNS QKASKACCVPTKLEPISILYLDKGVVTYKFKYEGMAVSECG CR | 63 |
| BMP-11/GDF-11 | MVLAAPLLLGFLLLALELRPRGEAAEGPAAAAAAAAAAA AGVGGERSSRPAPSVAPEPDGCPVCVWRQHSRELRLESIKSQ ILSKLRLKEAPNISREVVKQLLPKAPPLQQILDLHDFQGDALQ PEDFLEEDEYHATTETVISMAQETDPAVQTDGSPLCCHFHFS PKVMFTKVLKAQLWVYLRPVPRPATVYLQILRLKPLTGEGT AGGGGGGRRHIRIRSLKIELHSRSGHWQSIDFKQVLHSWFRQ PQSNWGIEINAFDPSGTDLAVTSLGPGAEGLHPFMELRVLEN TKRSRRNLGLDCDEHSSESRCCRYPLTVDFEAFGWDWIIAPK RYKANYCSGQCEYMFMQKYPHTHLVQQANPRGSAGPCCTP TKMSPINMLYFNDKQQIIYGKIPGMVVDRCGCS | 64 |
| BMP-12 | MDLSAAAALCLWLLSACRPRDGLEAAAVLRAAGAGPVRSP GGGGGGGGGGRTLAQAAGAAAVPAAAVPRARAARRAAGS GFRNGSVVPHHFMMSLYRSLAGRAPAGAAAVSASGHGRAD TITGFTDQATQDESAAETGQSFLFDVSSLNDADEVVGAELRV LRRGSPESGPGSWTSPPLLLLSTCPGAARAPRLLYSRAAEPLV GQRWEAFDVADAMRRHRREPRPPRAFCLLLRAVAGPVPSPL ALRRLGFGWPGGGSAAEERAVLVVSSRTQRKESLFREIRA QARALGAALASEPLPDPGTGTASPRAVIGGRRRRRTALAGTR TAQGSGGGAGRGHGRRGRSRCSRKPLHVDFKELGWDDWII APLDYEAYHCEGLCDFPLRSHLEPTNHAIIQTLLNSMAPDAA PASCCVPARLSPISILYIDAANNVVYKQYEDMVVEACGCR | 65 |

TABLE B-continued

| Exemplary human growth factors | | |
|---|---|---|
| Name | Exemplary Human Protein Sequence | SEQ ID NO: |
| BMP-13/GDF-6 | MDTPRVLLSAVFLISFLWDLPGFQQASISSSSSSAELGSTKGM<br>RSRKEGKMQRAPRDSDAGREGQEPQPRPQDEPRAQQPRAQE<br>PPGRGPRVVPHEYMLSIYRTYSIAEKLGINASFFQSSKSANTIT<br>SFVDRGLDDLSHTPLRRQKYLFDVSMLSDKEELVGAELRLFR<br>QAPSAPWGPPAGPLHVQLFPCLSPLLLDARTLDPQGAPPAG<br>WEVFDVWQGLRHQPWKQLCLELRAAWGELDAGEAEARAR<br>GPQQPPPPDLRSLGFGRRVRPPQERALLVVFTRSQRKNLFAE<br>MREQLGSAEAAGPGAGAEGSWPPPSGAPDARPWLPSPGRRR<br>RRTAFASRHGKRHGKKSRLRCSKKPLHVNFKELGWDDWIIA<br>PLEYEAYHCEGVCDFPLRSHLEPTNHAIIQTLMNSMDPGSTPP<br>SCCVPTKLTPISILYIDAGNNVVYKQYEDMVVESCGCR | 66 |
| BMP-15 | MVLLSILRILFLCELVLFMEHRAQMAEGGQSSIALLAEAPTLP<br>LIEELLEESPGEQPRKPRLLGHSLRYMLELYRRSADSHGHPRE<br>NRTIGATMVRLVKPLTNVARPHRGTWHIQILGFPLRPNRGLY<br>QLVRATVVYRHHLQLTRFNLSCHVEPWVQKNPTNHFPSSEG<br>DSSKPSLMSNAWKEMDITQLVQQRFWNNKGHRILRLRFMC<br>QQQKDSGGLELWHGTSSLDIAFLLLYFNDTHKSIRKAKFLPR<br>GMEEFMERESLLRRTRQADGISAEVTASSSKHSGPENNQCSL<br>HPFQISFRQLGWDHWIIAPPFYTPNYCKGTCLRVLRDGLNSP<br>NHAIIQNLINQLVDQSVPRPSCVPYKYVPISVLMIEANGSILY<br>KEYEGMIAESCTCR | 67 |
| DPP | MKIITYFCIWAVAWAIPVPQSKPLERHVEKSMNLHLLARSNV<br>SVQDELNASGTIKESGVLVHEGDRGRQENTQDGHKGEGNGS<br>KWAEVGGKSFSTYSTLANEEGNIEGWNGDTGKAETYGHDGI<br>HGKEENITANGIQGQVSIIDNAGATNRSNTNGNTDKNTQNG<br>DVGDAGHNEDVAVVQEDGPQVAGSNNSTDNEDEIIENSCRN<br>EGNTSEITPQINSKRNGTKEAEVTPGTGEDAGLDNSDGSPSG<br>NGADEDEDEGSGDDEDEEAGNGKDSSNNSKGQEGQDHGKE<br>DDHDSSIGQNSDSKEYYDPEGKEDPHNEVDGDKTSKSEENS<br>AGIPEDNGSQRIEDTQKLNHRESKRVENRITKESETHAVGKS<br>QDKGIEIKGPSSGNRNITKEVGKGNEGKEDKGQHGMILGKG<br>NVKTQGEVVNIEGPGQKSEPGNKVGHSNTGSDSNSDGYDSY<br>DFDDKSMQGDDPNSSDESNGNDDANSESDNNSSSRGDASYN<br>SDESKDNGNGSDSKGAEDDDSDSTSDTNNSDSNGNGNNGN<br>DDNDKSDSGKGKSDSSDSDSSDSSNSSDSSDSSDSDSSDSNSS<br>SDSDSSDSDSSDSSDSDSSDSSNSSDSSDSSDSSDSSDSSD<br>SKSDSSKSESDSSDSDSKSDSSDSNSSDSSDNSDSSDSSNSSNS<br>SDSSDSSDSSDSSSSSDSSNSSDSSDSSDSSNSSESSDSSDSSDS<br>DSSDSSDSSNSNSSDSDSSNSSDSSDSSNSSDSSDSSDSSNSSD<br>SSDSSDSSNSSDSSDSSDSSDSSDSSNSSDSNDSSNSSDSSDSS<br>NSSDSSNSSDSSDSSDSSDSDSSNSSDSSNSSDSSDSSNSSDSS<br>DSSDSSDGSDSDSSNRSDSSNSSDSSDSSDSSNSSDSSDSSDSN<br>ESSNSSDSSDSSNSSDSDSSDSSNSSDSSDSSNSSDSSESSNSSD<br>NSNSSDSSNSSDSSDSSDSSNSSDSSNSSDSSNSSDSSDSNSSD<br>SSDSSNSSDSSDSSDSSDSSDSSDSSNSSDSSDSSDSSDSSNSSD<br>SSNSSDSSNSSDSSDSSDSSDSSDSSDSSDSSDSSNSSDSSDSSD<br>SSDSSDSSDSSDSSDSSESSDSSDSSNSSDSSDSSDSSDSSDSSD<br>SSDSSDSSDSSNSSDSSDSSDSSDSSDSSNSSDSSDSSESSDSSD<br>SSDSSDSSDSSDSSDSSDSSDSSNSSDSSDSSDSSDSSDSSDSSD<br>SSDSSDSSDSSDSSDSSDSSDSSDSSDSSDSNESSDSSDSSDSSD<br>SSNSSDSSDSSDSSDSTSDSNDESDSQSKSGNGNNNGSDSDSD<br>SEGSDSNHSTSDD | 68 |
| GDF-1 | MPPPQQGPCGHHLLLLLALLLPSLPLTRAPVPPGPAAALLQA<br>LGLRDEPQGAPRLRPVPPVMWRLFRRRDPQETRSGSRRTSPG<br>VTLQPCHVEELGVAGNIVRHIPDRGAPTRASEPASAAGHCPE<br>WTVVFDLSAVEPAERPSRARLELRFAAAAAAAPEGGWELSV<br>AQAGQGAGADPGPVLLRQLVPALGPPVRAELLGAAWARNA<br>SWPRSLRLALALRPRAPAACARLAEASLLLVTLDPRLCHPLA<br>RPRRDAEPVLGGGPGGACRARRLYVSFREVGWHRWVIAPR<br>GFLANYCQGQCALPVALSGSGGPPALNHAVLRALMHAAAP<br>GAADLPCCVPARLSPISVLFFDNSDNVVLRQYEDMVVDECG<br>CR | 69 |
| GDF-3 | MLRFLPDLAFSFLLILALGQAVQFQEYVFLQFLGLDKAPSPQ<br>KFQPVPYILKKIFQDREAAATTGVSRDLCYVKELGVRGNVLR<br>FLPDQGFFLYPKKISQASSCLQKLLYFNLSAIKEREQLTLAQL<br>GLDLGPNSYYNLGPELELALFLVQEPHVWGQTTPKPGKMFV<br>LRSVPWPQGAVHF'NLLDVAKDWNDNPRKNFGLFLEILVKED | 70 |

TABLE B-continued

| Exemplary human growth factors | | |
|---|---|---|
| Name | Exemplary Human Protein Sequence | SEQ ID NO: |
| | RDSGVNFQPEDTCARLRCSLHASLLVVTLNPDQCHPSRKRR<br>AAIPVPKLSCKNLCHRHQLFINFRDLGWHKWIIAPKGFMANY<br>CHGECPFSLTISLNSSNYAFMQALMHAVDPEIPQAVCIPTKLS<br>PISMLYQDNNDNVILRHYEDMVVDECGCG | |
| GDF-5 | MRLPKLLTELLWYLAWLDLEFICTVLGAPDLGQRPQGTRPG<br>LAKAEAKERPPLARNVFRPGGHSYGGGATNANARAKGGTG<br>QTGGLTQPKKDEPKKLPPRPGGPEPKPGHPPQTRQATARTVT<br>PKGQLPGGKAPPKAGSVPSSELLKKAREPGPPREPKEPERPPPI<br>TPHEYMLSLYRTLSDADRKGGNSSVKLEAGLANTITSFIDKG<br>QDDRGPVVRKQRYVFDISALEKDGLLGAELRILRKKPSDTAK<br>PAAPGGGRAAQLKLSSCPSGRQPAALLDVRSVPGLDGSGWE<br>VEDIWKLERNEKNSAQLCLELEAWERGRAVDLRGLGEDRAA<br>RQVHEKALELVEGRTKKRDLEENEIKARSGQDDKTVYEYLES<br>QRRKRRAPLATRQGKRPSKNLKARCSRKALHVNFKDMGWD<br>DWIIAPLEYEAFHCEGLCEFPLRSHLEPTNHAVIQTLMNSMD<br>PESTPPTCCVPTRLSPISILFIDSANNVVYKQYEDMVVESCGC<br>R | 71 |
| GDF-7 | MDLSAAAALCLWLLSACRPRDGLEAAAVLRAAGAGPVRSP<br>GGGGGGGGGRTLAQAAGAAAVPAAAVPRARAARRAAGS<br>GFRNGSVVPHHEMMSLYRSLAGRAPAGAAAVSASGHGRAD<br>TITGETDQATQDESAAETGQSFLFDVSSLNDADEVVGAELRV<br>LRRGSPESGPGSWTSPPLLLLSTCPGAARAPRLLYSRAAEPLV<br>GQRWEAFDVADAMRRHRREPRPPRAFCLLLRAVAGPVPSPL<br>ALRRLGFGWPGGGGSAAEERAVLVVSSRTQRKESLFREIRA<br>QARALGAALASEPLPDPGTGTASPRAVIGGRRRRRTALAGTR<br>TAQGSGGGAGRGHGRRGRSRCSRKPLHVDFKELGWDDWII<br>APLDYEAYHCEGLCDFPLRSHLEPTNHAIIQTLLNSMAPDAA<br>PASCCVPARLSPISILYIDAANNVVYKQYEDMVVEACGCR | 72 |
| GDF8 | MQKLQLCVYIYLFMLIVAGPVDLNENSEQKENVEKEGLCNA<br>CTWRQNTKSSRIEAIKIQILSKLRLETAPNISKDVIRQLLPKAP<br>PLRELIDQYDVQRDDSSDGSLEDDDYHATTETIITMPTESDFL<br>MQVDGKPKCCFFKFSSKIQYNKVVKAQLWIYLRPVETPTTV<br>FVQILRLIKPMKDGTRYTGIRSLKLDMNPGTGIWQSIDVKTV<br>LQNWLKQPESNLGIEIKALDENGHDLAVTFPGPGEDGLNPFL<br>EVKVTDTPKRSRRDFGLDCDEHSTESRCCRYPLTVDFEAFG<br>WDWIIAPKRYKANYCSGECEFVFLQKYPHTHLVHQANPRGS<br>AGPCCTPTKMSPINMLYFNGKEQIIYGKIPAMVVDRCGCS | 73 |
| GDF15 | MPGQELRTVNGSQMLLVLLVLSWLPHGGALSLAEASRASFP<br>GPSELHSEDSRFRELRKRYEDLLTRLRANQSWEDSNTDLVPA<br>PAVRILTPEVRLGSGGHLHLRISRAALPEGLPEASRLHRALFR<br>LSPTASRSWDVTRPLRRQLSLARPQAPALHLRLSPPPSQSDQL<br>LAESSSARPQLELHLRPQAARGRRRARARNGDHCPLGPGRC<br>CRLHTVRASLEDLGWADWVLSPREVQVTMCIGACPSQFRAA<br>NMHAQIKTSLHRLKPDTVPAPCCVPASYNPMVLIQKTDTGV<br>SLQTYDDLLAKDCHCI | 74 |
| VEGF | MTDRQTDTAPSPSYHLLPGRRRTVDAAASRGQGPEPAPGGG<br>VEGVGARGVALKLFVQLLGCSRFGGAVVRAGEAEPSGAARS<br>ASSGREEPQPEEGEEEEEKEEERGPQWRLGARKPGSWTGEA<br>AVCADSAPAARAPQALARASGRGGRVARRGAEESGPPHSPS<br>RRGSASRAGPGRASETMNFLLSWVHWSLALLLYLHHAKWS<br>QAAPMAEGGGQNHHEVVKFMDVYQRSYCHPIETLVDIFQEY<br>PDEIEYIFKPSCVPLMRCGGCCNDEGLECVPTEESNITMQIMR<br>IKPHQGQHIGEMSFLQHNKCECRPKKDRARQEKKSVRGKGK<br>GQKRKRKKSRYKSWSVYVGARCCLMPWSLPGPHPCGPCSE<br>RRKHLFVQDPQTCKCSCKNTDSRCKARQLELNERTCRCDKP<br>RR | 75 |
| HABP | MFARMSDLHVLLLMALVGKTACGFSLMSLLESLDPDWTPD<br>QYDYSYEDYNQEENTSSTLTHAENPDWYYTEDQADPCQPNP<br>CEHGGDCLVHGSTFTCSCLAPFSGNKCQKVQNTCKDNPCGR<br>GQCLITQSPPYYRCVCKHPYTGPSCSQVVPVCRPNPCQNGAT<br>CSRHKRRSKFTCACPDQFKGKFCEIGSDDCYVGDGYSYRGK<br>MNRTVNQHACLYWNSHLLLQENYNMEMEDAETHGIGEHNF<br>CRNPDADEKPWCFIKVTNDKVKWEYCDVSACSAQDVAYPE<br>ESPTEPSTKLPGFDSCGKTEIAERKIKRIYGGEKSTAGKHPWQ<br>ASLQSSLPLTISMPQGHFCGGALIHPCWVLTAAHCTDIKTRH<br>LKVVLGDQDLKKEEFHEQSFRVEKIFKYSHYNERDEIPHNDI<br>ALLKLKPVDGHCALESKYVKTVCLPDGSFPSGSECHISGWG | 76 |

TABLE B-continued

Exemplary human growth factors

| Name | Exemplary Human Protein Sequence | SEQ ID NO: |
|---|---|---|
| | VTETGKGSRQLLDAKVKLIANTLCNSRQLYDHMIDDSMICA<br>GNLQKPGQDTCQGDSGGPLTCEKDGTYYVYGIVSWGLECG<br>KRPGVYTQVTKFLNWIKATIKSESGF | |
| CBP | MRSLLLLSAFCLLEAALAAEVKKPAAAAAPGTAEKLSPKAA<br>TLAERSAGLAFSLYQAMAKDQAVENILVSPVVVASSLGLVS<br>LGGKATTASQAKAVLSAEQLRDEEVHAGLGELLRSLSNSTA<br>RNVTWKLGSRLYGPSSVSFADDFVRSSKQHYNCEHSKINFR<br>DKRSALQSINEWAAQTTDGKLPEVTKDVERTDGALLVNAM<br>FFKPHWDEKEHHKMVDNRGEMVTRSYTVGVMMMHRTGLY<br>NYYDDEKEKLQIVEMPLAHKLSSLIILMPHHVEPLERLEKLLT<br>KEQLKIWMGKMQKKAVAISLPKGVVEVTHDLQKHLAGLGL<br>TEAIDKNKADLSRMSGKKDLYLASVFHATAFELDTDGNPFD<br>QDIYGREELRSPKLFYADHPFIFLVRDTQSGSLLFIGRLVRPK<br>GDKMRDEL | 77 |
| FGF-18 | MYSAPSACTCLCLHFLLLCFQVQVLVAEENVDFRIHVENQTR<br>ARDDVSRKQLRLYQLYSRTSGKHIQVLGRRISARGEDGDKY<br>AQLLVETDTFGSQVRIKGKETEFYLCMNRKGKLVGKPDGTS<br>KECVFIEKVLENNYTALMSAKYSGWYVGFTKKGRPRKGPKT<br>RENQQDVHFMKRYPKGQPELQKPFKYTTVTKRSRRIRPTHP<br>A | 78 |
| KGF | MHKWILTWILPTLLYRSCFHIICLVGTISLACNDMTPEQMAT<br>NVNCSSPERHTRSYDYMEGGDIRVRRLFCRTQWYLRIDKRG<br>KVKGTQEMKNNYNIMEIRTVAVGIVAIKGVESEFYLAMNKE<br>GKLYAKKECNEDCNFKELILENHYNTYASAKWTHNGGEMF<br>VALNQKGIPVRGKKTKKEQKTAHFLPMAIT | 79 |
| TNFα | MSTESMIRDVELAEEALPKKTGGPQGSRRCLFLSLFSFLIVAG<br>ATTLFCLLHFGVIGPQREEFPRDLSLISPLAQAVRSSSRTPSDK<br>PVAHVVANPQAEGQLQWLNRRANALLANGVELRDNQLVVP<br>SEGLYLIYSQVLFKGQGCPSTHVLLTHTISRIAVSYQTKVNLL<br>SAIKSPCQRETPEGAEAKPWYEPIYLGGVFQLEKGDRLSAEIN<br>RPDYLDFAESGQVYFGIIAL | 80 |
| TRAIL | MAMMEVQGGPSLGQTCVLIVIFTVLLQSLCVAVTYVYFTNE<br>LKQMQDKYSKSGIACFLKEDDSYWDPNDEESMNSPCWQVK<br>WQLRQLVRKMILRTSEETISTVQEKQQNISPLVRERGPQRVA<br>AHITGTRGRSNTLSSPNSKNEKALGRKINSWESSRSGHSFLSN<br>LHLRNGELVIHEKGFYYIYSQTYFRFQEEIKENTKNDKQMVQ<br>YIYKYTSYPDPILLMKSARNSCWSKDAEYGLYSIYQGGIFEL<br>KENDRIFVSVTNEHLIDMDHEASFFGAFLVG | 81 |
| WNT1 | MGLWALLPGWVSATLLLALAALPAALAANSSGRWWGIVNV<br>ASSTNLLTDSKSLQLVLEPSLQLLSRKQRRLIRQNPGILHSVS<br>GGLQSAVRECKWQFRNRRWNCPTAPGPHLFGKIVNRGCRET<br>AFIFAITSAGVTHSVARSCSEGSIESCTCDYRRRGPGGPDWH<br>WGGCSDNIDFGRLFGREFVDSGEKGRDLRFLMNLHNNEAGR<br>TTVFSEMRQECKCHGMSGSCTVRTCWMRLPTLRAVGDVLR<br>DRFDGASRVLYGNRGSNRASRAELLRLEPEDPAHKPPSPHDL<br>VYFEKSPNFCTYSGRLGTAGTAGRACNSSSPALDGCELLCCG<br>RGHRTRTQRVTERCNCTFHWCCHVSCRNCTHTRVLHECL | 82 |
| WNT2 | MNAPLGGIWLWLPLLLTWLTPEVNSSWWYMRATGGSSRV<br>MCDNVPGLVSSQRQLCHRHPDVMRAISQGVAEWTAECQHQ<br>FRQHRWNCNTLDRDHSLFGRVLLRSSRESAFVYAISSAGVVF<br>AITRACSQGEVKSCSCDPKKMGSAKDSKGIFDWGGCSDNID<br>YGIKFARAFVDAKERKGKDARALMNLHNNRAGRKAVKRFL<br>KQECKCHGVSGSCTLRTCWLAMADFRKTGDYLWRKYNGAI<br>QVVMNQDGTGFTVANERFKKPTKNDLVYFENSPDYCIRDRE<br>AGSLGTAGRVCNLTSRGMDSCEVMCCGRGYDTSHVTRMTK<br>CGCKFHWCCAVRCQDCLEALDVHTCKAPKNADWTTAT | 83 |
| WNT2B | MLRPGGAEEAAQLPLRRASAPVPVPSPAAPDGSRASARLGL<br>ACLLLLLLLTLPARVDTSWWYIGALGARVICDNIPGLVSRQR<br>QLCQRYPDIMRSVGEGAREWIRECQHQFRHHRWNCTTLDR<br>DHTVFGRVMLRSSREAAFVYAISSAGVVHAITRACSQGELSV<br>CSCDPYTRGRHHDQRGDFDWGGCSDNIHYGVRFAKAFVDA<br>KEKRLKDARALMNLHNNRCGRTAVRRFLKLECKCHGVSGS<br>CTLRTCWRALSDFRRTGDYLRRRYDGAVQVMATQDGANFT<br>AARQGYRRATRTDLVYFDNSPDYCVLDKAAGSLGTAGRVC<br>SKTSKGTDGCEEVICCGRGYDTTRVTRVTQCECKFHWCCAV<br>RCKECRNTVDVHTCKAPKKAEWLDQT | 84 |

TABLE B-continued

Exemplary human growth factors

| Name | Exemplary Human Protein Sequence | SEQ ID NO: |
|---|---|---|
| WNT3 | MEPHLLGLLLGLLLGGTRVLAGYPIWWSLALGQQYTSLGSQ PLLCGSIPGLVPKQLRFCRNYIEIMPSVAEGVKLGIQECQHQF RGRRWNCTTIDDSLAIFGPVLDKATRESAFVHAIASAGVAFA VTRSCAEGTSTICGCDSHHKGPPGEGWKWGGCSEDADFGVL VSREFADARENRPDARSAMNKHNNEAGRTTILDHMHLKCK CHGLSGSCEVKTCWWAQPDFRAIGDFLKDKYDSASEMVVE KHRESRGWVETLRAKYSLFKPPTERDLVYYENSPNFCEPNPE TGSFGTRDRTCNVTSHGIDGCDLLCCGRGHNTRTEKRKEKC HCIFHWCCYVSCQECIRIYDVHTCK | 85 |
| WNT3A | MAPLGYFLLLCSLKQALGSYPIWWSLAVGPQYSSLGSQPILC ASIPGLVPKQLRFCRNYVEIMPSVAEGIKIGIQECQHQFRGRR WNCTTVHDSLAIFGPVLDKATRESAFVHAIASAGVAFAVTRS CAEGTAAICGCSSRHQGSPGKGWKWGGCSEDIEFGGMVSRE FADARENRPDARSAMNRHNNEAGRQAIASHMHLKCKCHGL SGSCEVKTCWWSQPDFRAIGDFLKDKYDSASEMVVEKHRES RGWVETLRPRYTYFKVPTERDLVYYEASPNFCEPNPETGSFG TRDRTCNVSSHGIDGCDLLCCGRGHNARAERRREKCRCVFH WCCYVSCQECTRVYDVHTCK | 86 |
| WNT4 | MSPRSCLRSLRLLVFAVFSAAASNWLYLAKLSSVGSISEEETC EKLKGLIQRQVQMCKRNLEVMDSVRRGAQLAIEECQYQFRN RRWNCSTLDSLPVFGKVVTQGTREAAFVYAISSAGVAFAVT RACSSGELEKCGCDRTVHGVSPQGFQWSGCSDNIAYGVAFS QSFVDVRERSKGASSSRALMNLHNNEAGRKAILTHMRVECK CHGVSGSCEVKTCWRAVPPFRQVGHALKEKFDGATEVEPRR VGSSRALVPRNAQFKPHTDEDLVYLEPSPDFCEQDMRSGVL GTRGRTCNKTSKAIDGCELLCCGRGFHTAQVELAERCSCKF HWCCFVKCRQCQRLVELHTCR | 87 |
| WNT5A | MKKSIGILSPGVALGMAGSAMSSKFFLVALAIFFSFAQVVIEA NSWWSLGMNNPVQMSEVYIIGAQPLCSQLAGLSQGQKKLC HLYQDHMQYIGEGAKTGIKECQYQFRHRRWNCSTVDNTSV FGRVMQIGSRETAFTYAVSAAGVVNAMSRACREGELSTCGC SRAARPKDLPRDWLWGGCGDNIDYGYRFAKEFVDARERERI HAKGSYESARILMNLHNNEAGRRTVYNLADVACKCHGVSG SCSLKTCWLQLADFRKVGDALKEKYDSAAAMRLNSRGKLV QVNSRFNSPTTQDLVYIDPSPDYCVRNESTGSLGTQGRLCNK TSEGMDGCELMCCGRGYDQFKTVQTERCHCKFHWCCYVK CKKCTEIVDQFVCK | 88 |
| WNT5B | MPSLLLLFTAALLSSWAQLLTDANSWWSLALNPVQRPEMFII GAQPVCSQLPGLSPGQRKLCQLYQEHMAYIGEGAKTGIKEC QHQFRQRRWNCSTADNASVFGRVMQIGSRETAFTHAVSAA GVVNAISRACREGELSTCGCSRTARPKDLPRDWLWGGCGDN VEYGYRFAKEFVDAREREKNFAKGSEEQGRVLMNLQNNEA GRRAVYKMADVACKCHGVSGSCSLKTCWLQLAEFRKVGD RLKEKYDSAAAMRVTRKGRLELVNSRFTQPTPEDLVYVDPS PDYCLRNESTGSLGTQGRLCNKTSEGMDGCELMCCGRGYN QFKSVQVERCHCKFHWCCFVRCKKCTEIVDQYICK | 89 |
| WNT6 | MLPPLPSRLGLLLLLLLCPAHVGGLWWAVGSPLVMDPTSICR KARRLAGRQAELCQAEPEVVAELARGARLGVRECQFQFRFR RWNCSSHSKAFGRILQQDIRETAFVFAITAAGASHAVTQACS MGELLQCGCQAPRGRAPPRPSGLPGTPGPPGPAGSPEGSAA WEWGGCGDDVDFGDEKSRLFMDARHKRGRGDIRALVQLH NNEAGRLAVRSHTRTECKCHGLSGSCALRTCWQKLPPFREV GARLLERFHGASRVMGTNDGKALLPAVRTLKPPGRADLLYA ADSPDFCAPNRRTGSPGTRGRACNSSAPDLSGCDLLCCGRGH RQESVQLEENCLCRFHWCCVVQCHRCRVRKELSLCL | 90 |
| WNT7A | MNRKARRCLGHLFLSLGMVYLRIGGFSSVVALGASIICNKIP GLAPRQRAICQSRPDAIIVIGEGSQMGLDECQFQFRNGRWNC SALGERTVFGKELKVGSREAAFTYAIIAAGVAHAITAACTQG NLSDCGCDKEKQGQYHRDEGWKWGGCSADIRYGIGFAKVF VDAREIKQNARTLMNLHNNEAGRKILEENMKLECKCHGVS GSCTTKTCWTTLPQFRELGYVLKDKYNEAVHVEPVRASRNK RPTFLKIKKPLSYRKPMDTDLVYIEKSPNYCEEDPVTGSVGT QGRACNKTAPQASGCDLMCCGRGYNTHQYARVWQCNCKF HWCCYVKCNTCSERTEMYTCK | 91 |
| WNT7B | MHRNFRKWIFYVFLCFGVLYVKLGALSSVVALGANIICNKIP GLAPRQRAICQSRPDAIIVIGEGAQMGINECQYQFRFGRWNC SALGEKTVFGQELRVGSREAAFTYAITAAGVAHAVTAACSQ GNLSNCGCDREKQGYYNQAEGWKWGGCSADVRYGIDFSRR | 92 |

TABLE B-continued

Exemplary human growth factors

| Name | Exemplary Human Protein Sequence | SEQ ID NO: |
|---|---|---|
| | FVDAREIKKNARRLMNLHNNEAGRKVLEDRMQLECKCHGV SGSCTTKTCWTTLPKFREVGHLLKEKYNAAVQVEVVRASRL RQPTFLRIKQLRSYQKPMETDLVYIEKSPNYCEEDAATGSVG TQGRLCNRTSPGADGCDTMCCGRGYNTHQYTKVWQCNCK FHWCCFVKCNTCSERTEVFTCK | |
| WNT8A | MLCCIQCLCLVSPFPTLTPCQGGPHCLIPIHLCLTFSLFGRSVN NFLITGPKAYLTYTTSVALGAQSGIEECKFQFAWERWNCPEN ALQLSTHNRLRSATRETSFIHAISSAGVMYIITKNCSMGDFEN CGCDGSNNGKTGGHGWIWGGCSDNVEFGERISKLFVDSLEK GKDARALMNLHNNRAGRLAVRATMKRTCKCHGISGSCSIQT CWLQLAEFREMGDYLKAKYDQALKIEMDKRQLRAGNSAEG HWVPAEAFLPSAEAELIFLEESPDYCTCNSSLGIYGTEGRECL QNSHNTSRWERRSCGRLCTECGLQVEERKTEVISSCNCKFQ WCCTVKCDQCRHVTMSNPAVLLGIRRIEAKNERVLFRLLKS SLWLQIYADK | 93 |
| WNT8B | MFLSKPSVYICLFTCVLQLSHSWSVNNFLMTGPKAYLIYSSS VAAGAQSGIEECKYQFAWDRWNCPERALQLSSHGGLRSAN RETAFVHAISSAGVMYTLTRNCSLGDFDNCGCDDSRNGQLG GQGWLWGGCSDNVGFGEAISKQFVDALETGQDARAAMNL HNNEAGRKAVKGTMKRTCKCHGVSGSCTTQTCWLQLPEFR EVGAHLKEKYHAALKVDLLQGAGNSAAGRGAIADTFRSIST RELVHLEDSPDYCLENKTLGLLGTEGRECLRRGRALGRWER RSCRRLCGDCGLAVEERRAETVSSCNCKFHWCCAVRCEQCR RRVTKYFCSRAERPRGGAAHKPGRKP | 94 |
| WNT9A | MLDGSPLARWLAAAFGLTLLLAALRPSAAYFGLTGSEPLTIL PLTLEPEAAAQAHYKACDRLKLERKQRRMCRRDPGVAETL VEAVSMSALECQFQFRFERWNCTLEGRYRASLLKRGFKETA FLYAISSAGLTHALAKACSAGRMERCTCDEAPDLENREAWQ WGGCGDNLKYSSKFVKEFLGRRSSKDLRARVDFHNNLVGV KVIKAGVETTCKCHGVSGSCTVRTCWRQLAPFHEVGKHLKH KYETALKVGSTTNEAAGEAGAISPPRGRASGAGGSDPLPRTP ELVHLDDSPSFCLAGRFSPGTAGRRCHREKNCESICCGRGHN TQSRVVTRPCQCQVRWCCYVECRQCTQREEVYTCKG | 95 |
| WNT9B | MRPPPALALAGLCLLALPAAAASYFGLTGREVLTPFPGLGTA AAPAQGGAHLKQCDLLKLSRRQKQLCRREPGLAETLRDAA HLGLLECQFQFRHERWNCSLEGRMGLLKRGFKETAFLYAVS SAALTHTLARACSAGRMERCTCDDSPGLESRQAWQWGVCG DNLKYSTKFLSNFLGSKRGNKDLRARADAHNTHVGIKAVKS GLRTTCKCHGVSGSCAVRTCWKQLSPFRETGQVLKLRYDSA VKVSSATNEALGRLELWAPARQGSLTKGLAPRSGDLVYME DSPSFCRPSKYSPGTAGRVCSREASCSSLCCGRGYDTQSRLV AFSCHCQVQWCCYVECQQCVQEELVYTCKH | 96 |
| WNT10A | MGSAHPRPWLRLRPQPQPRPALWVLLFFLLLLAAAMPRSAP NDILDLRLPPEPVLNANTVCLTLPGLSRRQMEVCVRHPDVAA SAIQGIQIAIHECQHQFRDQRWNCSSLETRNKIPYESPIFSRGF RESAFAYAIAAAGVVHAVSNACALGKLKACGCDASRRGDE EAFRRKLHRLQLDALQRGKGLSHGVPEHPALPTASPGLQDS WEWGGCSPDMGFGERFSKDFLDSREPHRDIHARMRLHNNR VGRQAVMENMRRKCKCHGTSGSCQLKTCWQVTPEFRTVGA LLRSRFHRATLIRPHNRNGGQLEPGPAGAPSPAPGAPGPRRR ASPADLVYFEKSPDFCEREPRLDSAGTVGRLCNKSSAGSDGC GSMCCGRGHNILRQTRSERCHCRFHWCCFVVCEECRITEWV SVCK | 97 |
| WNT10B | MLEEPRPRPPPSGLAGLLFLALCSRALSNEILGLKLPGEPPLTA NTVCLTLSGLSKRQLGLCLRNPDVTASALQGLHIAVHECQH QLRDQRWNCSALEGGGRLPHHSAILKRGFRESAFSFSMLAA GVMHAVATACSLGKLVSCGCGWKGSGEQDRLRAKLLQLQ ALSRGKSFPHSLPSPGPGSSPSPGPQDTWEWGGCNHDMDFG EKFSRDFLDSREAPRDIQARMRIHNNRVGRQVVTENLKRKC KCHGTSGSCQFKTCWRAAPEFRAVGAALRERLGRAIFIDTHN RNSGAFQPRLRPRRLSGELVYFEKSPDFCERDPTMGSPGTRG RACNKTSRLLDGCGSLCCGRGHNVLRQTRVERCHCRFHWC CYVLCDECKVTEWVNVCK | 98 |
| WNT11 | MRARPQVCEALLFALALQTGVCYGIKWLALSKTPSALALNQ TQHCKQLEGLVSAQVQLCRSNLELMHTVVHAAREVMKACR RAFADMRWNCSSIELAPNYLLDLERGTRESAFVYALSAAAIS HAIARACTSGDLPGCSCGPVPGEPPGPGNRWGGCADNLSYG LLMGAKFSDAPMKVKKTGSQANKLMRLHNSEVGRQALRAS | 99 |

TABLE B-continued

| Exemplary human growth factors | | |
|---|---|---|
| Name | Exemplary Human Protein Sequence | SEQ ID NO: |
| | LEMKCKCHGVSGSCSIRTCWKGLQELQDVAADLKTRYLSAT KVVHRPMGTRKHLVPKDLDIRPVKDSELVYLQSSPDFCMKN EKVGSHGTQDRQCNKTSNGSDSCDLMCCGRGYNPYTDRVV ERCHCKYHWCCYVTCRRCERTVERYVCK | |
| WNT16 | MDRAALLGLARLCALWAALLVLFPYGAQGNWMWLGIASF GVPEKLGCANLPLNSRQKELCKRKPYLLPSIREGARLGIQEC GSQFRHERWNCMITAAATTAPMGASPLFGYELSSGTKETAFI YAVMAAGLVHSVTRSCSAGNMTECSCDTTLQNGGSASEGW HWGGCSDDVQYGMWFSRKFLDEPIGNTTGKENKVLLAMNL HNNEAGRQAVAKLMSVDCRCHGVSGSCAVKTCWKTMSSFE KIGHLLKDKYENSIQISDKTKRKMRRREKDQRKIPIHKDDLL YVNKSPNYCVEDKKLGIPGTQGRECNRTSEGADGCNLLCCG RGYNTHVVRHVERCECKFIWCCYVRCRRCESMTDVHTCK | 100 |

In some embodiments, the mammalian growth factor is a secreted human growth factor. In some embodiments, the mammalian growth factor is an active fragment (e.g., a fragment of a secreted human growth factor, e.g., any of the exemplary growth factors described herein) that has osteogenic activity). Non-limiting in vitro assays to determine whether a fragment of a secreted human growth factor, e.g., any of the exemplary growth factors described herein, has osteogenic activity are described in Kim et al., *Amino Acids* 42:1455-1465, 2012; Lee et al., *ACS Med. Chem. Lett.* 2(3):248-251, 2011; and Wang et al., *Genetics Mol. Res.* 13(2):4456-4465, 2014.

In some embodiments, a fragment of a secreted human growth factor having osteogenic activity can have 1 amino to about 40 amino acids (e.g., 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acid, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, or about 1 amino acid to about 3 amino acids) removed from the N-terminus of the secreted human growth factor and/or 1 amino acid to about 20 amino acids (e.g., 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, or about 1 amino acid to about 3 amino acids) removed from the C-terminus of the secreted human growth factor.

In some embodiments, the mammalian growth factor can have a sequence that is at least 70% identical (e.g., at least 75% identical, at least 80% identical, at least 85% identical, at least 90% identical, at least 95% identical, or at least 99% identical) to any of the sequences in Table B or any secreted human growth factor, and has osteogenic activity. As one skilled in the art can appreciate, the amino acids in a mammalian growth factor that are conserved between different species are likely important for osteogenic activity and should not be mutated, while amino acids in a mammalian growth factor that are not conserved between different species are not likely important for osteogenic activity and can be mutated.

β-TCP-Binding Polypeptides

Also provided herein are β-tricalcium phosphate (β-TCP)-binding polypeptides that include at least one (e.g., two, three, four, five, six, seven, eight, nine, ten, eleven, twelve, thirteen, fourteen, fifteen, sixteen, seventeen, eighteen, nineteen, or twenty) sequence selected from the group consisting of: VIGESTHHRPWS (SEQ ID NO: 2), LIADSTHHSPWT (SEQ ID NO: 3), ILAESTHHKPWT (SEQ ID NO: 4), ILAETTHHRPWS (SEQ ID NO: 5), IIGESSHHKPFT (SEQ ID NO: 6), GLGDTTHHRPWG (SEQ ID NO: 7), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTTHHRPAT (SEQ ID NO: 18), and GGADTTHHRPGT (SEQ ID NO: 19).

Also provided herein are β-TCP-binding polypeptides that include an amino acid sequence of Formula I:

$A_0B_0C_0D_0E_0F_0G_0H_0I_0J_0K_0L_0$ (Formula I) (SEQ ID NO: 35), where:

$A_0$ is V, L, I, G, S, T, or A;
$B_0$ is I, L, V, Q, T, S, G, or A;
$C_0$ is G, A, V, or S;
$D_0$ is E, D, L, or G;
$E_0$ is S, T, P T, E, or D;
$F_0$ is T or S;
$G_0$ is H, T, or S;
$H_0$ is H or T;
$I_0$ is R, S, K, P, or H;
$J_0$ is P, S, R, or K;
$K_0$ is W, F, S, P, V, A, or G; and
$L_0$ is absent or is S, T, G, (or A);

wherein Formula I does not include LLADTTHHRPWT (SEQ ID NO: 1).

In some embodiments, any of the β-TCP-binding polypeptides described herein can include two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, 20, 21, or 22) of any of SEQ ID NOs: 2-19 and a sequence of Formula I (not including SEQ ID NO: 1). In some embodiments, each neighboring pair of SEQ ID NOs: 2-19 and a sequence of Formula I (not including SEQ ID NO: 1) directly abut each other. In some embodiments, each neighboring pair of any of SEQ ID NOs: 2-19 and a sequence of Formula I (not including SEQ ID NO: 1) are separated by a linker sequence.

In some embodiments, the chimeric polypeptides can include at least two (e.g., at least three, at least four, at least five, at least six, at least seven, at least eight, at least nine, or at least ten; or 2, 3, 4, 5, 6, 7, 8, 9, or 10) different sequences selected from SEQ ID NOs: 2-19 and a sequence of Formula I (not including SEQ ID NO: 1).

In some embodiments, the β-TCP-binding polypeptide includes LLADTTHHRPWT (SEQ ID NO: 1) or GQVLPTTTPSSP (SEQ ID NO: 103). In some embodiments, the 3-TCP-binding polypeptide includes LLADTTHHRPWT (SEQ ID NO: 1) and VIGESTHHRPWS (SEQ ID NO: 2). In some embodiments, the β-TCP-binding polypeptide includes the sequence of (SEQ ID NO: 20)
LLADTTHHRPWTVIGESTHHRPWS.

In some embodiments, the β-TCP-binding polypeptide includes LLADTTHHRPWT (SEQ ID NO: 1), VIGESTHHRPWS (SEQ ID NO: 2), and IIGESSHHKPFT (SEQ ID NO: 6).

In some embodiments, the β-TCP-binding polypeptide includes the sequence of (SEQ ID NO: 21)
LLADTTHHRPWTVIGESTHHRPWSIIGESSHHKPFT.

In some embodiments, the β-TCP-binding polypeptide includes LLADTTHHRPWT (SEQ ID NO: 1), VIGESTHHRPWS (SEQ ID NO: 2), IIGESSHHKPFT (SEQ ID NO: 6), GLGDTTHHRPWG (SEQ ID NO: 7), and ILAESTHHKPWT (SEQ ID NO: 4). In some embodiments, the β-TCP-binding polypeptide includes the sequence of:

(SEQ ID NO: 22)
LLADTTHHRPWTVIGESTHHRPWSIIGESSHHKPFTGLGDTTHHRPWGI

LAESTHHKPWT.

In some embodiments, the β-TCP-binding polypeptide includes LLADTTHHRPWT (SEQ ID NO: 1) and ILAESTHHKPWT (SEQ ID NO: 4). In some embodiments, the R-TCP-binding polypeptide includes at least one copy of the sequence LLADTTHHRPWTILAESTHHKPWT (SEQ ID NO: 23). In some embodiments, the R-TCP-binding polypeptide includes the sequence of (SEQ ID NO: 24)
LLADTTHHRPWTILAESTHHKPWTLLADTTHHRPWTILAESTHHKPWTL

LADTTHHRPWT.

In some embodiments, the β-TCP-binding polypeptide includes LLADTTHHRPWT (SEQ ID NO: 1) and GLGDTTHHRPWG (SEQ ID NO: 7). In some embodiments, the R-TCP-binding polypeptide includes at least one copy of the sequence of LLADTTHHRPWTGLGDTTHHRPWG (SEQ ID NO: 25). In some embodiments, the 3-TCP-binding polypeptide includes the sequence of LLADTTHHRPWTGLGDTTHHRPWGL-LADTTHHRPWT (SEQ ID NO: 26). In some embodiments, the β-TCP-binding polypeptide includes the sequence of LLADTTHHRPWTGLGDTTHHRPWGL-LADTTHHRPWTGLGDTTHHRPWGLLADTTTHHR PWT (SEQ ID NO: 27). In some embodiments, the β-TCP-binding polypeptide includes the sequence of (SEQ ID NO: 28)
LLADTTHHRPWTGLGDTTHHRPWGLLADTTHHRPWTGLGDTTHHRPWGLL

ADTTHHRPWTGLGDTTHHRPWGLLADTTHHRPWT.

In some embodiments, the β-TCP-binding polypeptide includes STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), and GSSGESTHHKPST (SEQ ID NO: 14). In some embodiments, the β-TCP-binding polypeptide includes the sequence of (SEQ ID NO: 29)
STADTSHHRPSTSGGESTHHRPSTSGGESSHHKPSTGSGDSSHHRPSGSS

GESTHHKPST.

In some embodiments, the β-TCP-binding polypeptide includes VGADSTHHRPVT (SEQ ID NO: 15), GAADTTHHRPVT SEQ ID NO: 16), AGADTTHHRPVT (SEQ ID NO: 17), GGADTTHHRPAT (SEQ ID NO: 18) and GGADTTHHRPGT (SEQ ID NO: 19). In some embodiments, the β-TCP-binding polypeptide includes the sequence of (SEQ ID NO: 30)
VGADSTHHRPVTGAADTTHHRPVTAGADTTHHRPVTGGADTTHHRPATGG

ADTTHHRPGT.

In some embodiments, the β-TCP-binding polypeptide includes STADTSHHRPS (SEQ ID NO: 10), LLADTTHHRPWT (SEQ ID NO: 1), TSGGESTHHRPS (SEQ ID NO: 11), VGADSTHHRPVT (SEQ ID NO: 15), TSGGESSHHKPS (SEQ ID NO: 12), GAADTTHHRPVT (SEQ ID NO: 16), TGSGDSSHHRPS (SEQ ID NO: 13), GSSGESTHHKPS (SEQ ID NO: 101), and TGGADTTHHRPAT (SEQ ID NO: 102). In some embodiments, the β-TCP-binding polypeptide includes the sequence of:

(SEQ ID NO: 31)
STADTSHHRPSLLADTTHHRPWTTSGGESTHHRPSVGADSTHHRPVTTSG

GESSHHKPSGAADTTHHRPVTTGSGDSSHHRPSGSSGESTHHKPSTGGAD

TTHHRPAT.

In some embodiments, the β-TCP-binding polypeptides can include two or more (e.g., three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more; or 2, 3, 4, 5, 6, 7, 8, 9, 10, 11, 12, 13, 14, 15, 16, 17, 18, 19, or 20) copies of any one of SEQ ID NOs: 2-19 or a sequence of Formula I (excluding SEQ ID NO: 1).

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 1 (but excluding SEQ ID NO: 1).

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 2.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 3.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 4.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 5.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 6.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 7.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 8.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 9.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 10.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 11.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 12.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 13.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 14.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 15.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 16.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 17.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 18.

In some embodiments, the β-TCP-binding polypeptides can include an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 19.

In some embodiments, the β-TCP-binding polypeptide further comprises a linker sequence (e.g., any of the exemplary linker sequences described herein or known in the art) between a neighboring pair of any of SEQ ID NOs. 2-19 and a sequence of Formula I (excluding SEQ ID NO: 1). In some embodiments, the linker sequence can include the sequence of TGGSGEGGT-GASTGGSAGTGGSGGTTSGEAGGSSGAG (SEQ ID NO: 33). In some embodiments, the linker sequence consists of TGGSGEGGT-GASTGGSAGTGGSGGTTSGEAGGSSGAG (SEQ ID NO: 33). In some embodiments, the linker sequence includes the sequence of GSGATG (SEQ ID NO: 34). In some embodiments, the linker sequence consists of GSGATG (SEQ ID NO: 34).

In some embodiments, where the β-TCP-binding polypeptide comprises two or more or any of SEQ ID Nos. 2-19 and a sequence of Formula I (excluding SEQ ID NO: 1), a linker sequence (e.g., any of the exemplary linker sequences described herein or known in the art) can be between any of the pairs (e.g., all of the pairs) of neighboring sequences selected from the group of SEQ ID NOs: 2-19 and a sequence of Formula I (excluding SEQ ID NO: 1).

In some embodiments, the β-TCP-binding polypeptide can include a signal sequence at its N-terminus. In some embodiments, the β-TCP-binding polypeptide can further include a tag sequence (e.g., a poly-His tag, chitin-binding protein (CBP), maltose-binding protein (MBP), strep-tag, glutathione-S-transferase (GST), thioredoxin, or Fc region). Additional examples of tags are known in the art.

The β-TCP-binding polypeptides described herein can bind to β-TCP (e.g., any of the types of β-TCP described herein) with a dissociation equilibrium constant ($K_d$) of about 1 pM to about 100 μM (or any of the subranges of this range described herein) (e.g., as measured using SPR in phosphate buffered saline).

In some embodiments, the β-TCP-binding polypeptides described herein can have a total length of about 11 amino acids to about 1400 amino acids, about 11 amino acids to about 1350 amino acids, about 11 amino acids to about 1300 amino acids, about 11 amino acids to about 1250 amino acids, about 11 amino acids to about 1200 amino acids, about 11 amino acids to about 1150 amino acids, about 11 amino acids to about 1100 amino acids, about 11 amino acid to about 1050 amino acids, about 11 amino acids to about 1000 amino acids, about 11 amino acids to about 950 amino acids, about 11 amino acids to about 900 amino acids, about 11 amino acids to about 850 amino acids, about 11 amino acids to about 800 amino acids, about 11 amino acids to about 750 amino acids, about 11 amino acids to about 700 amino acids, about 11 amino acids to about 650 amino acids, about 11 amino acids to about 600 amino acids, about 11 amino acids to about 550 amino acids, about 11 amino acids to about 500 amino acids, about 11 amino acids to about 450 amino acids, about 11 amino acids to about 400 amino acids, about 11 amino acids to about 350 amino acids, about 11 amino acids to about 300 amino acids, about 11 amino acids to about 250 amino acids, about 11 amino acids to about 200 amino acids, about 11 amino acids to about 150 amino acids, about 11 amino acids to about 100 amino acids, about 11 amino acids to about 90 amino acids, about 11 amino acids to about 80 amino acids, about 11 amino acids to about 70 amino acids, about 11 amino acids to about 60 amino acids, about 11 amino acids to about 50 amino acids, about 11 amino acids to about 45 amino acids, about 11 amino acids to about 40 amino acids, about 11 amino acids to about 35 amino acids, about 11 amino acids to about 30 amino acids, about 11 amino acids to about 25 amino acids, about 11 amino acids to about 20 amino acids, about 11 amino acids to about 18 amino acids, about 11 amino acids to about 16 amino acids, about 11 amino acids to about 14 amino acids, about 12 amino acids to about 1400 amino acids, about 12 amino acids to about 1350 amino acids, about 12 amino acids to about 1300 amino acids, about 12 amino acids to about 1250 amino acids, about 12 amino acids to about 1200 amino acids, about 12 amino acids to about 1150 amino acids, about 12 amino acids to about 1100 amino acids, about 12 amino acid to about 1050 amino acids, about 12 amino acids to about 1000 amino acids, about 12 amino acids to about 950 amino acids, about 12 amino acids to about 900 amino acids, about 12 amino acids to about 850 amino acids, about 12 amino acids to about 800 amino acids, about 12 amino acids to about 750 amino acids, about 12 amino acids to about 700 amino acids, about 12 amino acids to about 650 amino acids, about 12 amino acids to about 600 amino acids, about 12 amino acids to about 550 amino acids, about 12 amino acids to about 500 amino acids, about 12 amino acids to about 450 amino acids, about 12 amino acids to about 400 amino acids, about 12 amino acids to about 350 amino acids, about 12 amino acids to about 300 amino acids, about 12 amino acids to about 250 amino acids, about 12 amino acids to about 200 amino acids, about 12 amino acids to about 150 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 20 amino acids, about 12 amino acids to about 18 amino acids, about 12 amino acids to about 16 amino acids, about 12 amino acids to about 14 amino acids, about 14 amino acids to about 1400 amino acids, about 14 amino acids to about 1350 amino acids, about 14 amino acids to about 1300 amino acids, about 14 amino acids to about 1250 amino acids, about 14 amino acids to about 1200 amino acids, about 14 amino acids to about 1150 amino acids, about 14 amino acids to about 1100 amino acids, about 14 amino acid to about 1050 amino acids, about 14 amino acids to about 1000 amino acids, about 14 amino acids to about 950 amino acids, about 14 amino acids to about 900 amino acids, about 14 amino acids to about 850 amino acids, about 14 amino acids to about 800 amino acids, about 14 amino acids to about 750 amino acids, about 14 amino acids to about 700 amino acids, about 14 amino acids to about 650 amino acids, about 14 amino acids to about 600 amino acids, about 14 amino acids to about 550 amino acids, about 14 amino acids to about 500 amino acids, about 14 amino acids to about 450 amino acids, about 14 amino acids to about 400 amino acids, about 14 amino acids to about 350 amino acids, about 14 amino acids to about 300 amino acids, about 14 amino acids to about 250 amino acids, about 14 amino acids to about 200 amino acids, about 14 amino acids to about 150 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 20 amino acids, about 14 amino acids to about 18 amino acids, about 14 amino acids to about 16 amino acids, about 16 amino acids to about 1400 amino acids, about 16 amino acids to about 1350 amino acids, about 16 amino acids to about 1300 amino acids, about 16 amino acids to about 1250 amino acids, about 16 amino acids to about 1200 amino acids, about 16 amino acids to about 1150 amino acids, about 16 amino acids to about 1100 amino acids, about 16 amino acid to about 1050 amino acids, about 16 amino acids to about 1000 amino acids, about 16 amino acids to about 950 amino acids, about 16 amino acids to about 900 amino acids, about 16 amino acids to about 850 amino acids, about 16 amino acids to about 800 amino acids, about 16 amino acids to about 750 amino acids, about 16 amino acids to about 700 amino acids, about 16 amino acids to about 650 amino acids, about 16 amino acids to about 600 amino acids, about 16 amino acids to about 550 amino acids, about 16 amino acids to about 500 amino acids, about 16 amino acids to about 450 amino acids, about 16 amino acids to about 400 amino acids, about 16 amino acids to about 350 amino acids, about 16 amino acids to about 300 amino acids, about 16 amino acids to about 250 amino acids, about 16 amino acids to about 200 amino acids, about 16 amino acids to about 150 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 20 amino acids, about 16 amino acids to about 18 amino acids, about 18 amino acids to about 1400 amino acids, about 18 amino acids to about 1350 amino acids, about 18 amino acids to about 1300 amino acids, about 18 amino acids to about 1250 amino acids, about 18 amino acids to about 1200 amino acids, about 18 amino acids to about 1150 amino acids, about 18 amino acids to about 1100 amino acids, about 18 amino acid to about 1050 amino acids, about 18 amino acids to about 1000 amino acids, about 18 amino acids to about 950 amino acids, about 18 amino acids to about 900 amino acids, about 18 amino acids to about 850 amino acids, about 18 amino acids to about 800 amino acids, about 18 amino acids to about 750 amino acids, about 18 amino acids to about 700 amino acids, about 18 amino acids to about 650 amino acids, about 18 amino acids to about 600 amino acids, about 18 amino acids to about 550 amino acids, about 18 amino acids to about 500 amino acids, about 18 amino acids to about 450 amino acids, about 18 amino acids to about 400 amino acids, about 18 amino acids to about 350 amino acids, about 18 amino acids to about 300 amino acids, about 18 amino acids to about 250 amino acids, about 18 amino acids to about 200 amino acids, about 18 amino acids to about 150 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 20 amino acids, about 20 amino acids to about 1400 amino acids, about 20 amino acids to about 1350 amino acids, about 20 amino acids to about 1300 amino acids, about 20 amino acids to about 1250 amino acids, about 20 amino acids to about 1200 amino acids, about 20 amino acids to about 1150 amino acids, about 20 amino acids to about 1100 amino acids, about 20 amino acid to about 1050 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 250 amino acids, about 20 amino acids to about 200 amino acids, about 20 amino acids to about 150 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1400 amino acids, about 25 amino acids to about 1350 amino acids, about 25 amino acids to about 1300 amino acids, about 25 amino acids to about 1250 amino acids, about 25 amino acids to about 1200 amino acids, about 25 amino acids to about 1150 amino acids, about 25 amino acids to about 1100 amino acids, about 25 amino acid to about 1050 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 250 amino acids, about 25 amino acids to about 200 amino acids, about 25 amino acids to about 150 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1400 amino acids, about 30 amino acids to about 1350 amino acids, about 30 amino acids to about 1300 amino acids, about 30 amino acids to about 1250 amino acids, about 30 amino acids to about 1200 amino acids, about 30 amino acids to about 1150 amino acids, about 30 amino acids to about 1100 amino acids, about 30 amino acid to about 1050 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 250 amino acids, about 30 amino acids to about 200 amino acids, about 30 amino acids to about 150 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1400 amino acids, about 35 amino acids to about 1350 amino acids, about 35 amino acids to about 1300 amino acids, about 35 amino acids to about 1250 amino acids, about 35 amino acids to about 1200 amino acids, about 35 amino acids to about 1150 amino acids, about 35 amino acids to about 1100 amino acids, about 35 amino acid to about 1050 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 250 amino acids, about 35 amino acids to about 200 amino acids, about 35 amino acids to about 150 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 1400 amino acids, about 40 amino acids to about 1350 amino acids, about 40 amino acids to about 1300 amino acids, about 40 amino acids to about 1250 amino acids, about 40 amino acids to about 1200 amino acids, about 40 amino acids to about 1150 amino acids, about 40 amino acids to about 1100 amino acids, about 40 amino acid to about 1050 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 250 amino acids, about 40 amino acids to about 200 amino acids, about 40 amino acids to about 150 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 1400 amino acids, about 45 amino acids to about 1350 amino acids, about 45 amino acids to about 1300 amino acids, about 45 amino acids to about 1250 amino acids, about 45 amino acids to about 1200 amino acids, about 45 amino acids to about 1150 amino acids, about 45 amino acids to about 1100 amino acids, about 45 amino acid to about 1050 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 250 amino acids, about 45 amino acids to about 200 amino acids, about 45 amino acids to about 150 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 1400 amino acids, about 50 amino acids to about 1350 amino acids, about 50 amino acids to about 1300 amino acids, about 50 amino acids to about 1250 amino acids, about 50 amino acids to about 1200 amino acids, about 50 amino acids to about 1150 amino acids, about 50 amino acids to about 1100 amino acids, about 50 amino acid to about 1050 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 1400 amino acids, about 60 amino acids to about 1350 amino acids, about 60 amino acids to about 1300 amino acids, about 60 amino acids to about 1250 amino acids, about 60 amino acids to about 1200 amino acids, about 60 amino acids to about 1150 amino acids, about 60 amino acids to about 1100 amino acids, about 60 amino acid to about 1050 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 250 amino acids, about 60 amino acids to about 200 amino acids, about 60 amino acids to about 150 amino acids, about 60 amino acids to about 100 amino acids, about 60 amino acids to about 90 amino acids, about 60 amino acids to about 80 amino acids, about 60 amino acids to about 70 amino acids, about 70 amino acids to about 1400 amino acids, about 70 amino acids to about 1350 amino acids, about 70 amino acids to about 1300 amino acids, about 70 amino acids to about 1250 amino acids, about 70 amino acids to about 1200 amino acids, about 70 amino acids to about 1150 amino acids, about 70 amino acids to about 1100 amino acids, about 70 amino acid to about 1050 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 250 amino acids, about 70 amino acids to about 200 amino acids, about 70 amino acids to about 150 amino acids, about 70 amino acids to about 100 amino acids, about 70 amino acids to about 90 amino acids, about 70 amino acids to about 80 amino acids, about 80 amino acids to about 1400 amino acids, about 80 amino acids to about 1350 amino acids, about 80 amino acids to about 1300 amino acids, about 80 amino acids to about 1250 amino acids, about 80 amino acids to about 1200 amino acids, about 80 amino acids to about 1150 amino acids, about 80 amino acids to about 1100 amino acids, about 80 amino acid to about 1050 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 250 amino acids, about 80 amino acids to about 200 amino acids, about 80 amino acids to about 150 amino acids, about 80 amino acids to about 100 amino acids, about 80 amino acids to about 90 amino acids, about 90 amino acids to about 1400 amino acids, about 90 amino acids to about 1350 amino acids, about 90 amino acids to about 1300 amino acids, about 90 amino acids to about 1250 amino acids, about 90 amino acids to about 1200 amino acids, about 90 amino acids to about 1150 amino acids, about 90 amino acids to about 1100 amino acids, about 90 amino acid to about 1050 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 250 amino acids, about 90 amino acids to about 200 amino acids, about 90 amino acids to about 150 amino acids, about 90 amino acids to about 100 amino acids, about 100 amino acids to about 1400 amino acids, about 100 amino acids to about 1350 amino acids, about 100 amino acids to about 1300 amino acids, about 100 amino acids to about 1250 amino acids, about 100 amino acids to about 1200 amino acids, about 100 amino acids to about 1150 amino acids, about 100 amino acids to about 1100 amino acids, about 100 amino acid to about 1050 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 1400 amino acids, about 150 amino acids to about 1350 amino acids, about 150 amino acids to about 1300 amino acids, about 150 amino acids to about 1250 amino acids, about 150 amino acids to about 1200 amino acids, about 150 amino acids to about 1150 amino acids, about 150 amino acids to about 1100 amino acids, about 150 amino acid to about 1050 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 1400 amino acids, about 200 amino acids to about 1350 amino acids, about 200 amino acids to about 1300 amino acids, about 200 amino acids to about 1250 amino acids, about 200 amino acids to about 1200 amino acids, about 200 amino acids to about 1150 amino acids, about 200 amino acids to about 1100 amino acids, about 200 amino acid to about 1050 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 1400 amino acids, about 250 amino acids to about 1350 amino acids, about 250 amino acids to about 1300 amino acids, about 250 amino acids to about 1250 amino acids, about 250 amino acids to about 1200 amino acids, about 250 amino acids to about 1150 amino acids, about 250 amino acids to about 1100 amino acids, about 250 amino acid to about 1050 amino acids, about 250 amino acids to about 1000 amino acids, about 250 amino acids to about 950 amino acids, about 250 amino acids to about 900 amino acids, about 250 amino acids to about 850 amino acids, about 250 amino acids to about 800 amino acids, about 250 amino acids to about 750 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 1400 amino acids, about 300 amino acids to about 1350 amino acids, about 300 amino acids to about 1300 amino acids, about 300 amino acids to about 1250 amino acids, about 300 amino acids to about 1200 amino acids, about 300 amino acids to about 1150 amino acids, about 300 amino acids to about 1100 amino acids, about 300 amino acid to about 1050 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1400 amino acids, about 350 amino acids to about 1350 amino acids, about 350 amino acids to about 1300 amino acids, about 350 amino acids to about 1250 amino acids, about 350 amino acids to about 1200 amino acids, about 350 amino acids to about 1150 amino acids, about 350 amino acids to about 1100 amino acids, about 350 amino acid to about 1050 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1400 amino acids, about 400 amino acids to about 1350 amino acids, about 400 amino acids to about 1300 amino acids, about 400 amino acids to about 1250 amino acids, about 400 amino acids to about 1200 amino acids, about 400 amino acids to about 1150 amino acids, about 400 amino acids to about 1100 amino acids, about 400 amino acid to about 1050 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1400 amino acids, about 450 amino acids to about 1350 amino acids, about 450 amino acids to about 1300 amino acids, about 450 amino acids to about 1250 amino acids, about 450 amino acids to about 1200 amino acids, about 450 amino acids to about 1150 amino acids, about 450 amino acids to about 1100 amino acids, about 450 amino acid to about 1050 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1400 amino acids, about 500 amino acids to about 1350 amino acids, about 500 amino acids to about 1300 amino acids, about 500 amino acids to about 1250 amino acids, about 500 amino acids to about 1200 amino acids, about 500 amino acids to about 1150 amino acids, about 500 amino acids to about 1100 amino acids, about 500 amino acid to about 1050 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1400 amino acids, about 550 amino acids to about 1350 amino acids, about 550 amino acids to about 1300 amino acids, about 550 amino acids to about 1250 amino acids, about 550 amino acids to about 1200 amino acids, about 550 amino acids to about 1150 amino acids, about 550 amino acids to about 1100 amino acids, about 550 amino acid to about 1050 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1400 amino acids, about 600 amino acids to about 1350 amino acids, about 600 amino acids to about 1300 amino acids, about 600 amino acids to about 1250 amino acids, about 600 amino acids to about 1200 amino acids, about 600 amino acids to about 1150 amino acids, about 600 amino acids to about 1100 amino acids, about 600 amino acid to about 1050 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1400 amino acids, about 650 amino acids to about 1350 amino acids, about 650 amino acids to about 1300 amino acids, about 650 amino acids to about 1250 amino acids, about 650 amino acids to about 1200 amino acids, about 650 amino acids to about 1150 amino acids, about 650 amino acids to about 1100 amino acids, about 650 amino acid to about 1050 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1400 amino acids, about 700 amino acids to about 1350 amino acids, about 700 amino acids to about 1300 amino acids, about 700 amino acids to about 1250 amino acids, about 700 amino acids to about 1200 amino acids, about 700 amino acids to about 1150 amino acids, about 700 amino acids to about 1100 amino acids, about 700 amino acid to about 1050 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1400 amino acids, about 750 amino acids to about 1350 amino acids, about 750 amino acids to about 1300 amino acids, about 750 amino acids to about 1250 amino acids, about 750 amino acids to about 1200 amino acids, about 750 amino acids to about 1150 amino acids, about 750 amino acids to about 1100 amino acids, about 750 amino acid to about 1050 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1400 amino acids, about 800 amino acids to about 1350 amino acids, about 800 amino acids to about 1300 amino acids, about 800 amino acids to about 1250 amino acids, about 800 amino acids to about 1200 amino acids, about 800 amino acids to about 1150 amino acids, about 800 amino acids to about 1100 amino acids, about 800 amino acid to about 1050 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1400 amino acids, about 850 amino acids to about 1350 amino acids, about 850 amino acids to about 1300 amino acids, about 850 amino acids to about 1250 amino acids, about 850 amino acids to about 1200 amino acids, about 850 amino acids to about 1150 amino acids, about 850 amino acids to about 1100 amino acids, about 850 amino acid to about 1050 amino acids, about 850 amino acids to about 1000 amino acids, about 850 amino acids to about 950 amino acids, about 850 amino acids to about 900 amino acids, about 900 amino acids to about 1400 amino acids, about 900 amino acids to about 1350 amino acids, about 900 amino acids to about 1300 amino acids, about 900 amino acids to about 1250 amino acids, about 900 amino acids to about 1200 amino acids, about 900 amino acids to about 1150 amino acids, about 900 amino acids to about 1100 amino acids, about 900 amino acid to about 1050 amino acids, about 900 amino acids to about 1000 amino acids, about 900 amino acids to about 950 amino acids, about 950 amino acids to about 1400 amino acids, about 950 amino acids to about 1350 amino acids, about 950 amino acids to about 1300 amino acids, about 950 amino acids to about 1250 amino acids, about 950 amino acids to about 1200 amino acids, about 950 amino acids to about 1150 amino acids, about 950 amino acids to about 1100 amino acids, about 950 amino acid to about 1050 amino acids, about 950 amino acids to about 1000 amino acids, about 1000 amino acids to about 1400 amino acids, about 1000 amino acids to about 1350 amino acids, about 1000 amino acids to about 1300 amino acids, about 1000 amino acids to about 1250 amino acids, about 1000 amino acids to about 1200 amino acids, about 1000 amino acids to about 1150 amino acids, about 1000 amino acids to about 1100 amino acids, about 1000 amino acid to about 1050 amino acids, about 1050 amino acids to about 1400 amino acids, about 1050 amino acids to about 1350 amino acids, about 1050 amino acids to about 1300 amino acids, about 1050 amino acids to about 1250 amino acids, about 1050 amino acids to about 1200 amino acids, about 1050 amino acids to about 1150 amino acids, about 1050 amino acids to about 1100 amino acids, about 1100 amino acids to about 1400 amino acids, about 1100 amino acids to about 1350 amino acids, about 1100 amino acids to about 1300 amino acids, about 1100 amino acids to about 1250 amino acids, about 1100 amino acids to about 1200 amino acids, about 1100 amino acids to about 1150 amino acids, about 1150 amino acids to about 1400 amino acids, about 1150 amino acids to about 1350 amino acids, about 1150 amino acids to about 1300 amino acids, about 1150 amino acids to about 1250 amino acids, about 1150 amino acids to about 1200 amino acids, about 1200 amino acids to about 1400 amino acids, about 1200 amino acids to about 1350 amino acids, about 1200 amino acids to about 1300 amino acids, about 1200 amino acids to about 1250 amino acids, about 1250 amino acids to about 1400 amino acids, about 1250 amino acids to about 1350 amino acids, about 1250 amino acids to about 1300 amino acids, about 1300 amino acids to about 1400 amino acids, about 1300 amino acids to about 1350 amino acids, or about 1350 amino acids to about 1400 amino acids.

For example, the β-TCP-binding polypeptide can include the amino acid sequence of LLADTTHHRPWTVI-GESTHHRPWSIIGESSHHKPFTGLGDTTHHRPWGI-LAESTHHKPWT ATGGSGEGGT-GASTGGSAGTGGSGGTTSGEAGGSSGAG (SEQ ID NO: 44). In some instances the β-TCP-binding polypeptide includes an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 44.

For example, the β-TCP-binding polypeptide may include: LLADTTHHRPWTGLGDTTHHRPWGL-LADTTHHRPWTGLGDTTHHRPWGLLADTTHHR PWTTGGSGEGGT-GASTGGSAGTGGSGGTTSGEAGGSSGAG (SEQ ID NO: 45). In some instances the β-TCP-binding polypeptide includes an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 45.

A variety of different methods known in the art can be used to determine the $K_D$ values of any of the β-TCP-binding polypeptides described herein for binding to β-TCP (e.g., any of the types of β-TCP described herein) (e.g., an electrophoretic mobility shift assay, a filter binding assay, surface plasmon resonance, and a biomolecular binding kinetics assay, etc.)

Nucleic Acids/Vectors

Also provided herein are nucleic acids that encode any of the chimeric polypeptides or β-TCP-binding polypeptides described herein.

Also provided herein are vectors that include any of the nucleic acids provided herein. A "vector" according to the present disclosure is a polynucleotide capable of inducing the expression of a recombinant protein (e.g., any of the chimeric polypeptides or β-TCP-binding polypeptides described) in a host cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., *Exp. Hematol.* 28(10:1137-1146, 2000; Park et al., *Trends Biotechnol.* 29(11):550-557, 2011; and Alonso-Camino et al., *Mol. Ther. Nucleic Acids* 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., *BioTechniques* 7:980-990, 1989*; Miller, Human Gene Therapy* 1:5-14, 1990; Scarpa et al., *Virology* 180:849-852, 1991; Burns et al., *Proc. Natl. Acad. Sci. U.S.A.* 90:8033-8037, 1993; and Boris-Lawrie et al., *Cur. Opin. Genet. Develop.* 3:102-109, 1993. Exemplary lentiviral vectors are described in, e.g., Wang et al., *J. Immunother.* 35(9):689-701, 2003; Cooper et al., *Blood* 101:1637-1644, 2003; Verhoeyen et al., *Methods Mol. Biol.* 506:97-114, 2009; and Cavalieri et al., *Blood* 102(2):497-505, 2003.

Exemplary vectors, in which any of the nucleic acids provided herein can be inserted, are described in, e.g., Ausubel et al., Eds. "*Current Protocols in Molecular Biology" Current Protocols,* 1993; and Sambrook et al., Eds. "*Molecular Cloning: A Laboratory Manual,"* 2nd ed., Cold Spring Harbor Press, 1989.

In some embodiments, the vectors further include a promoter and/or enhancer operably linked to any of the nucleic acids described herein. Non-limiting examples of promoters include promoters from human cytomegalovirus (CMV), mouse phosphoglycerate kinase 1, polyoma adenovirus, thyroid stimulating hormone a, vimentin, simian virus 40 (SV40), tumor necrosis factor, β-globin, α-fetoprotein, 7-globin, 0-interferon, 7-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQα, HLA DQP, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the chimeric polypeptide or β-TCP-binding polypeptide. Non-limiting examples of a poly(A) sequence include those derived from bovine growth hormone (Woychik et al., *Proc. Natl. Acad. Sci. U.S.A.* 81(13): 3944-3948, 1984, and U.S. Pat. No. 5,122,458), mouse-β-globin, mouse-α-globin (Orkin et al., *EMBO J.* 4(2): 453-456, 1985), human collagen, polyoma virus (Batt et al., *Mol. Cell Biol.* 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., *Mol. Therapy* 15(7): 1340-1347, 2007), SV40 poly(A) site, e.g., SV40 late and early poly(A) site (Schek et al., *Mol. Cell Biol.* 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2). A poly(A) sequence can, e.g., be a synthetic polyadenylation site. See, e.g., Levitt el al, *Genes Dev.* 3(7): 1019-1025, 1989). In some examples, a poly(A) sequence can be the polyadenylation signal of soluble neuropilin-1: AAATAAAATACGAAATG (SEQ ID NO:111). Additional examples of poly(A) sequences are known in the art. Additional examples and aspects of vectors are also known in the art.

Methods of Making A Chimeric Polypeptide

Also provided herein are methods of making a chimeric polypeptide (e.g., any of the chimeric polypeptides described herein) or a β-TCP-binding polypeptide (e.g., any of the 3-TCP-binding polypeptides described herein) that include: introducing into a cell a nucleic acid sequence encoding the chimeric polypeptide or the β-TCP-binding polypeptide to produce a recombinant cell; and culturing the recombinant cell under conditions sufficient for the expression of the chimeric polypeptide or β-TCP-binding polypeptide. In some embodiments, the introducing step includes introducing into a cell an expression vector including a nucleic acid sequence encoding the chimeric polypeptide or the β-TCP-binding polypeptide to produce a recombinant cell. In some embodiments, the expression vector includes chaperones (e.g., GroES, GroEL) and glutathione to aid with in vitro folding.

A chimeric polypeptide or β-TCP-binding polypeptide described herein can be produced by any cell, e.g., a eukaryotic cell or a prokaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. In some embodiments, the eukaryotic cell is a mammalian cell (e.g., a Chinese Hamster Ovary (CHO) cell). As used herein, the term "prokaryotic cell" refers to a cell that does not have a distinct, membrane-bound nucleus. In some embodiments, the prokaryotic cell is a bacterial cell. In some embodiments, the bacterial cell is a chemically competent *E. coli* K12 cell (e.g., Shuffle® T7; New England BioLabs) or a BL21(DE3) pLysS chemically competent *E. coli* cell.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection.

Provided herein are methods that further include isolation of the chimeric polypeptide or the β-TCP-binding polypeptide from a cell (e.g., a eukaryotic cell) using techniques well-known in the art (e.g., ammonium sulfate precipitation, polyethylene glycol precipitation, cobalt column, heparin column, ion-exchange chromatography (anion or cation), chromatography based on hydrophobic interaction, metal-affinity chromatography, ligand-affinity chromatography, and size exclusion chromatography).

In some embodiments, a hydrophobicity/hydrophilicity plot is constructed to determine variant β-TCP binding sequences that can be included in any of the chimeric polypeptides described herein.

β-TCP

Sintering of tricalcium phosphate, $Ca_3(PO_4)_2$, causes its structure to convert to 3-TCP. β-TCP is an osteoconductive material that supports bone mineralization by easily dissolving at low pH and serves as a rigid substrate for cell attachment (see, e.g., Muschler et al., *J. Bone Joint Surgery* 86:1541-1558, 2004; Fleming Jr. et al., "Intraoperative Harvest and Concentration of Human Bone Marrow Osteoprogenitors for Enhancement of Spinal Fusion," in Orthopedic Tissue Engineering: Basic Science and Practice, 2004).

β-TCP as described herein can be in a variety of different forms. Examples of such forms include a granular form, a porous form, a powder, a putty (e.g., a moldable putty), a paste, a scaffold, and/or a coating on a solid surface (e.g., a coating on a medical device). In addition, the β-TCP can be used in a variety of different shapes (e.g., a cross, a ladder, a sphere, an ellipsoid, a square, a triangular pyramid, a rod, a cone, a torus, or a wedge, or any combination thereof) and sizes (e.g., largest average diameter of about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, about 5 cm, about 6 cm, about 7 cm, about 8 cm, about 9 cm, or about 10 cm). In some embodiments, β-TCP can be porous (e.g., about 20% to about 80% porous, about 20% to about 75% porous, about 20% to about 70% porous, about 20% to about 65% porous, about 20% to about 60% porous, about 20% to about 55% porous, about 20% to about 50% porous, about 20% to about 45% porous, about 20% to about 40% porous, about 20% to about 35% porous, about 20% to about 30% porous, about 20% to about 25% porous, about 25% to about 80% porous, about 25% to about 75% porous, about 25% to about 70% porous, about 25% to about 65% porous, about 25% to about 60% porous, about 25% to about 55% porous, about 25% to about 50% porous, about 25% to about 45% porous, about 25% to about 40% porous, about 25% to about 35% porous, about 25% to about 30% porous, about 30% to about 80% porous, about 30% to about 75% porous, about 30% to about 70% porous, about 30% to about 65% porous, about 30% to about 60% porous, about 30% to about 55% porous, about 30% to about 50% porous, about 30% to about 45% porous, about 30% to about 40% porous, about 30% to about 35% porous, about 35% to about 80% porous, about 35% to about 75% porous, about 35% to about 70% porous, about 35% to about 65% porous, about 35% to about 60% porous, about 35% to about 55% porous, about 35% to about 50% porous, about 35% to about 45% porous, about 35% to about 40% porous, about 40% to about 80% porous, about 40% to about 75% porous, about 40% to about 70% porous, about 40% to about 65% porous, about 40% to about 60% porous, about 40% to about 55% porous, about 40% to about 50% porous, about 40% to about 45% porous, about 45% to about 80% porous, about 45% to about 75% porous, about 45% to about 70% porous, about 45% to about 65% porous, about 45% to about 60% porous, about 45% to about 55% porous, about 45% to about 50% porous, about 50% to about 80% porous, about 50% to about 75% porous, about 50% to about 70% porous, about 50% to about 65% porous, about 50% to about 60% porous, about 50% to about 55% porous, about 55% to about 80% porous, about 55% to about 75% porous, about 55% to about 70% porous, about 55% to about 65% porous, about 55% to about 60% porous, about 60% to about 80% porous, about 60% to about 75% porous, about 60% to about 70% porous, about 60% to about 65% porous, about 65% to about 80% porous, about 65% to about 75% porous, about 65% to about 70% porous, about 70% to about 80% porous, about 70% to about 75% porous, or about 75% to about 80% porous). For example, β-TCP can have an average pore size of about 1 nm to about 50 mm, about 1 nm to about 45 mm, about 1 nm to about 40 mm, about 1 nm to about 35 mm, about 1 nm to about 30 mm, about 1 nm to about 25 mm, about 1 nm to about 20 mm, about 1 nm to about 15 mm, about 1 nm to about 10 mm, about 1 nm to about 5 mm, about 1 nm to about 1 mm, about 1 nm to about 900 Tm, about 1 nm to about 800 Tm, about 1 nm to about 700 Tm, about 1 nm to about 600 Tm, about 1 nm to about 500 Tm, about 1 nm to about 400 Tm, about 1 nm to about 300 Tm, about 1 nm to about 200 Tm, about 1 nm to about 100 Tm, about 1 nm to about 50 Tm, about 1 nm to about 10 Tm, about 1 nm to about 5 Tm, about 1 nm to about 1 Tm, about 1 nm to about 900 nm, about 1 nm to about 800 nm, about 1 nm to about 700 nm, about 1 nm to about 600 nm, about 1 nm to about 500 nm, about 1 nm to about 400 nm, about 1 nm to about 300 nm, about 1 nm to about 200 nm, about 1 nm to about 100 nm, about 1 nm to about 50 nm, about 1 nm to about 25 nm, about 1 nm to about 10 nm, about 1 nm to about 5 nm, about 5 nm to about 50 mm, about 5 nm to about 45 mm, about 5 nm to about 40 mm, about 5 nm to about 35 mm, about 5 nm to about 30 mm, about 5 nm to about 25 mm, about 5 nm to about 20 mm, about 5 nm to about 15 mm, about 5 nm to about 10 mm, about 5 nm to about 5 mm, about 5 nm to about 1 mm, about 5 nm to about 900 Tm, about 5 nm to about 800 Tm, about 5 nm to about 700 Tm, about 5 nm to about 600 Tm, about 5 nm to about 500 Tm, about 5 nm to about 400 Tm, about 5 nm to about 300 Tm, about 5 nm to about 200 Tm, about 5 nm to about 100 Tm, about 5 nm to about 50 Tm, about 5 nm to about 10 Tm, about 5 nm to about 5 Tm, about 5 nm to about 1 Tm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, about 5 nm to about 100 nm, about 5 nm to about 50 nm, about 5 nm to about 25 nm, about 5 nm to about 10 nm, about 10 nm to about 50 mm, about 10 nm to about 45 mm, about 10 nm to about 40 mm, about 10 nm to about 35 mm, about 10 nm to about 30 mm, about 10 nm to about 25 mm, about 10 nm to about 20 mm, about 10 nm to about 15 mm, about 10 nm to about 10 mm, about 10 nm to about 5 mm, about 10 nm to about 1 mm, about 10 nm to about 900 Tm, about 10 nm to about 800 Tm, about 10 nm to about 700 Tm, about 10 nm to about 600 Tm, about 10 nm to about 500 Tm, about 10 nm to about 400 Tm, about 10 nm to about 300 Tm, about 10 nm to about 200 Tm, about 10 nm to about 100 Tm, about 10 nm to about 50 Tm, about 10 nm to about 10 Tm, about 10 nm to about 5 Tm, about 10 nm to about 1 Tm, about 10 nm to about 900 nm, about 10 nm to about 800 nm, about 10 nm to about 700 nm, about 10 nm to about 600 nm, about 10 nm to about 500 nm, about 10 nm to about 400 nm, about 10 nm to about 300 nm, about 10 nm to about 200 nm, about 10 nm to about 100 nm, about 10 nm to about 50 nm, about 10 nm to about 25 nm, about 25 nm to about 50 mm, about 25 nm to about 45 mm, about 25 nm to about 40 mm, about 25 nm to about 35 mm, about 25 nm to about 30 mm, about 25 nm to about 25 mm, about 25 nm to about 20 mm, about 25 nm to about 15 mm, about 25 nm to about 10 mm, about 25 nm to about 5 mm, about 25 nm to about 1 mm, about 25 nm to about 900 Tm, about 25 nm to about 800 Tm, about 25 nm to about 700 Tm, about 25 nm to about 600 Tm, about 25 nm to about 500 Tm, about 25 nm to about 400 Tm, about 25 nm to about 300 Tm, about 25 nm to about 200 Tm, about 25 nm to about 100 Tm, about 25 nm to about 50 Tm, about 25 nm to about 10 Tm, about 25 nm to about 5 Tm, about 25 nm to about 1 Tm, about 25 nm to about 900 nm, about 25 nm to about 800 nm, about 25 nm to about 700 nm, about 25 nm to about 600 nm, about 25 nm to about 500 nm, about 25 nm to about 400 nm, about 25 nm to about 300 nm, about 25 nm to about 200 nm, about 25 nm to about 100 nm, about 25 nm to about 50 nm, about 50 nm to about 50 mm, about 50 nm to about 45 mm, about 50 nm to about 40 mm, about 50 nm to about 35 mm, about 50 nm to about 30 mm, about 50 nm to about 25 mm, about 50 nm to about 20 mm, about 50 nm to about 15 mm, about 50 nm to about 10 mm, about 50 nm to about 5 mm, about 50 nm to about 1 mm, about 50 nm to about 900 Tm, about 50 nm to about 800 Tm, about 50 nm to about 700 Tm, about 50 nm to about 600 Tm, about 50 nm to about 500 Tm, about 50 nm to about 400 Tm, about 50 nm to about 300 Tm, about 50 nm to about 200 Tm, about 50 nm to about 100 Tm, about 50 nm to about 50 Tm, about 50 nm to about 10 Tm, about 50 nm to about 5 Tm, about 50 nm to about 1 Tm, about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm, about 50 nm to about 100 nm, about 100 nm to about 50 mm, about 100 nm to about 45 mm, about 100 nm to about 40 mm, about 100 nm to about 35 mm, about 100 nm to about 30 mm, about 100 nm to about 25 mm, about 100 nm to about 20 mm, about 100 nm to about 15 mm, about 100 nm to about 10 mm, about 100 nm to about 5 mm, about 100 nm to about 1 mm, about 100 nm to about 900 Tm, about 100 nm to about 800 Tm, about 100 nm to about 700 Tm, about 100 nm to about 600 Tm, about 100 nm to about 500 Tm, about 100 nm to about 400 Tm, about 100 nm to about 300 Tm, about 100 nm to about 200 Tm, about 100 nm to about 100 Tm, about 100 nm to about 50 Tm, about 100 nm to about 10 Tm, about 100 nm to about 5 Tm, about 100 nm to about 1 Tm, about 100 nm to about 900 nm, about 100 nm to about 800 nm, about 100 nm to about 700 nm, about 100 nm to about 600 nm, about 100 nm to about 500 nm, about 100 nm to about 400 nm, about 100 nm to about 300 nm, about 100 nm to about 200 nm, about 200 nm to about 50 mm, about 200 nm to about 45 mm, about 200 nm to about 40 mm, about 200 nm to about 35 mm, about 200 nm to about 30 mm, about 200 nm to about 25 mm, about 200 nm to about 20 mm, about 200 nm to about 15 mm, about 200 nm to about 10 mm, about 200 nm to about 5 mm, about 200 nm to about 1 mm, about 200 nm to about 900 Tm, about 200 nm to about 800 Tm, about 200 nm to about 700 Tm, about 200 nm to about 600 Tm, about 200 nm to about 500 Tm, about 200 nm to about 400 Tm, about 200 nm to about 300 Tm, about 200 nm to about 200 Tm, about 200 nm to about 100 Tm, about 200 nm to about 50 Tm, about 200 nm to about 10 Tm, about 200 nm to about 5 Tm, about 200 nm to about 1 Tm, about 200 nm to about 900 nm, about 200 nm to about 800 nm, about 200 nm to about 700 nm, about 200 nm to about 600 nm, about 200 nm to about 500 nm, about 200 nm to about 400 nm, about 200 nm to about 300 nm, about 300 nm to about 50 mm, about 300 nm to about 45 mm, about 300 nm to about 40 mm, about 300 nm to about 35 mm, about 300 nm to about 30 mm, about 300 nm to about 25 mm, about 300 nm to about 20 mm, about 300 nm to about 15 mm, about 300 nm to about 10 mm, about 300 nm to about 5 mm, about 300 nm to about 1 mm, about 300 nm to about 900 Tm, about 300 nm to about 800 Tm, about 300 nm to about 700 Tm, about 300 nm to about 600 Tm, about 300 nm to about 500 Tm, about 300 nm to about 400 Tm, about 300 nm to about 300 Tm, about 300 nm to about 200 Tm, about 300 nm to about 100 Tm, about 300 nm to about 50 Tm, about 300 nm to about 10 Tm, about 300 nm to about 5 Tm, about 300 nm to about 1 Tm, about 300 nm to about 900 nm, about 300 nm to about 800 nm, about 300 nm to about 700 nm, about 300 nm to about 600 nm, about 300 nm to about 500 nm, about 300 nm to about 400 nm, about 400 nm to about 50 mm, about 400 nm to about 45 mm, about 400 nm to about 40 mm, about 400 nm to about 35 mm, about 400 nm to about 30 mm, about 400 nm to about 25 mm, about 400 nm to about 20 mm, about 400 nm to about 15 mm, about 400 nm to about 10 mm, about 400 nm to about 5 mm, about 400 nm to about 1 mm, about 400 nm to about 900 Tm, about 400 nm to about 800 Tm, about 400 nm to about 700 Tm, about 400 nm to about 600 Tm, about 400 nm to about 500 Tm, about 400 nm to about 400 Tm, about 400 nm to about 300 Tm, about 400 nm to about 200 Tm, about 400 nm to about 100 Tm, about 400 nm to about 50 Tm, about 400 nm to about 10 Tm, about 400 nm to about 5 Tm, about 400 nm to about 1 Tm, about 400 nm to about 900 nm, about 400 nm to about 800 nm, about 400 nm to about 700 nm, about 400 nm to about 600 nm, about 400 nm to about 500 nm, about 500 nm to about 50 mm, about 500 nm to about 45 mm, about 500 nm to about 40 mm, about 500 nm to about 35 mm, about 500 nm to about 30 mm, about 500 nm to about 25 mm, about 500 nm to about 20 mm, about 500 nm to about 15 mm, about 500 nm to about 10 mm, about 500 nm to about 5 mm, about 500 nm to about 1 mm, about 500 nm to about 900 Tm, about 500 nm to about 800 Tm, about 500 nm to about 700 Tm, about 500 nm to about 600 Tm, about 500 nm to about 500 Tm, about 500 nm to about 400 Tm, about 500 nm to about 300 Tm, about 500 nm to about 200 Tm, about 500 nm to about 100 Tm, about 500 nm to about 50 Tm, about 500 nm to about 10 Tm, about 500 nm to about 5 Tm, about 500 nm to about 1 Tm, about 500 nm to about 900 nm, about 500 nm to about 800 nm, about 500 nm to about 700 nm, about 500 nm to about 600 nm, about 600 nm to about 50 mm, about 600 nm to about 45 mm, about 600 nm to about 40 mm, about 600 nm to about 35 mm, about 600 nm to about 30 mm, about 600 nm to about 25 mm, about 600 nm to about 20 mm, about 600 nm to about 15 mm, about 600 nm to about 10 mm, about 600 nm to about 5 mm, about 600 nm to about 1 mm, about 600 nm to about 900 Tm, about 600 nm to about 800 Tm, about 600 nm to about 700 Tm, about 600 nm to about 600 Tm, about 600 nm to about 500 Tm, about 600 nm to about 400 Tm, about 600 nm to about 300 Tm, about 600 nm to about 200 Tm, about 600 nm to about 100 Tm, about 600 nm to about 50 Tm, about 600 nm to about 10 Tm, about 600 nm to about 5 Tm, about 600 nm to about 1 Tm, about 600 nm to about 900 nm, about 600 nm to about 800 nm, about 600 nm to about 700 nm, about 700 nm to about 50 mm, about 700 nm to about 45 mm, about 700 nm to about 40 mm, about 700 nm to about 35 mm, about 700 nm to about 30 mm, about 700 nm to about 25 mm, about 700 nm to about 20 mm, about 700 nm to about 15 mm, about 700 nm to about 10 mm, about 700 nm to about 5 mm, about 700 nm to about 1 mm, about 700 nm to about 900 Tm, about 700 nm to about 800 Tm, about 700 nm to about 700 Tm, about 700 nm to about 600 Tm, about 700 nm to about 500 Tm, about 700 nm to about 400 Tm, about 700 nm to about 300 Tm, about 700 nm to about 200 Tm, about 700 nm to about 100 Tm, about 700 nm to about 50 Tm, about 700 nm to about 10 Tm, about 700 nm to about 5 Tm, about 700 nm to about 1 Tm, about 700 nm to about 900 nm, about 700 nm to about 800 nm, about 800 nm to about 50 mm, about 800 nm to about 45 mm, about 800 nm to about 40 mm, about 800 nm to about 35 mm, about 800 nm to about 30 mm, about 800 nm to about 25 mm, about 800 nm to about 20 mm, about 800 nm to about 15 mm, about 800 nm to about 10 mm, about 800 nm to about 5 mm, about 800 nm to about 1 mm, about 800 nm to about 900 Tm, about 800 nm to about 800 Tm, about 800 nm to about 700 Tm, about 800 nm to about 600 Tm, about 800 nm to about 500 Tm, about 800 nm to about 400 Tm, about 800 nm to about 300 Tm, about 800 nm to about 200 Tm, about 800 nm to about 100 Tm, about 800 nm to about 50 Tm, about 800 nm to about 10 Tm, about 800 nm to about 5 Tm, about 800 nm to about 1 Tm, about 800 nm to about 900 nm, about 900 nm to about 50 mm, about 900 nm to about 45 mm, about 900 nm to about 40 mm, about 900 nm to about 35 mm, about 900 nm to about 30 mm, about 900 nm to about 25 mm, about 900 nm to about 20 mm, about 900 nm to about 15 mm, about 900 nm to about 10 mm, about 900 nm to about 5 mm, about 900 nm to about 1 mm, about 900 nm to about 900 Tm, about 900 nm to about 800 Tm, about 900 nm to about 700 Tm, about 900 nm to about 600 Tm, about 900 nm to about 500 Tm, about 900 nm to about 400 Tm, about 900 nm to about 300 Tm, about 900 nm to about 200 Tm, about 900 nm to about 100 Tm, about 900 nm to about 50 Tm, about 900 nm to about 10 Tm, about 900 nm to about 5 Tm, about 900 nm to about 1 Tm, about 1 Tm to about 50 mm, about 1 Tm to about 45 mm, about 1 Tm to about 40 mm, about 1 Tm to about 35 mm, about 1 Tm to about 30 mm, about 1 Tm to about 25 mm, about 1 Tm to about 20 mm, about 1 Tm to about 15 mm, about 1 Tm to about 10 mm, about 1 Tm to about 5 mm, about 1 Tm to about 1 mm, about 1 Tm to about 900 Tm, about 1 Tm to about 800 Tm, about 1 Tm to about 700 Tm, about 1 Tm to about 600 Tm, about 1 Tm to about 500 Tm, about 1 Tm to about 400 Tm, about 1 Tm to about 300 Tm, about 1 Tm to about 200 Tm, about 1 Tm to about 100 Tm, about 1 Tm to about 50 Tm, about 1 Tm to about 10 Tm, about 1 Tm to about 5 Tm, about 5 Tm to about 50 mm, about 5 Tm to about 45 mm, about 5 Tm to about 40 mm, about 5 Tm to about 35 mm, about 5 Tm to about 30 mm, about 5 Tm to about 25 mm, about 5 Tm to about 20 mm, about 5 Tm to about 15 mm, about 5 Tm to about 10 mm, about 5 Tm to about 5 mm, about 5 Tm to about 1 mm, about 5 Tm to about 900 Tm, about 5 Tm to about 800 Tm, about 5 Tm to about 700 Tm, about 5 Tm to about 600 Tm, about 5 Tm to about 500 Tm, about 5 Tm to about 400 Tm, about 5 Tm to about 300 Tm, about 5 Tm to about 200 Tm, about 5 Tm to about 100 Tm, about 5 Tm to about 50 Tm, about 5 Tm to about 10 Tm, about 10 Tm to about 50 mm, about 10 Tm to about 45 mm, about 10 Tm to about 40 mm, about 10 Tm to about 35 mm, about 10 Tm to about 30 mm, about 10 Tm to about 25 mm, about 10 Tm to about 20 mm, about 10 Tm to about 15 mm, about 10 Tm to about 10 mm, about 10 Tm to about 5 mm, about 10 Tm to about 1 mm, about 10 Tm to about 900 Tm, about 10 Tm to about 800 Tm, about 10 Tm to about 700 Tm, about 10 Tm to about 600 Tm, about 10 Tm to about 500 Tm, about 10 Tm to about 400 Tm, about 10 Tm to about 300 Tm, about 10 Tm to about 200 Tm, about 10 Tm to about 100 Tm, about 10 Tm to about 50 Tm, about 50 Tm to about 50 mm, about 50 Tm to about 45 mm, about 50 Tm to about 40 mm, about 50 Tm to about 35 mm, about 50 Tm to about 30 mm, about 50 Tm to about 25 mm, about 50 Tm to about 20 mm, about 50 Tm to about 15 mm, about 50 Tm to about 10 mm, about 50 Tm to about 5 mm, about 50 Tm to about 1 mm, about 50 Tm to about 900 Tm, about 50 Tm to about 800 Tm, about 50 Tm to about 700 Tm, about 50 Tm to about 600 Tm, about 50 Tm to about 500 Tm, about 50 Tm to about 400 Tm, about 50 Tm to about 300 Tm, about 50 Tm to about 200 Tm, about 50 Tm to about 100 Tm, about 100 Tm to about 50 mm, about 100 Tm to about 45 mm, about 100 Tm to about 40 mm, about 100 Tm to about 35 mm, about 100 Tm to about 30 mm, about 100 Tm to about 25 mm, about 100 Tm to about 20 mm, about 100 Tm to about 15 mm, about 100 Tm to about 10 mm, about 100 Tm to about 5 mm, about 100 Tm to about 1 mm, about 100 Tm to about 900 Tm, about 100 Tm to about 800 Tm, about 100 Tm to about 700 Tm, about 100 Tm to about 600 Tm, about 100 Tm to about 500 Tm, about 100 Tm to about 400 Tm, about 100 Tm to about 300 Tm, about 100 Tm to about 200 Tm, about 200 Tm to about 50 mm, about 200 Tm to about 45 mm, about 200 Tm to about 40 mm, about 200 Tm to about 35 mm, about 200 Tm to about 30 mm, about 200 Tm to about 25 mm, about 200 Tm to about 20 mm, about 200 Tm to about 15 mm, about 200 Tm to about 10 mm, about 200 Tm to about 5 mm, about 200 Tm to about 1 mm, about 200 Tm to about 900 Tm, about 200 Tm to about 800 Tm, about 200 Tm to about 700 Tm, about 200 Tm to about 600 Tm, about 200 Tm to about 500 Tm, about 200 Tm to about 400 Tm, about 200 Tm to about 300 Tm, about 300 Tm to about 50 mm, about 300 Tm to about 45 mm, about 300 Tm to about 40 mm, about 300 Tm to about 35 mm, about 300 Tm to about 30 mm, about 300 Tm to about 25 mm, about 300 Tm to about 20 mm, about 300 Tm to about 15 mm, about 300 Tm to about 10 mm, about 300 Tm to about 5 mm, about 300 Tm to about 1 mm, about 300 Tm to about 900 Tm, about 300 Tm to about 800 Tm, about 300 Tm to about 700 Tm, about 300 Tm to about 600 Tm, about 300 Tm to about 500 Tm, about 300 Tm to about 400 Tm, about 400 Tm to about 50 mm, about 400 Tm to about 45 mm, about 400 Tm to about 40 mm, about 400 Tm to about 35 mm, about 400 Tm to about 30 mm, about 400 Tm to about 25 mm, about 400 Tm to about 20 mm, about 400 Tm to about 15 mm, about 400 Tm to about 10 mm, about 400 Tm to about 5 mm, about 400 Tm to about 1 mm, about 400 Tm to about 900 Tm, about 400 Tm to about 800 Tm, about 400 Tm to about 700 Tm, about 400 Tm to about 600 Tm, about 400 Tm to about 500 Tm, about 500 Tm to about 50 mm, about 500 Tm to about 45 mm, about 500 Tm to about 40 mm, about 500 Tm to about 35 mm, about 500 Tm to about 30 mm, about 500 Tm to about 25 mm, about 500 Tm to about 20 mm, about 500 Tm to about 15 mm, about 500 Tm to about 10 mm, about 500 Tm to about 5 mm, about 500 Tm to about 1 mm, about 500 Tm to about 900 Tm, about 500 Tm to about 800 Tm, about 500 Tm to about 700 Tm, about 500 Tm to about 600 Tm, about 600 Tm to about 50 mm, about 600 Tm to about 45 mm, about 600 Tm to about 40 mm, about 600 Tm to about 35 mm, about 600 Tm to about 30 mm, about 600 Tm to about 25 mm, about 600 Tm to about 20 mm, about 600 Tm to about 15 mm, about 600 Tm to about 10 mm, about 600 Tm to about 5 mm, about 600 Tm to about 1 mm, about 600 Tm to about 900 Tm, about 600 Tm to about 800 Tm, about 600 Tm to about 700 Tm, about 700 Tm to about 50 mm, about 700 Tm to about 45 mm, about 700 Tm to about 40 mm, about 700 Tm to about 35 mm, about 700 Tm to about 30 mm, about 700 Tm to about 25 mm, about 700 Tm to about 20 mm, about 700 Tm to about 15 mm, about 700 Tm to about 10 mm, about 700 Tm to about 5 mm, about 700 Tm to about 1 mm, about 700 Tm to about 900 Tm, about 700 Tm to about 800 Tm, about 800 Tm to about 50 mm, about 800 Tm to about 45 mm, about 800 Tm to about 40 mm, about 800 Tm to about 35 mm, about 800 Tm to about 30 mm, about 800 Tm to about 25 mm, about 800 Tm to about 20 mm, about 800 Tm to about 15 mm, about 800 Tm to about 10 mm, about 800 Tm to about 5 mm, about 800 Tm to about 1 mm, about 800 Tm to about 900 Tm, about 900 Tm to about 50 mm, about 900 Tm to about 45 mm, about 900 Tm to about 40 mm, about 900 Tm to about 35 mm, about 900 Tm to about 30 mm, about 900 Tm to about 25 mm, about 900 Tm to about 20 mm, about 900 Tm to about 15 mm, about 900 Tm to about 10 mm, about 900 Tm to about 5 mm, about 900 Tm to about 1 mm, about 1 mm to about 50 mm, about 1 mm to about 45 mm, about 1 mm to about 40 mm, about 1 mm to about 35 mm, about 1 mm to about 30 mm, about 1 mm to about 25 mm, about 1 mm to about 20 mm, about 1 mm to about 15 mm, about 1 mm to about 10 mm, about 1 mm to about 5 mm, about 5 mm to about 50 mm, about 5 mm to about 45 mm, about 5 mm to about 40 mm, about 5 mm to about 35 mm, about 5 mm to about 30 mm, about 5 mm to about 25 mm, about 5 mm to about 20 mm, about 5 mm to about 15 mm, about 5 mm to about 10 mm, about 10 mm to about 50 mm, about 10 mm to about 45 mm, about 10 mm to about 40 mm, about 10 mm to about 35 mm, about 10 mm to about 30 mm, about 10 mm to about 25 mm, about 10 mm to about 20 mm, about 10 mm to about 15 mm, about 15 mm to about 50 mm, about 15 mm to about 45 mm, about 15 mm to about 40 mm, about 15 mm to about 35 mm, about 15 mm to about 30 mm, about 15 mm to about 25 mm, about 15 mm to about 20 mm, about 20 mm to about 50 mm, about 20 mm to about 45 mm, about 20 mm to about 40 mm, about 20 mm to about 35 mm, about 20 mm to about 30 mm, about 20 mm to about 25 mm, about 25 mm to about 50 mm, about 25 mm to about 45 mm, about 25 mm to about 40 mm, about 25 mm to about 35 mm, about 25 mm to about 30 mm, about 30 mm to about 50 mm, about 30 mm to about 45 mm, about 30 mm to about 40 mm, about 30 mm to about 35 mm, about 35 mm to about 50 mm, about 35 mm to about 45 mm, about 35 mm to about 40 mm, about 40 mm to about 50 mm, about 40 mm to about 45 mm, or about 45 mm to about 50 mm.

In some embodiments, the β-TCP is about 50% to about 70% porous, with the pores having a mean pore diameter of about 50 Tm to about 70 Tm (e.g., about 55 Tm to about 65 Tm, or about 60 Tm).

Compositions and Kits

Also provided herein are compositions (e.g., pharmaceutical compositions) that include any of the chimeric polypeptides or β-TCP-binding polypeptides described herein. In some examples, the compositions can further include β-TCP (e.g., any of the types of β-TCP described herein). In some examples, the β-TCP is formulated as a powder, a putty (e.g., a moldable putty), a paste, a scaffold (e.g., a porous scaffold), a sponge, and/or a coating on a solid surface (e.g., a coating on a medical device). In some examples, the β-TCP can be disposed on or in a scaffold, a mesh, or a sponge (e.g., a resorbable sponge).

In some instances, the compositions (e.g., pharmaceutical compositions) are disposed in a sterile vial or a pre-loaded syringe.

In some instances, the compositions (e.g., pharmaceutical compositions) are formulated for different routes of administration (e.g., intraarticular, injection into a joint, or injection proximal to a bone fissue or fracture). Single or multiple administrations of any of the pharmaceutical compositions described herein can be given to a subject depend on, for example: the dosage and frequency as required and tolerated by the subject. A dosage of the pharmaceutical composition should provide a sufficient quantity of the chimeric polypeptide to effective treat or ameliorate conditions (e.g., bone defects, bone fractures, cartilage defects, or cartilage loss), or symptoms.

Also provided herein are kits that include any of the chimeric polypeptides or any of the β-TCP-binding polypeptides described herein, or any of the compositions (e.g., pharmaceutical compositions) described herein. In some embodiments, the kits can include instructions for performing any of the methods described herein. In some instances, the kits can include at least one dose of any of the compositions (e.g., pharmaceutical compositions) described herein. In some embodiments, the kits can include a syringe for administering any of the pharmaceutical compositions described herein. The kits described herein are not so limited; other variations will be apparent to one of ordinary skill in the art.

Methods of Making a Composition

Also provided herein are methods of producing any of the compositions described herein. Any of the compositions provided herein can be produced using the methods described herein or methods known in the art. For example, to create a β-TCP scaffold, granulated β-TCP powder can be sintered, sieved, and fabricated into a desired shape (e.g., any of the shapes described herein). In some examples, the purity of the β-TCP present in any of the compositions described herein can be greater than about 75%, greater than 80%, greater than 85%, greater than 90%, greater than 95%, or greater than 99% pure. In some examples, the purity of β-TCP present in any of the compositions described herein can be greater than 1%, greater than 2%, greater than 3%, greater than 4%, greater than 5%, greater than 6%, greater than 7%, greater than 8%, greater than 9%, greater than 10%, greater than 12%, greater than 14%, greater than 15%, greater than 16%, greater than 18%, greater than 20%, greater than 22%, greater than 24%, greater than 25%, greater than 26%, greater than 28%, greater than 30%, greater than 32%, greater than 34%, greater than 35%, greater than 36%, greater 38%, greater 40%, greater than 42%, greater than 44%, greater than 45%, greater than 46%, greater than 48%, greater than 50%, greater than 52%, greater than 54%, greater than 55%, greater than 56%, greater than 58%, greater than 60%, greater than 62%, greater than 64%, greater than 65%, greater than 66%, greater than 68%, greater than 70%, greater than 72%, greater than 74%. In some examples, the β-TCP is made using a similar method but as a composite with other agents, such as a biocompatible polymer, e.g., polylactide-co-glycolide.

As will be apparent to those of skill in the art, the composition can further include one or more pore forming agents. Examples of pore forming agents include, e.g., inorganic salts, such as sodium chloride, saccharides (e.g., sucrose or glucose), gelatin (e.g., gelatin spheres), or paraffin (e.g., paraffin spheres).

The compositions described herein can be generated by contacting any of the chimeric polypeptides or any of the β-TCP-binding polypeptides to any of the types of β-TCP described herein. In some embodiments, the β-TCP can be in the form of a granular/powder form, a porous form, a putty (e.g., a moldable putty), a paste, a scaffold, and/or a coating on a solid surface (e.g., a coating on a medical device).

Methods of Treatment

Provided herein are methods of promoting bone or cartilage formation in a subject in need thereof that include: administering to the subject a therapeutically effective amount of any of the compositions described herein. Some embodiments of these methods can further include first selecting a subject in need of bone or cartilage formation. In some embodiments, the composition is administered to the subject proximal to the desired site of bone or cartilage formation in the subject.

Also provided herein are methods of replacing and/or repairing bone or cartilage in a subject in need thereof that include: administering to the subject a therapeutically effective amount of any of the compositions described herein. Some embodiments of these methods can further include first selecting a subject in need of bone replacement, bone repair, cartilage replacement, or cartilage repair. In some embodiments, the composition is administered to the subject proximal to the desired site of bone or cartilage replacement or repair in the subject.

Also provided herein are methods of treating a bone fracture or bone loss in a subject in need thereof, the method comprising administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

Also provided herein are methods of repairing soft tissue in a subject in need thereof that include: administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

Also provided herein are methods of localized delivery of a therapeutic to a subject in need thereof that include: administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

In some instances, the subject has a bone fracture or a bone defect.

In some instances, the subject requires a vertebral fusion of the spine.

In some instances, the subject has a cartilage tear or cartilage defect.

In other instances, the subject has cartilage loss.

Methods of determining the efficacy of treatment of a bone fracture or bone loss in a subject are known in the art and include, e.g., imaging techniques (e.g., magnetic resonance imaging, X-ray, or computed tomography).

Methods of detecting bone or cartilage formation, or replacement or repair of bone or cartilage in a subject are also known in the art and include, e.g., imaging techniques (e.g., magnetic resonance imaging, X-ray, or computed tomography).

Suitable animal models for treatment of a bone fraction or bone loss, bone or cartilage formation, or bone or cartilage replacement or repair are known in the art. Non-limiting examples of such animal models are described in the Examples and in, e.g., Drosse et al., *Tissue Engineering Part C* 14(1):79-88, 2008; Histing et al., *Bone* 49:591-599, 2011; and Poser et al., Hindawi Publishing Corporation, BioMed Research International; Article ID 348635, 2014.

The invention is further described in the following examples, which do not limit the scope of the invention described in the claims.

EXAMPLES

Example 1. A Preclinical Study of tBMP-2 in a β-TCP Carrier in a Rat Critical Size Femoral Defect Model The aim of this study was to examine the safety and effect of modified recombinant human bone morphogenetic protein (rhBMP) known as tBMP in a beta-tricalcium phosphate ((β-TCP) putty matrix in the replacement and repair of bone in a rat critical size defect model. The tBMP-2 variant exhibits very tight binding to calcium phosphate ceramics and thus allows for targeted delivery of tBMP-2 to implant sites. This was achieved by surgically creating the defect using the RatFix internal fixator system, then filling that defect with tBMP+β-TCP putty, or β-TCP putty alone as a control. The positive control was a dose-adjusted commercially available (Medtronic) preparation for human use of rhBMP with an absorbable collagen sponge (ACS). The animals were monitored clinically and had bi-weekly radiographs until their scheduled end-points at four or eight weeks post-administration of treatment. Ex vivo histology was conducted on organs and tissues, and the treated leg was subjected to CT, histomorphometry, and/or mechanical strength testing.

This report covers animal arrival, assignment to groups, surgical creation of defect and administration of test, reference or control item. In addition, this report covers the post-operative period up to and including Week 8, and end-point in vivo and ex vivo measurements. Included are the clinical summaries, radiographs, end-point clinical pathology and organ histopathology, histomorphometry of treated legs (odd-numbered animals), and mechanical strength testing of treated legs (even-numbered animals).

On arrival at the Test Facility, all animals underwent a Veterinary health check and were weighed. Based on the weights, the animals were assigned to groups A) tBMP+β-TCP putty; B) rhBMP+ACS; or C) β-TCP putty alone. The animals then had at least five days to acclimatize to their new surroundings and diet.

On the day of surgery, the animals were anaesthetized, the defect was created and the bone supported with the internal fixator following the method supplied by the manufacturer with some refinements to the surgical procedure. The pre-prepared test, reference or control item was then inserted into the defect. The surgical site was closed and the animal went immediately for X-ray. Following completion of the baseline radiograph, post-operative pain relief was administered and the animal was returned to its cage for recovery. Post-operative analgesia and antibiotic therapy were continued for at least two days, and longer when required.

A number of the original animals were removed from the study and replaced prior to surgery as they were getting too large for the fixator system specifications. The second, replacement group also had a thorough Veterinary health check and were weighed prior to being assigned to groups. The allocation of animals to either four or eight-week end-point groups was adjusted to include animals from both weight ranges at both end-points.

A total of 61 animals were successfully administered assigned treatment and recovered from surgery. Of these, one animal was euthanized five days post-operatively due to poor recovery and inappetence. The animal was replaced.

Two animals which were found to have dislodged bone plates during their 2-week post-operative radiographs were humanely killed and not replaced. Two animals did not successfully recover from surgery, one died immediately post-surgery, and the other had an unstable bone plate which could not be fixed, and so was humanely killed. Both of these animals were replaced immediately.

The animals were monitored at least once daily, and their clinical signs scored. Any animal with unusual findings, or considered to be not eating and gaining weight normally was monitored more frequently, and veterinary advice was sought. When unusual findings were noted, this resulted in possible treatment with additional antibiotic or analgesic therapy, fluid supplementation), and in four cases euthanasia (three broken bones and one with continued weight loss).

All relevant animals received bone-labelling dyes at 10 days (calcein green) and 3 days (xylenol orange) prior to their scheduled end-point date. All animals had end-point blood samples collected. There were no clinically significant differences found between any of the groups for any biochemical or haematological parameter at either end-point time. Three haematology samples were clotted and could not be analysed.

In all specimens examined, there was evidence of extensive mineralization akin to mature trabecular bone in samples from animals in the tBMP+β-TCP putty group (Group A). This mineralization appears to be lamella (mature) bone rather than the woven bone that occurs in early callus formation (presence of osteocytes). Group A animals also had osteoclasts present (suggesting active remodelling), and red blood cells and adipocytes, indicating angiogenesis and infiltration of cells to most regions of the callus. Whilst there is mineralized bone in the specimens from the rhBMP+ACS group animals, there are extensive regions of unmineralized fibrous and cartilaginous tissue within the callus region. The callus development in these samples appears to be at an earlier stage than that observed in the Group A animals. The Group C (β-TCP putty) samples show no evidence of mineralization, bone formation or bone remodeling even at eight weeks post-application of treatment.

The mechanical testing analyses showed the tBMP+β-TCP group animals (Group A) had significantly stronger bones at the four and eight week end-point times than either of the other treatment groups.

In conclusion, the bone specimens form the tBMP+β-TCP putty group clearly demonstrated vastly improved bone healing at 4 and 8 weeks post-surgery when compared to samples from animals in the rhBMP+ACS or the β-TCP putty alone treatment groups. The aim of this study was to evaluate the performance of a modified variant of recombinant human BMP-2 (rhBMP-2) called tBMP-2. The tBMP-2 variant exhibits very tight binding to calcium phosphate ceramics and thus allows for targeted delivery of tBMP-2 to implant sites. The ability to tether BMP-2 in this manner will allow for longer persistence times, lower doses, and, it is expected, superior outcomes.

Animals

The rat is a validated animal model for assessing the effect of treatments on critical-sized defects in the femur (4-6). Sixty male rats (plus spares) were required: ten animals in each group per time point. One animal was replaced after successful administration of the test item at day 5 post-surgery as he was losing weight and not eating. Animals that were euthanized or humanely killed after successful administration of the test item were necropsied and had tissue collected for histopathology. The number of animals used in this study was considered sufficient for evaluation of results.

The animals were housed in conventional conditions (targeted temperature 22±3° C., 12/12-hour light/dark cycle) in standard open top cages that satisfy the size requirements specified in the Animal Welfare Regulations (Animal Welfare Act 1985, v 15.10.2015. Attorney General's Department, Government of South Australia). Animals were housed individually for the entirety of the experiment. The animals had access to standard laboratory rat chow (Specialty Feeds, Glen Forest, Australia) 25-30 g/day. Immediately post-operatively, and when rats were not thriving, the food was soaked in water for easier palatability. Chlorinated tap water was provided to the animals ad libitum. Food and water were not withheld at any time.

Each animal was uniquely identified by a subcutaneously implanted microchip which was scanned using a barcode reader. For the purpose of the study, each animal was also given a number from 1-70 (to include replacement and spared required). As the initial batch of animals gained weight too quickly, some animals were replaced prior to surgery. The replacement animals were given the number of the animal they replaced and the suffix (a) was added. Numbers went up to 68a with a couple of gaps.

Animals were assigned to groups by a weight-ordered distribution. The heavier animals were used first. The animals gained weight rapidly, even on the restricted food allowance. Two weeks into the surgeries, it was deemed necessary to remove some animals from the study (n=16) as these animals were already too heavy (>425 g). These animals were replaced with animals in the 250-300 g range. The replacement animals were also assigned to treatment groups on a weight-ordered distribution. As the first surgical group had originally been assigned to the 8-week end-point group, animals were reassigned to either 4- or 8-week end-points to ensure the lighter animals were evenly distributed amongst the treatment and end-point times.

Analgesia/Antibiotic Therapy

All interventional procedures were performed under isoflurane in 02 anaesthesia. Induction and maintenance of surgical depth anesthesia was at 24% isoflurane (Baxter International, Sydney, Australia) in a flow of 1-2 L/minute 02. Post-operatively, after closure of the wound, a topical application of local anesthetic in the form of Marcaine (Bupivacaine, 0.5%, AstraZeneca, Frewville, SA, Australia) up to 2.5 mg/Kg was applied to the area around the wound. The animals received 0.1 mg/kg buprenorphine (Temgesic, Reckitt-Benckiser, Melrose Park, Australia) subcutaneously post-operatively after X-ray. They also received 0.1 mg/kg subcutaneously twice daily for two days post-operatively. Additionally, they were given a non-steroidal anti-inflammatory treatment in the form of Carprieve (Carprofen, 50 mg/mL, Norbrook Laboratories, Tullamarine, Australia) at a dose of 5 mg/kg subcutaneously post-operatively and once daily for at least two days post-surgery.

All animals received cephalosporin (Cefazolin, Hospira Inc, Lake Forest IL, USA) 20 mg/kg subcutaneously intra-operatively and twice daily for two days post-operatively. Any animals that needed re-suturing of their wounds received antibiotic treatment for up to fourteen days post-repair. Antibiotic therapy was ceased if suspected to be causing diarrhea and/or weight loss.

Microchip Implantation

The microchip was inserted into the scruff of the neck (after clipping hair) using a microchip implanter. The microchip was inserted until completely covered by skin. The wounds were closed with one or two wound clips if required. The area was swabbed with betadine. This was performed under isoflurane in 02 anaesthesia at the same time as the defect surgery and test- or reference-item placement.

Critical-Size Defect Creation

The defects were created in the right femur of all rats as described for the RatFix RISystem. Briefly, all anaesthetized rats were placed on a warming pad in lateral recumbency with the right leg facing upwards. The surgical site was shaved and aseptically prepared with iodine or chlorhexidine scrub and solution. A skin incision between the greater trochanter and the knee joint was made and the superficial fascia incised. The intermuscular plane between the vastus lateralis and the biceps femoris was separated and the periosteum of the femur incised. The PEEK plate was fitter into the jug and secured with suture material. The jig-plate assembly was fixed to the craniolateral surface of the femur by pulling the sutures through under the femur, allowing the assembly to be tightened to the femur.

After predilling the holes in the PEEL plate using the supplied drill bit, the plate was attached to the femur by six bicortical titanium screws. Standardised 6-mm defects were created (marked on the plate) using the Gigli wire saw guided by the sawing device of the jig. After defect sawing, the jig and bone piece were removed. The fresh defect was flushed with sterile saline and dried with gauze in preparation of test item or reference item, or vehicle administration into the defect size. In the event that the plate itself was damaged with the cutting wire, reducing stability, that animal would be replaced. No replacements due to plate damage were required.

Baseline Radiographs

Baseline radiographs were taken immediately after creation of the defect and administration of the test or reference item to show position of treatment articles (where visible), and placement of the plate, whilst the animal was still under anaesthesia.

Radiographic Assessments

X-rays were taken on the anaesthetized animals (isoflurane) immediately after surgery, and at 2, 4 (end-point for half of the animals), 6 and 8 weeks (end-point for the remaining animals) post-operatively. The radiographs were taken in lateromedial and craiocaudal projections for assessment of bone healing and to exclude implant loosening or failure. All in-life radiographs were taken using a Villa Visitor Mobile X-ray Unit (Villa Sistemi Medicali, Buccinasco, Italy), using a dental image capture device (Soredex, Digora Optime, Tuusula, Finland). The images were transferred to the PIRL picture archiving and communication system (PACS, Carestream Vue Motion, Rochester, USA) by the radiographer for storage and access.

Bone Labelling

At 10 days prior to their prescribed end-point, all animals received an intraperitoneal injection of calcein green (25 mg/kg in saline). At 3 days prior to their prescribed end-point all animals received an injection of xylenol orange (10 mg/mL, 25 mg/kg, intraperitoneal) to double-label the bone for histomorphometric analyses.

Blood Collection Haematology

All blood collections were performed on anaesthetized animals at their end-point radiograph. Blood was collected via cardiac puncture.

Blood samples were evaluated for the parameters specified in Tables 1 and 2. For Table 1, samples of approximately 2 mL were collected into tubes containing $K_2EDTA$ anticoagulant for haemotological analyses. Analyses were performed on an Abbott Cell Dyn. 3700 (Abbott Laboratories, North Ryde, Australia). For Table 2, samples of approximately 5 mL were collected into tubes containing a clot activator for biochemical analysis. Analyses were performed on a Siemens Advia 1800 (Siemens Healthcare Diagnostics Inc., Flanders, NJ, USA).

TABLE 1

| Haematology Parameters to be reported | |
|---|---|
| Haemoglobin (Hb) | White Cell Count (WCC) |
| Erythrocyte count (RBC) | Mean Corpuscular Volume (MCV) |
| Packed Cell Volume (PCV)/ Haematocrit (HCT) | Mean Corpuscular Haemoglobin (MCH)* |
| Mean Corpuscular Haemoglobin Concentration (MCHC)* | Red Cell Distribution Width (RDW) |
| Platelets (Plt) | |
| White Blood Cell Differential: Neutrophils, Lymphocytes, Monocytes, Eosinophils, Basophils | |

*Calculated values

TABLE 2

| Serum Chemistry Parameters to be reported | | |
|---|---|---|
| Electrolytes: Sodium (Sod) Potassium (Pot) Chloride (Chl) Bicarbonate (Bicarb) | Anion Gap* (AG) Glucose (Gluc) Urea Creatinine (Creat) Cholesterol (Chol) | Albumin (Alb) Globulin* (Glob) Protein (Tot Prot) Total bilirubin (Tot Bili) Lactate Dehydrogenase (LD) |
| Lipid Studies: Triglycerides (Trig) High Density Lipoproteins (HDL) Low Density Lipoproteins (LDL) Chol/HDL* | Urate (Uric Acid, UA) Phosphate (Phos) Gamma glutamyltransferase (GGT) Asparatate aminotransferase (AST) | Alkaline phosphatase (ALP) Total Calcium (Tot. Ca) Alanine aminotransferase (ALT) |

*Calculated values

Mechanical Strength Testing

This was performed on half of the animals at each time point. All tissue was placed in 0.9% NaCl-soaked gauzed in 50-mL sterile urine pots to avoid freezer burn and stored frozen at −20° C. until testing. Tissue was prepared immediately and frozen within one hour of collection to avoid autolysis. Immediately before testing, tissues were thawed, and the internal fixator device carefully cut in the middle section. Tissue was test at room temperature (approximately 23° C.). The ultimate breaking strength was measured by using a load frame (model 5542, Instron, Canton, MA) and a 3-point bend fixture (model 2810-400, Instron) at a crosshead speed of 10 mm/min. The load cell for this testing (Instron 2530-416) had a maximum capacity of 500 N. The data (force in kg and extension in mm) was collected and analysed with a vendor-provided commercial mathematical software package (Bluehill2, Instron).

Histological Analyses

Specimen were fixed in 10% formalin for 7 days prior to processing. Formalin-fixed bones were cut using a slow-speed saw (Buehler Ltd, IL, USA) along the sagittal plane using a diamond-tipped cutting blade before being submerged in 70% ethanol. Subsequently, bones were processed for resin embedding via several dehydration steps. Briefly, bones were submerged in 2×90% ethanol and 1×100% ethanol steps over 48 hours. Bones were then transferred into a solution containing methymethacrylate (MMA) and 10% v/v polyethylene glycol (PEG) and stored at room temperature for 10-14 days. Resin embedding then occurs by preparing a solution of MMA, 10% PEG, and 0.4% peroxydicarbonate (Perkadox) and incubation at 37° C. for 24 hours to allow the resin to harden. The exposed cut surface was placed facing down in the tube. The resin-set bones were then removed from their tubes and fixed to stubs for sectioning. For each bone, 5-μm thick sections were cut using a tungsten-carbide blade (Leica RM2255, Wetzlar, GER). Sections were placed on to gel-coated slides and dipped 2 times in a spreading solution (70% ethanol/30% 2-ethoxyethanol) heated to 70° C. To ensure adherence to the slide, sections were flattended, covered by strips of polyethylene and clamped together separated by blotting paper, before being placed into a 37° C. oven. Prior to commencing staining procedures, sections were placed in acetone for 15 minutes, unless otherwise stated. All sections were digitally scanned at 100× magnification (3D Histech scanner, TMA-MASTER01).

Von Koss+Haemaotoxylin and Eosin (H&E) Staining

Acetone treated sections were rinsed in demineralised water for 2 minutes. Sections were then placed in a 1% silver nitrate solution and placed in front of a UV lamp for 60 minutes. Washed slides were then treated with 2.5% sodium thiosulphate solution for 5 minutes. Washed slides were then counterstained with H&E. To stain for H&E, sections were placed in haematoxylin for 8 minutes to stain cell nuclei before being rinsed in demineralised water for 2 minutes and dipped in acid alcohol (%), typically, 4-5 minutes. After rinsing in demineralised water, sections were dipped in lithium carbonate 4-5 times and placed in eosin for 4 minutes. Once removed, excess eosin was removed with a squeeze bottle of absolute alcohol, sections were hydrated, placed in xylene and mounted in xylene-based mounting medium.

Tartrate-Resistant Acid Phosphatase (TRAP) Stain for Analysis of Osteoclasts

Acetone treated sections underwent a 60-minute incubation in Tris-HCL buffer (pH 9.4) at 37° C. for 60 minutes in an acid phosphatase (AcP) stain prepared by adding 0.0355 g of tartaric acid dissolved in 35 mL of sodium acetate (pH 5.2) to 100 μL basic fucshin in a 100 μL solution containing 0.4 mg of sodium nitrite. This solution was then added to a solution containing 0.04 g Napthol ASBI phosphate (Sigma-Aldrich, Missouri, USA) in 2 mL dimethylformamide. Subsequently, two washed were performed before the sections were counterstained in haematoxylin for 8 minutes, then rinsed in demineralised water, then dipped in acid alcohol 4 times, rinsed again, dipped in lithium carbonate 4 times and then dehydrated, placed in xylene and mounted in DPX. Quantification of osteoclast number per bone perimeter mm was performed by identifying cells (stained pink-red) on the surface of bone (stained blue-purple) and calculated by the OsteoMeasure histomorphometry system.

Double Fluorochrome Labelling of Bone Sections for Measures of Bone Formation

Acetone sections were immediately placed in xylene and mounted in DPX. Slides were viewed under a fluorescent microscope (Olympus BX53; Olympus, Tokyo, JP).

Histomorphometry

Those animals which did not have mechanical testing of femurs will undergo histological analysis of the defect and treatments. Following CT of the femurs, they were opened at the wound site, and the internal fixator device carefully removed. They were placed in 70% ethanol. Femurs were placed in PMMA, polymethyl methacrylate (10% polyethylene glycol [PEG] in methylmethacrylate) for 10-14 days, then polymerized in PMMA containing 10% Perkadox 16 (di[4-tert-butylcyclohexyl] peroxydicarbonate) at 37° C. for 24 hours. Sections were stained with H&E, and tartrate resistant acid phosphatase (TRAP) for analysis.

Humane Killing

Animals were humanely killed on day 28±2 days (n=30) or day 56±3 (n=30) immediately following their end-point radiograph and blood collection, and whilst still under anaesthesia, with an intracariac injection of a lethal dose of sodium pentobarbitone of 60 mg/mL formulation (Lethabarb®) at 200 mg/kg. Death was confirmed by lack of respiration and palpable heartbeat, loss of corneal reflex and loss of colour of mucous membranes.

Necropsy

All animals were subjected to a comprehensive necropsy. A comprehensive necropsy is defined as examination of the external surface of the body, all orifices, and the cranial, thoracic, and abdominal cavities, and their contents. If abnormalities were found in tissues or organs other than those listed below, they were also collected for histology.

Organ and Tissue Collection

Whole organs, sections of the issues listed in Table 3 below were dissected free and fixed in 10% neutral buffered formalin. This was done for twelve animals from each groups (six animals from each group at each time-point). The animals were selected such that at least one from each group was selected at each end-point (staggered as surgeries were staggered).

TABLE 3

Organ and Tissue Samples Collected From Each Animal

| | | |
|---|---|---|
| Adrenal gland | Lesions | Skin (containing implant[s]) |
| Brain | Liver | |
| Cecum | Lymph node (mesenteric) | Spinal cord (cervical, thoracic, and lumbar) |
| Duodenum | Pancreas | |
| Eye | Pituitary Gland | Spleen |
| Heart | Rectum | Sternum (+bone marrow) |
| Ileum | Salivary gland (mandibular) | Stomach |
| Jejunum | Sciatic nerve | Thymus |
| Kidney | Skeletal muscle (thigh) | Tongue |
| Femur with bone marrow(articular surface of the distal end) | Lung (with mainstem bronchi) | Epididymis |
| | | Prostate/seminal vesicles, bladder, testes |

Treated Limb Collection and Storage

Immediately following confirmation of death, the treated leg was removed and placed in either 1000 neutral buffered formalin (n=5 animals/group/time point), or wrapped in saline-soaked gauze and placed at −20° C. for at least 48 hours (n=10 animals/group/time point).

μCT

All legs had μCT measurements (Bruker Skyscan 1076, Brussels, Belgium) of the defect performed to quantify newly mineralized bone volume. This was done on all animals at each end-point time. The bones were either formalin-fixed (105 neutral buffered formalin) or frozen at −20° C. for 3-5 days prior to testing. The plate was adjusted to the longitudinal axis of the device. Scanning parameters and intensity were recorded and were in the vicinity of a source voltage of 70 kV with an intensity of 114 μA. The end-point μCT was manually and subjectively scored as described by Chhabra et al. (2005) using the grading system described in Table 4.

TABLE 4

| Radiographic Grading Scale of Fracture Callus Formation | |
|---|---|
| Grade | Amount of Callus Formation |
| 0 | No callus |
| 1 | Little-to-moderate callus |
| 2 | Profuse callus tissue |
| 3 | Bridging periosteal callus |
| 4 | Mature callus with interfragmentary bridging |
| 5 | Callus resorption after solid union |

Study Design

The study was performed as outlined in Table 5. There were three groups with 20 animals/group. All animals underwent surgery to create a critical-size defect (6-mm) in the mid diaphysis of the right femur (RatFix RISystem), and had inserted into the defect test item, reference item or vehicle. The animals were monitored at least once daily and were weighed at least twice weekly. They underwent radiographic evaluation immediately post-operatively, and at 2, 4, 6, and 8 weeks post-surgery. Ten animals from each group (n=30 animals) were scheduled to have end-point data (CT, mechanical testing, histomorphometry, clinical pathology) collected 4 weeks post-operatively and the remaining animals (n=30 animals) were scheduled for end-point data collection 8-weeks post operatively. Of these, six from each group (chosen such that there was a representative from each group from the majority of surgical days) at each end-point had tissues and organs collected for histology.

TABLE 5

| Study design | | | | |
|---|---|---|---|---|
| | | | End-Point (n) | |
| Group | Treatment | Nomenclature | Week 4 | Week 8 |
| A | tBMβ-2 + β-TCP putty | tBMβ-2 + β-TCP putty | 10 | 10 |
| B | rhBMβ-2 + absorbable collagen sponge (ACS) | rhBMP2 + ACS | 10 | 10 |
| C | β-TCP putty | β-TCP putty | 10 | 10 |

Group A animals received tBMP-2+β-TCP (0.615-0.620 mg tBMP-2 in β-TCP putty to fill defect); Group B animals received InFUSE™ Bone Graft of rhBMP-2+ACS (2 μg rhBMP-2 on ACS to fill defect); Group C animals received β-TCP to fill the defect. All test and control items were mixed on the day of surgery (tBMP-coated β-TCP to putty or rhBMP to ACS). Following administration of the treatment article, the wounds were closed in two muscle layers with subcutis and intracutaneous vicryl sutures. The wounds were closed exteriorly with intradermal sutures to prevent chewing by the rats. The wounds were washed with liberal amounts chlorhexidine solution. A small amount of tea tree oil was applied to the area surrounding the actual wound to prevent the animals from worrying the suture side.

Route of Administration

The anticipated route of human administration is by surgical implantation into a bone defect. Therefore, that route was used in this study. The bone defects were surgically created, the area flushed with saline, then the test or control items were placed in the defect immediately.

Preparation of Test Item (tBMP-2+β-TCP Putty)

For each rat, 195 μL of tBMP-2 (stock 3.53 mg/mL) were added to a pre-weighed aliquot of 47 mg β-TCP granules and mixed gently for 2-3 hours. All liquid was removed, and retained for analysis. The pellet was washed with 1 mL of sterile phosphate-buffered saline (PBS pH 7.4) and mixed gently to wash away any excess unbound protein. As much as possible of the liquid was removed with a pipette, and sterile pre-weighed putty was added to the protein-coated β-TCP. β-TCP and putty were mixed 1:1. The entire tBMP-2+β-TCP putty formulation was placed in the surgically-created defect. Assuming approximately 90% binding, the final dose of tBMP which was administered to the rat in the defect was 615-620 μg. Sterility was maintained at all steps. β-TCP binding to tBMP-2 was done no more than 48 hours prior to surgery. If β-TCP was bound/washed the day before surgery, it was stored at 4° C. β-TCP and putty were not mixed more than one hour prior to implantation, as it will dehydrate with time and become less malleable.

Reference Item

Recombinant human bone morphogenetic protein+absorbable collagen sponge (InFUSE™ Bone Graft; size XX small; Medtronic Sofamor Danek, Inc) was used as per packet insert with modifications as described below. BMP-2 vial contents were reconstituted with the provided sterile water to give 1.5 mg/mL rhBMP-2. This concentration is intended for human use. To bring this concentration to the range typically used in rats, it was diluted 1 in 60 with PBS (25 μg/mL). A defect volume of approximately 75.5 $mm^3$ was assumed, therefore the ACS was trimmed to form a 6-mm×4-mm block for insertion into the defect. Diluted rhBMP solution (80 μL) were added to the ACS in a dropwise fashion at least 15 minutes prior to insertion into the defect. This resulted in 2 μg tBMP-2 in the defect. Sterility was maintained.

μ-TCP Putty

β-TCP granules (46-48 mg aliquots), carboxymethyl cellulose putty (48-50 mg aliquots). Under sterile conditions, the β-TCP granules were washed with 1 mL of sterile PBS and mixed gently. As much as possible of the liquid was removed using a pipette. Pre-weighed sterile carboxymethyl cellulose (approximately 2 mg more than the β-TCP putty formulation was inserted into the defect.

Dose Formulation

The rhBMP-2+absorbable collagen sponge and the tBMP-2+β-TCP putty were prepared as described above. The final dose each rat received of the BMP-2 formulations was 2 μg rhBMP-2 for the reference item and approximately 615-620 μg tBMP of the test item.

Animal Assignments and Body Weights

On arrival, the initial animals were numbered 1-63, of which 60 were assigned to the study. The animals were fed ad lib on arrival, but this was reduced to 35-30 g when it was found at their third weighing that they were gaining weight too quickly. The initial surgeries were delayed by one week, and as the animals weights continued to increase, the decision was made to remove the heaviest sixteen animals from the study and get replacement animals. The replacement animals were assigned numbers.

Figure 1B:
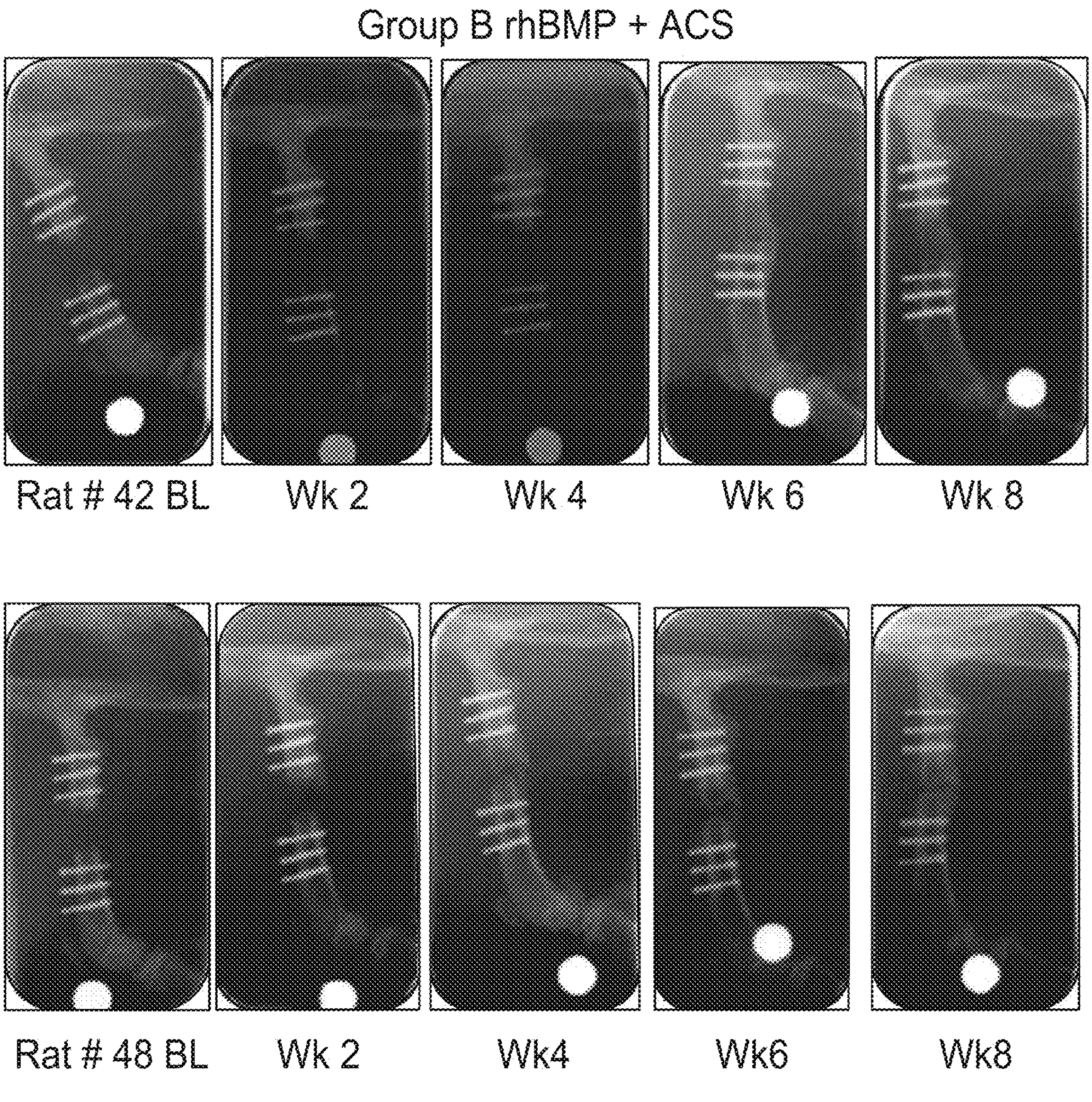
FIG. 1B are representative in vivo radiographs (lateromedial orientation) of animals from experimental Group B.
Figure 1C:
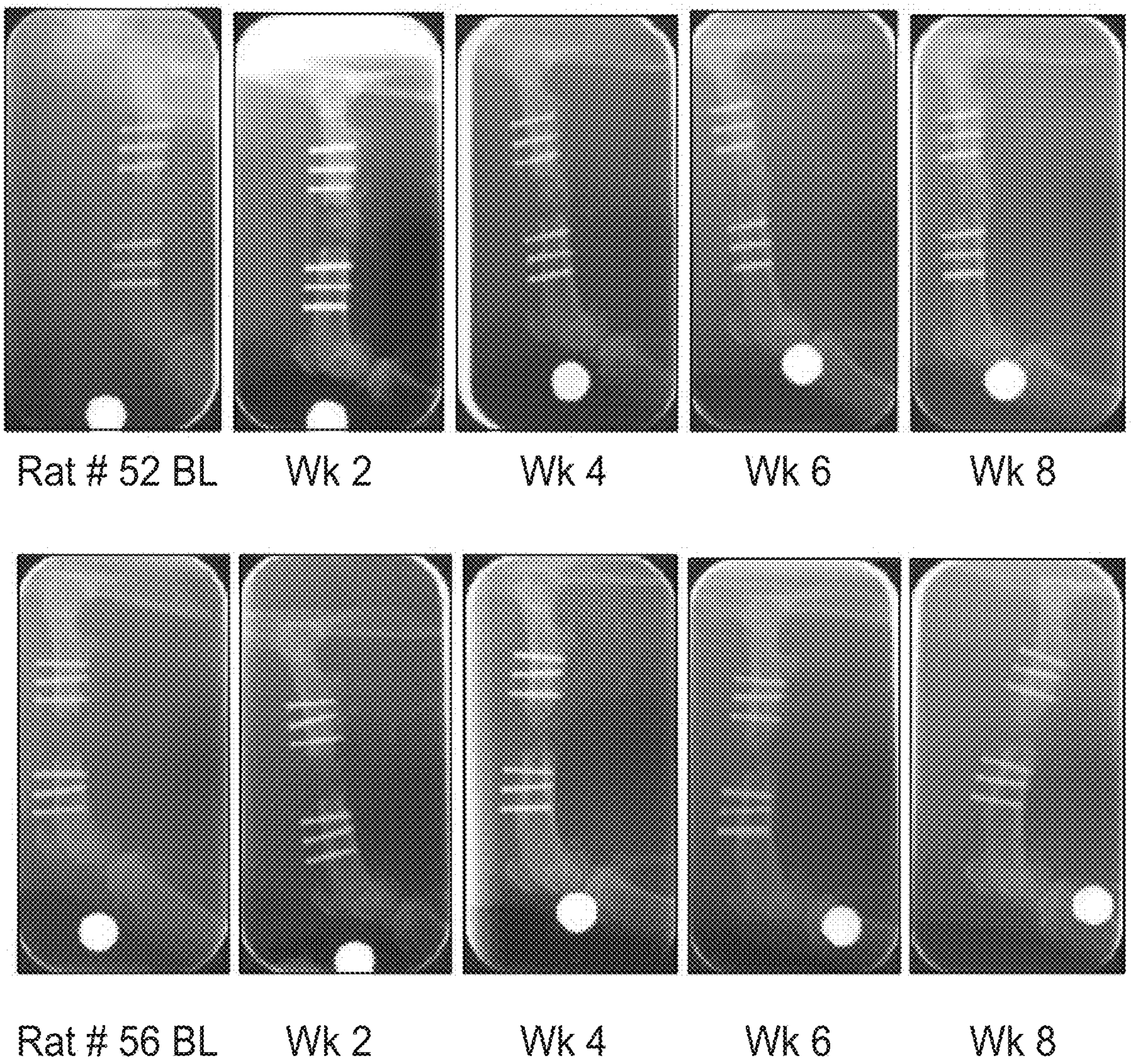
FIG. 1C are representative in vivo radiographs (lateromedial orientation) of animals from experimental Group C.

All animals were weighed on arrival and assigned to one of three groups on a weight-ordered distribution. All allocations to group and end-point times were done to ensure there were no significant differences in weight prior to the surgical intervention between any of the groups in terms of treatment to be administered, or time to end-point (either 4- or 8-weeks post-surgery). There were no significant differences in weights at assignment to study between any of the groups for either the initial group of animals or the replacement group, or at any time for the duration of the study (FIG. 1A, FIG. 1B and FIG. 1C).

Example 2. Radiographic, Mechanical, Histomorphometric and Histological

Analyses of 4 and 8 week post-fracture healing in three experimental rat fracture groups (A, B and C)

To assess the extent of mineralized bone material within the callus region of fractures in three experimental rat groups (A, B and C), radiographic scoring of callus formation, mechanical testing of the callus strength, high resolution micro computed tomography (CT), and quantitative histological analyses of bone formation and resorption were conducted.

Radiographic Assessment

Sagittal radiographic images were generated using a Faxitron X-ray with fixed exposure settings. Radiographic scoring specifically on callus formation healing was based on Chhabra et al. (2005) *J Orthop Trauma* 19(9): 629-634, and modified from Marino et al. (1979) *Clin Orthop Relat Res* (145): 239-244 and Makley et al. (1967) *J Bone Joint Surg Am* 49(5): 903-914 (Table 4). Scoring was performed in one session on de-identified, randomised radiographs. Both the posterior and anterior aspect of the cortex at the site of fracture was scored. The average score for each specimen was recorded.

Figure 2:
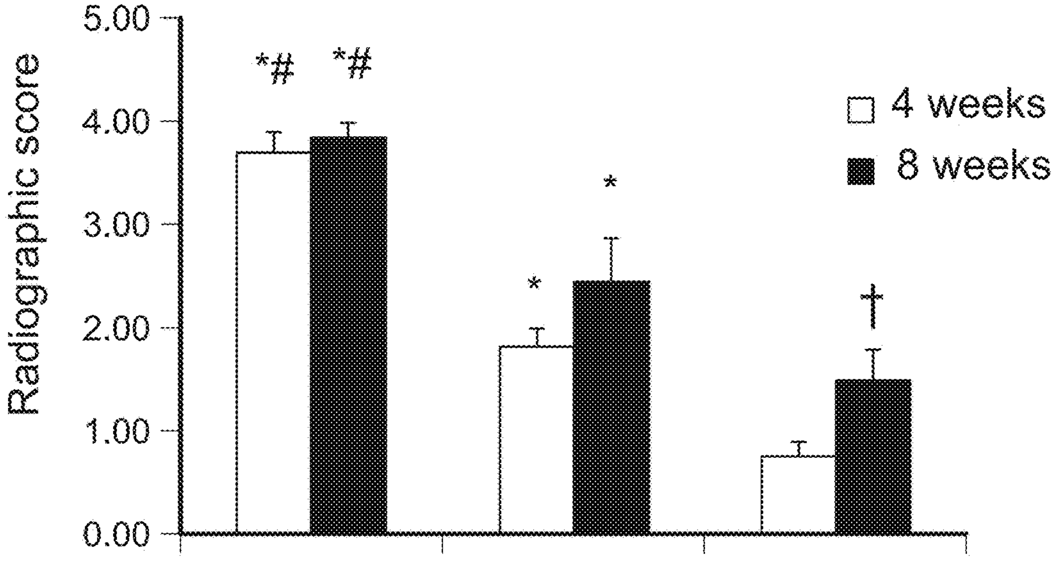
FIG. 2 is a representative graph of the mean radiographic score (+SEM, n=9-10) of animals from each Group at four weeks- and eight weeks-post-surgery. * P<0.01 vs Group Cl #P<0.01 vs Group V; +P<0.01 vs Group C at 4 weeks.

Baseline radiographs were taken on all animals as soon as possible after surgery whilst still under anaesthetic, at two weeks, four weeks (end-point for half of the animals), six weeks and eight weeks (end-point for remaining animals) post-surgery. They were taken in lateromedial and craniocaudal views. FIG. 2 shows representative radiographs of animals from all groups at 0, 2, 4, 6, and 8 weeks post-surgery. The defect was only visible in Group B animals that received the rhBMP+ACS. The putty (with or without protein) in animals from Groups A and C appear to be outside the confines of the defect (more obvious in mediolateral view). This was the case in all animals, even when the surgeon reported that the putty appeared to be completely contained within the defect, and touching the muscle tissue had been completely avoided on insertion of the test or control items.

Ex vivo radiographs, as with the in vivo radiographs showed that the putty and/or bone growth was not confined to the defect area in Groups A and C, as it was in Group B images (FIG. 2).

Figure 3A:
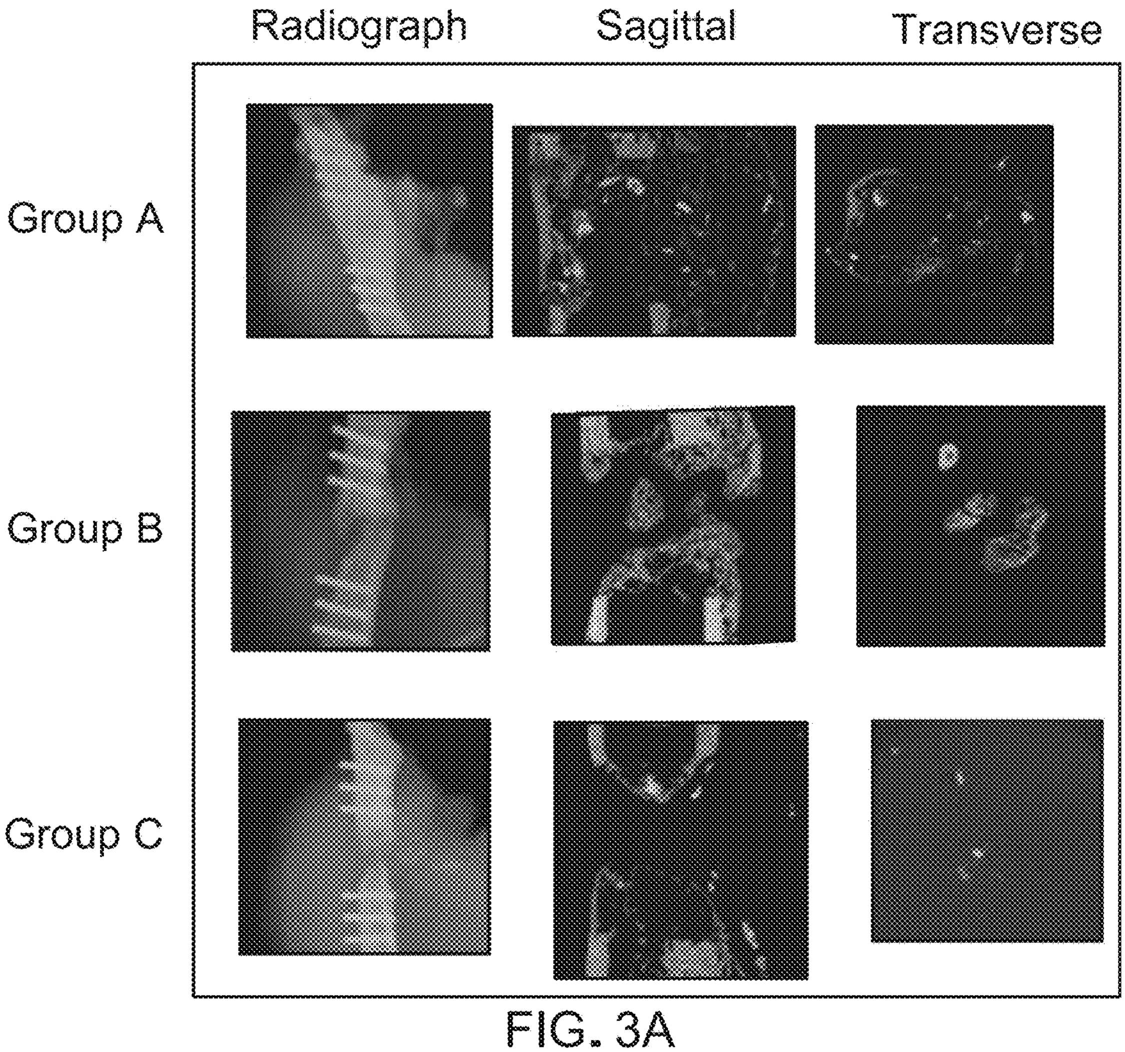
FIG. 3A are representative radiographs, sagittal, and transverse micro-CT images at 4-weeks post-operation from animals in Group A, B, or C.
Figure 3B:
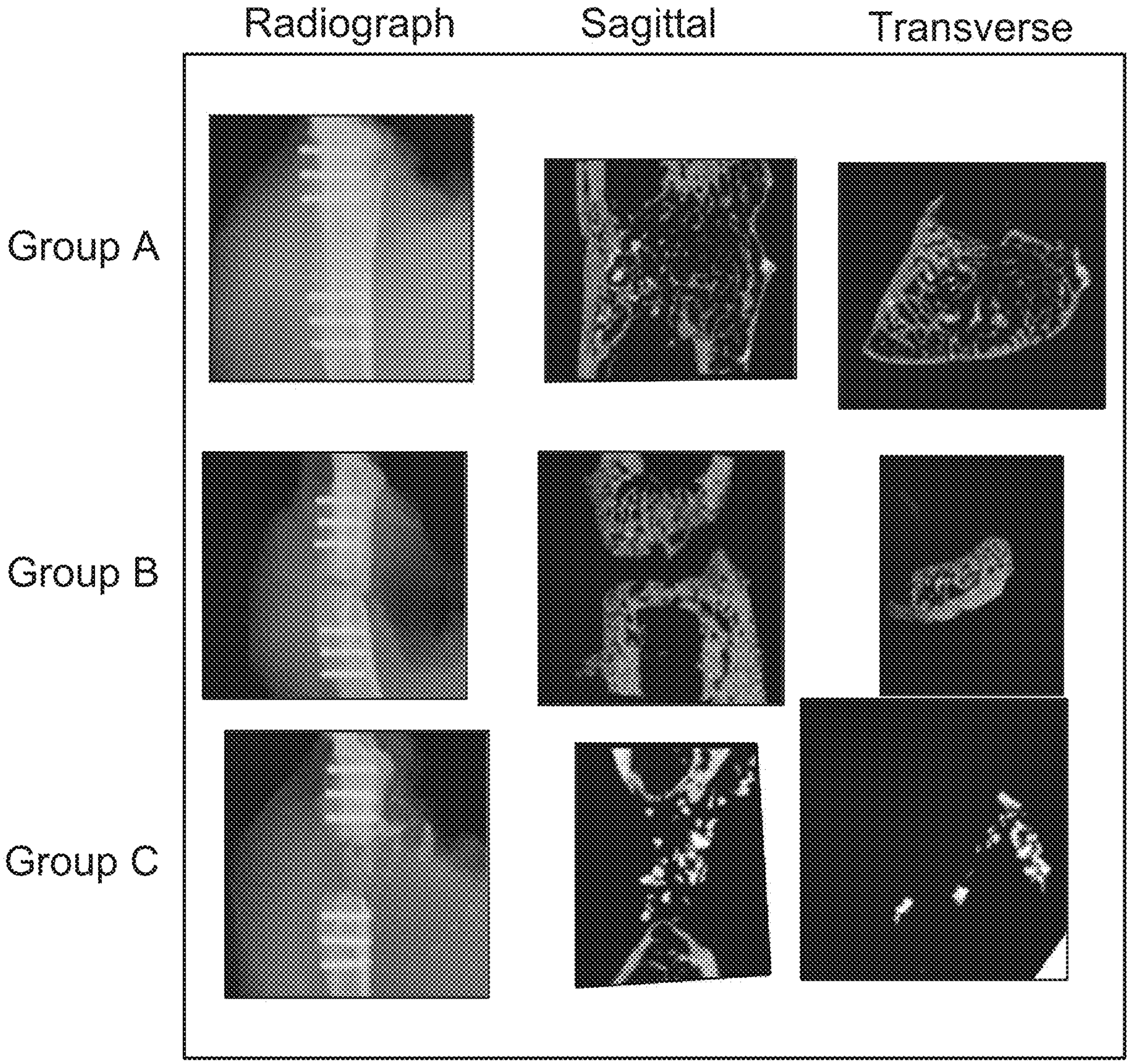
FIG. 3B are representative radiographs, sagittal, and transverse micro-CT images at 4-weeks post-operation from animals in Group A, B, or C.
Figure 4:
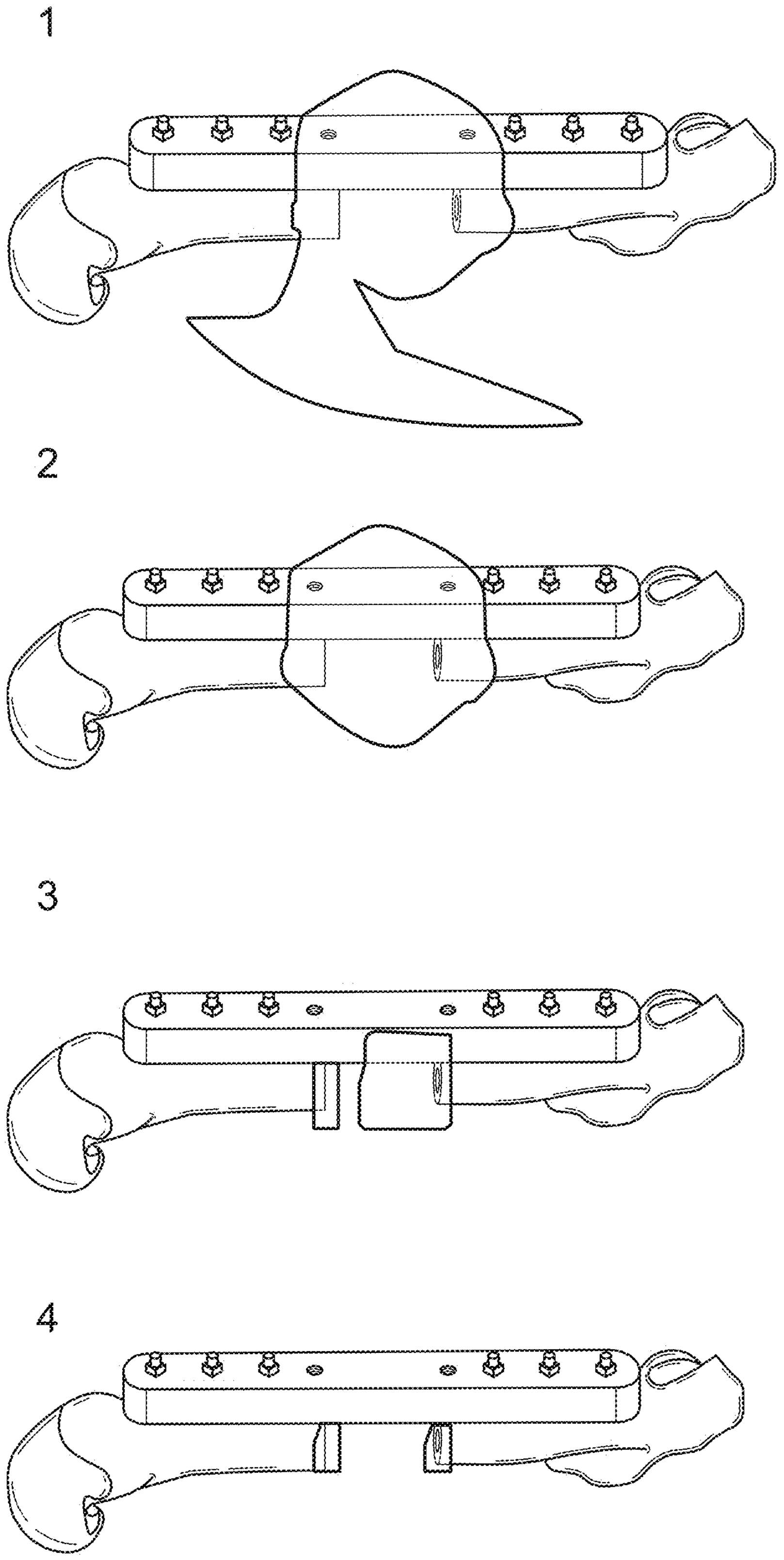
FIG. 4 is a schematic representation of the varied callus formation in animals from Group A, B, or C at 4 weeks post-surgery. The red-shaded area is an approximation of the mineralized callus volume.

At 4-weeks post-surgery, Group A routinely demonstrated bridging of the periosteal callus and frequently demonstrated mature callus with interfragmentary bridging (FIG. 3A). This as in clear constrast to Groups B and C where only callus tissue and little or no callus scores were observed respectively. At 8-weeks post-surgery, while there appears to be no significant radiographic change in the scoring of the mature callus, Group A remained advanced in the healing stage when compared to Group B and C, both of which only marginally improved their scores in the intervening 4 weeks (FIG. 3B). It is worth noting that in Group A, frequent larger boney callus volumes were observed intact but distal to the fracture site suggesting that the treatment in this group was not contained to the fracture region. Representative images from each group at 4- and 8-weeks post-surgery are located in FIGS. 3A and 3B. A schematic of the varied callus formations is represented in FIG. 4.

Micro-Computed Tomography

To quantify the total callus and bone mineral volumes, each specimen was scanned by high resolution CT (Skyscan, Model 1174, Bruker microCT). Specimens were wrapped in PBS-soaked gauze and secured within a humidified tube prior to scanning. All scans were performed at 6.4 m voxel resolution and X-ray tube potential of 50 kV and 800 μA. Images were acquired over 180 degrees with intervals of 0.8 degrees and frames were averaged from 2 images taken at each step. For each scan, the images were then reconstructed into a z-stack of images to represent the transverse plane of the femur (N-Recon software, Bruker microCT). All reconstructions used a modified Feldkamp cone-beam algorithm with a smoothing setting of 1, a ring artefact reduction level set to 12, a beam hardening level of 20% and a post-alignment balue of no greater than +1.0. Reconstructions of the callus region excluded the adjacent screws which secured the rat-fix plate, in order to remove the interfering signal of the titanium screws from subsequent analyses. Uniform realignment of datasets were performed using Dataviewer v.1.5.1 (Bruker, BEL). Reconstructed z-stack images for each specimen were then analysed using CTan software (Bruker microCT). Analyses of bone volume in the fracture region were performed by three manually defined volumes of interest (VOI's). Prior to 3D analyses, all volumes of interest binarised using an adaptive thresholding technique using a specimen-specific hydroxyapatite standard control. 3D analyses were performed to establish total volume and bone volume fractions in each volume of interest.

During necropsy, all treated legs were removed, and placed in either 10% neutral-buffered formalin and kept at room temperature, or gauze-soaked saline and frozen at −20° C., for μCT imaging and mechanical strength testing. All legs were also X-rayed (Faxitron X-ray Imager) and the images graded as per Table 3 above. FIG. 4 shows a graphical representation of bridging of periosteal callus. Moderate callus was observed in Group B samples, whereas Group C samples showed little or no callus.

Figure 5A:
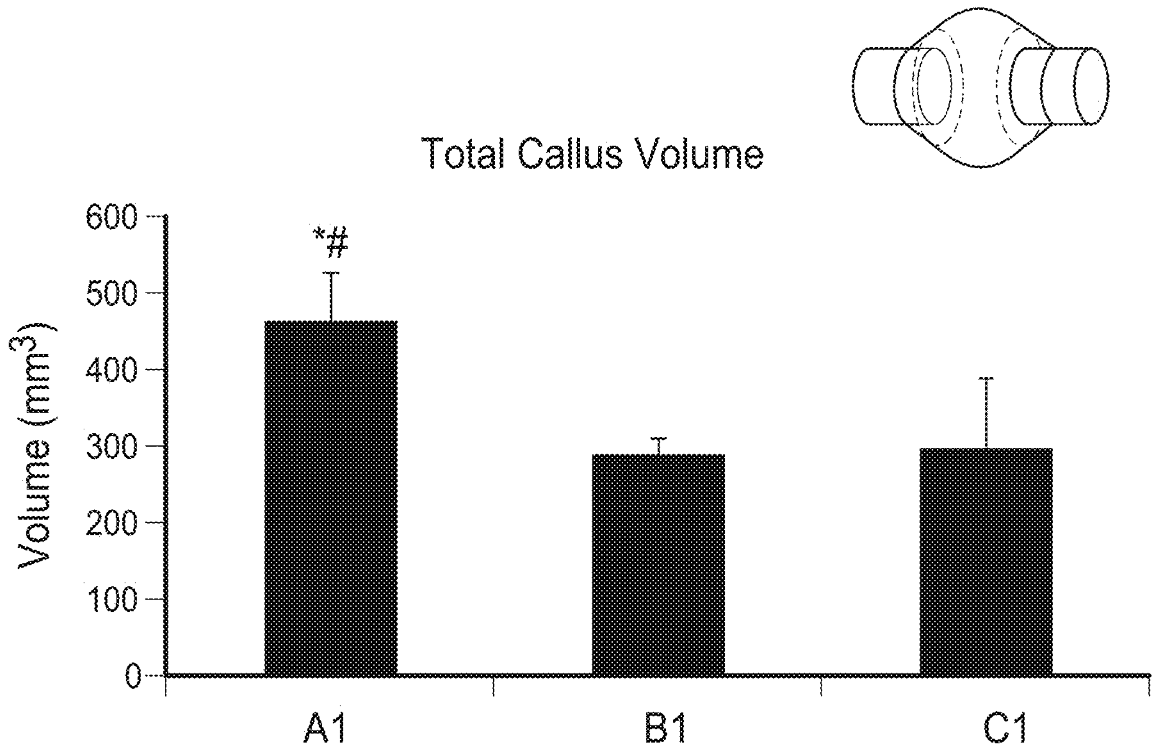
FIG. 5A is a representative graph of micro-CT analyses showing total callus volume in bone specimens obtained at 8 weeks post-surgery from animals in Group A (n=9), B (=n-7), or C (n=8). The data are represented as Mean±SEM; * P<0.01 vs B, #P<0.0.1 vs C.
Figure 5B:
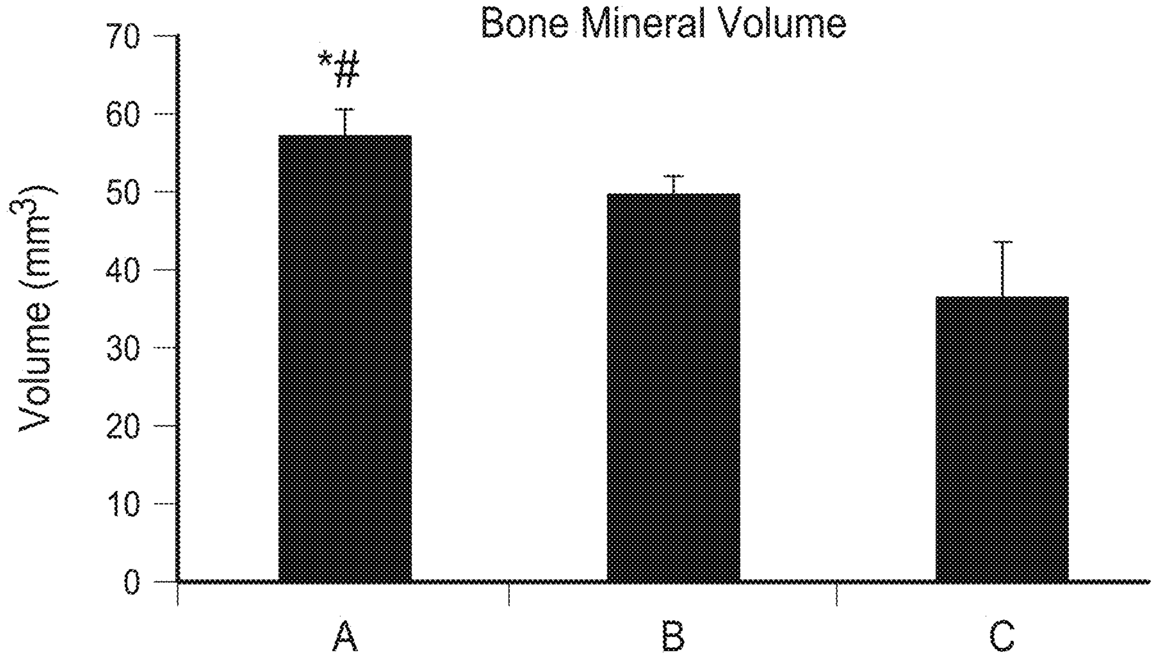
FIG. 5B is a representative graph of micro-CT analyses showing bone mineral volume in bone specimens obtained 8 weeks post-surgery from animals in Group A (n=9), B (=n-7), or C (n=8). The data are represented as Mean±SEM; * P<0.01 vs B, #P<0.0.1 vs C.
Figure 6A:
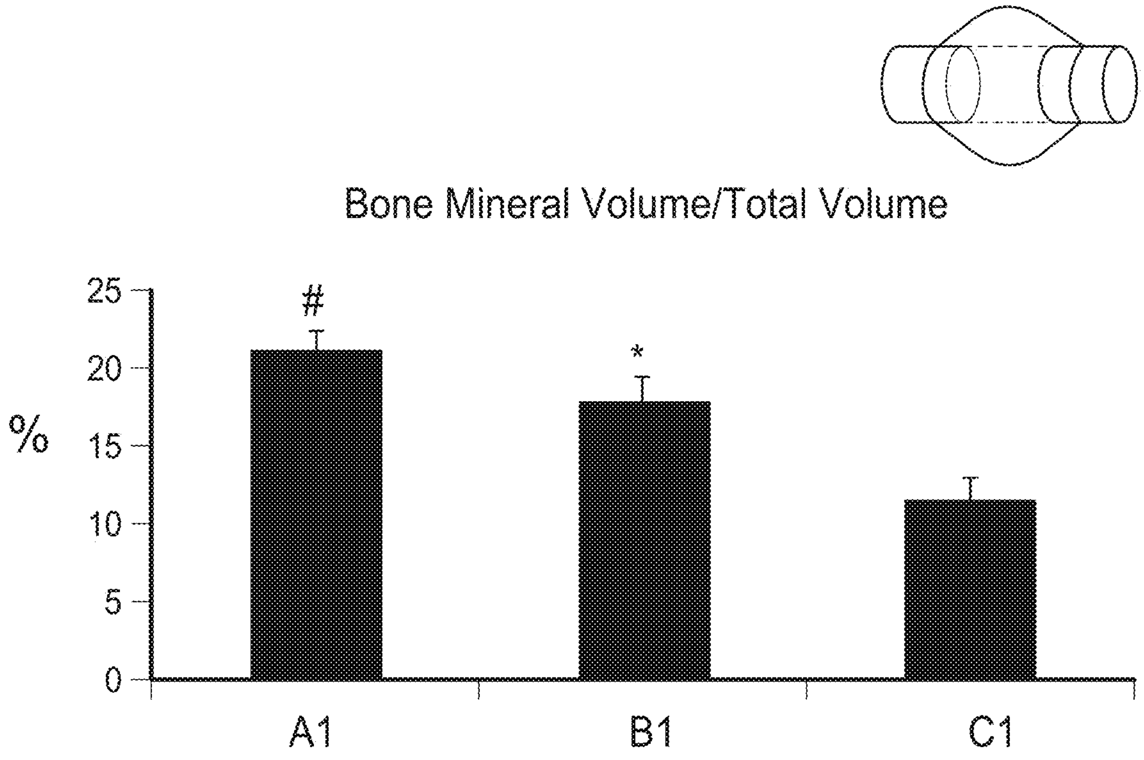
FIG. 6A is a representative graph of micro-CT analyses of the diaphyseal region volume of bone speciments obtained 4 weeks post-surgery in animals from Group A (n=10), B (n=8), or C (n=7). Bone mineral volume is expressed as the percentage of bone mineral volume to total volume. The data are represented as Mean±SEM; * P<0.05 vs B, #P<0.0.5 vs C. A1 vs B1; p=0.059.
Figure 6B:
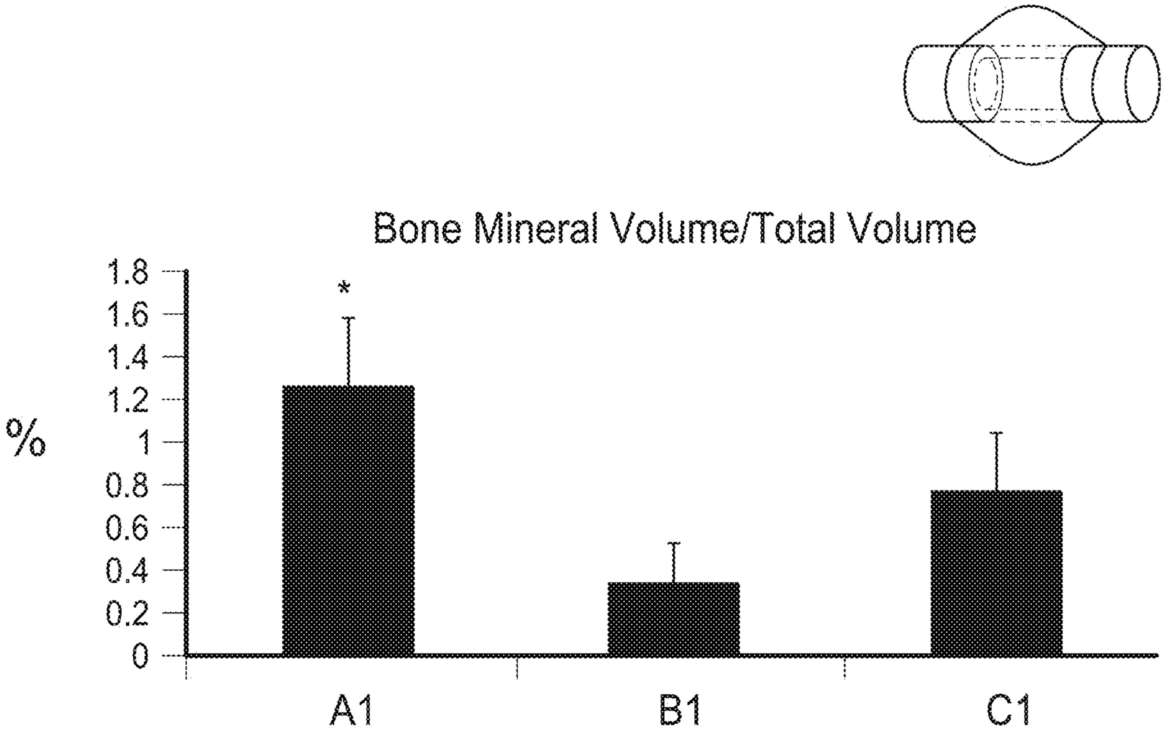
FIG. 6B is a representative graph of micro-CT analyses of the cortical bone volume of bone specimens obtained 4 weeks post-surgery in animals from Group A (n=10), B (n=8), or C (n=7). Bone mineral volume is expressed as the percentage of bone mineral volume to total volume. The data are represented as Mean±SEM; * P<0.05 vs B, #P<0.0.5 vs C.

Analyses of the CT images for bone volume in the fracture region showed that the total callus volume and the bone mineral volume were significantly higher in Group A (tBMP+(β-TCP putty-treated) animals than in either the β-TCP putty (Group C) or the rhBMP+ACS-treated animals ($p<0.01$ in both cases). There were no significant differences between the Group B and Group C animals for either total callus volume or bone mineral volume. These are shown in FIG. 5A and FIG. 5B. When restricting the region to the interpolated shaft region, in both Group A and Group B, the bone mineral volume as a percentage of the tissue volume (BV/TV) was approximately 2-fold greater than Group C ($P<0.05$). The BV/TV for Group A was trending to be increased by 15% when compared to Group B ($P=0.059$) (FIG. 6A). When restricting the region to the interpolated cortical bone region only, in Group A, the cortical bone mineral volume, in BV/TV terms, was 4-fold greater than levels in Group B ($P<0.05$) but not significantly greater than in Group C (FIG. 6B).

At 8-weeks post-surgery, TCB was markedly increased in Group A when compared to Groups B and C (FIG. 7A and FIG. 7B). However, BMV in Group A is not significantly increased when compared to Group B. These data suggested that while a larger bony callus existed in Group A, the density of bone mineral was more comparable to Group B.

Mechanical Strength Testing of Treated Femur

The mechanical strength testing of femoral callus was performed using 3 point bending method (5940 and BlueHill 3 software, v3.25, Instron, MA, USA). Each specimen was stored in PBS-soaked gauze at −80° C. until ready for testing. Prior to testing, specimens were gradually thawed to 4° C. over three days to maintain tissue integrity. On the day of testing, samples were scanned by micro-CT in a humidified chamber and kept cool prior to allowing specimens to reach room temperature for mechanical testing. For each specimen, the rat-fix plate was cut immediately prior to testing using a slow speed rotary diamond tipped saw lubricated with cooled phosphate buffered saline. The mid-point of the rat-fix plate was cut to remove the support of the plate in the fracture stabilization. This cut was done so as to cause minimal disturbance to the surrounding callus. After cutting the plate, each bone was then loaded into the 3-point jig with the rat-fix plate in contact with the low anvils with a 10 mm span such that the upper anvil was positioned directly above the cut-point on the plate. The downward motion of the upper anvil tests the resistance, and thus the strength, of the callus. As the bone deforms during testing, the plate separates at the mid-point cut, minimizing the contribution of the plate to the measure of Ultimate Load to Failure (ULF). T Compression testing was performed by gradually increasing the force applied, at a rate of 0.01 mm per second. ULF was determined by the peak force immediately prior to the failure of callus as determined by the force-displacement curve.

The mechanical testing of femoral strength in each fracture specimen required that the contribution of the rat-fix plate be removed without disturbing the callus. Typically this would involve removing the rat-fix plate altogether. However, in numerous samples, in particular in Group A, the extent of callus enveloped the plate making removal impractical. Thus, the compromise was to cut the plate exactly at the mid-point such that it no longer contributed to femoral support. The cut was done in such a way as to only cause minimal damage to the callus. The downward motion of the upper anvil thus tests the resistance, and thus the strength, of the callus. Group A exhibited markedly increased ULF at 4 and 8 week post-surgery when compared to Groups B and C (FIG. 8). At 8 weeks post-surgery, Group A exhibited 2.5-fold increase in ULF when compared to Group B at the same time point ($P<0.001$). Group B demonstrated increased ULF when compared to Group C and both time points. At 8 weeks post-surgery, in Group B, a trend for increased ULF was observed when compared to 4 weeks post-surgery ($P=0.059$).

Histomorphometry of Treated Femur

At ten days prior to end-point, all animals were administered calcein green (25 mg/kg of 10 mg/mL), with the exception of Rat #6, 8, 9, 10, 18, 20, 23, 30 and 50, which were inadvertently administered 12.5 mg/Kg of 10 mg/mL solution. All rats received 100 mg/Kg of xylenol orange (100 mg/mL solution) at three days prior to end-point. All administrations were intraperitoneal.

At 4 weeks post-surgery, Group A exhibits extensive evidence of mineralization akin to mature trabecular bone (FIG. 9A). Significant remodelling of bone was observed by the presence of osteoclasts (FIG. 9B, white arrows), and the presence of osteocytes in Group A specimens (FIG. 9B, yellow arrows) which is indicative of mature mineralized bone. Osteoblastic activity was observed in the form of double-fluorochrome labelled mineral accretion. The osteoblastic bone formation was frequently observed as 'lines' colored green and red which are in association with each other (FIG. 9B, blue arrows). This represented the formation of lamella (mature) bone, rather than the ad-hoc mineralization of woven bone that occurs in early callus formation, a common observation in Group B. Furthermore, the presence of red-blood cells, and adipocytes indicated that an angiogenesis has occurred and suggested good infiltration of cells to most regions of the callus in Group A specimens.

In Group B, while bone mineral was observed, there were extensive regions of fibrous and cartilage tissue which was unmineralized within the callus region (FIG. 9A). Where new bone mineral occurs, double labels were observed indicating bone formation. However, these double labels were frequently disorganized and often occurred as single labels suggesting that woven bone formation (i.e. initial bone callus formation) was continuing to be formed at this time point (FIG. 9B). While not quantified, it appeared that osteoclasts predominantly existed in regions between the unmineralized and mineralized portions of the callus which suggested an earlier stage of callus development than what was observed for Group A animals.

In Group C, there was no evidence of mineralization, bone formation or bone remodelling. Indeed, there was no evidence of cartilage formation. A fibrous-like material with foreign mineralized spicules existed within the fracture site. There were some instances where osteoclasts as present on the surface of the foreign material, suggesting that this material could be resorbed (FIG. 9B).

At 8 weeks post-surgery, the same pattern of activity between the groups was continued (FIG. 10A and FIG. 10B). Of note, however, in Group A, there appeared to be greater distribution of mature bone across all sections, consistent with CT analyses. Also, a degree of intra-trabecular, or intra-cortical labelling of mineral (FIG. 10B, orange arrows) suggested a further maturing of bone consistent with late-stage bone healing. Also of note, Group B specimens appeared to exhibit all stages of callus formation and remodelling. That is, there was evidence of lack of periosteal bridging at times, the presence of cartilage, woven bone, lamellae bone, and evidence of remodelling as well. In Group C, the persistent lack of healing suggested that this group contained a treatment which was most comparable to a critical-sized defect model without any scaffold of healing agents.

In summary, sixty-one animals were successfully treated with one of three test items following surgical creation of a critical size defect in the right femur. The post operative recovery was unremarkable in the majority of animals. The test items were all placed within the defects, but on X-ray, it could be seen that the compounds containing the β-TCP putty were spread out of the defect area and into the surrounding tissue. As the collagen sponge was not visible on X-ray, it was not possible to judge if the sponge had moved out of the defect area.

Most animals recovered from surgery well and in most cases were moving as per usual within 24 hours of surgery. A number of the animals were larger than the recommended weight for the plates, but the femurs were not so large that the screws of the internal fixator system were not going through the whole bone, so there should not have been loss of stability while new bone was forming at the site. Two animals had evidence of displaced bones on the two week radiographs, these animals were not heavier than others. One animal was in the rhBMP+ACS group, the other was in the β-TCP putty group. Another animal (Group C) had a broken screw and displaced bone at the six-week post-operative time point. There was no obvious reason why this had occurred.

There were no differences between any of the groups in any clinical pathology parameters or histological analyses of organs and tissues.

Radiographic and histological examination of the treated femurs showed that the Group A animals (tBMP-2+β-TCP putty) had the most evidence of formation of mature bone in the defect site compared to the other two groups. This was shown by bridging of the periosteal callus, increased mineralization, presence of osteocytes, active remodelling of the bone (as shown by the presence of osteoclasts) and evidence of angiogenesis (shown by the presence of red blood cells and adipocytes). Whilst some evidence of mineralization of callus is present in the Group B (rhBMP+ACS) samples, this appeared to be less developed than for Group A. Group C (β-TCP putty) showed no evidence of mineralization, suggesting that having a scaffold alone could not induce new bone growth within eight weeks of application into a critical-sized defect.

Group A animals also had significantly stronger bones than either Group B or Group C animals as evidenced by ultimate load to failure tests. This was evident at both four and eight weeks post-treatment.

The differences in callus formation in the process of healing are distinct between all three groups, clearly indicating that there were unambiguous differences in the treatments of fracture in each group.

In Group C, a frank lack of periosteal bridging and minimal bony callus formation at both 4 and 8 weeks was associated with a lack of cellular activity within the fracture. These observations were consistent with the near complete absence of mechanical integrity at either time point.

In Group B, the mineralized callus was more extensive than the levels in Group C both 4 and 8 weeks post-surgery. This was evident in the radiographic and histomorphometric analyses. Furthermore, while periosteal bridging was observed only in some Group B specimens at 8 week post-surgery, there was a clear and overt difference in the histological assessment at both time points with regards to bone formation and cellular activity. Unlike in Group C, the presence of bone formation, frequently in the form of woven bone and occasionally as lamellae bone, was associated with increase in mechanical strength when compared to Group C. Interestingly, neither radiographic nor mechanical strength measures were significantly improved at 8 weeks when compared to 4 weeks post-surgery. This suggested that the majority of activity in callus formation and structural integrity occurred in the first 4 weeks.

Group A exhibited the most advanced healing when compared to the other groups. At 4 weeks post-surgery radiographic evidence of periosteal bridging was a measure that no samples achieved in Group C and often was not observed in Group B, even at 8 weeks post-surgery. Interestingly, while radiographic scores at 8 weeks post-surgery were comparable to 4 week scores, the mechanical strength of the callus was more than double the levels at 4 weeks post-surgery and at least 3-fold greater than levels in Group B, suggesting that considerable bone mineralization occurred within the callus region in the second 4 week period. This observation was consistent with high levels of lamellae bone formation in Group A at 4 and 8 weeks post-surgery, which was distinct from the weaker woven bone formation that occurred in Group B, even at 8 weeks post-surgery. It is important to note that callus volume at 8 weeks of age was lower than levels at 4 weeks post-surgery, suggesting that callus volume was being remodelled into a more compact callus at the site of fracture. In Group A, this was consistent with fewer observations of extraneous mineralized callus distal to the fracture site at 8 weeks post-surgery. With regards to the histological assessment of Group A specimens, observations of osteoclastic none resorption adjacent to regions of bone undergoing bone formation is entirely typical of bone undergoing remodelling which is known to be done to provide a stronger and more efficient structure for skeletal integrity. The additional observations of the presence of osteocytes as well as other cellular structures such as vascular structures and adipocytes clearly makes the bone often indistinguishable from endogenous trabecular micro-anatomy.

In conclusion, the bone specimens form the tBMP-2+β-TCP putty group clearly demonstrated vastly improved bone healing at 4- and 8-weeks post-surgery when compared to samples from animals in the rhBMP+ACS or the β-TCP putty alone treatment groups.

Example 3. Overview of Chimeric β-TCP Polypeptides

Figure 12:
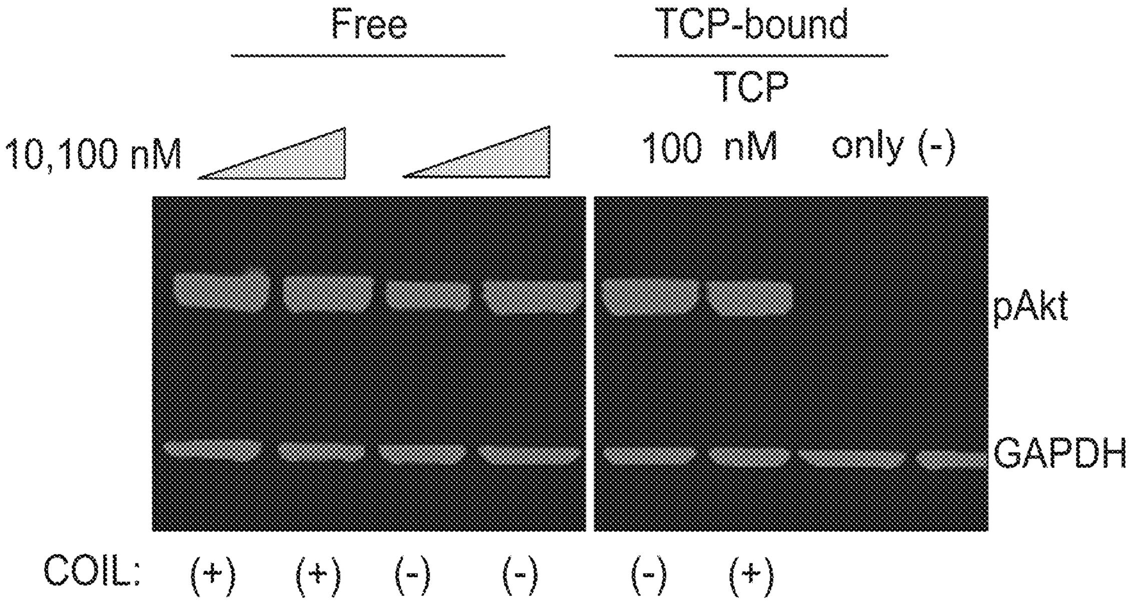
FIG. 12 is a representative immunoblot of MCF-7 lysate probed with an anti-P-Akt antibody, wherein the MCF-7 cells were incubated with β-TCBP-HRG (free) or β-TCBP-HRG (β-TCP-bound).

The present inventors found that chimeric polypeptides maintained activity of the tethered protein. The chimeric polypeptide (10× β-TCP-histidine rich glycoprotein HRG) refolded at 22° C. in buffer 10, and following incubation of the chimeric polypeptide with MCF-7 breast cancer cells, Akt activity was detected (FIG. 11). This result indicated that the chimeric polypeptide stimulated signalling activity in the target cell and was able to cause Akt phosphorylation. Next, the Akt activity was determined in 10× β-TCP-HRG bound to a β-TCP peptide (FIG. 12). The β-TCP peptide on its own was unable to cause Akt phosphorylation in MCF-7 cells, however, incubation of MCF-7 cells with β-TCP peptide bound to 10×3-TCP-HRG led to Akt phosphorylation. Interestingly, the extent of Akt phosphorylation was not affected whether the chimeric polypeptide was bound to a β-TCP peptide or not.

Example 4. Binding Affinity of tBMP2 to Various Substrate Materials

Binding assays were performed to quantify the affinity of tBMP2 protein to various substrates, including commercially available bone graft materials, ceramic powders, 3D printable scaffold materials, and a plasma-sprayed hydroxyapatite coating. First, 10 mg of each material was washed with deionized water followed by acetate buffer. Then either a 150 pg or 250 pg load of tBMP2 protein was applied to each material and allowed to bind under light agitation for 90-120 minutes. The flow through was aspirated (removing the tBMP2 which did not bind to the substrate material), and a wash was conducted with acetate buffer. A subsequent overnight elution was done by immersing the substrate material in a sodium phosphate buffer (100 mM NaPhos, 4 M Urea, 1 M NaCl, 10% 1,6 Hexanediol, pH=8) to remove the bound protein from the substrate for measurement.

The bound tBMP2 was quantified by either 1) running non-reducing SDS Page gel electrophoresis and comparing the eluted tBMP2 band to the tBMP2 load band with Image J Gel Analysis tool, or 2) conducting a Bradford assay (with a BSA standard curve) on the eluted tBMP2 and tBMP2 load. Dividing the eluted tBMP2 quantity by the original tBMP2 load quantity and multiplying by 100 gave the % of tBMP2 load that was strongly tethered to the substrate after the binding incubation step.

Table 6 summarizes the materials that were evaluated as well as the % of tBMP2 load which was effectively tethered to the substrate (% Bound).

TABLE 6

| Summary of Binding Activity | | | | | |
|---|---|---|---|---|---|
| Product | Description | Manu-facturer | Load tBMP2 Applied to Material | Method of measure-ment | % of tBMP2 load bound to material |
| Master-graft Strip | Biphasic TCP (85% β-Tricalcium Phosphate: 15% Hydro-xyapatite)/Type I bovine collagen composite | Med-tronic | 15 ug tBMP2/mg material | Bradford Assay | 69% |
| Vitoss Foam Pack | β-Tricalcium Phosphate/Type I bovine collagen composite | Stryker | 15 ug tBMP2/mg material | Bradford Assay | 82% |
| chronOS Strip | β-Tricalcium Phosphate/poly (lactide co-ε-caprolactone) composite | DePuy Synthes | 15 ug tBMP2/mg material | Image J Gel Analysis Tool | 75% |
| Vitoss Micro-morsels | β-Tricalcium Phosphate granules (1 mm-2 mm) | Stryker | 15 ug tBMP2/mg material | Image J Gel Analysis Tool | 74% |
| LifeInk 500 | Calcium Phosphate Cement 3D printable ink | Advanced Biomatrix | 15 ug tBMP2/mg material | Image J Gel Analysis Tool | 87% |
| Hyper-elastic Bone | Hydro-xapatite/Poly(lactic-co-glycolic acid) 3D printable ink | Di-mension Inx | 15 ug tBMP2/mg material | Image J Gel Analysis Tool | 58% |
| Bioactive Glass | Combeite 45S5 Bioactive Glass powder | Stryker | 25 ug tBMP2/mg material | Image J Gel Analysis Tool | 49% |
| Silicon Nitride Powder | $Si_3N_4$ powder, 99% purity | Chem-savers | 25 ug tBMP2/mg material | Image J Gel Analysis Tool | 54% |
| β-TCP Powder | β-Tricalcium Phosphate powder, 3-5 µm particle size | CaP Bio-materials | 25 ug tBMP2/mg material | Image J Gel Analysis Tool | 79% |
| β-TCP Spray Dried Powder | β-Tricalcium Phosphate spray dried powder, <38 µm particle size | CaP Bio-materials | 25 ug tBMP2/mg material | Image J Gel Analysis Tool | 78% |
| Hydro-xyapatite Powder | Hydro-xyapatite powder, 3-5 µm particle size | CaP Bio-materials | 25 ug tBMP2/mg material | Image J Gel Analysis Tool | 57% |
| HA-coated Bone Screw | Hydro-xyapatite plasma spray-coated stainless steel bone screw (6 mm dia × 5 mm long piece cut from screw) | Citieffe material | 25 ug tBMP2/mg material | Bradford Assay | 44% |
| β-TCP Granules | β-Tricalcium Phosphate granules, 250-1000 µm particle size | CaP Bio-materials | 15 ug tBMP2/mg material | Bradford Assay | 70% |
| Hydro-xyapatite Granules | Hydro-xyapatite granules, 250-1000 µm particle size | CaP Bio-materials | 15 ug tBMP2/mg material | Bradford Assay | 52% |
| Re-BOSSIS | Cotton-like bone void filler. Main ingredients are β-Tricalcium Phosphate, bioabsorbable polymer, and SiV (silicon-containing calcium carbonate) | Ortho-rebirth | 15 ug tBMP2/mg material | Bradford Assay | 83% |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising LIADSTHHSPWT (SEQ ID NO: 3), ILAETTHHRPWS (SEQ ID NO: 5), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), or GGADTTHHRPGT (SEQ ID NO: 19), or a combination of two or more thereof.

2. The composition of claim 1, comprising LIADSTHHSPWT (SEQ ID NO: 3).

3. The composition of claim 1, comprising ILAETTHHRPWS (SEQ ID NO: 5).

4. The composition of claim 1, comprising VGADSTHHRPVT (SEQ ID NO: 15).

5. The composition of claim 1, comprising β-tricalcium phosphate.

6. The composition of claim 5, wherein the β-tricalcium phosphate is in the form of a granule.

7. The composition of claim 5, wherein the LIADSTHHSPWT (SEQ ID NO: 3), ILAETTHHRPWS (SEQ ID NO: 5), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13) GSSGESTHHKPST (SEQ ID NO: 15), VGADSTHHRPVT (SEQ ID NO: 15), GAADTTHHRPVT (SEQ ID NO: 16), AGADTTHHRPVT (SEQ ID NO: 17) GGADTTHHRPAT (SEQ ID NO: 18), or GGADTTHHRPGT (SEQ ID NO: 19), or the combination of two or more thereof is bound to the β-tricalcium phosphate.

8. A method of delivering the LIADSTHHSPWT (SEQ ID NO: 3), ILAETTHHRPWS (SEQ ID NO: 5), VLGDTTHHKPWT (SEQ ID NO: 8) IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), or GGADTTHHRPGT (SEQ ID NO: 19), or the combination of two or more thereof to a subject, the method comprising administering to the subject the composition of claim 7.

9. The method of claim 8, wherein the subject is a mammal.

10. The method of claim 9, wherein the mammal is a dog.

11. A nucleic acid encoding a polypeptide, the polypeptide comprising LIADSTHHSPWT (SEQ ID NO: 3), ILAETTHHRPWS (SEQ ID NO: 5), VLGDTTHHKPWT (SEQ ID NO: 8), IVADSTHHRPWT (SEQ ID NO: 9); STADTSHHRPS (SEQ ID NO: 10), TSGGESTHHRPS (SEQ ID NO: 11), TSGGESSHHKPS (SEQ ID NO: 12), TGSGDSSHHRPS (SEQ ID NO: 13), GSSGESTHHKPST (SEQ ID NO: 14), VGADSTHHRPVT (SEQ ID NO: 15), GAADTTHHRPVT (SEQ ID NO: 16), AGADTTHHRPVT (SEQ ID NO: 17), GGADTTHHRPAT (SEQ ID NO: 18), or GGADTTHHRPGT (SEQ ID NO: 19), or a combination of two or more thereof.

* * * * *

SEQUENCE LISTING

```
Sequence total quantity: 112
SEQ ID NO: 1            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 1
LLADTTHHRP WT                                                          12

SEQ ID NO: 2            moltype = AA  length = 12
```

```
FEATURE                Location/Qualifiers
REGION                 1..12
                       note = Description of Artificial Sequence: Synthetic peptide
source                 1..12
                       mol_type = protein
                       organism = synthetic construct
SEQUENCE: 2
VIGESTHHRP WS                                                            12

SEQ ID NO: 3           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 3
LIADSTHHSP WT                                                            12

SEQ ID NO: 4           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 4
ILAESTHHKP WT                                                            12

SEQ ID NO: 5           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 5
ILAETTHHRP WS                                                            12

SEQ ID NO: 6           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 6
IIGESSHHKP FT                                                            12

SEQ ID NO: 7           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 7
GLGDTTHHRP WG                                                            12

SEQ ID NO: 8           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 8
VLGDTTHHKP WT                                                            12

SEQ ID NO: 9           moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 9
IVADSTHHRP WT                                                            12
```

```
SEQ ID NO: 10           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 10
STADTSHHRP S                                                           11

SEQ ID NO: 11           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 11
TSGGESTHHR PS                                                          12

SEQ ID NO: 12           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 12
TSGGESSHHK PS                                                          12

SEQ ID NO: 13           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 13
TGSGDSSHHR PS                                                          12

SEQ ID NO: 14           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 14
GSSGESTHHK PST                                                         13

SEQ ID NO: 15           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 15
VGADSTHHRP VT                                                          12

SEQ ID NO: 16           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 16
GAADTTHHRP VT                                                          12

SEQ ID NO: 17           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 17
AGADTTHHRP VT                                                          12
```

```
SEQ ID NO: 18          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 18
GGADTTHHRP AT                                                          12

SEQ ID NO: 19          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 19
GGADTTHHRP GT                                                          12

SEQ ID NO: 20          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 20
LLADTTHHRP WTVIGESTHH RPWS                                             24

SEQ ID NO: 21          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 21
LLADTTHHRP WTVIGESTHH RPWSIIGESS HHKPFT                                36

SEQ ID NO: 22          moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 22
LLADTTHHRP WTVIGESTHH RPWSIIGESS HHKPFTGLGD TTHHRPWGIL AESTHHKPWT  60

SEQ ID NO: 23          moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 23
LLADTTHHRP WTILAESTHH KPWT                                             24

SEQ ID NO: 24          moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 24
LLADTTHHRP WTILAESTHH KPWTLLADTT HHRPWTILAE STHHKPWTLL ADTTHHRPWT  60

SEQ ID NO: 25          moltype = AA  length = 24
FEATURE                Location/Qualifiers
REGION                 1..24
                       note = Description of Artificial Sequence: Synthetic peptide
source                 1..24
```

```
                         mol_type = protein
                         organism = synthetic construct
SEQUENCE: 25
LLADTTHHRP WTGLGDTTHH RPWG                                            24

SEQ ID NO: 26            moltype = AA  length = 36
FEATURE                  Location/Qualifiers
REGION                   1..36
                         note = Description of Artificial Sequence: Synthetic
                          polypeptide
source                   1..36
                         mol_type = protein
                         organism = synthetic construct
SEQUENCE: 26
LLADTTHHRP WTGLGDTTHH RPWGLLADTT HHRPWT                               36

SEQ ID NO: 27            moltype = AA  length = 60
FEATURE                  Location/Qualifiers
REGION                   1..60
                         note = Description of Artificial Sequence: Synthetic
                          polypeptide
source                   1..60
                         mol_type = protein
                         organism = synthetic construct
SEQUENCE: 27
LLADTTHHRP WTGLGDTTHH RPWGLLADTT HHRPWTGLGD TTHHRPWGLL ADTTHHRPWT  60

SEQ ID NO: 28            moltype = AA  length = 84
FEATURE                  Location/Qualifiers
REGION                   1..84
                         note = Description of Artificial Sequence: Synthetic
                          polypeptide
source                   1..84
                         mol_type = protein
                         organism = synthetic construct
SEQUENCE: 28
LLADTTHHRP WTGLGDTTHH RPWGLLADTT HHRPWTGLGD TTHHRPWGLL ADTTHHRPWT  60
GLGDTTHHRP WGLLADTTHH RPWT                                            84

SEQ ID NO: 29            moltype = AA  length = 60
FEATURE                  Location/Qualifiers
REGION                   1..60
                         note = Description of Artificial Sequence: Synthetic
                          polypeptide
source                   1..60
                         mol_type = protein
                         organism = synthetic construct
SEQUENCE: 29
STADTSHHRP STSGGESTHH RPSTSGGESS HHKPSTGSGD SSHHRPSGSS GESTHHKPST  60

SEQ ID NO: 30            moltype = AA  length = 60
FEATURE                  Location/Qualifiers
REGION                   1..60
                         note = Description of Artificial Sequence: Synthetic
                          polypeptide
source                   1..60
                         mol_type = protein
                         organism = synthetic construct
SEQUENCE: 30
VGADSTHHRP VTGAADTTHH RPVTAGADTT HHRPVTGGAD TTHHRPATGG ADTTHHRPGT  60

SEQ ID NO: 31            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 31
STADTSHHRP SLLADTTHHR PWTTSGGEST HHRPSVGADS THHRPVTTSG GESSHHKPSG  60
AADTTHHRPV TTGSGDSSHH RPSGSSGEST HHKPSTGGAD TTHHRPAT                 108

SEQ ID NO: 32            moltype = AA  length = 396
FEATURE                  Location/Qualifiers
source                   1..396
                         mol_type = protein
                         organism = Homo sapiens
SEQUENCE: 32
```

```
MVAGTRCLLA LLLPQVLLGG AAGLVPELGR RKFAAASSGR PSSQPSDEVL SEFELRLLSM  60
FGLKQRPTPS RDAVVPPYML DLYRRHSGQP GSPAPDHRLE RAASRANTVR SFHHEESLEE  120
LPETSGKTTR RFFFNLSSIP TEEFITSAEL QVFREQMQDA LGNNSSFHHR INIYEIIKPA  180
TANSKFPVTR LLDTRLVNQN ASRWESFDVT PAVMRWTAQG HANHGFVVEV AHLEEKQGVS  240
KRHVRISRSL HQDEHSWSQI RPLLVTFGHD GKGHPLHKRE KRQAKHKQRK RLKSSCKRHP  300
LYVDFSDVGW NDWIVAPPGY HAFYCHGECP FPLADHLNST NHAIVQTLVN SVNSKIPKAC  360
CVPTELSAIS MLYLDENEKV VLKNYQDMVV EGCGCR                            396

SEQ ID NO: 33          moltype = AA  length = 37
FEATURE                Location/Qualifiers
REGION                 1..37
                       note = Description of Artificial Sequence: Synthetic
                        polypeptide
REGION                 1..37
                       note = Linker sequence
source                 1..37
                       mol_type = protein
                       organism = synthetic construct
SEQUENCE: 33
TGGSGEGGTG ASTGGSAGTG GSGGTTSGEA GGSSGAG                           37

SEQ ID NO: 34          moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 34
GSGATG                                                             6

SEQ ID NO: 35          moltype =   length =
SEQUENCE: 35
000

SEQ ID NO: 36          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 36
AAADTTHHRP WT                                                      12

SEQ ID NO: 37          moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 37
AAADTTHHRP WTAAADTTHH RPWTAAADTT HHRPWTAAAD TTHHRPWTAA ADTTHHRPWT  60

SEQ ID NO: 38          moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 38
LLADAAHHRP WTLLADAAHH RPWTLLADAA HHRPWTLLAD AAHHRPWTLL ADAAHHRPWT  60

SEQ ID NO: 39          moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 39
LLADTTAARP WTLLADTTAA RPWTLLADTT AARPWTLLAD TTAARPWTLL ADTTAARPWT  60

SEQ ID NO: 40          moltype = AA  length = 24
```

```
FEATURE                Location/Qualifiers
REGION                 1..24
                       note = Description of Artificial Sequence: Synthetic peptide
source                 1..24
                       mol_type = protein
                       organism = synthetic construct
SEQUENCE: 40
LLADTTHHRP WTLLADTTHH RPWT                                         24

SEQ ID NO: 41          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 41
LLADTTHHRP WTLLADTTHH RPWTLLADTT HHRPWT                            36

SEQ ID NO: 42          moltype = AA  length = 60
FEATURE                Location/Qualifiers
REGION                 1..60
                       note = Description of Artificial Sequence: Synthetic
                        polypeptide
source                 1..60
                       mol_type = protein
                       organism = synthetic construct
SEQUENCE: 42
LLADTTHHRP WTLLADTTHH RPWTLLADTT HHRPWTLLAD TTHHRPWTLL ADTTHHRPWT  60

SEQ ID NO: 43          moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 43
STSGSTVIGE STHHRPWSLI ADSTHHSPWT ILAESTHHKP WTILAETTHH RPWSIIGESS  60
HHKPFTGLGD TTHHRPWGVL GDTTHHKPWT IVADSTHHRP WTGQVLPTTT PSSPSTTSGS  120

SEQ ID NO: 44          moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 44
LLADTTHHRP WTVIGESTHH RPWSIIGESS HHKPFTGLGD TTHHRPWGIL AESTHHKPWT  60
ATGGSGEGGT GASTGGSAGT GGSGGTTSGE AGGSSGAG                          98

SEQ ID NO: 45          moltype = AA  length = 97
FEATURE                Location/Qualifiers
REGION                 1..97
                       note = Description of Artificial Sequence: Synthetic
                        polypeptide
source                 1..97
                       mol_type = protein
                       organism = synthetic construct
SEQUENCE: 45
LLADTTHHRP WTGLGDTTHH RPWGLLADTT HHRPWTGLGD TTHHRPWGLL ADTTHHRPWT  60
TGGSGEGGTG ASTGGSAGTG GSGGTTSGEA GGSSGAG                           97

SEQ ID NO: 46          moltype = AA  length = 1207
FEATURE                Location/Qualifiers
source                 1..1207
                       mol_type = protein
                       organism = Homo sapiens
SEQUENCE: 46
MLLTLIILLP VVSKFSFVSL SAPQHWSCPE GTLAGNGNST CVGPAPFLIF SHGNSIFRID  60
TEGTNYEQLV VDAGVSVIMD FHYNEKRIYW VDLERQLLQR VFLNGSRQER VCNIEKNVSG  120
MAINWINEEV IWSNQQEGII TVTDMKGNNS HILLSALKYP ANVAVDPVER FIFWSSEVAG  180
SLYRADLDGV GVKALLETSE KITAVSLDVL DKRLFWIQYN REGSNSLICS CDYDGGSVHI  240
SKHPTQHNLF AMSLFGDRIF YSTWKMKTIW IANKHTGKDM VRINLHSSFV PLGELKVVHP  300
LAQPKAEDDT WEPEQKLCKL RKGNCSSTVC GQDLQSHLCM CAEGYALSRD RKYCEDVNEC  360
```

```
AFWNHGCTLG CKNTPGSYYC TCPVGFVLLP DGKRCHQLVS CPRNVSECSH DCVLTSEGPL  420
CFCPEGSVLE RDGKTCSGCS SPDNGGCSQL CVPLSPVSWE CDCFPGYDLQ LDEKSCAASG  480
PQPFLLFANS QDIRHMHFDG TDYGTLLSQQ MGMVYALDHD PVENKIYFAH TALKWIERAN  540
MDGSQRERLI EEGVDVPEGL AVDWIGRRFY WTDRGKSLIG RSDLNGKRSK IITKENISQP  600
RGIAVHPMAK RLFWTDTGIN PRIESSSLQG LGRLVIASSD LIWPSGITID FLTDKLYWCD  660
AKQSVIEMAN LDGSKRRRLT QNDVGHPFAV AVFEDYVWFS DWAMPSVMRV NKRTGKDRVR  720
LQGSMLKPSS LVVVHPLAKP GADPCLYQNG GCEHICKKRL GTAWCSCREG FMKASDGKTC  780
LALDGHQLLA GGEVDLKNQV TPLDILSKTR VSEDNITESQ HMLVAEIMVS DQDDCAPVGC  840
SMYARCISEG EDATCQCLKG FAGDGKLCSD IDECEMGVPV CPPASSKCIN TEGGYVCRCS  900
EGYQGDGIHC LDIDECQLGE HSCGENASCT NTEGGYTCMC AGRLSEPGLI CPDSTPPPHL  960
REDDHHYSVR NSDSECPLSH DGYCLHDGVC MYIEALDKYA CNCVVGYIGE RCQYRDLKWW  1020
ELRHAGHGQQ QKVIVVAVCV VVLVMLLLLS LWGAHYYRTQ KLLSKNPKNP YEESSRDVRS  1080
RRPADTEDGM SSCPQPWFVV IKEHQDLKNG GQPVAGEDGQ AADGSMQPTS WRQEPQLCGM  1140
GTEQGCWIPV SSDKGSCPQV MERSFHMPSY GTQTLEGGVE KPHSLLSANP LWQQRALDPP  1200
HQMELTQ                                                            1207

SEQ ID NO: 47          moltype = AA  length = 211
FEATURE                Location/Qualifiers
source                 1..211
                       mol_type = protein
                       organism = Homo sapiens
SEQUENCE: 47
MRTLACLLLL GCGYLAHVLA EEAEIPREVI ERLARSQIHS IRDLQRLLEI DSVGSEDSLD  60
TSLRAHGVHA TKHVPEKRPL PIRRKRSIEE AVPAVCKTRT VIYEIPRSQV DPTSANFLIW  120
PPCVEVKRCT GCCNTSSVKC QPSRVHHRSV KVAKVEYVRK KPKLKEVQVR LEEHLECACA  180
TTSLNPDYRE EDTGRPRESG KKRKRKRLKP T                                211

SEQ ID NO: 48          moltype = AA  length = 158
FEATURE                Location/Qualifiers
source                 1..158
                       mol_type = protein
                       organism = Homo sapiens
SEQUENCE: 48
MGKISSLPTQ LFKCCFCDFL KVKMHTMSSS HLFYLALCLL TFTSSATAGP ETLCGAELVD  60
ALQFVCGDRG FYFNKPTGYG SSSRRAPQTG IVDECCFRSC DLRRLEMYCA PLKPAKSARS  120
VRAQRHTDMP KTQKYQPPST NKNTKSQRRK GSTFEERK                         158

SEQ ID NO: 49          moltype = AA  length = 155
FEATURE                Location/Qualifiers
source                 1..155
                       mol_type = protein
                       organism = Homo sapiens
SEQUENCE: 49
MAEGEITTFT ALTEKFNLPP GNYKKPKLLY CSNGGHFLRI LPDGTVDGTR DRSDQHIQLQ  60
LSAESVGEVY IKSTETGQYL AMDTDGLLYG SQTPNEECLF LERLEENHYN TYISKKHAEK  120
NWFVGLKKNG SCKRGPRTHY GQKAILFLPL PVSSD                            155

SEQ ID NO: 50          moltype = AA  length = 288
FEATURE                Location/Qualifiers
source                 1..288
                       mol_type = protein
                       organism = Homo sapiens
SEQUENCE: 50
MVGVGGGDVE DVTPRPGGCQ ISGRGARGCN GIPGAAAWEA ALPRRRPRRH PSVNPRSRAA  60
GSPRTRGRRT EERPSGSRLG DRGRGRALPG GRLGGRGRGR APERVGGRGR GRGTAAPRAA  120
PAARGSRPGP AGTMAAGSIT TLPALPEDGG SGAFPPGHFK DPKRLYCKNG GFFLRIHPDG  180
RVDGVREKSD PHIKLQLQAE ERGVVSIKGV CANRYLAMKE DGRLLASKCV TDECFFFERL  240
ESNNYNTYRS RKYTSWYVAL KRTGQYKLGS KTGPGQKAIL FLPMSAKS               288

SEQ ID NO: 51          moltype = AA  length = 207
FEATURE                Location/Qualifiers
source                 1..207
                       mol_type = protein
                       organism = Homo sapiens
SEQUENCE: 51
MYSAPSACTC LCLHFLLLCF QVQVLVAEEN VDFRIHVENQ TRARDDVSRK QLRLYQLYSR  60
TSGKHIQVLG RRISARGEDG DKYAQLLVET DTFGSQVRIK GKETEFYLCM NRKGKLVGKP  120
DGTSKECVFI EKVLENNYTA LMSAKYSGWY VGFTKKGRPR KGPKTRENQQ DVHFMKRYPK  180
GQPELQKPFK YTTVTKRSRR IRPTHPA                                     207

SEQ ID NO: 52          moltype = AA  length = 160
FEATURE                Location/Qualifiers
source                 1..160
                       mol_type = protein
                       organism = Homo sapiens
SEQUENCE: 52
MVPSAGQLAL FALGIVLAAC QALENSTSPL SADPPVAAAV VSHFNDCPDS HTQFCFHGTC  60
RFLVQEDKPA CVCHSGYVGA RCEHADLLAV VAASQKKQAI TALVVVSIVA LAVLIITCVL  120
IHCCQVRKHC EWCRALICRH EKPSALLKGR TACCHSETVV                       160
```

```
SEQ ID NO: 53          moltype = AA  length = 390
FEATURE                Location/Qualifiers
source                 1..390
                       mol_type = protein
                       organism = Homo sapiens
SEQUENCE: 53
MPPSGLRLLP LLLPLLWLLV LTPGRPAAGL STCKTIDMEL VKRKRIEAIR GQILSKLRLA  60
SPPSQGEVPP GPLPEAVLAL YNSTRDRVAG ESAEPEPEPE ADYYAKEVTR VLMVETHNEI  120
YDKFKQSTHS IYMFFNTSEL REAVPEPVLL SRAELRLLRL KLKVEQHVEL YQKYSNNSWR  180
YLSNRLLAPS DSPEWLSFDV TGVVRQWLSR GGEIEGFRLS AHCSCDSRDN TLQVDINGFT  240
TGRRGDLATI HGMNRPFLLL MATPLERAQH LQSSRHRRAL DTNYCFSSTE KNCCVRQLYI  300
DFRKDLGWKW IHEPKGYHAN FCLGPCPYIW SLDTQYSKVL ALYNQHNPGA SAAPCCVPQA  360
LEPLPIVYYV GRKPKVEQLS NMIVRSCKCS                                  390

SEQ ID NO: 54          moltype = AA  length = 412
FEATURE                Location/Qualifiers
source                 1..412
                       mol_type = protein
                       organism = Homo sapiens
SEQUENCE: 54
MKMHLQRALV VLALLNFATV SLSLSTCTTL DFGHIKKKRV EAIRGQILSK LRLTSPPEPT  60
VMTHVPYQVL ALYNSTRELL EEMHGEREEG CTQENTESEY YAKEIHKFDM IQGLAEHNEL  120
AVCPKGITSK VFRFNVSSVE KNRTNLFRAE FRVLRVPNPS SKRNEQRIEL FQILRPDEHI  180
AKQRYIGGKN LPTRGTAEWL SFDVTDTVRE WLLRRESNLG LEISIHCPCH TFQPNGDILE  240
NIHEVMEIKF KGVDNEDDHG RGDLGRLKKQ KDHHNPHLIL MMIPPHRLDN PGQGGQRKKR  300
ALDTNYCFRN LEENCCVRPL YIDFRQDLGW KWVHEPKGYY ANFCSGPCPY LRSADTTHST  360
VLGLYNTLNP EASASPCCVP QDLEPLTILY YVGRTPKVEQ LSNMVVKSCK CS          412

SEQ ID NO: 55          moltype = AA  length = 402
FEATURE                Location/Qualifiers
source                 1..402
                       mol_type = protein
                       organism = Homo sapiens
SEQUENCE: 55
MTALPGPLWL LGLALCALGG GGPGLRPPPG CPQRRLGARE RRDVQREILA VLGLPGRPRP  60
RAPPAASRLP ASAPLFMLDL YHAMAGDDDE DGAPAERRLG RADLVMSFVN MVERDRALGH  120
QEPHWKEFRF DLTQIPAGEA VTAAEFRIYK VPSIHLLNRT LHVSMFQVVQ EQSNRESDLF  180
FLDLQTLRAG DEGWLVLDVT AASDCWLLKR HKDLGLRLYV ETEDGHSVDP GLAGLLGQRA  240
PRSQQPFVVT FFRASPSPIR TPRAVRPLRR RQPKKSNELP QANRLPGIFD DVHGSHGRQV  300
CRRHELYVSF QDLGWLDWVI APQGYSAYYC EGECSFPLDS CMNATNHAIL QSLVHLMMPD  360
AVPKACCAPT KLSATSVLYY DSSNNVILRK HRNMVVKACG CH                    402

SEQ ID NO: 56          moltype = AA  length = 399
FEATURE                Location/Qualifiers
source                 1..399
                       mol_type = protein
                       organism = Homo sapiens
SEQUENCE: 56
MAARPGLLWL LGLALCVLGG GHLSHPPHVF PQRRLGVREP RDMQREIREV LGLPGRPRSR  60
APVGAAQQPA SAPLFMLDLY RAMTDDSGGG TPQPHLDRAD LIMSFVNIVE RDRTLGYQEP  120
HWKEFHFDLT QIPAGEAVTA AEFRIYKEPS THPLNTTLHI SMFEVVQEHS NRESDLFFLD  180
LQTLRSGDEG WLVLDITAAS DRWLLNHHKD LGLRLYVETE DGHSIDPGLA GLLGRQAPRS  240
RQPFMVGFFR ANQSPVRAPR TARPLKKKQL NQINQLPHSN KHLGILDDGH GSHGREVCRR  300
HELYVSFRDL GWLDSVIAPQ GYSAYYCAGE CIYPLNSCMN STNHATMQAL VHLMKPDIIP  360
KVCCVPTELS AISLLYYDRN NNVILRRERN MVVQACGCH                        399

SEQ ID NO: 57          moltype = AA  length = 472
FEATURE                Location/Qualifiers
source                 1..472
                       mol_type = protein
                       organism = Homo sapiens
SEQUENCE: 57
MAGASRLLFL WLGCFCVSLA QGERPKPPFP ELRKAVPGDR TAGGGPDSEL QPQDKVSEHM  60
LRLYDRYSTV QAARTPGSLE GGSQPWRPRL LREGNTVRSF RAAAAETLER KGLYIFNLTS  120
LTKSENILSA TLYFCIGELG NISLSCPVSG GCSHHAQRKH IQIDLSAWTL KFSRNQSQLL  180
GHLSVDMAKS HRDIMSWLSK DITQFLRKAK ENEEFLIGFN ITSKGRQLPK RRLPFPEPYI  240
LVYANDAAIS EPESVVSSLQ GHRNFPTGTV PKWDSHIRAA LSIERRKKRS TGVLLPLQNN  300
ELPGAEYQYK KDEVWEERKP YKTLQAQAPE KSKNKKKQRK GPHRKSQTLQ FDEQTLKKAR  360
RKQWIEPRNC ARRYLKVDFA DIGWSEWIIS PKSFDAYYCS GACQFPMPKS LKPSNHATIQ  420
SIVRAVGVVP GIPEPCCVPE KMSSLSILFF DENKNVVLKV YPNMTVESCA CR          472

SEQ ID NO: 58          moltype = AA  length = 408
FEATURE                Location/Qualifiers
source                 1..408
                       mol_type = protein
                       organism = Homo sapiens
SEQUENCE: 58
MIPGNRMLMV VLLCQVLLGG ASHASLIPET GKKKVAEIQG HAGGRRSGQS HELLRDFEAT  60
```

```
LLQMFGLRRR PQPSKSAVIP DYMRDLYRLQ SGEEEEEQIH STGLEYPERP ASRANTVRSF  120
HHEEHLENIP GTSENSAFRF LFNLSSIPEN EVISSAELRL FREQVDQGPD WERGFHRINI  180
YEVMKPPAEV VPGHLITRLL DTRLVHHNVT RWETFDVSPA VLRWTREKQP NYGLAIEVTH  240
LHQTRTHQGQ HVRISRSLPQ GSGNWAQLRP LLVTFGHDGR GHALTRRRRA KRSPKHHSQR  300
ARKKNKNCRR HSLYVDFSDV GWNDWIVAPP GYQAFYCHGD CPFPLADHLN STNHAIVQTL  360
VNSVNSSIPK ACCVPTELSA ISMLYLDEYD KVVLKNYQEM VVEGCGCR                408

SEQ ID NO: 59          moltype = AA  length = 454
FEATURE                Location/Qualifiers
source                 1..454
                       mol_type = protein
                       organism = Homo sapiens
SEQUENCE: 59
MHLTVFLLKG IVGFLWSCWV LVGYAKGGLG DNHVHSSFIY RRLRNHERRE IQREILSILG  60
LPHRPRPFSP GKQASSAPLF MLDLYNAMTN EENPEESEYS VRASLAEETR GARKGYPASP  120
NGYPRRIQLS RTTPLTTQSP PLASLHDTNF LNDADMVMSF VNLVERDKDF SHQRRHYKEF  180
RFDLTQIPHG EAVTAAEFRI YKDRSNNRFE NETIKISIYQ IIKEYTNRDA DLFLLDTRKA  240
QALDVGWLVF DITVTSNHWV INPQNNLGLQ LCAETGDGRS INVKSAGLVG RQGPQSKQPF  300
MVAFFKASEV LLRSVRAANK RKNQNRNKSS SHQDSSRMSS VGDYNTSEQK QACKKHELYV  360
SFRDLGWQDW IIAPEGYAAF YCDGECSFPL NAHMNATNHA IVQTLVHLMF PDHVPKPCCA  420
PTKLNAISVL YFDDSSNVIL KKYRNMVVRS CGCH                              454

SEQ ID NO: 60          moltype = AA  length = 513
FEATURE                Location/Qualifiers
source                 1..513
                       mol_type = protein
                       organism = Homo sapiens
SEQUENCE: 60
MPGLGRRAQW LCWWWGLLCS CCGPPPLRPP LPAAAAAAAG GQLLGDGGSP GRTEQPPPSP  60
QSSSGFLYRR LKTQEKREMQ KEILSVLGLP HRPRPLHGLQ QPQPPALRQQ EEQQQQQQLP  120
RGEPPPGRLK SAPLFMLDLY NALSADNDED GASEGERQQS WPHEAASSSQ RRQPPPGAAH  180
PLNRKSLLAP GSGSGGASPL TSAQDSAFLN DADMVMSFVN LVEYDKEFSP RQRHHKEFKF  240
NLSQIPEGEV VTAAEFRIYK DCVMGSFKNQ TFLISIYQVL QEHQHRDSDL FLLDTRVVWA  300
SEEGWLEFDI TATSNLWVVT PQHNMGLQLS VVTRDGVHVH PRAAGLVGRD GPYDKQPFMV  360
AFFKVSEVHV RTTRSASSRR RQQSRNRSTQ SQDVARVSSA SDYNSSELKT ACRKHELYVS  420
FQDLGWQDWI IAPKGYAANY CDGECSFPLN AHMNATNHAI VQTLVHLMNP EYVPKPCCAP  480
TKLNAISVLY FDDNSNVILK KYRNMVVRAC GCH                               513

SEQ ID NO: 61          moltype = AA  length = 431
FEATURE                Location/Qualifiers
source                 1..431
                       mol_type = protein
                       organism = Homo sapiens
SEQUENCE: 61
MHVRSLRAAA PHSFVALWAP LFLLRSALAD FSLDNEVHSS FIHRRLRSQE RREMQREILS  60
ILGLPHRPRP HLQGKHNSAP MFMLDLYNAM AVEEGGGPGG QGFSYPYKAV FSTQGPPLAS  120
LQDSHFLTDA DMVMSFVNLV EHDKEFFHPR YHHREFRFDL SKIPEGEAVT AAEFRIYKDY  180
IRERFDNETF RISVYQVLQE HLGRESDLFL LDSRTLWASE EGWLVFDITA TSNHWVVNPR  240
HNLGLQLSVE TLDGQSINPK LAGLIGRHGP QNKQPFMVAF FKATEVHFRS IRSTGSKQRS  300
QNRSKTPKNQ EALRMANVAE NSSSDQRQAC KKHELYVSFR DLGWQDWIIA PEGYAAYYCE  360
GECAFPLNSY MNATNHAIVQ TLVHFINPET VPKPCCAPTQ LNAISVLYFD DSSNVILKKY  420
RNMVVRACGC H                                                       431

SEQ ID NO: 62          moltype = AA  length = 429
FEATURE                Location/Qualifiers
source                 1..429
                       mol_type = protein
                       organism = Homo sapiens
SEQUENCE: 62
MCPGALWVAL PLLSLLAGSL QGKPLQSWGR GSAGGNAHSP LGVPGGGLPE HTFNLKMFLE  60
NVKVDFLRSL NLSGVPSQDK TRVEPPQYMI DLYNRYTSDK STTPASNIVR SFSMEDAISI  120
TATEDFPFQK HILLFNISIP RHEQITRAEL RLYVSCQNHV DPSHDLKGSV VIYDVLDGTD  180
AWDSATETKT FLVSQDIQDE GWETLEVSSA VKRWVRSDST KSKNKLEVTV ESHRKGCDTL  240
DISVPPGSRN LPFFVVFSND HSSGTKETRL ELREMISHEQ ESVLKKLSKD GSTEAGESSH  300
EEDTDGHVAA GSTLARRKRS AGAGSHCQKT SLRVNFEDIG WDSWIIAPKE YEAYECKGGC  360
FFPLADDVTP TKHAIVQTLV HLKFPTKVGK ACCVPTKLSP ISVLYKDDMG VPTLKYHYEG  420
MSVAECGCR                                                          429

SEQ ID NO: 63          moltype = AA  length = 424
FEATURE                Location/Qualifiers
source                 1..424
                       mol_type = protein
                       organism = Homo sapiens
SEQUENCE: 63
MGSLVLTLCA LFCLAAYLVS GSPIMNLEQS PLEEDMSLFG DVFSEQDGVD FNTLLQSMKD  60
EFLKTLNLSD IPTQDSAKVD PPEYMLELYN KFATDRTSMP SANIIRSFKN EDLFSQPVSF  120
NGLRKYPLLF NVSIPHHEEV IMAELRLYTL VQRDRMIYDG VDRKITIFEV LESKGDNEGE  180
RNMLVLVSGE IYGTNSEWET FDVTDAIRRW QKSGSSTHQL EVHIESKHDE AEDASSGRLE  240
IDTSAQNKHN PLLIVFSDDQ SSDKERKEEL NEMISHEQLP ELDNLGLDSF SSGPGEEALL  300
```

```
QMRSNIIYDS TARIRRNAKG NYCKRTPLYI DFKEIGWDSW IIAPPGYEAY ECRGVCNYPL  360
AEHLTPTKHA IIQALVHLKN SQKASKACCV PTKLEPISIL YLDKGVVTYK FKYEGMAVSE  420
CGCR                                                              424

SEQ ID NO: 64          moltype = AA  length = 407
FEATURE                Location/Qualifiers
source                 1..407
                       mol_type = protein
                       organism = Homo sapiens
SEQUENCE: 64
MVLAAPLLLG FLLLALELRP RGEAAEGPAA AAAAAAAAAA AGVGGERSSR PAPSVAPEPD  60
GCPVCVWRQH SRELRLESIK SQILSKLRLK EAPNISREVV KQLLPKAPPL QQILDLHDFQ  120
GDALQPEDFL EEDEYHATTE TVISMAQETD PAVQTDGSPL CCHFHFSPKV MFTKVLKAQL  180
WVYLRPVPRP ATVYLQILRL KPLTGEGTAG GGGGGRRHIR IRSLKIELHS RSGHWQSIDF  240
KQVLHSWFRQ PQSNWGIEIN AFDPSGTDLA VTSLGPGAEG LHPFMELRVL ENTKRSRRNL  300
GLDCDEHSSE SRCCRYPLTV DFEAFGWDWI IAPKRYKANY CSGQCEYMFM QKYPHTHLVQ  360
QANPRGSAGP CCTPTKMSPI NMLYFNDKQQ IIYGKIPGMV VDRCGCS                407

SEQ ID NO: 65          moltype = AA  length = 450
FEATURE                Location/Qualifiers
source                 1..450
                       mol_type = protein
                       organism = Homo sapiens
SEQUENCE: 65
MDLSAAAALC LWLLSACRPR DGLEAAAVLR AAGAGPVRSP GGGGGGGGGG RTLAQAAGAA  60
AVPAAAVPRA RAARRAAGSG FRNGSVVPHH FMMSLYRSLA GRAPAGAAAV SASGHGRADT  120
ITGFTDQATQ DESAAETGQS FLFDVSSLND ADEVVGAELR VLRRGSPESG PGSWTSPPLL  180
LLSTCPGAAR APRLLYSRAA EPLVGQRWEA FDVADAMRRH RREPRPPRAF CLLLRAVAGP  240
VPSPLALRRL GFGWPGGGGS AAEERAVLVV SSRTQRKESL FREIRAQARA LGAALASEPL  300
PDPGTGTASP RAVIGGRRRR RTALAGTRTA QGSGGGAGRG HGRRGRSRCS RKPLHVDFKE  360
LGWDDWIIAP LDYEAYHCEG LCDFPLRSHL EPTNHAIIQT LLNSMAPDAA PASCCVPARL  420
SPISILYIDA ANNVVYKQYE DMVVEACGCR                                   450

SEQ ID NO: 66          moltype = AA  length = 455
FEATURE                Location/Qualifiers
source                 1..455
                       mol_type = protein
                       organism = Homo sapiens
SEQUENCE: 66
MDTPRVLLSA VFLISFLWDL PGFQQASISS SSSSAELGST KGMRSRKEGK MQRAPRDSDA  60
GREGQEPQPR PQDEPRAQQP RAQEPPGRGP RVVPHEYMLS IYRTYSIAEK LGINASFFQS  120
SKSANTITSF VDRGLDDLSH TPLRRQKYLF DVSMLSDKEE LVGAELRLFR QAPSAPWGPP  180
AGPLHVQLFP CLSPLLLDAR TLDPQGAPPA GWEVFDVWQG LRHQPWKQLC LELRAAWGEL  240
DAGEAEARAR GPQQPPPPDL RSLGFGRRVR PPQERALLVV FTRSQRKNLF AEMREQLGSA  300
EAAGPGAGAE GSWPPPSGAP DARPWLPSPG RRRRRTAFAS RHGKRHGKKS RLRCSKKPLH  360
VNFKELGWDD WIIAPLEYEA YHCEGVCDFP LRSHLEPTNH AIIQTLMNSM DPGSTPPSCC  420
VPTKLTPISI LYIDAGNNVV YKQYEDMVVE SCGCR                             455

SEQ ID NO: 67          moltype = AA  length = 392
FEATURE                Location/Qualifiers
source                 1..392
                       mol_type = protein
                       organism = Homo sapiens
SEQUENCE: 67
MVLLSILRIL FLCELVLFME HRAQMAEGGQ SSIALLAEAP TLPLIEELLE ESPGEQPRKP  60
RLLGHSLRYM LELYRRSADS HGHPRENRTI GATMVRLVKP LTNVARPHRG TWHIQILGFP  120
LRPNRGLYQL VRATVVYRHH LQLTRFNLSC HVEPWVQKNP TNHFPSSEGD SSKPSLMSNA  180
WKEMDITQLV QQRFWNNKGH RILRLRFMCQ QQKDSGGLEL WHGTSSLDIA FLLLYFNDTH  240
KSIRKAKFLP RGMEEFMERE SLLRRTRQAD GISAEVTASS SKHSGPENNQ CSLHPFQISF  300
RQLGWDHWII APPFYTPNYC KGTCLRVLRD GLNSPNHAII QNLINQLVDQ SVPRPSCVPY  360
KYVPISVLMI EANGSILYKE YEGMIAESCT CR                                392

SEQ ID NO: 68          moltype = AA  length = 1301
FEATURE                Location/Qualifiers
source                 1..1301
                       mol_type = protein
                       organism = Homo sapiens
SEQUENCE: 68
MKIITYFCIW AVAWAIPVPQ SKPLERHVEK SMNLHLLARS NVSVQDELNA SGTIKESGVL  60
VHEGDRGRQE NTQDGHKGEG NGSKWAEVGG KSFSTYSTLA NEEGNIEGWN GDTGKAETYG  120
HDGIHGKEEN ITANGIQGQV SIIDNAGATN RSNTNGNTDK NTQNGDVGDA GHNEDVAVVQ  180
EDGPQVAGSN NSTDNEDEII ENSCRNEGNT SEITPQINSK RNGTKEAEVT PGTGEDAGLD  240
NSDGSPSGNG ADEDEDEGSG DDEDEEAGNG KDSSNNSKGQ EGQDHGKEDD HDSSIGQNSD  300
SKEYYDPEGK EDPHNEVDGD KTSKSEENSA GIPEDNGSQR IEDTQKLNHR ESKRVENRIT  360
KESETHAVGK SQDKGIEIKG PSSGNRNITK EVGKGNEGKE DKGQHGMILG KGNVKTQGEV  420
VNIEGPGQKS EPGNKVGHSN TGSDSNSDGY DSYDFDDKSM QGDDPNSSDE SNGNDDANSE  480
SDNNSSSRGD ASYNSDESKD NGNGSDSKGA EDDDSDSTSD TNNSDSNGNG NNGNDDNDKS  540
DSGKGKSDSS DSDSSDSSNS SDSSDSSDSD SSDSNSSSDS DSSDSDSSDS SDSDSSDSSN  600
SSDSSDSSDS SDSSDSSDSS DSKSDSSKSE SDSSDSDSKS DSSDSNSSDS SDNSDSSDSS  660
```

```
NSSNSSDSSD SSDSSDSSSS SDSSNSSDSS DSSDSSNSSE SSDSSDSSDS DSSDSSDSSN  720
SNSSDSDSSN SSDSSDSSNS SDSSDSSDSS NSSDSSDSSD SSNSSDSSDS SDSSDSSDSS  780
NSSDSNDSSN SSDSSDSSNS SDSSNSSDSS DSSDSSDSDS SNSSDSSNSS DSSDSSNSSD  840
SSDSSDSSDG SDSDSSNRSD SSNSSDSSDS SDSSNSSDSS DSSDSNESSN SSDSSDSSNS  900
SDSDSSDSSN SSDSSDSSNS SDSSESSNSS DNSNSSDSSN SSDSSDSSDS SNSSDSSNSS  960
DSSNSSDSSD SNSSDSSDSS NSSDSSDSSD SSDSSDSSDS SNSSDSSDSS DSSDSSNSSD  1020
SSNSSDSSNS SDSSDSSDSS DSSDSSDSSD SSDSSNSSDS SDSSDSSDSS DSSDSSDSSD  1080
SSESSDSSDS SNSSDSSDSS DSSDSSDSSD SSDSSDSSDS SNSSDSSDSS DSSDSSDSSN  1140
SSDSSDSSES SDSSDSSDSS DSSDSSDSSD SSDSSDSSNS SDSSDSSDSS DSSDSSDSSD  1200
SSDSSDSSDS SDSSDSSDSS DSSDSSDSSD SNESSDSSDS SDSSDSSNSS DSSDSSDSSD  1260
STSDSNDESD SQSKSGNGNN NGSDSDSDSE GSDSNHSTSD D                      1301

SEQ ID NO: 69          moltype = AA  length = 372
FEATURE                Location/Qualifiers
source                 1..372
                       mol_type = protein
                       organism = Homo sapiens
SEQUENCE: 69
MPPPQQGPCG HHLLLLLALL LPSLPLTRAP VPPGPAAALL QALGLRDEPQ GAPRLRPVPP  60
VMWRLFRRRD PQETRSGSRR TSPGVTLQPC HVEELGVAGN IVRHIPDRGA PTRASEPASA  120
AGHCPEWTVV FDLSAVEPAE RPSRARLELR FAAAAAAAPE GGWELSVAQA GQGAGADPGP  180
VLLRQLVPAL GPPVRAELLG AAWARNASWP RSLRLALALR PRAPAACARL AEASLLLVTL  240
DPRLCHPLAR PRRDAEPVLG GGPGGACRAR RLYVSFREVG WHRWVIAPRG FLANYCQGQC  300
ALPVALSGSG GPPALNHAVL RALMHAAAPG AADLPCCVPA RLSPISVLFF DNSDNVVLRQ  360
YEDMVVDECG CR                                                      372

SEQ ID NO: 70          moltype = AA  length = 364
FEATURE                Location/Qualifiers
source                 1..364
                       mol_type = protein
                       organism = Homo sapiens
SEQUENCE: 70
MLRFLPDLAF SFLLILALGQ AVQFQEYVFL QFLGLDKAPS PQKFQPVPYI LKKIFQDREA  60
AATTGVSRDL CYVKELGVRG NVLRFLPDQG FFLYPKKISQ ASSCLQKLLY FNLSAIKERE  120
QLTLAQLGLD LGPNSYYNLG PELELALFLV QEPHVWGQTT PKPGKMFVLR SVPWPQGAVH  180
FNLLDVAKDW NDNPRKNFGL FLEILVKEDR DSGVNFQPED TCARLRCSLH ASLLVVTLNP  240
DQCHPSRKRR AAIPVPKLSC KNLCHRHQLF INFRDLGWHK WIIAPKGFMA NYCHGECPFS  300
LTISLNSSNY AFMQALMHAV DPEIPQAVCI PTKLSPISML YQDNNDNVIL RHYEDMVVDE  360
CGCG                                                               364

SEQ ID NO: 71          moltype = AA  length = 501
FEATURE                Location/Qualifiers
source                 1..501
                       mol_type = protein
                       organism = Homo sapiens
SEQUENCE: 71
MRLPKLLTFL LWYLAWLDLE FICTVLGAPD LGQRPQGTRP GLAKAEAKER PPLARNVFRP  60
GGHSYGGGAT NANARAKGGT GQTGGLTQPK KDEPKKLPPR PGGPEPKPGH PPQTRQATAR  120
TVTPKGQLPG GKAPPKAGSV PSSFLLKKAR EPGPPREPKE PFRPPPITPH EYMLSLYRTL  180
SDADRKGGNS SVKLEAGLAN TITSFIDKGQ DDRGPVVRKQ RYVFDISALE KDGLLGAELR  240
ILRKKPSDTA KPAAPGGGRA AQLKLSSCPS GRQPAALLDV RSVPGLDGSG WEVFDIWKLF  300
RNFKNSAQLC LELEAWERGR AVDLRGLGFD RAARQVHEKA LFLVFGRTKK RDLFFNEIKA  360
RSGQDDKTVY EYLFSQRRKR RAPLATRQGK RPSKNLKARC SRKALHVNFK DMGWDDWIIA  420
PLEYEAFHCE GLCEFPLRSH LEPTNHAVIQ TLMNSMDPES TPPTCCVPTR LSPISILFID  480
SANNVVYKQY EDMVVESCGC R                                            501

SEQ ID NO: 72          moltype = AA  length = 450
FEATURE                Location/Qualifiers
source                 1..450
                       mol_type = protein
                       organism = Homo sapiens
SEQUENCE: 72
MDLSAAAALC LWLLSACRPR DGLEAAAVLR AAGAGPVRSP GGGGGGGGGG RTLAQAAGAA  60
AVPAAAVPRA RAARRAAGSG FRNGSVVPHH FMMSLYRSLA GRAPAGAAAV SASGHGRADT  120
ITGFTDQATQ DESAAETGQS FLFDVSSLND ADEVVGAELR VLRRGSPESG PGSWTSPPLL  180
LLSTCPGAAR APRLLYSRAA EPLVGQRWEA FDVADAMRRH RREPRPPRAF CLLLRAVAGP  240
VPSPLALRRL GFGWPGGGGS AAEERAVLVV SSRTQRKESL FREIRAQARA LGAALASEPL  300
PDPGTGTASP RAVIGGRRRR RTALAGTRTA QGSGGGAGRG HGRRGRSRCS RKPLHVDFKE  360
LGWDDWIIAP LDYEAYHCEG LCDFPLRSHL EPTNHAIIQT LLNSMAPDAA PASCCVPARL  420
SPISILYIDA ANNVVYKQYE DMVVEACGCR                                   450

SEQ ID NO: 73          moltype = AA  length = 375
FEATURE                Location/Qualifiers
source                 1..375
                       mol_type = protein
                       organism = Homo sapiens
SEQUENCE: 73
MQKLQLCVYI YLFMLIVAGP VDLNENSEQK ENVEKEGLCN ACTWRQNTKS SRIEAIKIQI  60
LSKLRLETAP NISKDVIRQL LPKAPPLREL IDQYDVQRDD SSDGSLEDDD YHATTETIIT  120
```

```
MPTESDFLMQ VDGKPKCCFF KFSSKIQYNK VVKAQLWIYL RPVETPTTVF VQILRLIKPM  180
KDGTRYTGIR SLKLDMNPGT GIWQSIDVKT VLQNWLKQPE SNLGIEIKAL DENGHDLAVT  240
FPGPGEDGLN PFLEVKVTDT PKRSRRDFGL DCDEHSTESR CCRYPLTVDF EAFGWDWIIA  300
PKRYKANYCS GECEFVFLQK YPHTHLVHQA NPRGSAGPCC TPTKMSPINM LYFNGKEQII  360
YGKIPAMVVD RCGCS                                                   375

SEQ ID NO: 74           moltype = AA  length = 308
FEATURE                 Location/Qualifiers
source                  1..308
                        mol_type = protein
                        organism = Homo sapiens
SEQUENCE: 74
MPGQELRTVN GSQMLLVLLV LSWLPHGGAL SLAEASRASF PGPSELHSED SRFRELRKRY  60
EDLLTRLRAN QSWEDSNTDL VPAPAVRILT PEVRLGSGGH LHLRISRAAL PEGLPEASRL  120
HRALFRLSPT ASRSWDVTRP LRRQLSLARP QAPALHLRLS PPPSQSDQLL AESSSARPQL  180
ELHLRPQAAR GRRRARARNG DHCPLGPGRC CRLHTVRASL EDLGWADWVL SPREVQVTMC  240
IGACPSQFRA ANMHAQIKTS LHRLKPDTVP APCCVPASYN PMVLIQKTDT GVSLQTYDDL  300
LAKDCHCI                                                           308

SEQ ID NO: 75           moltype = AA  length = 412
FEATURE                 Location/Qualifiers
source                  1..412
                        mol_type = protein
                        organism = Homo sapiens
SEQUENCE: 75
MTDRQTDTAP SPSYHLLPGR RRTVDAAASR GQGPEPAPGG GVEGVGARGV ALKLFVQLLG  60
CSRFGGAVVR AGEAEPSGAA RSASSGREEP QPEEGEEEEE KEEERGPQWR LGARKPGSWT  120
GEAAVCADSA PAARAPQALA RASGRGGRVA RRGAEESGPP HSPSRRGSAS RAGPGRASET  180
MNFLLSWVHW SLALLLYLHH AKWSQAAPMA EGGGQNHHEV VKFMDVYQRS YCHPIETLVD  240
IFQEYPDEIE YIFKPSCVPL MRCGGCCNDE GLECVPTEES NITMQIMRIK PHQGQHIGEM  300
SFLQHNKCEC RPKKDRARQE KKSVRGKGKG QKRKRKKSRY KSWSVYVGAR CCLMPWSLPG  360
PHPCGPCSER RKHLFVQDPQ TCKCSCKNTD SRCKARQLEL NERTCRCDKP RR          412

SEQ ID NO: 76           moltype = AA  length = 560
FEATURE                 Location/Qualifiers
source                  1..560
                        mol_type = protein
                        organism = Homo sapiens
SEQUENCE: 76
MFARMSDLHV LLLMALVGKT ACGFSLMSLL ESLDPDWTPD QYDYSYEDYN QEENTSSTLT  60
HAENPDWYYT EDQADPCQPN PCEHGGDCLV HGSTFTCSCL APFSGNKCQK VQNTCKDNPC  120
GRGQCLITQS PPYYRCVCKH PYTGPSCSQV VPVCRPNPCQ NGATCSRHKR RSKFTCACPD  180
QFKGKFCEIG SDDCYVGDGY SYRGKMNRTV NQHACLYWNS HLLLQENYNM FMEDAETHGI  240
GEHNFCRNPD ADEKPWCFIK VTNDKVKWEY CDVSACSAQD VAYPEESPTE PSTKLPGFDS  300
CGKTEIAERK IKRIYGGFKS TAGKHPWQAS LQSSLPLTIS MPQGHFCGGA LIHPCWVLTA  360
AHCTDIKTRH LKVVLGDQDL KKEEFHEQSF RVEKIFKYSH YNERDEIPHN DIALLKLKPV  420
DGHCALESKY VKTVCLPDGS FPSGSECHIS GWGVTETGKG SRQLLDAKVK LIANTLCNSR  480
QLYDHMIDDS MICAGNLQKP GQDTCQGDSG GPLTCEKDGT YYVYGIVSWG LECGKRPGVY  540
TQVTKFLNWI KATIKSESGF                                              560

SEQ ID NO: 77           moltype = AA  length = 418
FEATURE                 Location/Qualifiers
source                  1..418
                        mol_type = protein
                        organism = Homo sapiens
SEQUENCE: 77
MRSLLLLSAF CLLEAALAAE VKKPAAAAAP GTAEKLSPKA ATLAERSAGL AFSLYQAMAK  60
DQAVENILVS PVVVASSLGL VSLGGKATTA SQAKAVLSAE QLRDEEVHAG LGELLRSLSN  120
STARNVTWKL GSRLYGPSSV SFADDFVRSS KQHYNCEHSK INFRDKRSAL QSINEWAAQT  180
TDGKLPEVTK DVERTDGALL VNAMFFKPHW DEKFHHKMVD NRGFMVTRSY TVGVMMMHRT  240
GLYNYYDDEK EKLQIVEMPL AHKLSSLIIL MPHHVEPLER LEKLLTKEQL KIWMGKMQKK  300
AVAISLPKGV VEVTHDLQKH LAGLGLTEAI DKNKADLSRM SGKKDLYLAS VFHATAFELD  360
TDGNPFDQDI YGREELRSPK LFYADHPFIF LVRDTQSGSL LFIGRLVRPK GDKMRDEL    418

SEQ ID NO: 78           moltype = AA  length = 207
FEATURE                 Location/Qualifiers
source                  1..207
                        mol_type = protein
                        organism = Homo sapiens
SEQUENCE: 78
MYSAPSACTC LCLHFLLLCF QVQVLVAEEN VDFRIHVENQ TRARDDVSRK QLRLYQLYSR  60
TSGKHIQVLG RRISARGEDG DKYAQLLVET DTFGSQVRIK GKETEFYLCM NRKGKLVGKP  120
DGTSKECVFI EKVLENNYTA LMSAKYSGWY VGFTKKGRPR KGPKTRENQQ DVHFMKRYPK  180
GQPELQKPFK YTTVTKRSRR IRPTHPA                                      207

SEQ ID NO: 79           moltype = AA  length = 194
FEATURE                 Location/Qualifiers
source                  1..194
                        mol_type = protein
```

```
                         organism = Homo sapiens
SEQUENCE: 79
MHKWILTWIL PTLLYRSCFH IICLVGTISL ACNDMTPEQM ATNVNCSSPE RHTRSYDYME  60
GGDIRVRRLF CRTQWYLRID KRGKVKGTQE MKNNYNIMEI RTVAVGIVAI KGVESEFYLA  120
MNKEGKLYAK KECNEDCNFK ELILENHYNT YASAKWTHNG GEMFVALNQK GIPVRGKKTK  180
KEQKTAHFLP MAIT                                                    194

SEQ ID NO: 80            moltype = AA  length = 233
FEATURE                  Location/Qualifiers
source                   1..233
                         mol_type = protein
                         organism = Homo sapiens
SEQUENCE: 80
MSTESMIRDV ELAEEALPKK TGGPQGSRRC LFLSLFSFLI VAGATTLFCL LHFGVIGPQR  60
EEFPRDLSLI SPLAQAVRSS SRTPSDKPVA HVVANPQAEG QLQWLNRRAN ALLANGVELR  120
DNQLVVPSEG LYLIYSQVLF KGQGCPSTHV LLTHTISRIA VSYQTKVNLL SAIKSPCQRE  180
TPEGAEAKPW YEPIYLGGVF QLEKGDRLSA EINRPDYLDF AESGQVYFGI IAL         233

SEQ ID NO: 81            moltype = AA  length = 281
FEATURE                  Location/Qualifiers
source                   1..281
                         mol_type = protein
                         organism = Homo sapiens
SEQUENCE: 81
MAMMEVQGGP SLGQTCVLIV IFTVLLQSLC VAVTYVYFTN ELKQMQDKYS KSGIACFLKE  60
DDSYWDPNDE ESMNSPCWQV KWQLRQLVRK MILRTSEETI STVQEKQQNI SPLVRERGPQ  120
RVAAHITGTR GRSNTLSSPN SKNEKALGRK INSWESSRSG HSFLSNLHLR NGELVIHEKG  180
FYYIYSQTYF RFQEEIKENT KNDKQMVQYI YKYTSYPDPI LLMKSARNSC WSKDAEYGLY  240
SIYQGGIFEL KENDRIFVSV TNEHLIDMDH EASFFGAFLV G                      281

SEQ ID NO: 82            moltype = AA  length = 370
FEATURE                  Location/Qualifiers
source                   1..370
                         mol_type = protein
                         organism = Homo sapiens
SEQUENCE: 82
MGLWALLPGW VSATLLLALA ALPAALAANS SGRWWGIVNV ASSTNLLTDS KSLQLVLEPS  60
LQLLSRKQRR LIRQNPGILH SVSGGLQSAV RECKWQFRNR RWNCPTAPGP HLFGKIVNRG  120
CRETAFIFAI TSAGVTHSVA RSCSEGSIES CTCDYRRRGP GGPDWHWGGC SDNIDFGRLF  180
GREFVDSGEK GRDLRFLMNL HNNEAGRTTV FSEMRQECKC HGMSGSCTVR TCWMRLPTLR  240
AVGDVLRDRF DGASRVLYGN RGSNRASRAE LLRLEPEDPA HKPPSPHDLV YFEKSPNFCT  300
YSGRLGTAGT AGRACNSSSP ALDGCELLCC GRGHRTRTQR VTERCNCTFH WCCHVSCRNC  360
THTRVLHECL                                                         370

SEQ ID NO: 83            moltype = AA  length = 360
FEATURE                  Location/Qualifiers
source                   1..360
                         mol_type = protein
                         organism = Homo sapiens
SEQUENCE: 83
MNAPLGGIWL WLPLLLTWLT PEVNSSWWYM RATGGSSRVM CDNVPGLVSS QRQLCHRHPD  60
VMRAISQGVA EWTAECQHQF RQHRWNCNTL DRDHSLFGRV LLRSSRESAF VYAISSAGVV  120
FAITRACSQG EVKSCSCDPK KMGSAKDSKG IFDWGGCSDN IDYGIKFARA FVDAKERKGK  180
DARALMNLHN NRAGRKAVKR FLKQECKCHG VSGSCTLRTC WLAMADFRKT GDYLWRKYNG  240
AIQVVMNQDG TGFTVANERF KKPTKNDLVY FENSPDYCIR DREAGSLGTA GRVCNLTSRG  300
MDSCEVMCCG RGYDTSHVTR MTKCGCKFHW CCAVRCQDCL EALDVHTCKA PKNADWTTAT  360

SEQ ID NO: 84            moltype = AA  length = 391
FEATURE                  Location/Qualifiers
source                   1..391
                         mol_type = protein
                         organism = Homo sapiens
SEQUENCE: 84
MLRPGGAEEA AQLPLRRASA PVPVPSPAAP DGSRASARLG LACLLLLLLL TLPARVDTSW  60
WYIGALGARV ICDNIPGLVS RQRQLCQRYP DIMRSVGEGA REWIRECQHQ FRHHRWNCTT  120
LDRDHTVFGR VMLRSSREAA FVYAISSAGV VHAITRACSQ GELSVCSCDP YTRGRHHDQR  180
GDFDWGGCSD NIHYGVRFAK AFVDAKEKRL KDARALMNLH NNRCGRTAVR RFLKLECKCH  240
GVSGSCTLRT CWRALSDFRR TGDYLRRRYD GAVQVMATQD GANFTAARQG YRRATRTDLV  300
YFDNSPDYCV LDKAAGSLGT AGRVCSKTSK GTDGCEIMCC GRGYDTTRVT RVTQCECKFH  360
WCCAVRCKEC RNTVDVHTCK APKKAEWLDQ T                                 391

SEQ ID NO: 85            moltype = AA  length = 355
FEATURE                  Location/Qualifiers
source                   1..355
                         mol_type = protein
                         organism = Homo sapiens
SEQUENCE: 85
MEPHLLGLLL GLLLGGTRVL AGYPIWWSLA LGQQYTSLGS QPLLCGSIPG LVPKQLRFCR  60
NYIEIMPSVA EGVKLGIQEC QHQFRGRRWN CTTIDDSLAI FGPVLDKATR ESAFVHAIAS  120
```

```
AGVAFAVTRS CAEGTSTICG CDSHHKGPPG EGWKWGGCSE DADFGVLVSR EFADARENRP  180
DARSAMNKHN NEAGRTTILD HMHLKCKCHG LSGSCEVKTC WWAQPDFRAI GDFLKDKYDS  240
ASEMVVEKHR ESRGWVETLR AKYSLFKPPT ERDLVYYENS PNFCEPNPET GSFGTRDRTC  300
NVTSHGIDGC DLLCCGRGHN TRTEKRKEKC HCIFHWCCYV SCQECIRIYD VHTCK       355

SEQ ID NO: 86          moltype = AA  length = 352
FEATURE                Location/Qualifiers
source                 1..352
                       mol_type = protein
                       organism = Homo sapiens
SEQUENCE: 86
MAPLGYFLLL CSLKQALGSY PIWWSLAVGP QYSSLGSQPI LCASIPGLVP KQLRFCRNYV  60
EIMPSVAEGI KIGIQECQHQ FRGRRWNCTT VHDSLAIFGP VLDKATRESA FVHAIASAGV  120
AFAVTRSCAE GTAAICGCSS RHQGSPGKGW KWGGCSEDIE FGGMVSREFA DARENRPDAR  180
SAMNRHNNEA GRQAIASHMH LKCKCHGLSG SCEVKTCWWS QPDFRAIGDF LKDKYDSASE  240
MVVEKHRESR GWVETLRPRY TYFKVPTERD LVYYEASPNF CEPNPETGSF GTRDRTCNVS  300
SHGIDGCDLL CCGRGHNARA ERRREKCRCV FHWCCYVSCQ ECTRVYDVHT CK          352

SEQ ID NO: 87          moltype = AA  length = 351
FEATURE                Location/Qualifiers
source                 1..351
                       mol_type = protein
                       organism = Homo sapiens
SEQUENCE: 87
MSPRSCLRSL RLLVFAVFSA AASNWLYLAK LSSVGSISEE ETCEKLKGLI QRQVQMCKRN  60
LEVMDSVRRG AQLAIEECQY QFRNRRWNCS TLDSLPVFGK VVTQGTREAA FVYAISSAGV  120
AFAVTRACSS GELEKCGCDR TVHGVSPQGF QWSGCSDNIA YGVAFSQSFV DVRERSKGAS  180
SSRALMNLHN NEAGRKAILT HMRVECKCHG VSGSCEVKTC WRAVPPFRQV GHALKEKFDG  240
ATEVEPRRVG SSRALVPRNA QFKPHTDEDL VYLEPSPDFC EQDMRSGVLG TRGRTCNKTS  300
KAIDGCELLC CGRGFHTAQV ELAERCSCKF HWCCFVKCRQ CQRLVELHTC R           351

SEQ ID NO: 88          moltype = AA  length = 380
FEATURE                Location/Qualifiers
source                 1..380
                       mol_type = protein
                       organism = Homo sapiens
SEQUENCE: 88
MKKSIGILSP GVALGMAGSA MSSKFFLVAL AIFFSFAQVV IEANSWWSLG MNNPVQMSEV  60
YIIGAQPLCS QLAGLSQGQK KLCHLYQDHM QYIGEGAKTG IKECQYQFRH RRWNCSTVDN  120
TSVFGRVMQI GSRETAFTYA VSAAGVVNAM SRACREGELS TCGCSRAARP KDLPRDWLWG  180
GCGDNIDYGY RFAKEFVDAR ERERIHAKGS YESARILMNL HNNEAGRRTV YNLADVACKC  240
HGVSGSCSLK TCWLQLADFR KVGDALKEKY DSAAAMRLNS RGKLVQVNSR FNSPTTQDLV  300
YIDPSPDYCV RNESTGSLGT QGRLCNKTSE GMDGCELMCC GRGYDQFKTV QTERCHCKFH  360
WCCYVKCKKC TEIVDQFVCK                                              380

SEQ ID NO: 89          moltype = AA  length = 359
FEATURE                Location/Qualifiers
source                 1..359
                       mol_type = protein
                       organism = Homo sapiens
SEQUENCE: 89
MPSLLLLFTA ALLSSWAQLL TDANSWWSLA LNPVQRPEMF IIGAQPVCSQ LPGLSPGQRK  60
LCQLYQEHMA YIGEGAKTGI KECQHQFRQR RWNCSTADNA SVFGRVMQIG SRETAFTHAV  120
SAAGVVNAIS RACREGELST CGCSRTARPK DLPRDWLWGG CGDNVEYGYR FAKEFVDARE  180
REKNFAKGSE EQGRVLMNLQ NNEAGRRAVY KMADVACKCH GVSGSCSLKT CWLQLAEFRK  240
VGDRLKEKYD SAAAMRVTRK GRLELVNSRF TQPTPEDLVY VDPSPDYCLR NESTGSLGTQ  300
GRLCNKTSEG MDGCELMCCG RGYNQFKSVQ VERCHCKFHW CCFVRCKKCT EIVDQYICK   359

SEQ ID NO: 90          moltype = AA  length = 365
FEATURE                Location/Qualifiers
source                 1..365
                       mol_type = protein
                       organism = Homo sapiens
SEQUENCE: 90
MLPPLPSRLG LLLLLLLCPA HVGGLWWAVG SPLVMDPTSI CRKARRLAGR QAELCQAEPE  60
VVAELARGAR LGVRECQFQF RFRRWNCSSH SKAFGRILQQ DIRETAFVFA ITAAGASHAV  120
TQACSMGELL QCGCQAPRGR APPRPSGLPG TPGPPGPAGS PEGSAAWEWG GCGDDVDFGD  180
EKSRLFMDAR HKRGRGDIRA LVQLHNNEAG RLAVRSHTRT ECKCHGLSGS CALRTCWQKL  240
PPFREVGARL LERFHGASRV MGTNDGKALL PAVRTLKPPG RADLLYAADS PDFCAPNRRT  300
GSPGTRGRAC NSSAPDLSGC DLLCCGRGHR QESVQLEENC LCRFHWCCVV QCHRCRVRKE  360
LSLCL                                                              365

SEQ ID NO: 91          moltype = AA  length = 349
FEATURE                Location/Qualifiers
source                 1..349
                       mol_type = protein
                       organism = Homo sapiens
SEQUENCE: 91
MNRKARRCLG HLFLSLGMVY LRIGGFSSVV ALGASIICNK IPGLAPRQRA ICQSRPDAII  60
```

```
VIGEGSQMGL DECQFQFRNG RWNCSALGER TVFGKELKVG SREAAFTYAI IAAGVAHAIT  120
AACTQGNLSD CGCDKEKQGQ YHRDEGWKWG GCSADIRYGI GFAKVFVDAR EIKQNARTLM  180
NLHNNEAGRK ILEENMKLEC KCHGVSGSCT TKTCWTTLPQ FRELGYVLKD KYNEAVHVEP  240
VRASRNKRPT FLKIKKPLSY RKPMDTDLVY IEKSPNYCEE DPVTGSVGTQ GRACNKTAPQ  300
ASGCDLMCCG RGYNTHQYAR VWQCNCKFHW CCYVKCNTCS ERTEMYTCK             349

SEQ ID NO: 92          moltype = AA  length = 349
FEATURE                Location/Qualifiers
source                 1..349
                       mol_type = protein
                       organism = Homo sapiens
SEQUENCE: 92
MHRNFRKWIF YVFLCFGVLY VKLGALSSVV ALGANIICNK IPGLAPRQRA ICQSRPDAII  60
VIGEGAQMGI NECQYQFRFG RWNCSALGEK TVFGQELRVG SREAAFTYAI TAAGVAHAVT  120
AACSQGNLSN CGCDREKQGY YNQAEGWKWG GCSADVRYGI DFSRRFVDAR EIKKNARRLM  180
NLHNNEAGRK VLEDRMQLEC KCHGVSGSCT TKTCWTTLPK FREVGHLLKE KYNAAVQVEV  240
VRASRLRQPT FLRIKQLRSY QKPMETDLVY IEKSPNYCEE DAATGSVGTQ GRLCNRTSPG  300
ADGCDTMCCG RGYNTHQYTK VWQCNCKFHW CCFVKCNTCS ERTEVFTCK             349

SEQ ID NO: 93          moltype = AA  length = 386
FEATURE                Location/Qualifiers
source                 1..386
                       mol_type = protein
                       organism = Homo sapiens
SEQUENCE: 93
MLCCIQCLCL VSPFPTLTPC QGGPHCLIPI HLCLTFSLFG RSVNNFLITG PKAYLTYTTS  60
VALGAQSGIE ECKFQFAWER WNCPENALQL STHNRLRSAT RETSFIHAIS SAGVMYIITK  120
NCSMGDFENC GCDGSNNGKT GGHGWIWGGC SDNVEFGERI SKLFVDSLEK GKDARALMNL  180
HNNRAGRLAV RATMKRTCKC HGISGSCSIQ TCWLQLAEFR EMGDYLKAKY DQALKIEMDK  240
RQLRAGNSAE GHWVPAEAFL PSAEAELIFL EESPDYCTCN SSLGIYGTEG RECLQNSHNT  300
SRWERRSCGR LCTECGLQVE ERKTEVISSC NCKFQWCCTV KCDQCRHVTM SNPAVLLGIR  360
RIEAKNERVL FRLLKSSLWL QIYADK                                      386

SEQ ID NO: 94          moltype = AA  length = 351
FEATURE                Location/Qualifiers
source                 1..351
                       mol_type = protein
                       organism = Homo sapiens
SEQUENCE: 94
MFLSKPSVYI CLFTCVLQLS HSWSVNNFLM TGPKAYLIYS SSVAAGAQSG IEECKYQFAW  60
DRWNCPERAL QLSSHGGLRS ANRETAFVHA ISSAGVMYTL TRNCSLGDFD NCGCDDSRNG  120
QLGGQGWLWG GCSDNVGFGE AISKQFVDAL ETGQDARAAM NLHNNEAGRK AVKGTMKRTC  180
KCHGVSGSCT TQTCWLQLPE FREVGAHLKE KYHAALKVDL LQGAGNSAAG RGAIADTFRS  240
ISTRELVHLE DSPDYCLENK TLGLLGTEGR ECLRRGRALG RWERRSCRRL CGDCGLAVEE  300
RRAETVSSCN CKFHWCCAVR CEQCRRRVTK YFCSRAERPR GGAAHKPGRK P           351

SEQ ID NO: 95          moltype = AA  length = 365
FEATURE                Location/Qualifiers
source                 1..365
                       mol_type = protein
                       organism = Homo sapiens
SEQUENCE: 95
MLDGSPLARW LAAAFGLTLL LAALRPSAAY FGLTGSEPLT ILPLTLEPEA AAQAHYKACD  60
RLKLERKQRR MCRRDPGVAE TLVEAVSMSA LECQFQFRFE RWNCTLEGRY RASLLKRGFK  120
ETAFLYAISS AGLTHALAKA CSAGRMERCT CDEAPDLENR EAWQWGGCGD NLKYSSKFVK  180
EFLGRRSSKD LRARVDFHNN LVGVKVIKAG VETTCKCHGV SGSCTVRTCW RQLAPFHEVG  240
KHLKHKYETA LKVGSTTNEA AGEAGAISPP RGRASGAGGS DPLPRTPELV HLDDSPSFCL  300
AGRFSPGTAG RRCHREKNCE SICCGRGHNT QSRVVTRPCQ CQVRWCCYVE CRQCTQREEV  360
YTCKG                                                             365

SEQ ID NO: 96          moltype = AA  length = 357
FEATURE                Location/Qualifiers
source                 1..357
                       mol_type = protein
                       organism = Homo sapiens
SEQUENCE: 96
MRPPPALALA GLCLLALPAA AASYFGLTGR EVLTPFPGLG TAAAPAQGGA HLKQCDLLKL  60
SRRQKQLCRR EPGLAETLRD AAHLGLLECQ FQFRHERWNC SLEGRMGLLK RGFKETAFLY  120
AVSSAALTHT LARACSAGRM ERCTCDDSPG LESRQAWQWG VCGDNLKYST KFLSNFLGSK  180
RGNKDLRARA DAHNTHVGIK AVKSGLRTTC KCHGVSGSCA VRTCWKQLSP FRETGQVLKL  240
RYDSAVKVSS ATNEALGRLE LWAPARQGSL TKGLAPRSGD LVYMEDSPSF CRPSKYSPGT  300
AGRVCSREAS CSSLCCGRGY DTQSRLVAFS CHCQVQWCCY VECQQCVQEE LVYTCKH     357

SEQ ID NO: 97          moltype = AA  length = 417
FEATURE                Location/Qualifiers
source                 1..417
                       mol_type = protein
                       organism = Homo sapiens
SEQUENCE: 97
```

```
MGSAHPRPWL RLRPQPQPRP ALWVLLFFLL LLAAAMPRSA PNDILDLRLP PEPVLNANTV  60
CLTLPGLSRR QMEVCVRHPD VAASAIQGIQ IAIHECQHQF RDQRWNCSSL ETRNKIPYES  120
PIFSRGFRES AFAYAIAAAG VVHAVSNACA LGKLKACGCD ASRRGDEEAF RRKLHRLQLD  180
ALQRGKGLSH GVPEHPALPT ASPGLQDSWE WGGCSPDMGF GERFSKDFLD SREPHRDIHA  240
RMRLHNNRVG RQAVMENMRR KCKCHGTSGS CQLKTCWQVT PEFRTVGALL RSRFHRATLI  300
RPHNRNGGQL EPGPAGAPSP APGAPGPRRR ASPADLVYFE KSPDFCEREP RLDSAGTVGR  360
LCNKSSAGSD GCGSMCCGRG HNILRQTRSE RCHCRFHWCC FVVCEECRIT EWVSVCK     417

SEQ ID NO: 98          moltype = AA  length = 389
FEATURE                Location/Qualifiers
source                 1..389
                       mol_type = protein
                       organism = Homo sapiens
SEQUENCE: 98
MLEEPRPRPP PSGLAGLLFL ALCSRALSNE ILGLKLPGEP PLTANTVCLT LSGLSKRQLG  60
LCLRNPDVTA SALQGLHIAV HECQHQLRDQ RWNCSALEGG GRLPHHSAIL KRGFRESAFS  120
FSMLAAGVMH AVATACSLGK LVSCGCGWKG SGEQDRLRAK LLQLQALSRG KSFPHSLPSP  180
GPGSSPSPGP QDTWEWGGCN HDMDFGEKFS RDFLDSREAP RDIQARMRIH NNRVGRQVVT  240
ENLKRKCKCH GTSGSCQFKT CWRAAPEFRA VGAALRERLG RAIFIDTHNR NSGAFQPRLR  300
PRRLSGELVY FEKSPDFCER DPTMGSPGTR GRACNKTSRL LDGCGSLCCG RGHNVLRQTR  360
VERCHCRFHW CCYVLCDECK VTEWVNVCK                                    389

SEQ ID NO: 99          moltype = AA  length = 354
FEATURE                Location/Qualifiers
source                 1..354
                       mol_type = protein
                       organism = Homo sapiens
SEQUENCE: 99
MRARPQVCEA LLFALALQTG VCYGIKWLAL SKTPSALALN QTQHCKQLEG LVSAQVQLCR  60
SNLELMHTVV HAAREVMKAC RRAFADMRWN CSSIELAPNY LLDLERGTRE SAFVYALSAA  120
AISHAIARAC TSGDLPGCSC GPVPGEPPGP GNRWGGCADN LSYGLLMGAK FSDAPMKVKK  180
TGSQANKLMR LHNSEVGRQA LRASLEMKCK CHGVSGSCSI RTCWKGLQEL QDVAADLKTR  240
YLSATKVVHR PMGTRKHLVP KDLDIRPVKD SELVYLQSSP DFCMKNEKVG SHGTQDRQCN  300
KTSNGSDSCD LMCCGRGYNP YTDRVVERCH CKYHWCCYVT CRRCERTVER YVCK        354

SEQ ID NO: 100         moltype = AA  length = 365
FEATURE                Location/Qualifiers
source                 1..365
                       mol_type = protein
                       organism = Homo sapiens
SEQUENCE: 100
MDRAALLGLA RLCALWAALL VLFPYGAQGN WMWLGIASFG VPEKLGCANL PLNSRQKELC  60
KRKPYLLPSI REGARLGIQE CGSQFRHERW NCMITAAATT APMGASPLFG YELSSGTKET  120
AFIYAVMAAG LVHSVTRSCS AGNMTECSCD TTLQNGGSAS EGWHWGGCSD DVQYGMWFSR  180
KFLDFPIGNT TGKENKVLLA MNLHNNEAGR QAVAKLMSVD CRCHGVSGSC AVKTCWKTMS  240
SFEKIGHLLK DKYENSIQIS DKTKRKMRRR EKDQRKIPIH KDDLLYVNKS PNYCVEDKKL  300
GIPGTQGREC NRTSEGADGC NLLCCGRGYN THVVRHVERC ECKFIWCCYV RCRRCESMTD  360
VHTCK                                                              365

SEQ ID NO: 101         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 101
GSSGESTHHK PS                                                      12

SEQ ID NO: 102         moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 102
TGGADTTHHR PAT                                                     13

SEQ ID NO: 103         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 103
GQVLPTTTPS SP                                                      12
```

```
SEQ ID NO: 104          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 104
GAGTG                                                                       5

SEQ ID NO: 105          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 105
GSGS                                                                        4

SEQ ID NO: 106          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 106
GSGSGS                                                                      6

SEQ ID NO: 107          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 107
SGSG                                                                        4

SEQ ID NO: 108          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 108
SGSGSG                                                                      6

SEQ ID NO: 109          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 109
GSSG                                                                        4

SEQ ID NO: 110          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 110
GGGGS                                                                       5

SEQ ID NO: 111          moltype = DNA  length = 17
FEATURE                 Location/Qualifiers
misc_feature            1..17
                        note = Description of Artificial Sequence: Synthetic
                         oligonucleotide
source                  1..17
                        mol_type = other DNA
                        organism = synthetic construct
SEQUENCE: 111
```

```
aaataaaata cgaaatg                                                   17

SEQ ID NO: 112          moltype =   length =
SEQUENCE: 112
000
```